(12) United States Patent
Yu et al.

(10) Patent No.: US 9,260,722 B2
(45) Date of Patent: Feb. 16, 2016

(54) HEPATOCYTE PRODUCTION BY FORWARD PROGRAMMING

(71) Applicant: CELLULAR DYNAMICS INTERNATIONAL, INC., Madison, WI (US)

(72) Inventors: Junying Yu, Madison, WI (US); Fongching Kevin Chau, Madison, WI (US); Jinlan Jiang, Madison, WI (US); Yong Jiang, Madison, WI (US); Maksym A. Vodyanyk, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 307 days.

(21) Appl. No.: 13/910,510

(22) Filed: Jun. 5, 2013

(65) Prior Publication Data
US 2013/0251694 A1    Sep. 26, 2013

Related U.S. Application Data

(62) Division of application No. 13/086,159, filed on Apr. 13, 2011, now Pat. No. 8,481,317.

(60) Provisional application No. 61/323,689, filed on Apr. 13, 2010.

(51) Int. Cl.
| | | |
|---|---|---|
| C12N 5/00 | (2006.01) |
| C12N 15/85 | (2006.01) |
| C12N 5/071 | (2010.01) |
| A61K 35/407 | (2015.01) |
| G01N 33/50 | (2006.01) |

(52) U.S. Cl.
CPC .............. *C12N 15/85* (2013.01); *A61K 35/407* (2013.01); *C12N 5/067* (2013.01); *G01N 33/5067* (2013.01); *C12N 2501/12* (2013.01); *C12N 2501/237* (2013.01); *C12N 2501/60* (2013.01); *C12N 2506/02* (2013.01); *C12N 2506/45* (2013.01)

(58) Field of Classification Search
CPC .... C12N 15/85; C12N 5/067; G01N 33/5067; A61K 35/407
See application file for complete search history.

(56) References Cited

U.S. PATENT DOCUMENTS

| | | |
|---|---|---|
| 5,486,359 A | 1/1996 | Caplan et al. |
| 5,736,396 A | 4/1998 | Bruder et al. |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 6,833,269 B2 | 12/2004 | Carpenter |
| 7,015,036 B2 | 3/2006 | Prachumsri et al. |
| 7,473,555 B2 | 1/2009 | Mandalam et al. |
| 7,781,214 B2 | 8/2010 | Smith et al. |
| 2009/0130064 A1 | 5/2009 | Rogiers et al. |
| 2009/0317365 A1 | 12/2009 | Lee et al. |

FOREIGN PATENT DOCUMENTS

| | | |
|---|---|---|
| EP | 0412700 | 2/1991 |
| EP | 2495320 | 9/2012 |
| EP | 2532741 | 12/2012 |
| JP | 2008-546417 | 12/2008 |
| WO | WO 03/042405 | 5/2003 |
| WO | WO 2007-002568 | 1/2007 |
| WO | WO 2010/014949 | 2/2010 |
| WO | WO 2011-052504 | 5/2011 |
| WO | WO 2011-096223 | 8/2011 |

OTHER PUBLICATIONS

"ERG v-ets erythroblastosis virus E26 oncogene homolog (avian) [Homo sapiens]" Gene ID: 2078. Entrez Gene. Updated May 29, 2010.
Amit et al., "Clonally derived human embryonic stem cell lines maintain pluripotency and proliferative potential for prolonged periods of culture," *Dev. Bio.*, 227:271-278, 2000.
Bailey et al., "Transplanted adult hematopoietic stem cells differentiate into functional endothelial cells,"*Blood*, 103(1):13-19, 2004.
Bhatia et al., "Bone morphogenetic proteins regulate the developmental program of human hematopoietic stem cells," *J. Exp. Med.*, 189:1139-1148, 1999.
Boyer et al., "Core transcriptional regulatory circuitry in human embryonic stem cells," *Cell*, 122(6):947-56, 2005.
Chadwick et al.., "Cytokines and BMP-4 promote hematopoietic differentiation of human embryonic stem cells," *Blood*, 102(3):906-915, 2003.
Chambers et al., "Functional expression cloning of Nanog, a pluripotency sustaining factor in embryonic stem cells," *Cell*, 113(5):643-55, 2003.
David et al., "Foward programming of pluripotent stem cells towards distinct cardiovascular cell types," *Cardiovascular Research*, 84:263-272, 2009.
De Val and Black, "Transcriptional control of endothelial cell development," *Developmental Cell*, 16:180-195, 2009.
Dzau et al., "Therapeutic potential of endothelial progenitor cells in cardiovascular diseases," *Hypertension*, 46-7-18, 2005.
Genbank Accession No. NM 000545.4 "Homo sapiens HNF-1A homeobox A (HNF1A), mRNA", 1990.
Genbank Accession No. NM_000457.3 "Homo sapiens hepatocyte nuclear factor 4, alpha (HNF4A), transcript variant 2, mRNA," 1994.
Genbank Accession No. NM_005996.3, "Homo sapiens T-box 3 (TBX3), transcript variant 1, mRNA," 1997.

(Continued)

*Primary Examiner* — Marcia S Noble
(74) *Attorney, Agent, or Firm* — Parker Highlander PLLC

(57) ABSTRACT

The invention generally features methods for providing hepatocytes from a variety of cell sources, particularly pluripotent stem cells, therapeutic compositions featuring such cells, and methods of using them for the treatment of subjects.

3 Claims, 9 Drawing Sheets

(56) References Cited

OTHER PUBLICATIONS

Genbank Accession No. NM_153675.2, "Homo sapiens forkhead box A2 (FOXA2), transcript variant 2, mRNA," 1997.
Genbank Accession No. NM_178849.1, "Homo sapiens hepatocyte nuclear factor 4, alpha (HNF4A), transcript variant 1, mRNA" 1994.
Genbank Accession No. NM_1788501.1, "Homo sapiens hepatocyte nuclear factor 4, alpha (HNF4A), transcript variant 3, mRNA," 1994.
Genbank Accession No. NM_001030003.1, "Homo sapiens hepatocyte nuclear factor 4, alpha (HNF4A), transcript variant 5, mRNA," 1994.
Genbank Accession No. NM_001030004.1, "Homo sapiens hepatocyte nuclear factor 4, alpha (HNF4A), transcript varient 6, mRNA," 1994.
Hayhurst et al., "Hepatocyte nuclear factor 4alpha (nuclear receptor 2A1) is essential for maintenance of hepatic gene expression and lipid homeostasis," *Mol. Cell Biol.*, 21(4):1393-403, 2001.
Huang et al., "Induction of functional hepatocyte-like cells from mouse fibroblasts by defined factors," *Nature*, 475(7356):386-389, 2011.
Huber et al., "Cooperative effects of growth factors involved in the induction of hematopoietic mesoderm," *Blood*, 92: 4128-4137, 1998.
Ishizaka et al., "Development of hepatocytes from embryonic stem cells after transfection with the HNF-3β gene," *The FASEB Journal* express article, doi:10.1096/fj.01-0806fje. Published online Jul. 1, 2002.
Kheolamai and Dickson, "Liver-enriched transcription factors are critical for the expression of hepatocyte marker genes in mES-derived hepatocyte-lineage cells," *BMC Molecular Biology*, 10:35, doi:10.11861/1471-2199-10-35, 2009.
Kuzuya et al., "VEGF protects against oxidized LDL toxicity to endothelial cells by an intracellular glutathione-dependent mechanism through the KDR receptor," *Arterioscl., Thromb. Vascular Biol.*, 21:765-70, 2001.
Li et al., "Mammalian hepatocyte differentiation requires the transcription factor HNF-4alpha," *Genes Dev.*, 14(4):464-74, 2000.
Li et al., "Transplantation of human embryonic stem cell-derived endothelial cells for vascular diseases," *J. Cell Biochem.*, 106:194-199, 2009.
Marshall et al., "Polarized expression of bone morphogenetic protein-4 in the human aorta-gonad-mesonephros region," *Blood*, 96:1591-1593, 2000.
Nagaki and Moriwaki, "Transcription factor HNF and hepatocyte differentiation," *Hepatology Research*, 38:961-969, 2008.
Sekiya and Suzuki, "Direct conversion of mouse fibroblasts to hepatocyte-like cells by defined factors," *Nature*, 475(7356):390-393, 2011.
Sullivan et al., "Generation of functional human hepatic endoderm from human induced pluripotent stem cells," *Hepatology*, 51(1):329-335, 2010.
Takahashi and Yamanaka, "Induction of pluripotent stem cells from mouse embryonic and adult fibroblast cultures by defined factors," *Cell*, 126(4):663-676, 2006.
Takahashi et al., "Induction of pluripotent stem cells from adult human fibroblasts by defined factors," *Cell*, 131:861-872, 2007.
Thomson et al. "Isolation of a primate embryonic stem cell line," *Proc. Natl. Acad. Scie. USA*, 92:7844-7848, 1995.
Thomson et al., "Embryonic stem cell lines derived from human blastocysts," *Science*, 282:1145, 1998.
U.S. Appl. No. 61/058,858 entitled Methods for the Production of iPS Cells Using Non VIral Approach, by Amanda Mack, filed Jun. 4, 2008.
U.S. Appl. No. 61/184,546 entitled "Reprogramming T Cells," by Matthew Brown et al., filed Jun. 5, 2009.
Watt et al., "HNF4: A central regulator of hepatocyte differentiation and function," *Hepatology*, 37(6): 1249-1253, 2003.
Yu and Thompson, "Pluripotent stem cell lines," *Genes Dev.*, 22(15):1987-97, 2008.
Yu et al., "Human induced pluripotent stem cells free of vector and transgene sequences," *Science*, 324(5928):797-801, 2009.
Yu et al., *Science*, "Induced pluripotent stem cell lines derived from human somatic cells," 318(5858):1917-1920, 2007.
PCT International Search Report and Written Opinion issued in International application No. PCT/US2011/032309, dated Dec. 9, 2011.
Lavon et al., "Study of hepatocyte differentiation using embryonic stem cells," *Journal of Cellular Biochemistry*, 96:1193-1202, 2005.
Levinson-Dushnik et al., "Involvement of hepatocyte nuclear factor 3 in endoderm differentiation of embryonic stem cells," *Molecular and Cellular Biology*, 17(7):3817-3822, 1997.
Si-Tayeb et al., "Highly efficient generation of human hepatocyte-like cells from induced pluripotent stem cells," *Hepatology*, 51(1):297-305, 2010.
Zhao et al., "Derivation and characterization of hepatic progenitor cells from human embryonic stem cells," *PLoSONE*, 4(7):e6468, pp. 1010, 2009.
Nikolova-Krstevski et al., "ERG is required for the differentiation of embryonic stem cells along the endothelial lineage," *BMC Developmental Biology*, 9:72, 2009.
PCT International Search Report and Written Opinion issued in International application No. PCT/US2001/043218, dated Feb. 17, 2012.
Ria et al., "Endothelial differentiation of hematopoietic stem and progenitor cells from patients with multiple myeloma," *Clinical Cancer Research*, 14:1678-1685, 2008.
Wong et al., "Identification of vasculature-specific genes by microarray analysis of Etsrp/Etv2 overexpressing zebrafish embryos," *Developmental Dynamics*, 238(7):1836-1850, 2009.
Harding and Gibson, "Therapeutic liver repopulation for phenylketonuria," *J Inherit Metab Dis.*, 33:681-687, 2010.
Office Communication issued in U.S. Appl. No. 13/086,159, dated Aug. 17, 2012.
Office Communication issued in U.S. Appl. No. 13/086,159, dated Oct. 10, 2012.
PCT International Preliminary Report on Patentability issued in International application No. PCT/US2011/032309, dated Oct. 16, 2012.
Office Action issued in Japanese Application No. 2013-505093, mailed Jun. 12, 2015.

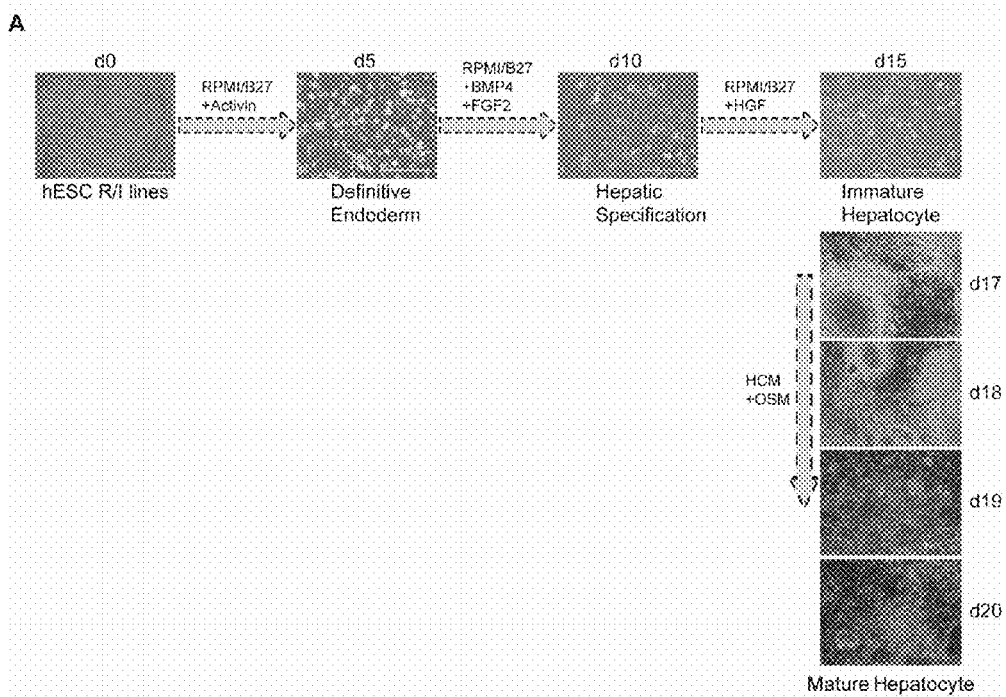

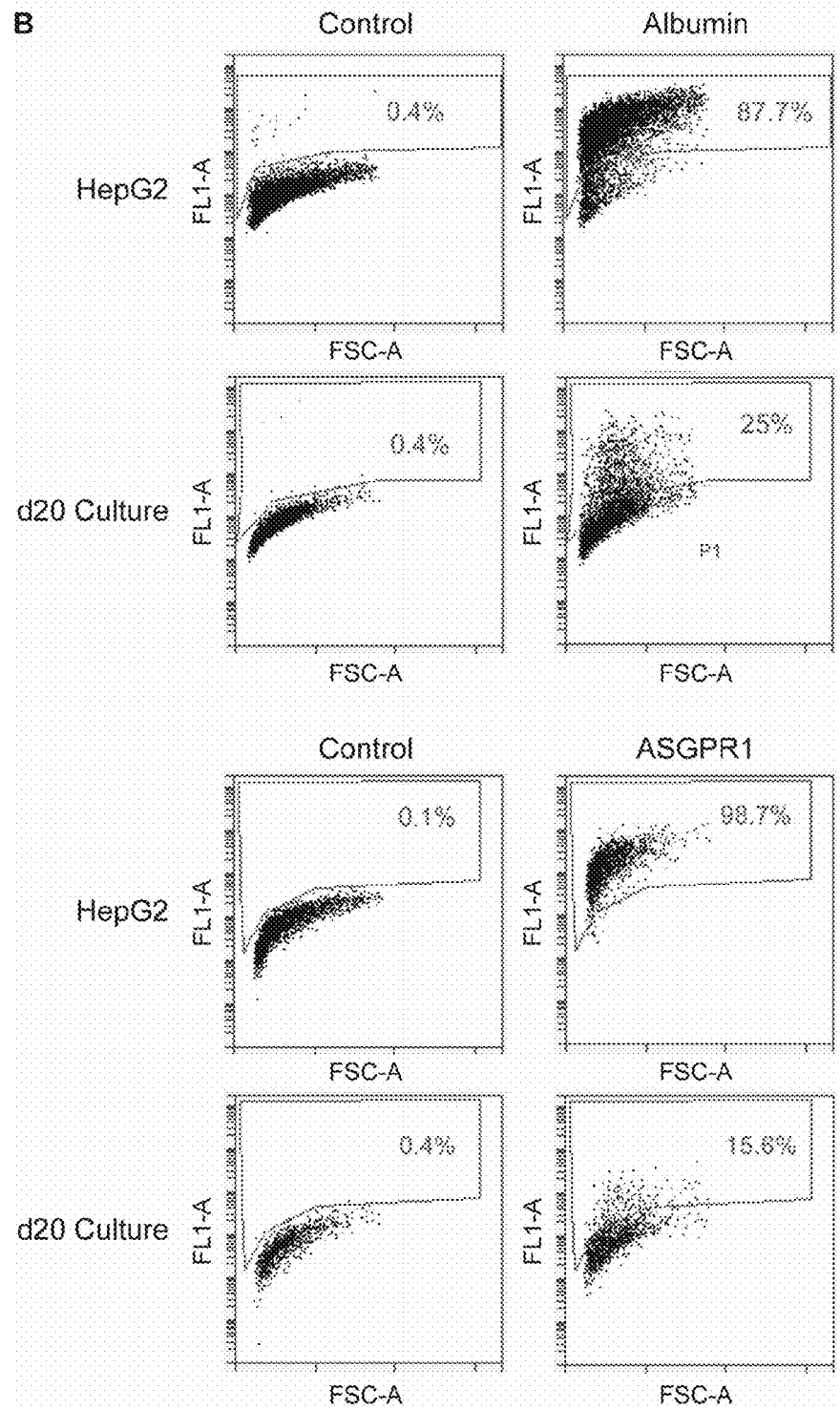

SEQUENCE LISTING

<160> NUMBER OF SEQ ID NOS: 53

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Arg Lys Lys Arg Arg Gln Arg Arg Arg
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Tyr Gly Arg Lys Lys Arg Arg Gln Arg Arg Arg
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Ala Lys Ile Trp Phe Gln Asn Arg Arg Met Lys Trp Lys Lys Glu Asn
1               5                   10                  15

Asn

<210> SEQ ID NO 4
<211> LENGTH: 34
<212> TYPE: PRT
<213> ORGANISM: Artificial Sequence
<220> FEATURE:
<223> OTHER INFORMATION: Synthetic peptide

<400> SEQUENCE: 4

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Tyr Ala Arg Lys Ala Arg Arg Gln Ala Arg Arg
1               5                   10

<210> SEQ ID NO 6
<211> LENGTH: 11
<212> TYPE: PRT
<213> ORGANISM: Artificial Sequence

```
<220> FEATURE:
<223> OTHER INFORMATION: Synthetic peptide

<400> SEQUENCE: 6

Tyr Ala Arg Ala Ala Arg Arg Ala Ala Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Tyr Ala Arg Ala Ala Arg Arg Ala Ala Arg Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Tyr Ala Arg Ala Ala Ala Arg Gln Ala Arg Ala
1               5                   10

<210> SEQ ID NO 9
<211> LENGTH: 2350
<212> TYPE: DNA
<213> ORGANISM: Homo sapiens

<400> SEQUENCE: 9
gcagtgtcac taggccggct gggggccctg ggtacgctgt agaccagacc gcgacaggcc      60
agaacacggg cggcggcttc gggccgggag acccgcgcag ccctcgggac atctcagtgc     120
ctcactcccc accccctccc ccgggtcggg ggaggcggcg cgtccggcgg agggttgagg     180
ggagcgggggc aggcctggag cgccatgagc agcccggatg cgggatacgc cagtgacgac     240
cagagccaga cccagagcgc gctgcccgcg gtgatggccg ggctgggccc ctgcccctgg     300
gccgagtcgc tgagccccat cggggacatg aaggtgaagg cgaggcgcc ggcgaacagc      360
ggagcaccgg ccgggggccgc gggccgagcc aagggcgagt cccgtatccg gcggccgatg     420
aacgctttca tggtgtgggc taaggacgag cgcaagcggc tggcgcagca gaatccagac     480
ctgcacaacg ccgagttgag caagatgctg ggcaagtcgt ggaaggcgct gacgctggcg     540
gagaagcggc ccttcgtgga ggaggcagag cggctgcgcg tgcagcacat gcaggaccac     600
cccaactaca agtaccggcc gcggcggcgc aagcaggtga agcggctgaa gcgggtggag     660
ggcggcttcc tgcacggcct ggctgagccg caggcggccg cgctgggccc cgagggcggc     720
cgcgtggcca tggacggcct gggcctccag ttccccgagc agggcttccc cgccggcccg     780
ccgctgctgc ctccgcacat gggcggccac taccgcgact gccagagtct gggcgcgcct     840
ccgctcgacg gctacccgtt gcccacgccc gacacgtccc cgctgacgg cgtggacccc     900
gacccggctt tcttcgccgc cccgatgccc ggggactgcc cggcggccgg cacctacagc     960
tacgcgcagg tctcggacta cgctggcccc ccggagcctc ccgccggtcc catgcacccc    1020
cgactcggcc cagagcccgc gggtcccctcg attccgggcc tcctggcgcc acccagcgcc    1080
cttcacgtgt actacggcgc gatgggctcg cccgggggcgg gcggcgggcg cggcttccag    1140
```

```
atgcagccgc aacaccagca ccagcaccag caccagcacc accccccggg ccccggacag    1200
ccgtcgcccc ctccggaggc actgccctgc cgggacggca cggaccccag tcagcccgcc    1260
gagctcctcg gggaggtgga ccgcacggaa tttgaacagt atctgcactt cgtgtgcaag    1320
cctgagatgg gcctccccta ccaggggcat gactccggtg tgaatctccc cgacagccac    1380
ggggccattt cctcggtggt gtccgacgcc agctccgcgg tatattactg caactatcct    1440
gacgtgtgac aggtccctga tccgccccag cctgcaggcc agaagcagtg ttacacactt    1500
cctggaggag ctaaggaaat cctcagactc ctgggttttt gttgttgctg ttgttgtttt    1560
ttaaaaggtg tgttggcata taatttatgg taatttattt tgtctgccac ttgaacagtt    1620
tgggggggtg aggtttcatt taaaatttgt tcagagattt gtttcccata gttggattgt    1680
caaaacccta tttccaagtt caagttaact agctttgaat gtgtcccaaa acagcttcct    1740
ccatttcctg aaagtttatt gatcaaagaa atgttgtcct gggtgtgttt tttcaatctt    1800
ctaaaaaata aaatctggaa tcctgctttt ttgctctact agtacctctg tcacactagt    1860
cttatcaaaa accagttctt aagatcaatg ttaagtttat tagttaatgt aaatttctca    1920
tcctcgaaaa gggtgaacat aaatgccttt aaggagtata tctaaaaata aacattagga    1980
tatctaagtt tgatgtaatt gtttcaggaa ggaaaaaaga aaagcattct ggaatgagcc    2040
tacttcaagt aatcttagtt tctaaaacta acagttaata tttcaattc cagtatatca     2100 ctttaagtag aaggggatgt ccaagtaatt ttggttttct aactgttgaa tcataagctt    2160
gacctgcccc cagaggcttt ttggatgttt ttatctgtgt tttgccatct ctttacactc    2220
ctcgacattc agtttacctt aatcttcaca tttttacacc ttgggaagtg gcaagcatcg    2280
ctgggtttaa gataaaggag tcacaaaaac taatcaaaat aaaatttgca ttatgacaac    2340
ttttaataca                                                            2350

<210> SEQ ID NO 10
<211> LENGTH: 3124
<212> TYPE: DNA
<213> ORGANISM: Homo sapiens

<400> SEQUENCE: 10
taagatccac atcagctcaa ctgcacttgc ctcgcagagg cagcccgctc acttcccgcg      60
gaggcgctcc ccggcgccgc gctccgcggc agccgcctgc ccccggcgct gccccgcgcc     120
gccgcgccgc cgccgccgcc gcgcacgccg cgcccgcag ctctgggctt cctcttcgcc      180
cgggtggcgt tgggccgcg cggggcgctcg ggtgactgca gctgctcagc tcccctcccc     240
cgccccgcgc cgcgcggccg cccgtcgctt cgcacagggc tggatggttg tattgggcag    300
ggtggctcca ggatgttagg aactgtgaag atggaagggc atgaaaccag cgactggaac    360
agctactacg cagacacgca ggaggcctac tcctccgtcc cggtcagcaa catgaactca    420
ggcctgggct ccatgaactc catgaacacc tacatgacca tgaacaccat gactacgagc    480
ggcaacatga ccccggcgtc cttcaacatg tcctatgcca acccgggcct aggggccggc    540
ctgagtcccg gcgcagtagc cggcatgccg ggggctcgg cggcgccat gaacagcatg     600 actgcggccg gcgtgacggc catgggtacg gcgctgagcc cgagcggcat gggcgccatg    660
ggtgcgcagc aggcggcctc catgaatggc ctgggcccct acgcggccgc catgaacccg    720
tgcatgagcc ccatggcgta cgcgccgtcc aacctgggcc gcagccgcgc gggcggcggc    780
ggcgacgcca agacgttcaa gcgcagctac ccgcacgcca gccgccctac ctcgtacatc    840
```

```
tcgctcatca ccatggccat ccagcaggcg cccagcaaga tgctcacgct gagcgagatc    900
taccagtgga tcatggacct cttcccctat taccggcaga accagcagcg ctggcagaac    960
tccatccgcc actcgctgtc cttcaatgac tgcttcgtca aggtggcacg ctccccggac   1020
aagccgggca agggctccta ctggacgctg cacccggact ccggcaacat gttcgagaac   1080
ggctgctact tgcgccgcca gaagcgcttc aagtgcgaga agcagccggg ggccggcggc   1140
gggggcggga gcggaagcgg gggcagcggc gccaagggcg gccctgagag ccgcaaggac   1200
ccctctggcg cctctaaccc cagcgccgac tcgcccctcc atcggggtgt gcacgggaag   1260
accggccagc tagagggcgc gccggccccc gggcccgccg ccagccccca gactctggac   1320
cacagtgggg cgacggcgac agggggcgcc tcggagttga agactccagc ctcctcaact   1380
gcgcccccca taagctccgg gccgggggcg ctggcctctg tgcccgcctc tcacccggca   1440
cacggcttgg caccccacga gtcccagctg cacctgaaag gggaccccca ctactccttc   1500
aaccacccgt tctccatcaa caacctcatg tcctcctcgg agcagcagca taagctggac   1560
ttcaaggcat acgaacaggc actgcaatac tcgccttacg gctctacgtt gcccgccagc   1620
ctgcctctag gcagcgcctc ggtgaccacc aggagcccca tcgagccctc agccctggag   1680
ccggcgtact accaaggtgt gtattccaga cccgtcctaa acacttccta gctcccggga   1740
ctgggggggtt tgtctggcat agccatgctg gtagcaagag agaaaaaatc aacagcaaac   1800
aaaaccacac aaaaccaaacc gtcaacagca taataaaatc ccaacaacta tttttatttc   1860
attttttcatg cacaacctttt ccccccagtgc aaaagactgt tactttatta ttgtattcaa   1920
aattcattgt gtatattact acaaagacaa ccccaaacca attttttttcc tgcgaagttt   1980
aatgatccac aagtgtatat atgaaattct cctccttcct tgccccccctc tctttcttcc   2040
ctctttcccc tccagacatt ctagtttgtg gagggttatt taaaaaaaca aaaaaggaag   2100
atggtcaagt ttgtaaaata tttgtttgtg ctttttcccc ctccttacct gacccccctac   2160
gagtttacag gtctgtggca atactcttaa ccataagaat tgaaatggtg aagaaacaag   2220
tatacactag aggctcttaa aagtattgaa agacaatact gctgttatat agcaagacat   2280
aaacagatta taaacatcag agccatttgc ttctcagttt acatttctga tacatgcaga   2340
tagcagatgt ctttaaatga aatacatgta tattgtgtat ggacttaatt atgcacatgc   2400
tcagatgtgt agacatcctc cgtatatttta cataacatat agaggtaata gataggtgat   2460
atacatgata cattctcaag agttgcttga ccgaaagtta caaggacccc aaccccttttg   2520
tcctctctac ccacagatgg ccctgggaat caattcctca ggaattgccc tcaagaactc   2580
tgcttcttgc tttgcagagt gccatggtca tgtcattctg aggtcacata acacataaaa   2640
ttagtttcta tgagtgtata ccatttaaag aatttttttt tcagtaaaag ggaatattac   2700
aatgttggag gagagataag ttatagggag ctggatttca aaacgtggtc caagattcaa   2760
aaatcctatt gatagtggcc atttttaatca ttgccatcgt gtgcttgttt catccagtgt   2820
tatgcacttt ccacagttgg acatggtgtt agtatagcca gacgggtttc attattattt   2880
ctctttgctt tctcaatgtt aatttattgc atggtttatt cttttttcttt acagctgaaa   2940
ttgctttaaa tgatggttaa aattacaaat taaattgtta atttttatca atgtgattgt   3000
aattaaaaat atttttgattt aaataacaaa aataatacca gatttttaagc cgtggaaaat   3060
gttcttgatc atttgcagtt aaggacttta aataaatcaa atgttaacaa aaaaaaaaaa   3120
aaaa                                                                3124
```

```
<210> SEQ ID NO 11
<211> LENGTH: 2428
<212> TYPE: DNA
<213> ORGANISM: Homo sapiens

<400> SEQUENCE: 11
cccgcccact tccaactacc gcctccggcc tgcccaggga gagagaggga gtggagccca        60
gggagaggga gcgcgagaga gggagggagg aggggacggt gctttggctg acttttttt       120 aaaagagggt gggggtgggg ggtgattgct ggtcgtttgt tgtggctgtt aaattttaaa       180
ctgccatgca ctcggcttcc agtatgctgg gagcggtgaa gatggaaggg cacgagccgt       240
ccgactggag cagctactat gcagagcccg agggctactc ctccgtgagc aacatgaacg       300
ccggcctggg gatgaacggc atgaacacgt acatgagcat gtcggcggcc gccatgggca       360
gcggctcggg caacatgagc gcgggctcca tgaacatgtc gtcgtacgtg ggcgctggca       420
tgagcccgtc cctggcgggg atgtccccccg cgcgggcgc catggcgggc atgggcggct       480
cggccggggc ggccggcgtg gcgggcatgg ggccgcactt gagtcccagc ctgagcccgc       540
tcggggggca ggcggccggg gccatgggcg gcctggcccc ctacgccaac atgaactcca       600
tgagccccat gtacgggcag gcgggcctga ccgcgcccg cgaccccaag acctacaggc       660
gcagctacac gcacgcaaag ccgccctact cgtacatctc gctcatcacc atggccatcc       720
agcagagccc caacaagatg ctgacgctga gcgagatcta ccagtggatc atggaccctc       780
tccccttcta ccggcagaac cagcagcgct ggcagaactc catccgccac tcgctctcct       840
tcaacgactt tttcctgaag gtgccccgct cgcccgacaa gcccggcaag ggctccttct       900
ggaccctgca ccctgactcg ggcaacatgt tcgagaacgg ctgctacctg cgccgccaga       960 gcgcttcaa gtgcgagaag cagctggcgc tgaaggaggc cgcaggcgcc gccggcagcg      1020
gcaagaaggc ggccgccgga gcccaggcct cacaggctca actcggggag gccgccgggc      1080
cggcctccga gactccggcg ggcaccgagt cgcctcactc gagcgcctcc ccgtgccagg      1140
agcacaagcg agggggcctg ggagagctga aggggacgcc ggctgcggcg ctgagccccc      1200
cagagccggc gccctctccc gggcagcagc agcaggccgc ggcccacctg ctgggccccg      1260
cccaccaccc gggcctgccg cctgaggccc acctgaagcc ggaacaccac tacgccttca      1320 accaccgtt ctccatcaac aacctcatgt cctcggagca gcagcaccac cacagccacc      1380
accaccacca accccacaaa atggacctca aggcctacga caggtgatg cactaccccg      1440 gctacggttc ccccatgcct ggcagcttgg ccatgggccc ggtcacgaac aaaacgggcc      1500
tggacgcctc gcccctggcc gcagatacct cctactacca gggggtgtac tcccggccca      1560
ttatgaactc ctcttaagaa gacgacggct tcaggcccgg ctaactctgg cacccggat      1620 cgaggacaag tgagagagca agtggggtc gagactttgg ggagacgtg ttgcagagac      1680 gcaagggaga agaaatccat aacaccccca ccccaacacc cccaagacag cagtcttctt      1740
cacccgctgc agccgttccg tcccaaacag agggccacac agatacccca cgttctatat      1800
aaggaggaaa acgggaaaga atataaagtt aaaaaaaagc ctccggtttc cactactgtg      1860
tagactcctg cttcttcaag cacctgcaga ttctgatttt tttgttgttg ttgttctcct      1920
ccattgctgt tgttgcaggg aagtcttact taaaaaaaaa aaaaattttt gtgagtgact      1980
cggtgtaaaa ccatgtagtt ttaacagaac cagagggttg tactattgtt taaaaacagg      2040
aaaaaaaata atgtaagggt ctgttgtaaa tgaccaagaa aaagaaaaaa aaagcattcc      2100
caatcttgac acggtgaaat ccaggtctcg ggtccgatta atttatggtt tctgcgtgct      2160
```

-continued

| | |
|---|---|
| ttatttatgg cttataaatg tgtattctgg ctgcaagggc cagagttcca caaatctata | 2220 |
| ttaaagtgtt atacccggtt ttatcccttg aatcttttct tccagatttt tcttttcttt | 2280 |
| acttggctta caaaatatac aggcttggaa attatttcaa gaaggaggga gggataccct | 2340 |
| gtctggttgc aggttgtatt ttattttggc ccagggagtg ttgctgtttt cccaacattt | 2400 |
| tattaataaa attttcagac ataaaaaa | 2428 |

<210> SEQ ID NO 12
<211> LENGTH: 2415
<212> TYPE: DNA
<213> ORGANISM: Homo sapiens

<400> SEQUENCE: 12

| | |
|---|---|
| cggccgctgc tagaggggct gcttgcgcca ggcgccggcc gccccactgc gggtccctgg | 60 |
| cggccggtgt ctgaggagtc ggagagccga ggcggccaga ccgtgcgccc cgcgcttctc | 120 |
| ccgaggccgt tccgggtctg aactgtaaca gggaggggcc tcgcaggagc agcagcgggc | 180 |
| gagttaaagt atgctgggag cggtgaagat ggaagggcac gagccgtccg actgagcag | 240 |
| ctactatgca gagcccgagg gctactcctc cgtgagcaac atgaacgccg gcctggggat | 300 |
| gaacggcatg aacacgtaca tgagcatgtc ggcggccgcc atgggcagcg gctcgggcaa | 360 |
| catgagcgcg ggctccatga acatgtcgtc gtacgtgggc gtggcatga gcccgtccct | 420 |
| ggcggggatg tcccccggcg cgggcgccat ggcgggcatg ggcggctcgg ccggggcggc | 480 |
| cggcgtggcg ggcatggggc cgcacttgag tcccagcctg agcccgctcg gggggcaggc | 540 |
| ggccggggcc atgggcggcc tggcccccta cgccaacatg aactccatga gccccatgta | 600 |
| cgggcaggcg ggcctgagcc gcgcccgcga ccccaagacc tacaggcgca gctacacgca | 660 |
| cgcaaagccg ccctactcgt acatctcgct catcaccatg gccatccagc agagccccaa | 720 |
| caagatgctg acgctgagcg agatctacca gtggatcatg gacctcttcc ccttctaccg | 780 |
| gcagaaccag cagcgctggc agaactccat ccgccactcg ctctccttca cgactgttt | 840 |
| cctgaaggtg ccccgctcgc ccgacaagcc cggcaagggc tccttctgga ccctgcaccc | 900 |
| tgactcgggc aacatgttcg agaacggctg ctacctgcgc cgccagaagc gcttcaagtg | 960 |
| cgagaagcag ctggcgctga aggaggccgc aggcgccgcc ggcagcggca agaaggcggc | 1020 |
| cgccggagcc caggcctcac aggctcaact cggggaggcc gccgggccgg cctccgagac | 1080 |
| tccggcgggc accgagtcgc tcactcgag cgcctccccg tgccaggagc acaagcgagg | 1140 |
| gggcctggga gagctgaagg ggacgccggc tgcggcgctg agcccccag agccggcgcc | 1200 |
| ctctcccggg cagcagcagc aggccgcggc ccacctgctg ggcccgcccc accacccggg | 1260 |
| cctgccgcct gaggcccacc tgaagccgga acaccactac gccttcaacc cccgttctc | 1320 |
| catcaacaac ctcatgtcct cggagcagca gcaccaccac agccaccacc accaccaacc | 1380 |
| ccacaaaatg gacctcaagg cctacgaaca ggtgatgcac taccccсggct acggttcccc | 1440 |
| catgcctggc agcttggcca tgggcccggt cacgaacaaa acgggcctgg acgcctcgcc | 1500 |
| cctggccgca gatacctcct actaccaggg ggtgtactcc cggcccatta tgaactcctc | 1560 |
| ttaagaagac gacggcttca ggcccggcta actctggcac cccggatcga ggacaagtga | 1620 |
| gagagcaagt gggggtcgag actttgggga gacggtgttg cagagacgca agggagaaga | 1680 |
| aatccataac acccccaccc caacacccccc aagacagcag tcttcttcac ccgctgcagc | 1740 |
| cgttccgtcc caaacagagg gccacacaga taccccacgt tctatataag gaggaaaacg | 1800 |
| ggaaagaata taaagttaaa aaaaagcctc cggtttccac tactgtgtag actcctgctt | 1860 |

```
cttcaagcac ctgcagattc tgattttttt gttgttgttg ttctcctcca ttgctgttgt    1920
tgcagggaag tcttacttaa aaaaaaaaaa aaattttgtg agtgactcgg tgtaaaacca    1980 tgtagttttta acagaaccag agggttgtac tattgtttaa aaacaggaaa aaaaataatg    2040
taagggtctg ttgtaaatga ccaagaaaaa gaaaaaaaaa gcattcccaa tcttgacacg    2100
gtgaaatcca ggtctcgggt ccgattaatt tatggtttct gcgtgcttta tttatggctt    2160
ataaatgtgt attctggctg caagggccag agttccacaa atctatatta aagtgttata    2220
cccggtttta tcccttgaat ctttctcttcc agatttttct tttctttact tggcttacaa    2280
aatatacagg cttggaaatt atttcaagaa ggagggaggg ataccctgtc tggttgcagg    2340 ttgtattttta ttttggccca gggagtgttg ctgttttccc aacattttat taataaaatt    2400
ttcagacata aaaaa                                                     2415

<210> SEQ ID NO 13
<211> LENGTH: 1772
<212> TYPE: DNA
<213> ORGANISM: Homo sapiens

<400> SEQUENCE: 13
ggataaatgt agcgccgcgg cgcgggccag cagctctgcg aggggccgga gcgcggcgga     60
gccatgcagt accgcacccc cgggccggcg cggggcgccg tggggggtgcc gctgtacgcg    120 cccacgccgc tgctgcaacc cgcacacccg acgcccttt acatcgagga catcctgggc    180
cgcgggcccg ccgcgcccac gcccgccccc acgctgccgt cccccaactc ctccttcacc    240
agcctcgtgt cccctaccg gaccccggtg tacgagccca cgccgatcca tccagccttc    300
tcgcaccact ccgccgccgc gctggccgct gcctacggac ccggcggctt cgggggccct    360 ctgtaccccct tcccgcggac ggtgaacgac tacacgcacg ccctgctccg ccacgacccc    420
ctgggcaaac ctctactctg gagccccttc ttgcagaggc ctctgcataa aaggaaaggc    480
ggccaggtga gattctccaa cgaccagacc atcgagctgg agaagaaatt cgagacgcag    540
aaatatctct ctccgcccga gaggaagcgt ctggccaaga tgctgcagct cagcgagaga    600
caggtcaaaa cctggtttca gaatcgacgc gctaaatgga gagactaaa acaggagaac    660 cctcaaagca ataaaaaga gaactggaa agtttggaca gttcctgtga tcagaggcaa    720
gatttgccca gtgaacagaa taaggtgct tctttggata gctctcaatg ttcgccctcc    780
cctgcctccc aggaagacct tgaatcagag atttcagagg attctgatca ggaagtggac    840
attgagggcg ataaaagcta ttttaatgct ggatgatgac cactggcatt ggcatgttca    900
gaaaactgga tttaggaata atgttttgct acagaaaatc ttcatagaag aactggaagg    960
ctatataaga aagggaatca attctctggt attctggaaa cctaaaaata tttggtgcac   1020
tgctcaatta acaaacctac atggagacct taattttgac ttaacaaata gtttatgtac   1080
tgctcttagg ttgttttgat aaagtgacat tatagtgatt aaattcttcc ccctttaaaa   1140
aaacagttag tggttttcac tatttataaa aaattaattt tgaactttt gttaaatttt   1200 taagttatag ctttaaaggt tttaatagga ccttcttgaa cgacttttct gtaatctgtt   1260
tatctcccac ttaatggaaa ggcaaggggg taccccaaat ccagaggtgc ctacatttca   1320
ggcagccttg gagtatttta aaaggaaaac attcttact tttatatgac attcttatac   1380
tgctgtctca aatccaaaaa catttcgag ctccttgtctc agatgtgt gttcttttg   1440 tcagagatat ggttgatgag aatcttaaat gcttgttttg cactatcact tagtacctgt   1500
```

```
ttgaccaagg tgttaagggg atagtacctc ccaattcaag cagagaaact gacctgacta   1560
aagttaatcg cagatgaact agaagtcaca ggttaattaa atgtaagtag attgtagata   1620
ctgttttata tcaaacaatg tttataatgt gtatatagaa ttgttcactg taaaaaaaat   1680
ggccaaaatg tgttttttt ttaataagta acttgactat aaaataaagc cgtccgtggg   1740
acgactgacc tcgttgcaaa aaaaaaaaaa aa                                1772

<210> SEQ ID NO 14
<211> LENGTH: 3419
<212> TYPE: DNA
<213> ORGANISM: Homo sapiens

<400> SEQUENCE: 14
ttggaggcgg ccggcgcagg ggccgcgaga ggcttcgtcg ccgctgcagc tccgggggct     60
cccaggggag cgtgcgcgga acctccaggc ccagcaggac cccggctgcg gcgaggagga    120
aggagccagc ctagcagctt ctgcgcctgt ggccgcgggt gtcctggagg cctctcggtg    180
tgacgagtgg gggacccgaa ggctcgtgcg ccacctccag gcctgacgc tgccctccgt     240 cttctgcccc caataggtgc gccggacctt caggccctgg ggtgaattca gctgctccta    300
catcagcttc cggaaccacc aaaaattcaa attgggattt ccggagtaa acaagagcct     360 agagcccttt gctcaatgct ggatttaata cgtatatatt tttaagcgag ttggtttttt    420
cccctttgat ttttgatctt cgcgacagtt cctcccacgc atattatcgt tgttgccgtc    480
gttttctctc cccgcgtggc tccttgacct gcgagggaga gagaggacac cgaagccggg    540
agctcgcagg gaccatgtat cagagcttgg ccatggccgc caaccacggg ccgcccccg     600 gtgcctacga ggcgggcggc cccggcgcct tcatgcacgg cgcgggcgcc gcgtcctcgc    660
cagtctacgt gcccacaccg cgggtgccct cctccgtgct gggcctgtcc tacctccagg    720
gcggaggcgc gggctctgcg tccggaggcg cctcgggcgg cagctccggt ggggccgcgt    780
ctggtgcggg gccggggacc cagcagggca gcccgggatg gagccaggcg ggagccgacg    840
gagccgctta caccccgccg ccggtgtcgc cgcgcttctc cttcccgggg accaccgggt    900
ccctggcggc cgccgccgcc gctgccgcgg cccgggaagc tgcggcctac agcagtggcg    960
gcggagcggc gggtgcgggc ctggcgggcc gcagcagta cgggcgcgcc ggcttcgcgg   1020
gctcctactc cagcccctac ccggcttaca tggccgacgt gggcgcgtcc tgggccgcag   1080
ccgccgccgc ctccgccggc cccttcgaca gcccggtcct gcacagcctg cccggccggg   1140
ccaacccggc cgcccgacac cccaatctcg atatgtttga cgacttctca gaaggcagag   1200
agtgtgtcaa ctgtggggct atgtccaccc cgctctggag gcgagatggg acgggtcact   1260
atctgtgcaa cgcctgcggc ctctaccaca gatgaacgg catcaaccgg ccgctcatca    1320
agcctcagcg ccggctgtcc gcctcccgcc gagtgggcct ctcctgtgcc aactgccaga   1380
ccaccaccac cacgctgtgg cgccgcaatg cggagggcga gcctgtgtgc aatgcctgcg   1440
gcctctacat gaagctccac ggggtcccca ggcctcttgc aatgcggaaa gagggatcc    1500 aaaccagaaa acggaagccc aagaacctga ataaatctaa gacaccagca gctccttcag   1560
gcagtgagag ccttcctccc gccagcgtg cttccagcaa ctccagcaac gccaccacca    1620
gcagcagcga ggagatgcgt cccatcaaga cggagcctgg cctgtcatct cactacgggc   1680
acagcagctc cgtgtcccag acgttctcag tcagtgcgat gtctggccat gggcctccca   1740
tccaccctgt cctctcggcc ctgaagctct ccccacaagg ctatgcgtct cccgtcagcc   1800
agtctccaca gaccagctcc aagcaggact cttggaacag cctggtcttg gccgacagtc   1860
```

```
acggggacat aatcactgcg taatcttccc tcttccctcc tcaaattcct gcacggacct    1920
gggacttgga ggatagcaaa gaaggaggcc ctgggctccc aggggccggc ctcctctgcc    1980
tggtaatgac tccagaacaa caactgggaa gaaacttgaa gtcgacaatc tggttagggg    2040
aagcgggtgt tggattttct cagatgcctt tacacgctga tgggactgga gggagcccac    2100
ccttcagcac gagcacactg catctctcct gtgagttgga gacttctttc ccaagatgtc    2160
cttgtcccct gcgttcccca ctgtggccta ccgtgtgggt tttgcattgt gtttctagca    2220
ccgaggatct gagaacaagc ggagggccgg gccctgggac ccctgctcca gcccgaatga    2280
cggcatctgt ttgccatgta cctggatgcg acgggcccct ggggacaggc ccttgcccca    2340
tccatccgct tgaggcatgg caccgccctg catccctaat accaaatctg actccaaaat    2400
tgtggggtgt gacatacaag tgactgaaca cttcctgggg agctacaggg gcacttaacc    2460
caccacagca cagcctcatc aaaatgcagc tggcaacttc tccccaggt gccttccccc    2520
tgctgccggc ctttgctcct tcacttccaa catctctcaa aataaaaatc cctcttcccg    2580
ctctgagcga ttcagctctg cccgcagctt gtacatgtct ctcccctggc aaaacaagag    2640
ctgggtagtt tagccaaacg gcaccccctc gagttcactg cagacccttc gttcaccgtg    2700
tcacacatag aggggttctg agtaagaaca aaacgttctg ctgctcaagc cagtctggca    2760
agcactcagc ccagcctcga ggtccttctg gggagagtgt aagtggacag agtcctggtc    2820
agggggcagg agtgtcccaa gggctggccc acctgctgtc tgtctgctcc tcctagccct    2880
tggtcagatg gcagccagag tccctcagga cctgcagcct cgccccggca gaagtctttt    2940
gtccaggagg caaaaagcca gagattctgc aacacgaatt cgaagcaaac aaacacaaca    3000
caacagaatt cctggaaaga agacgactgc taagacacgg caggggggcc tggagggagc    3060
ctccgactct gagctgctcc gggatctgcc gcgttctcct ctgcacattg ctgtttctgc    3120
ccctgatgct ggagctcaag gagactcctt cctctttctc agcagagctg tagctgactg    3180
tggcattact acgcctcccc acacgcccag accctcact ccaaaatcct actggctgta    3240
gcagagaata ccttgaacc aagattctgt tttaatcatc atttacattg ttttcttcca    3300
aaggcccct cgtatacct ccctaaccca caaacctgtt aacattgtct taggtgaaa    3360
tggctggaaa atcagtattt aactaataaa tttatctgta ttcctcttaa aaaaaaaa    3419
```

<210> SEQ ID NO 15
<211> LENGTH: 3494
<212> TYPE: DNA
<213> ORGANISM: Homo sapiens

<400> SEQUENCE: 15

```
ggcacccttc ggcgagcgct gtttgtttag ggctcggtga gtccaatcag gagcccaggc      60
tgcagttttc cggcagagca gtaagaggcg cctcctctct ccttttttatt caccagcagc     120
gcggcgcaga ccccggactc gcgctcgccc gctggcgccc tcggcttctc tccgcgcctg     180
ggagcaccct ccgccgcggc cgttctccat gcgcagcgcc cgcccgagga gctagacgtc     240
agcttggagc ggcgccggac cgtggatggc cttgactgac ggcggctggt gcttgccgaa     300
gcgcttcggg gccgcgggtg cggacgccag cgactccaga gccttccag cgcgggagcc     360
ctccacgccg ccttcccca tctcttcctc gtcctcctcc tgctcccggg gcggagagcg     420
gggcccggc ggcgccagca actgcgggac gcctcagctc gacacggagg cggcggccgg     480
acccccggcc cgctcgctgc tgctcagttc ctacgcttcg catcccttcg gggctcccca     540
```

```
cggaccttcg gcgcctgggg tcgcgggccc cgggggcaac ctgtcgagct gggaggactt    600
gctgctgttc actgacctcg accaagccgc gaccgccagc aagctgctgt ggtccagccg    660
cggcgccaag ctgagcccct tcgcacccga gcagccggag gagatgtacc agaccctcgc    720
cgctctctcc agccagggtc cggccgccta cgacggcgcg cccggcggct tcgtgcactc    780
tgcggccgcg gcggcagcag ccgcggcggc ggccagctcc ccggtctacg tgcccaccac    840
ccgcgtgggt tccatgctgc ccggcctacc gtaccacctg caggggtcgg gcagtgggcc    900
agccaaccac gcgggcggcg cgggcgcgca ccccggctgg cctcaggcct cggccgacag    960
ccctccatac ggcagcggag gcggcgcggc tggcggcggg gccgcggggc ctggcggcgc   1020
tggctcagcc gcggcgcacg tctcggcgcg cttcccctac tctcccagcc cgcccatggc   1080
caacggcgcc gcgcgggagc cgggaggcta cgcggcggcg ggcagtgggg gcgcgggagg   1140
cgtgagcggc ggcggcagta gcctggcggc catgggcggc cgcgagcccc agtacagctc   1200
gctgtcggcc gcgcggccgc tgaacgggac gtaccaccac caccaccacc accaccacca   1260
ccatccgagc ccctactcgc cctacgtggg ggcgccactg acgcctgcct ggcccgccgg   1320
acccttcgag accccggtgc tgcacagcct gcagagccgc gccggagccc cgctcccggt   1380
gccccggggt cccagtgcag acctgctgga ggacctgtcc gagagccgcg agtgcgtgaa   1440
ctgcggctcc atccagacgc cgctgtggcg gcgggacggc accggccact acctgtgcaa   1500
cgcctgcggg ctctacagca agatgaacgg cctcagccgg cccctcatca agccgcagaa   1560
gcgcgtgcct tcatcacggc ggcttggatt gtcctgtgcc aactgtcaca ccacaactac   1620
caccttatgg cgcagaaacg ccgagggtga accgtgtgc aatgcttgtg gactctacat    1680
gaaactccat ggggtgccca gaccacttgc tatgaaaaaa gagggaattc aaaccaggaa   1740
acgaaaacct aagaacataa ataaatcaaa gacttgctct ggtaatagca ataattccat   1800
tcccatgact ccaacttcca cctcttctaa ctcagatgat tgcagcaaaa atacttcccc   1860
cacaacacaa cctacagcct caggggcggg tgccccggtg atgactggtg cgggagagag   1920
caccaatccc gagaacagcg agctcaagta ttcgggtcaa gatgggctct acataggcgt   1980
cagtctcgcc tcgccggccg aagtcacgtc ctccgtgcga ccggattcct ggtgcgccct   2040
ggccctggcc tgagcccacg ccgccaggag gcagggaggg ctccgccgcg ggcctcactc   2100
cactcgtgtc tgcttttgtg cagcggtcca gacagtggcg actgcgctga cagaacgtga   2160
ttctcgtgcc tttattttga aagagatgtt tttcccaaga ggcttgctga agagtgaga   2220
gaagatggaa gggaagggcc agtgcaactg ggcgcttggg ccactccagc cagcccgcct   2280
ccggggcgga ccctgctcca cttccagaag ccaggactag gacctgggcc ttgcctgcta   2340
tggaatattg agagagattt tttaaaaaag attttgcatt ttgtccaaaa tcatgtgctt   2400
cttctgatca attttggttg ttccagaatt tcttcatacc ttttccacat ccagatttca   2460
tgtgcgttca tggagaagat cacttgaggc catttggtac acatctctgg aggctgagtc   2520
ggttcatgag gtctcttatc aaaaatatta ctcagtttgc aagactgcat tgtaacttta   2580
acatacactg tgactgacgt ttctcaaagt tcatattgtg tggctgatct gaagtcagtc   2640
ggaatttgta aacagggtag caaacaagat atttttcttc catgtataca ataatttttt   2700
taaaaagtgc aatttgcgtt gcagcaatca gtgttaaatc atttgcataa gatttaacag   2760
cattttttat aatgaatgta aacattttaa cttaatggta cttaaaataa tttaaaagaa   2820
aaatgttaac ttagcattc ttatgcttct tttacaacta catcccattt tatatttcca    2880
attgttaaag aaaaatattt caagaacaaa tcttctctca ggaaaattgc ctttctctat   2940
```

| | |
|---|---|
| ttgttaagaa tttttataca agaacaccaa tatacccoct ttattttact gtggaatatg | 3000 |
| tgctggaaaa attgcaacaa cactttacta cctaacggat agcatttgta aatactctag | 3060 |
| gtatctgtaa acactctgat gaagtctgta tagtgtgact aacccacagg caggttggtt | 3120 |
| tacattaatt ttttttttg aatgggatgt cctatgaaaa cctatttcac cagagtttta | 3180 |
| aaaataaaaa gggtattgtt ttgtcttctg tacagtgagt tccttcccctt ttcaaagctt | 3240 |
| tcttttatg ctgtatgtga ctatagatat tcatataaaa caagtgcacg tgaagtttgc | 3300 |
| aaaatgcttt aaggccttcc tttcaaagca tagtccttttt ggagccgttt tgtaccttttt | 3360 |
| ataccttggc ttatttgaag ttgacacatg gggttagtta ctactctcca tgtgcattgg | 3420 |
| ggacagtttt tataagtggg aaggactcag tattattata tttgagatga taagcatttt | 3480 |
| gtttgggaac aatg | 3494 |

<210> SEQ ID NO 16
<211> LENGTH: 3088
<212> TYPE: DNA
<213> ORGANISM: Homo sapiens

<400> SEQUENCE: 16

| | |
|---|---|
| cccctttttcc agaatcactt gcactgtctt gttcttgaat gagaaaggaa gaaaagagcc | 60 |
| tcccattact cagacccgtg taaacattat tccccccagg agaaaatggt gttattcaaa | 120 |
| tgaatcataa taaaatagcc tctaaacagt ttctaagcgg gagcctccgt ggaactcagc | 180 |
| gctccgctcc tcccagttcc taagaggtcc cgggattctt gagctgtgcc cagctgacga | 240 |
| gcttttgaag atggcacaat aaccgtccag tgatgcctga ccatgacagc acagccctct | 300 |
| taagccggca aaccaagagg agaagagttg acattggagt gaaaaggacg gtagggacag | 360 |
| catctgcatt ttttgctaag gcaagagcaa cgtttttttag tgccatgaat ccccaaggtt | 420 |
| ctgagcagga tgttgagtat tcagtggtgc agcatgcaga tggggaaaag tcaaatgtac | 480 |
| tccgcaagct gctgaagagg gcgaactcgt atgaagatgc catgatgcct tttccaggag | 540 |
| caaccataat ttcccagctg ttgaaaaata acatgaacaa aaatggtggc acggagccca | 600 |
| gtttccaagc cagcggtctc tctagtacag gctccgaagt acatcaggag gatatatgca | 660 |
| gcaactcttc aagagacagc cccccagagt gtctttcccc ttttggcagg cctactatga | 720 |
| gccagtttga tatggatcgc ttatgtgatg agcacctgag agcaaagcgc gcccgggttg | 780 |
| agaatataat tcggggtatg agccattccc ccagtgtggc attaaggggc aatgaaaatg | 840 |
| aaagagagat ggccccgcag tctgtgagtc cccgagaaag ttacagagaa aacaaacgca | 900 |
| agcaaaagct tccccagcag cagcaacaga gtttccagca gctggtttca gcccgaaaag | 960 |
| aacagaagcg agaggagcgc cgacagctga acagcagct ggaggacatg cagaaacagc | 1020 |
| tgcgccagct gcaggaaaag ttctaccaaa tctatgacag cactgattcg gaaaatgatg | 1080 |
| aagatggtaa cctgtctgaa gacagcatgc gctcggagat cctggatgcc agggcccagg | 1140 |
| actctgtcgg aaggtcagat aatgagatgt gcgagctaga cccaggacag tttattgacc | 1200 |
| gagctcgagc cctgatcaga gagcaggaaa tggctgaaaa caagccgaag cgagaaggca | 1260 |
| acaacaaaga aagagaccat gggccaaact ccttacaacc ggaaggcaaa catttggctg | 1320 |
| agaccttgaa acaggaactg aacactgcca tgtcgcaagt tgtggacact gtggtcaaag | 1380 |
| tcttttcggc caagccctcc cgccaggttc ctcaggtctt cccacctctc cagatccccc | 1440 |
| aggccagatt tgcagtcaat ggggaaaacc acaatttcca caccgccaac cagcgcctgc | 1500 |

```
agtgctttgg cgacgtcatc attccgaacc ccctggacac ctttggcaat gtgcagatgg    1560
ccagttccac tgaccagaca gaagcactgc ccctggttgt ccgcaaaaac tcctctgacc    1620
agtctgcctc cggccctgcc gctggcggcc accaccagcc cctgcaccag tcgcctctct    1680
ctgccaccac gggcttcacc acgtccacct tccgccaccc cttccccctt cccttgatgg    1740
cctatccatt tcagagccca ttaggtgctc cctccggctc cttctctgga aaagacagag    1800
cctctcctga atccttagac ttaactaggg ataccacgag tctgaggacc aagatgtcat    1860
ctcaccacct gagccaccac ccttgttcac cagcacaccc gcccagcacc gccgaagggc    1920
tctccttgtc gctcataaag tccgagtgcg gcgatcttca agatatgtct gaaatatcac    1980
cttattcggg aagtgcaatg caggaaggat tgtcacccaa tcacttgaaa aaagcaaagc    2040
tcatgttttt ttatacccgt tatcccagct ccaatatgct gaagacctac ttctccgacg    2100
taaagttcaa cagatgcatt acctctcagc tcatcaagtg gtttagcaat ttccgtgagt    2160
tttactacat tcagatggag aagtacgcac gtcaagccat caacgatggg gtcaccagta    2220
ctgaagagct gtctataacc agagactgtg agctgtacag ggctctgaac atgcactaca    2280
ataaagcaaa tgactttgag gttccagaga gattcctgga agttgctcag atcacattac    2340
gggagttttt caatgccatt atcgcaggca agatgttga tccttcctgg aagaaggcca    2400
tatacaaggt catctgcaag ctggatagtg aagtccctga gattttcaaa tccccgaact    2460
gcctacaaga gctgcttcat gagtagaaat ttcaacaact cttttgaat gtatgaagag    2520 tagcagtccc ctttggatgt ccaagttata tgtgtctaga ttttgatttc atatatatgt    2580
gtatgggagg catggatatg ttatgaaatc agctggtaat tcctcctcat cacgtttctc    2640
tcattttctt ttgttttcca ttgcaagggg atggttgttt tctttctgcc tttagtttgc    2700
ttttgcccaa ggcccttaac atttggacac ttaaaatagg gttaattttc agggaaaaag    2760
aatgttggcg tgtgtaaagt ctctattagc aatgaaggga atttgttaac gatgcatcca    2820
cttgattgat gacttattgc aaatggcggt tggctgagga aaacccatga cacagcacaa    2880
ctctacagac agtgatgtgt ctcttgtttc tactgctaag aaggtctgaa aatttaatga    2940
aaccacttca tacatttaag tattttgttt ggtttgaact caatcagtag cttttcctta    3000
catgtttaaa aataattcca atgacagatg agcagctcac ttttccaaag taccccaaaa    3060
ggccaaatta aaaaaaaaaa aaaaaaaa                                       3088
```

<210> SEQ ID NO 17
<211> LENGTH: 4754
<212> TYPE: DNA
<213> ORGANISM: Homo sapiens

<400> SEQUENCE: 17

```
gaattctaga ggcggcggag ggtggcgagg agctctcgct ttctctcgct ccctccctct      60
ccgactccgt ctctctctct ctctctctct ctccccctccc tctctttccc tctgttccat     120
ttttcccccc tctaaatcct ccctgccctg cgcgcctgga cacagattta ggaagcgaat     180
tcgctcacgt tttaggacaa ggaagagaga gaggcacggg agaagagccc agcaagattt     240
ggattgaaac cgagacaccc tccgaggct cggagcagag aaggaggag agggcggcg        300 aacggaagcc agtttgcaat tcaagttttg atagcgctgg tagaagggg tttaaatcag      360 attttttttt tttaaagga gagagacttt ttccgctctc tcgctcccctg ttaaagccgg     420 gtctagcaca gctgcagacg ccaccagcga gaaagaggga gaggaagaca gatgggggc     480 gggggaagaa gaaaaagaaa ggtaaaaagt cttctaggag aacctttcac atttgcaaca    540
```

```
aaagacctag gggctggaga gagattcctg ggacgcaggg ctggagtgtc tatttcgagc    600
tcagcggcag ggctcgggcg cgagtcgaga ccctgctcgc tcctctcgct tctgaaaccg    660
acgttcagga gcggcttttt aaaaacgcaa ggcacaagga cggtcacccg cgcgactatg    720
tttgctgatt tttcgccttg ccctctttaa aagcggcctc ccattctcca aaagacactt    780
cccctcctcc ctttgaagtg cattagttgt gatttctgcc tccttttctt ttttctttct    840
tttttgtttt gcttttctcc ccctttttgaa ttatgtgctg ctgttaaaca acaacaaaaa    900
aacaacaaaa cacagcagct gcggacttgt ccccggctgg agcccagcgc ccgcctgga     960 gtggatgagc ctctccatga gagatccggt cattcctggg acaagcatgg cctaccatcc    1020
gttcctacct caccgggcgc cggacttcgc catgagcgcg gtgctgggtc accagccgcc    1080
gttcttcccc gcgctgacgc tgcctcccaa cggcgcggcg gcgctctcgc tgccgggcgc    1140
cctggccaag ccgatcatgg atcaattggt gggggcggcc gagaccggca tcccgttctc    1200
ctccctgggg ccccaggcgc atctgaggcc tttgaagacc atggagcccg aagaagaggt    1260
ggaggacgac cccaaggtgc acctggaggc taaagaactt tgggatcagt ttcacaagcg    1320
gggcaccgga atggtcatta ccaagtcggg aaggcgaatg tttcctccat ttaaagtgag    1380
atgttctggg ctggataaaa aagccaaata cattttattg atggacatta tagctgctga    1440
tgactgtcgt tataaatttc acaattctcg gtggatggtg gctggtaagg ccgaccccga    1500
aatgccaaag aggatgtaca ttcacccgga cagccccgct actggggaac agtggatgtc    1560
caaagtcgtc actttccaca aactgaaact caccaacaac atttcagaca acatggatt     1620 tactatattg aactccatgc acaaatacca gccccggttc cacattgtaa gagccaatga    1680
catcttgaaa ctcccttata gtacatttcg gacatacttg ttccccgaaa ctgaattcat    1740
cgctgtgact gcataccaga atgataagat aacccagtta aaaatagaca caaccccttt    1800
tgcaaaaggt ttccgggaca ctggaaatgg ccgaagagaa aaagaaaac agctcaccct     1860 gcagtccatg agggtgtttg atgaaagaca caaaaggag aatgggacct ctgatgagtc     1920
ctccagtgaa caagcagctt tcaactgctt cgcccaggct tcttctccag ccgcctccac    1980
tgtagggaca tcgaacctca agatttatg tcccagcgag ggtgagagcg acgccgaggc    2040
cgagagcaaa gaggagcatg gccccgaggc ctgcgacgcg gccaagatct ccaccaccac    2100
gtcggaggag ccctgccgtg acaagggcag ccccgcggtc aaggctcacc ttttcgctgc    2160
tgagcggccc cgggacagcg ggcggctgga caaagcgtcg cccgactcac gccatagccc    2220
cgccaccatc tcgtccagca ctcgcggcct gggcgcggag gagcgcagga gcccggttcg    2280
cgagggcaca gcgccggcca aggtggaaga ggcgcgcgcg ctcccgggca aggaggcctt    2340
cgcgccgctc acggtgcaga cggacgcggc cgccgcgcac ctggcccagg gcccctgcc    2400 tggcctcggc ttcgccccgg gcctggcggg ccaacagttc ttcaacgggc acccgctctt    2460
cctgcacccc agccagtttg ccatgggggg cgccttctcc agcatggcgg ccgctggcat    2520
gggtcccctc ctggccacgg tttctggggc ctccaccggt gtctcgggcc tggattccac    2580
ggccatggcc tctgccgctg cggcgcaggg actgtccggg gcgtccgcgg ccaccctgcc    2640
cttccacctc agcagcacg tcctggcctc tcagggcctg gccatgtccc ctttcggaag     2700
cctgttccct taccctaca cgtacatggc cgcagcggcg gccgcctcct ctgcggcagc    2760
ctccagctcg gtgcaccgcc acccttcct caatctgaac accatgcgcc gcggctgcg     2820 ctacagcccc tactccatcc cggtgccggt cccggacggc agcagtctgc tcaccaccgc    2880
```

```
cctgccctcc atggcggcgg ccgcggggcc cctggacggc aaagtcgccg ccctggccgc    2940
cagcccggcc tcggtggcag tggactcggg ctctgaactc aacagccgct cctccacgct    3000
ctcctccagc tccatgtcct tgtcgcccaa actctgcgcg gagaaagagg cggccaccag    3060
cgaactgcag agcatccagc ggttggttag cggcttggaa gccaagccgg acaggtcccg    3120
cagcgcgtcc ccgtagaccc gtcccagaca cgtcttttca ttccagtcca gttcaggctg    3180
ccgtgcactt tgtcggatat aaaataaacc acgggcccgc catggcgtta gcccttcctt    3240
ttgcagttgc gtctgggaag gggccccgga ctccctcgag agaatgtgct agagacagcc    3300
cctgtcttct tggcgtggtt tatatgtccg ggatctggat cagattctgg gggctcagaa    3360
acgtcggttg cattgagcta ctgggggtag gagttccaac atttatgtcc agagcaactt    3420
ccagcaaggc tggtctgggt ctctgcccac caggcgggga ggtgttcaaa gacatctccc    3480
tcagtgcgga tttatatata tattttttcct tcactgtgtc aagtggaaac aaaaacaaaa    3540
tctttcaaaa aaaaaatcgg gacaagtgaa cacattaaca tgattctgtt tgtgcagatt    3600
aaaaacttta tagggacttg cattatcggt tctcaataaa ttactgagca gctttgtttg    3660
gggagggaag tccctaccat ccttgtttag tctatattaa gaaaatctgt gtcttttaa     3720
tattcttgtg atgttttcag agccgctgta ggtctcttct tgcatgtcca cagtaatgta    3780
tttgtggttt ttattttgaa cgcttgcttt tagagagaaa acaatatagc cccctaccct    3840
tttcccaatc ctttgccctc aaatcagtga cccaagggag gggggatttt aagggaagg    3900
agtgggcaaa acacataaaa tgaatttatt atatctaagc tctgtagcag gattcatgtc    3960
gttctttgac agttctttct ctttcctgta tatgcaataa caaggttttta aaaaataat    4020
aaagaagtga gactattaga caaagtatttt atgtaattat ttgataactc ttgtaaatag    4080
gtggaatatg aatgcttgga aaattaaact ttaatttatt gacattgtac atagctctgt    4140
gtaaatagaa ttgcaactgt caggttttgt gttcttgttt tcctttagtt gggtttattt    4200
ccaggtcaca gaattgctgt taacactaga aaacacactt cctgcaccaa caccaatacc    4260
cttttcaaaag agttgtctgc aacatttttg ttttctttttt taatgtccaa aagtggggga    4320
aagtgctatt tcctattttc accaaaattg gggaaggagt gccactttcc agctccactt    4380
caaattcctt aaaatataac tgagattgct gtggggaggg aggagggcag aggctgcggt    4440
ttgactttttt aatttttctt ttgttatttg tatttgctag tctctgattt cctcaaaacg    4500
aagtggaatt tactactgtt gtcagtatcg gtgttttgaa ttggtgcctg cctatagaga    4560
tatattcaca gttcaaaagt caggtgctga gagatggttt aaagacaaat tcatgaaggt    4620
atattttgtg ttatagttgt tgatgagttc tttggttttc tgtattttttc ccctctctt    4680
taaaacatca ctgaaatttc aataaatttt tattgaaatg tctaaaaaaa aaaaaaaaa    4740
aaaaaaaaa aaaa                                                      4754

<210> SEQ ID NO 18
<211> LENGTH: 4814
<212> TYPE: DNA
<213> ORGANISM: Homo sapiens

<400> SEQUENCE: 18
gaattctaga ggcggcggag ggtggcgagg agctctcgct ttctctcgct ccctcccttct     60 ccgactccgt ctctctctct ctctctctct ctccccctccc tctctttccc tctgttccat    120
tttttccccc tctaaatcct ccctgccctg cgcgcctgga cacagattta ggaagcgaat    180
tcgctcacgt tttaggacaa ggaagagaga gaggcacggg agaagagccc agcaagattt    240
```

```
ggattgaaac cgagacaccc tccggaggct cggagcagag gaaggaggag gagggcggcg      300
aacggaagcc agtttgcaat tcaagttttg atagcgctgg tagaaggggg tttaaatcag      360 atttttttt tttttaaagga gagagacttt ttccgctctc tcgctccctg ttaaagccgg      420
gtctagcaca gctgcagacg ccaccagcga gaaagaggga gaggaagaca gatagggggc      480 ggggggaagaa gaaaaagaaa ggtaaaaagt cttctaggag aacctttcac atttgcaaca     540
aaagacctag gggctggaga gagattcctg ggacgcaggg ctggagtgtc tatttcgagc      600
tcagcggcag ggctcgggcg cgagtcgaga ccctgctcgc tcctctcgct tctgaaaccg      660
acgttcagga gcggcttttt aaaaacgcaa ggcacaagga cggtcacccg cgcgactatg      720
tttgctgatt tttcgccttg ccctctttaa aagcggcctc ccattctcca aaagacactt      780 ccctcctcc ctttgaagtg cattagttgt gatttctgcc tccttttctt ttttcttcct      840
tttttgtttt gcttttccc cccttttgaa ttatgtgctg ctgttaaaca acaacaaaaa       900
aacaacaaaa cacagcagct gcggacttgt ccccggctgg agcccagcgc ccgcctgga      960 gtggatgagc ctctccatga gagatccggt cattcctggg acaagcatgg cctaccatcc     1020
gttcctacct caccgggcgc cggacttcgc catgagcgcg gtgctgggtc accagccgcc     1080
gttcttcccc gcgctgacgc tgcctcccaa cggcgcggcg gcgctctcgc tgccgggcgc     1140
cctggccaag ccgatcatgg atcaattggt ggggcggcc gagaccggca tcccgttctc      1200
ctccctgggg ccccaggcgc atctgaggcc tttgaagacc atggagcccg aagaagaggt     1260
ggaggacgac cccaaggtgc acctggaggc taaagaactt tgggatcagt ttcacaagcg     1320
gggcaccgag atggtcatta ccaagtcggg aaggcgaatg tttcctccat ttaaagtgag     1380
atgttctggg ctggataaaa aagccaaata cattttattg atggacatta tagctgctga     1440
tgactgtcgt tataaatttc acaattctcg gtggatggtg gctggtaagg ccgaccccga     1500
aatgccaaag aggatgtaca ttcacccgga cagccccgct actggggaac agtggatgtc     1560
caaagtcgtc actttccaca aactgaaact caccaacaac atttcagaca acatggatt     1620 tactttggcc ttcccaagtg atcacgctac gtggcagggg aattatagtt ttggtactca     1680
gactatattg aactccatgc acaaatacca gccccggttc cacattgtaa gagccaatga     1740
catcttgaaa ctcccttata gtacatttcg gacatacttg ttccccgaaa ctgaattcat     1800
cgctgtgact gcataccaga atgataagat aacccagtta aaaatagaca acaacccttt     1860
tgcaaaaggt ttccgggaca ctggaaatgg ccgaagagaa aaagaaaac agctcaccct     1920 gcagtccatg agggtgtttg atgaaagaca caaaaggaa aatgggacct ctgatgagtc     1980
ctccagtgaa caagcagctt tcaactgctt cgcccaggct tcttctccag ccgcctccac     2040
tgtagggaca tcgaacctca agatttatg tcccagcgag ggtgagagcg acgccgaggc     2100
cgagagcaaa gaggagcatg gcccgaggc ctgcgacgcg gccaagatct ccaccaccac     2160
gtcggaggag ccctgccgtg acaagggcag ccccgcggtc aaggctcacc tttttcgctgc    2220 tgagcggccc cgggacagcg ggcggctgga caaagcgtcg cccgactcac gccatagccc     2280
cgccaccatc tcgtccagca ctcgcggcct gggcgcggag gagcgcagga gcccggttcg     2340
cgagggcaca gcgccggcca aggtggaaga ggcgcgcgcg ctcccgggca aggaggcctt     2400
cgcgccgctc acggtgcaga cggacgcggc cgccgcgcac ctggcccagg gccccctgcc     2460
tggcctcggc ttcgccccgg gcctgcgggg ccaacagttc ttcaacgggc acccgctctt     2520 cctgcaccccc agccagtttg ccatggggggg cgccttctcc agcatggcgg ccgctggcat     2580
```

```
gggtcccctc ctggccacgg tttctggggc ctccaccggt gtctcgggcc tggattccac    2640
ggccatggcc tctgccgctg cggcgcaggg actgtccggg gcgtccgcgg ccaccctgcc    2700
cttccacctc cagcagcacg tcctggcctc tcagggcctg gccatgtccc ctttcggaag    2760
cctgttccct taccctaca cgtacatggc cgcagcggcg gccgcctcct ctgcggcagc     2820
ctccagctcg gtgcaccgcc accccttcct caatctgaac accatgcgcc cgcggctgcg    2880
ctacagcccc tactccatcc cggtgccggt cccggacggc agcagtctgc tcaccaccgc    2940
cctgccctcc atggcggcgg ccgcggggcc cctggacggc aaagtcgccg ccctggccgc    3000
cagcccggcc tcggtggcag tggactcggg ctctgaactc aacagccgct cctccacgct    3060
ctcctccagc tccatgtcct tgtcgcccaa actctgcgcg gagaaagagg cggccaccag    3120
cgaactgcag agcatccagc ggttggttag cggcttggaa gccaagccgg acaggtcccg    3180
cagcgcgtcc ccgtagaccc gtcccagaca cgtcttttca ttccagtcca gttcaggctg    3240
ccgtgcactt tgtcggatat aaaataaacc acgggcccgc catggcgtta gcccttcctt    3300
ttgcagttgc gtctgggaag gggccccgga ctccctcgag agaatgtgct agagacagcc    3360
cctgtcttct tggcgtggtt tatatgtccg ggatctggat cagattctgg gggctcagaa    3420
acgtcggttg cattgagcta ctgggggtag gagttccaac atttatgtcc agagcaactt    3480
ccagcaaggc tggtctgggt ctctgcccac caggcgggga ggtgttcaaa gacatctccc    3540
tcagtgcgga tttatatata tattttttcct tcactgtgtc aagtggaaac aaaaacaaaa    3600
tctttcaaaa aaaaaatcgg gacaagtgaa cacattaaca tgattctgtt tgtgcagatt    3660
aaaaacttta tagggacttg cattatcggt tctcaataaa ttactgagca gctttgtttg    3720
gggagggaag tccctaccat ccttgtttag tctatattaa gaaaatctgt gtcttttttaa    3780 tattcttgtg atgttttcag agccgctgta ggtctcttct tgcatgtcca cagtaatgta    3840
tttgtggttt ttattttgaa cgcttgcttt tagagagaaa acaatatagc cccctaccct    3900
tttcccaatc ctttgccctc aaatcagtga cccaagggag gggggggattt aaagggaagg   3960 agtgggcaaa acacataaaa tgaatttatt atatctaagc tctgtagcag gattcatgtc    4020
gttctttgac agttctttct ctttcctgta tatgcaataa caaggtttta aaaaaataat    4080
aaagaagtga gactattaga caaagtattt atgtaattat ttgataactc ttgtaaatag    4140
gtggaatatg aatgcttgga aaattaaact ttaatttatt gacattgtac atagctctgt    4200
gtaaatagaa ttgcaactgt caggttttgt gttcttgttt tcctttagtt gggtttatttt   4260 ccaggtcaca gaattgctgt taacactaga aaacacactt cctgcaccaa caccaatacc    4320 cttttcaaaag agttgtctgc aacatttttg ttttcttttt taatgtccaa aagtgggga    4380 aagtgctatt tcctatttttc accaaaattg gggaaggagt gccactttcc agctccactt    4440
caaattcctt aaaatataac tgagattgct gtggggaggg aggagggcag aggctgcggt    4500 ttgactttt aatttttctt ttgttatttg tatttgctag tctctgatt cctcaaaacg     4560 aagtggaatt tactactgtt gtcagtatcg gtgttttgaa ttggtgcctg cctatagaga    4620
tatattcaca gttcaaaagt caggtgctga gagatggttt aaagacaaat tcatgaaggt    4680
atattttgtg ttatagttgt tgatgagttc tttggttttc tgtattttc cccctctctt     4740 taaaacatca ctgaaatttc aataaatttt tattgaaatg tctaaaaaaa aaaaaaaaaa    4800
aaaaaaaaaa aaaa                                                       4814

<210> SEQ ID NO 19
<211> LENGTH: 2308
```

<212> TYPE: DNA
<213> ORGANISM: Homo sapiens

<400> SEQUENCE: 19

| | | | | | |
|---|---|---|---|---|---|
| aaaactttgg | gagtttttag | agacgagttt | tttttttttt | ctattacttt | tccccccccc | 60 |
| taactaacgg | actattattg | ttgttgtttt | aaatttagct | cttagggctt | agctatttgg | 120 |
| gttttcttgc | ggtgtccggc | tcccgtctcc | ctggctcccc | cgcccgccct | gcggccccag | 180 |
| cgcccctcgc | tctcatccag | cccgcgagga | gtgcgggcgc | cgcgccgcct | ttaaagcgag | 240 |
| gccagggagc | gaggcggtga | ccggccgaga | tccggccctc | gcctcctccc | tcggtggcgc | 300 |
| tagggctccc | ggcctctctt | cctcagtgcg | ggcggagaag | cgaaagcgga | tcgtcctcgg | 360 |
| ctgccgccgc | cttctccggg | actcgcgcgc | ccctccccgc | gcgcccaccc | acccagtccg | 420 |
| gctggactgc | ggcagccgcg | cggctcaccc | cggcaggatg | ttcgcagccg | ggctggctcc | 480 |
| cttctacgcc | tccaacttca | gcctctggtc | ggccgcttac | tgctcctcgg | ccggcccagg | 540 |
| cggctgctcc | ttccccttgg | acccgccgc | cgtcaaaaag | ccctccttct | gcatcgcaga | 600 |
| cattctgcac | gccggcgtgg | gggatctggg | ggcggccccg | gagggcctgg | cagggggcctc | 660 |
| ggccgccgcc | ctcaccgcgc | acttgggctc | ggttcacccg | cacgcctctt | tccaagcggc | 720 |
| ggccagatcc | ccgcttcgac | ccaccccagt | ggtggcgccc | tccgaagtcc | cggctggctt | 780 |
| cccgcagcgg | ctgtctccgc | tctcagccgc | ctaccaccac | catcacccgc | aacaacaaca | 840 |
| gcagcagcaa | cagccgcagc | agcaacagcc | tccgcctccg | cccccgggctg | gcgccctgca | 900 |
| gcccccggcc | tcggggacgc | gagtggttcc | gaacccccac | cacagtggct | ctgccccggc | 960 |
| ccccctccagc | aaagacctca | aatttggaat | tgaccgcatt | ttatctgcag | aatttgaccc | 1020 |
| aaaagtcaaa | gaaggcaaca | cgctgagaga | tctcacttcc | ctgctaaccg | gtgggcggcc | 1080 |
| cgccggggtg | cacctctcag | gcctgcagcc | ctcggccggc | cagttcttcg | catctctaga | 1140 |
| tcccattaac | gaggcttctg | caatcctgag | tcccttaaac | tcgaacccaa | gaaattcagt | 1200 |
| tcagcatcag | ttccaagaca | cgtttccagg | tccctatgct | gtgctcacga | aggacaccat | 1260 |
| gccgcagacg | tacaaaagga | agcgttcatg | gtcgcgcgct | gtgttctcca | acctgcagag | 1320 |
| gaaaggcctg | gagaaaaggt | ttgagattca | gaagtacgtg | accaagccgg | accgaaagca | 1380 |
| gctggcggcg | atgctgggcc | tcacggacgc | acaggtgaag | gtgtggttcc | agaaccggcg | 1440 |
| gatgaagtgg | cggcactcca | aggaggccca | ggcccaaaag | gacaaggaca | aggaggctgg | 1500 |
| cgagaagcca | tcaggtggag | ccccggctgc | ggatggcgag | caggacgaga | ggagccccag | 1560 |
| ccgttctgaa | ggcgaggctg | agagcgagag | cagcgactcc | gagtccctgg | acatggcccc | 1620 |
| cagcgacacg | gagcggactg | agggagtga | gcgttctctg | caccaaacaa | cagttattaa | 1680 |
| ggccccggtc | actggcgccc | tcattaccgc | cagcagtgct | gggagtggtg | ggagcagcgg | 1740 |
| cggcggcggc | aatagtttca | gcttcagcag | cgccagcagt | cttagtagca | gcagcaccag | 1800 |
| tgcgggttgc | gccagcagcc | ttggcggcgg | cggcgcctcg | gagcttctcc | ctgcaacaca | 1860 |
| gcccacagcc | agcagcgctc | ccaaaagccc | cgagccagcc | caaggcgcgc | ttggctgctt | 1920 |
| atagactgta | ctagggcgga | ggggatccgg | gccttgcgtg | cagcctccca | accatgggct | 1980 |
| gggttttgtg | cttactgtat | gttggcgact | tggtagggca | ggagacgcag | cgtgagcct | 2040 |
| acctcccgac | attcacgctt | cgccccacgc | tgctccgact | ggctgcagcg | gacactgccc | 2100 |
| aaagcagagg | ggagtctcag | tgtcctgcta | gccagccgaa | cacttctctc | cggaagcagg | 2160 |
| ctggttcgac | tgtgaggtgt | ttgactaaac | tgtttctctg | actcgcccca | gaggtcgtgg | 2220 |

-continued

```
ctcaaaggca cttaggacgc cttaaatttg taaataaaat gtttactacg gtttgtaaaa    2280
aaaaaaaaaa aaaaaaaaaa aaaaaaaa                                       2308

<210> SEQ ID NO 20
<211> LENGTH: 1925
<212> TYPE: DNA
<213> ORGANISM: Homo sapiens

<400> SEQUENCE: 20
ccccacagtg agaggaagga aggcaacagt cgccagcagc cgatgtgaag accggactcc      60
gtgcgcccct cgccgcctct gcctggccac atcgatgttg tgtccgccgc ctgctcgccc     120
ggatcacgat gaacgcgcag ctgaccatgg aagcgatcgg cgagctgcac ggggtgagcc     180
atgagccggt gcccgcccct gccgacctgc tgggcggcag ccccacgcg cgcagctccg      240 tggcgcaccg cggcagccac ctgccccccg cgcacccgcg ctccatgggc atggcgtccc     300
tgctggacgg cggcagcggc ggcggagatt accaccacca ccaccgggcc cctgagcaca     360
gcctggccgg cccctgcat cccaccatga ccatggcctg cgagactccc ccaggtatga      420
gcatgcccac cacctacacc accttgaccc ctctgcagcc gctgcctccc atctccacag     480
tctcggacaa gttcccccac catcaccacc accaccatca ccaccaccac ccgcaccacc     540
accagcgcct ggcgggcaac gtgagcggta gcttcacgct catgcgggat gagcgcgggc     600
tggcctccat gaataacctc tatacccct accacaagga cgtggccggc atgggccaga     660
gcctctcgcc cctctccagc tccggtctgg gcagcatcca caactcccag caagggctcc     720
cccactatgc ccaccggggg gccgccatgc ccaccgacaa gatgctcacc cccaacggct     780
tcgaagccca ccacccggcc atgctcggcc gccacgggga gcagcacctc acgcccacct     840
cggccggcat ggtgcccatc aacggccttc ctccgcacca tcccacgcc cacctgaacg      900 cccagggcca cggcaactc ctgggcacag cccgggagcc caacccttcg gtgaccggcg      960
cgcaggtcag caatggaagt aattcagggc agatggaaga gatcaatacc aaagaggtgg    1020
cgcagcgtat caccaccgag ctcaagcgct acagcatccc acaggccatc ttcgcgcaga    1080
gggtgctctg ccgctcccag gggacccttct cggacctgct cgcaaccccc aaaccctgga    1140
gcaaactcaa atccggccgg gagaccttcc ggaggatgtg gaagtggctg caggagccgg    1200
agttccagcg catgtccgcg ctccgcttag cagcatgcaa aaggaaagaa caagaacatg    1260
ggaaggatag aggcaacaca cccaaaaagc ccaggttggt cttcacagat gtccagcgtc    1320
gaactctaca tgcaatattc aaggaaaata agcgtccatc caagaattg caaatcacca     1380 tttcccagca gctggggttg gagctgagca ctgtcagcaa cttcttcatg aacgcaagaa    1440
ggaggagtct ggacaagtgg caggacgagg gcagctccaa ttcaggcaac tcatcttctt    1500
catcaagcac ttgtaccaaa gcatgaagga agaaccacaa actaaaacct cggtggaaaa    1560
gctttaaatt aaaaaaaatt tttaaaagac caggacctca agatagcagg tttatactta    1620
gaaatatttg aagaaaaaaa agcgttattt atagtccaaa gaaaccaaag acttagctca    1680
cctgcattct gactttgttt ggagacacac acttcagcag ggcggcgact tggcaagaca    1740
aatgatgagc aggaaaacac cactggatct cacaccttca atccatgacc atcctcgctg    1800
tgcttggctg tttagtggtt tggagcatag tgattttgag ccattgagcg gacatctttt    1860
aagatcgaac tttctcatct gttctaccat gccacgaagg tgtatggtgt ctcagtacta    1920
ccacc                                                                1925
```

<210> SEQ ID NO 21
<211> LENGTH: 16142
<212> TYPE: DNA
<213> ORGANISM: Homo sapiens

<400> SEQUENCE: 21

| | | | | | |
|---|---|---|---|---|---|
| gcccccgccg | ccccgggcc | ctgatggact | gaatgaaggc | tgcctacacc | gcctatcgat | 60 |
| gcctcaccaa | agacctagaa | ggctgcgcca | tgaacccgga | gctgacaatg | gaaagtctgg | 120 |
| gcactttgca | cgggccggcc | ggcggcggca | gtggcggggg | cggcggcggg | ggcggcgggg | 180 |
| gcggcggcgg | gggcccgggc | catgagcagg | agctgctggc | cagccccagc | ccccaccacg | 240 |
| cgggccgcgg | cgccgctggc | tcgctgcggg | gccctccgcc | gcctccaacc | gcgcaccagg | 300 |
| agctgggcac | ggcggcagcg | gcggcagcgg | cggcgtcgcg | ctcggccatg | gtcaccagca | 360 |
| tggcctcgat | cctggacggc | ggcgactacc | ggcccgagct | ctccatcccg | ctgcaccacg | 420 |
| ccatgagcat | gtcctgcgac | tcgtctccgc | ctggcatggg | catgagcaac | acctacacca | 480 |
| cgctgacacc | gctccagccg | ctgccaccca | tctccaccgt | gtctgacaag | ttccaccacc | 540 |
| ctcacccgca | ccaccatccg | caccaccacc | accaccacca | ccaccagcgc | ctgtccggca | 600 |
| acgtcagcgg | cagcttcacc | ctcatgcgcg | acgagcgcgg | gctcccggcc | atgaacaacc | 660 |
| tctacagtcc | ctacaaggag | atgcccggca | tgagccagag | cctgtccccg | ctggccgcca | 720 |
| cgccgctggg | caacgggcta | gcggcctcc | acaacgcgca | gcagagtctg | cccaactacg | 780 |
| gtccgccggg | ccacgacaaa | atgctcagcc | ccaacttcga | cgcgcaccac | actgccatgc | 840 |
| tgacccgcgt | tgagcaacac | ctgtcccgcg | gcctgggcac | cccacctgcg | gccatgatgt | 900 |
| cgcacctgaa | cggcctgcac | cacccgggcc | acactcagtc | tcacgggccg | gtgctggcac | 960 |
| ccagtcgcga | gcggccaccc | tcgtcctcat | cgggctcgca | ggtggccacg | tcgggccagc | 1020 |
| tggaagaaat | caacaccaaa | gaggtggccc | agcgcatcac | agcggagctg | aagcgctaca | 1080 |
| gtatccccca | ggcgatcttt | gcgcagaggg | tgctgtgccg | gtctcagggg | actctctccg | 1140 |
| acctgctccg | gaatccaaaa | ccgtggagta | aactcaaatc | tggcagggag | accttccgca | 1200 |
| ggatgtggaa | gtggcttcag | gagcccgagt | tccagcgcat | gtccgcctta | cgcctggcag | 1260 |
| cgtgcaaacg | caaagagcaa | gaaccaaaca | agacaggaa | caattcccag | aagaagtccc | 1320 |
| gcctggtgtt | cactgacctc | caacgccgaa | cactcttcgc | catcttcaag | gagaacaaac | 1380 |
| gcccgtcaaa | ggagatgcag | atcaccattt | cccagcagct | gggcctggag | ctcacaaccg | 1440 |
| tcagcaactt | cttcatgaac | gcccggcgcc | gcagcctgga | gaagtggcaa | gacgatctga | 1500 |
| gcacaggggg | ctcctcgtcc | acctccagca | cgtgtaccaa | agcatgatgg | aaggactctc | 1560 |
| acttgggcac | aagtcacctc | caaatgagga | aacagatac | caaagaaaa | caaggaaaa | 1620 |
| agacaccgga | ttcctagctg | gggcccttca | ctggtgattt | gaaagcacaa | ttctcttgca | 1680 |
| aagaaactta | tattctagct | gtaatcatag | gccaggtgtt | cttctttgt | ttttaatggc | 1740 |
| tatggagtcc | aagtgcaagc | tgaaaaatta | atctcttaga | accagacact | gttctctgag | 1800 |
| catgctaagc | atcccagaaa | cccaaatggg | gccttcctgg | agcgagttaa | ttccagtatg | 1860 |
| gtgtcaacca | agctcgggat | tgcttaaaat | atcatccatc | ccacttcagg | tcctgtcagc | 1920 |
| ttcttgcagt | cagagttcct | atgagtaaca | ataggagttt | ggcctatgta | aggactctga | 1980 |
| gtttaggctt | ccaagataca | acaataagag | aagaatctag | caacgagaat | gacctcattt | 2040 |
| gctttccaca | tgcttagcct | cattatacca | tgttatgtcc | aagttcacag | ccacaacatc | 2100 |
| agaatggtaa | ttactgagca | caagttttaa | atatggacgt | taaaaaaaaa | aatccaagga | 2160 |

```
cctgttttc  caacccagac  atcttttcat  tgaatgattt  agaaagcttt  aagttgatcc   2220
agcttacaat  ttttttttc   tttacctcct  ggaaatctca  tatggtcttg  gatccgtcaa   2280
aaaaaccagt  cagttcactt  gcgctcaaag  tatcaagcac  aacaaagata  aacagaagtg   2340
aggaaggttc  tgggttcact  acatctggat  tttcaagaca  cctattgtga  agtcattagg   2400
gaattgatga  gaatatggct  tcaagcacat  tttgcagttt  gctacaaatt  ctgttgtaca   2460
taatgcagac  gcacactcag  gaggccaatt  taactgttaa  cagtgcatgg  agcgaatgca   2520
gcattttaaa  agatctaggt  ttttttaggt  cattaatgtg  tccttggttg  atcagtcatc   2580
tggtccctcc  tactgtgtgt  tatgaccacc  acgtaatcca  ttctcgctct  ttctgatttg   2640 gggttttcc   tcatccatcc  cattagtagg  gatgttttct  gtgttttcta  gcaagaaaaa   2700
aaaatcaatc  aatcaaacct  gcatacatgt  tactcatgac  tgtcatctag  tcctaaatct   2760
cttctgttgt  tgaatcatcc  ttgcaaaaca  gctgaataca  tctggagaaa  acacagcaca   2820
ccaaagaagc  agaatactgc  aaaccaaaga  catttatgac  ttgtcatttt  ctagcctaaa   2880
aatactgtga  ttacttttag  aaatcagaaa  acctctgcaa  ctccgaatgg  cattcagctc   2940
ttgcatttgg  cgcatcatcg  ggctgagcgg  accagctaca  ccaaggacat  tagccaagcc   3000
acccagaggg  gtggctttgc  cacaccagtt  gtcaccttcc  catagcaagt  ggaagagcgc   3060
ccacagaact  ctgggagatt  gcaaaggtca  caatgtgcat  atttaccagt  gaatggcccc   3120
gggtggggcc  acgtggggt   gttcaaagca  agccaaacgc  tgcaatcatt  ctttacagac   3180
acttgagact  gacttttta   tgaattactt  agtcgaaacc  aaagaaactt  tttctgcacc   3240
tacttctgca  acaaacaaaa  ctgtcccatt  aaaatgaata  aataaatccg  taaatcaatg   3300
gaaatcacca  ccaataagaa  ggaagcacgc  cagaaaataa  acgaaaacaa  aaacagggag   3360
acacactgtg  ttcaaacaga  cctcttggga  catttttgg   aagcagattt  taaagaaagg   3420
gttgagacaa  agatagaaat  aaggaagagc  ctcagtggct  gctgcttcat  ttgacaactc   3480
acacggtaat  cttaaagctg  aagattgtct  ttaatttgtg  cctatgcagt  ttttcaaaag   3540
aacacggaac  agagcaacag  aaacctcaac  agctacaata  ccaaagatga  ggatttctca   3600 cacctttgt   ttcagttcat  tatctcctct  tgcctggcta  aaatactaat  agcgccattg   3660
aactgtataa  aggtaatcaa  ttatgtttct  ctgagcaaca  aaaggaaagg  gccatttatt   3720 tgatttatt   gtttcatttc  aattttgtct  tatggttttt  tgccccaaca  tggaatctct   3780
caaaagtttc  catggactcc  aagtttaaga  tgttgggata  ttgaacagtt  ctctctgctc   3840
agcagagggt  agggaataac  attatcactt  gaatgttctt  tgcttaaccc  ttagacttgg   3900
ttccttctat  gttcagagtc  tcatcatcag  gggaaggaaa  gggagtgagg  gtcagggata   3960
ggggtcttgg  tgatgcatcc  tctcccgagc  cacagaacca  aagagtttat  agaggaattt   4020
acagcctcgt  tttcatgtga  ttgctacatc  ctaacagggc  ttcatttggg  ggtgggggga   4080
aacatgtaaa  aataattgcc  agtttctact  tttctattag  ctttttaaaa  atcagctgta   4140
aagttgcatt  tctaaagaaa  gatatatata  atatataaaa  tacatatata  gatcaacttg   4200
acattggtga  taaccaaaat  tattgctgtc  caaattcatg  tcttgttttg  gtccagtgct   4260
tcatttgcta  agtattcggt  tcagaatttt  tctcatttct  catgccattc  cagagttaat   4320
ttgccactgt  ggatgatttg  aagtattcag  atctctatgg  aagtttctgg  gacaggttta   4380
aagtcaagat  caagcatttt  agcatttaac  ctgttgataa  atggatccat  ggtgtacatg   4440
agttttattt  gtattcggag  tcatctctat  tctatccctc  agcctcgatt  aaggtggtga   4500
gtgaagtgca  tccaacagac  tcggcccaga  actgggtcct  gacagtgggg  tgctcatctt   4560
```

```
ctgtaactgt tgggaaggct cggtggtcca ttttcaccag ttaaagaata tgaggccagc      4620
ccagaaatct gttctccagg agctgccctg tcccatctgg gtgtgccaga cccctcagt      4680 gagcaggtcc accaaaggga cttctcacag gggaagccca actcctgttg caatgggttg      4740
atagatttcc tcagggtggt aattaccaat tcgtattttg acaagccrat gtgcaaccac      4800
agctggcact ggggtgggca gtggtgttgg gtgggatggg ggagagtgtc tcaatcctga      4860
agagaaaata taaagcaggt tttggggaga cttctggagt cctgcccta gagagccca       4920 ttgttgttct ttgtgccccc tcctcattcc ccctatgtgg gtctccctat gcaggagctg      4980
tgagagaatg tgactctcca caattttat aattcatcct tcctaggaga ttgttcattg       5040
gctcttccct tgtgtccctt tgtcccttgc tcatactcca tgtttccttt gtcaaaggac      5100
taagaaaaga gcatatttca gcagaggagt gttcccatgt gggttgattt caacttgggt      5160
atttctaaaa gagtccttgt gacatgtgtc cagtggaaat ggttgctctt ttccagactg      5220
gattgaggaa tggagcctgt ttgatttggt tagtgattct ttgacatact aatctcagcg      5280
tttgggtctc cagcatcctc tgaagatgtc tagactagta gaggctgcct ttgtgacctg      5340
acattacaac attggtcaaa ccagtcctct gataatcaga agaacatgtc ataattgttt      5400
aaaaaaaaaa aaaaggcaag aatttctctc caaggagctt taataaatgt ctcattccag      5460
ataatgtcat accagagaaa agtgcttgct tttagaaaat tatttacata catatataaa      5520
tatatatgtg tatctataca gttatgtatc aaaattttaa gccctgcaga atttcaattt      5580
gttagaaatc taacagaaaa aaatttctat attgaaaggt aatagaattt aacccagtga      5640
gtttactcaa ggattttaa atttaagtta ataatttcag agaaaataac catttgggtg       5700
tggttatagt ttagtatcca ttacctcaat ccaaggaaaa ttccaggcat tcctcaacca      5760
tcaggaaaag gtacagtgtg aaggaacagt tctcagccaa atttcacatt cttgaggcaa      5820
cagaaatcaa aacactcaga gccattgagt ggaaaacaa tttactttat tcctttacac       5880
aaataggctt gcattgtttt tgttttaatg tgattttggt actagggata taattatttc      5940
attccaggaa ataataaaaa aaaacagaca gagccaatac atttctttt ttaaaggaaa       6000 cagcaacaac aataaaaact cagcaccaat atttaaaagc ttttccaaaa tgtaaaagaa      6060
gtgtttagct tgcaccatgc ataaaggtgc aggctagttg aaccaggaag catggcactt      6120
cctctggaga aatccagaaa gagttgcttc taagctccct ttccccctg caggctcttg       6180 gcaattgtag gctttagcaa atccagaata attttcaatt caagctaaaa taaaatcaac      6240
atttggaatg taaatctgat acacacacac ttttctaagt caaacaacat atttcaaaac      6300
caaaaataaa tacctttag ataatcagtt attttctttg tctatactgg gcacccacct       6360
actagtgcca gtaaattcaa gttgaacaga ttttaaaat cactattatc tgggtatggg       6420
ggaaacttcc ccacttttga aaatgttggt agaattatag gaatgtctgt ttgattatca      6480
ttaccaaagt gtcatgacag tatgcctttg tagtgaactc ggattttcag gagtttgaat      6540
agttggatat tttaaaatct aagaagaaaa ggcctgtttc caatgttgtt gaagaataat      6600
gaactctatt aaaagtggaa gaaaagata atacatgtgg tcaaggttga ccacaaggcc       6660
caggcacaac taccttggcg ataatcttct agattcgtaa caggttagag ctgactttt       6720 gttttgttg ttgctgatgc tgtgtgattc agacttctca gcctaaccag gaagagtaag       6780
tggaaatggt agatgaagaa ggggtagagc tggtgtatct ataactttct gatatttgtc      6840
tgccaaactt gatatattag taatttttt atctttagct aagatcaagt caccctgaa        6900
```

| | |
|---|---|
| acaacaggag attctagttt taaaataagg ccacaaaaat ccttacggaa tgaagaatgg | 6960 |
| caccccagtt ggttgtataa gtctcataag ataatgatgt tgattttaaa tatggatgtc | 7020 |
| tcaatgcctg ttttctatca atgatttgtt tgtttccaag gtcggggagg gaaagagggg | 7080 |
| agggtttatc tgttttagaa agtctcagaa tacttataaa atacagaagt agttattaaa | 7140 |
| atatatagga cctcacatag gtagatacag aacttaccat tgaggctgat gggctgttgt | 7200 |
| gtgaatcaca caggacctta aatgaggctc attattctca cacaccaaaa tgactctgac | 7260 |
| agcctgaagc agttattgct agagcccaag cttccttgg aggttttgga gttaggttga | 7320 |
| ttggaagtaa ccagctaata ccttttctag tggagaaaaa gacattgcta ccagcttgtt | 7380 |
| catcccatag aagtcttcca ctctgctcca tttttagcag caagcatttc atgtagcata | 7440 |
| aaccttggca gataagtgtg cctaaggttt atacagtctg tccgcttgga tgtatacaaa | 7500 |
| tttagataca tattttaaca tgtgttctca tagatgactt tataacaaca cacattacct | 7560 |
| ataggtgtct agactgtgta catacaagtg tgtacagaca agcttcatac gtatatactg | 7620 |
| taatccgtta caacaaataa atttaaatc atcgtttaac atgtatgtgg tacttctaca | 7680 |
| gtgtacattg ttttcattat ttattgtaac attgaaaacc acagtgcagg gaaaacaaaa | 7740 |
| gtatcccagc atcttcatcc tgtacacttg gaattaattt catttgggca tatccaagat | 7800 |
| aaactcaact ttcaagaaat cttgtatatt atttaatcat ctgtgttagg atgacaccta | 7860 |
| tgattgatga cttcggttga atagctttat tctggatttt tcataactaa agctaaatcc | 7920 |
| aaagacctga aaaaggacaa aaagaaaaaa aaaaaagaa aaacaaaga aaagaagaa | 7980 |
| aaaataataa agtcaagcgc aaactgatgg ggagacagtg ggctctggtt tccaggattg | 8040 |
| agacaatggt actgcggtct tggggagact gcgttagcta gtggggagtg gtgattttt | 8100 |
| tcatgcttgt cacatctaaa tggtctttaa catgagaaag ttttagaggt tataatttcc | 8160 |
| tgctttgttt ttatttagac tatcaaatga agttatacat gttgtcagtc aaaaaatgaa | 8220 |
| gacaccctct gccccacccc acagaatgct ttttatcttg tctctttggg ttatgaccca | 8280 |
| acaagctaag taccattaat gtaattaact tatttaaatt agttcctagt acataaatgt | 8340 |
| ataggatttg ggtaattatt taatcatcct tccttagttt gattctactc cttgtactta | 8400 |
| tttatcaaaa cctagaccaa tggtgcatca gagatgcaaa attctacttg gaatactctt | 8460 |
| gaagtttagt ttgctttata aagcagtgaa attctgttac agacagggaa gaaatacagg | 8520 |
| ttacaaaaag agaatttggg atattcttcc ctcttaaatt aacttttaaa atagtctaag | 8580 |
| taacaatttt taaattattt aacttaagtt cgcagcccca cctggtacca ggcgaacttc | 8640 |
| acctcttaat tattgtggcc ctcggagcct tcatattgta acttatttat ttaacttatt | 8700 |
| cagcatctgt gaaggtgca ctgtatagtt tatattttta atttaaaaca acagagagca | 8760 |
| ctgcagtttg tttgctgtca gaacaacaga gcaaattttg tggacaagca atgactattc | 8820 |
| agcctgaacc tgtgcattca gaaaacataa gctgagaccc tgcttcacca gcctggtttt | 8880 |
| cggggcttct atacagaaac tggaaaaata aattttaaaa aaatcgtaaa caaaagaga | 8940 |
| gaaacccta cactagctgc ttccaagaat gaactctgtg tgtatgtaaa gcaacaaaac | 9000 |
| aaaaaaggaa aaaacaaaa agcagaaaaa agaaaaaaaa aatgaaaaac tttctatttc | 9060 |
| tagtgagaac caagaaggc tacctcactg acttttccca tttgtaattt taatcgtgtt | 9120 |
| gatgacacca aagataccaa agatttcttt ctctgtgcgg tctgcatttt gcttgtgctc | 9180 |
| ttttataatt tgaacgattt tctctgacat atggtatgta cagccacagc tcagataccc | 9240 |
| caaagaaata attatctatg cgacggcggc tgctaatttg gaaagggata ttttctgtgt | 9300 |

```
ttctcttata tgtttgctgt ctgctcgaca tgttcaagat gcgagttcag atgctgctgt   9360
aattggattc cttaaattct gattacaaat tgaggaagga aactggttgg aaatggcctt   9420
cagtcctagc catggcctct atccccgctg ggacctgtca cagtaaagac tgccaattac   9480
tgaaccacag aagctctgac cattgagtag ttgagctgga agagaccttta ggaatcattt   9540
agtccaagcc ccggtggccc agaggaatga aatagttatc caaatcaaat aactcttgag   9600
agtgaaagcc cacacatgcc tcctggttcc tgccccagtg ctccgcttat tgtacagtgc   9660
tacctctgca tgagagcggt cccacattga caaataggat ggtggcaatc ctttagcaat   9720
gagcagggac tggggtttat ctcttaacat tttcagctgt aaaattagtc acaagcattt   9780
tcagtgtccc attagtacat agtcacatat ggtcggttgc ttcgtgaagg tggcctgtct   9840
tgaaatacta gggctcatac gggattttttg ccctaggaaa aacatgttga tcccaatgat   9900
gtgatcactt ttgaaccttt ccattacaaa gcattgtata gataactttt taattcagta   9960
ggaggagaaa gttcattctt ggcctgttgg ctttgattat tatgggtact ttaaagtcag  10020
tatttatcaa gaaagggaac ttgaccacca ttggcacatg tgacatttaa gctcttcagc  10080
cttttccttt ttagttgtag gtgtttacat ttcatttcta agccaactct gtatttatga  10140
gagaagttta agccttacat catttgatac taaagggtta tttgtggtaa atgaaaaatg  10200
accccaaaat tacagaggaa tatgccagtt taagaaatgg ctactaaaag ttgcttctct  10260
ctttccttct tactcatgaa attaattggt cttcttcaag tttctttaga ttccattaaa  10320
tgattaaatc actattaaga gccattcatc aacgtgattt tgtgttagc caatgaatct  10380
gtctcagctt ttgaccaaat gggttttaga caaatgcaaa gatctgcctc tagtccatat  10440
ggctcttttt gagtgctagt attttgcatt tcacataatg tagttatttt gagcttttaa  10500
agagagcatt tagacaaaga agcaaagaga ggaagggacc aatcaactca tcagttccat  10560
gcatcaacaa agcatagcta gtagaggaat ataaatgaca gattgacaaa ctgtaggaaa  10620
cactgttact ctcttttctga agttttcaag caccatccta tgtgaaagtt ccctcctgtc  10680
caaacaagct caaggcccat cttctcccta tacaaggcaa acctgtaagg ccttccttcc  10740
aaagagtaca ttgctttggt tttcttccta aattcctatt ggaattagaa ctctcagaat  10800
ccctgggaga cagagcaaag atgacttaat tcattgagca gcagagctcc ctataagtga  10860
acatcacctt cccccatctttt cctactgcca cacccatacg agagaggatc tagaaagagc  10920
gatggcagcc tgaacacaga aaacatcccc acttggcaga cctctcctca gcaatccccc  10980
cagcctcatg cttcacttgc aaagtgtgac ataaccacgg gacgagtgcc ttgcttgaac  11040
caaagcaacg atttagccag tctggacctc tctgtgcttt ttttaattct tcctgtgaat  11100
acctcagctt caactgggcc tccatacagt cagttggtgg gcttattgta ctgtggtgct  11160
ttgcaatgca accctgcaaa gaacaagatt tgtactaata ccaaaggttc tttctctatg  11220
tctcctcctc tgcctccctc gttcttccct tttttctagt tcttcacggt tccaaagctt  11280
tactatgaac ctgggcatgt tggcaatgca gaccgcgcaa ttccttaccg aattttctca  11340
gatatacctc atagacaata gtgtttagag taatgttatt atagcgtatg taataaatta  11400
ttcactgttt cttttggtaa ctgtgattta aaaaagaaa aagaaaaaa aagctttata  11460
cgttttaggt tgtgcttttg taatagatga aaaaggtgc gcttaaaaag aaaatgtatg  11520
ttttttttccc cctttggatt ttatttatgc tggattgggg aaagttgcag aatgagccca  11580
aagtttacag tttcatattt tgctgaagaa acaatctgtg ttcatttgct ctgttgaaaa  11640
```

```
gaataattat tttctacatt tgtgccactt ggtctgaaca attaattgtt ccgtgttaac   11700
agtgtagtat tatgattagc aactgccaat cagtgctata attttatgca tgaggctaaa   11760
aatttagcag tgtgatgcat tgtggtctta atagcaacat ttttcatttt gaactagatc   11820
ttcccctttg gttcaatgga ctttatttat gcatgggcgc ctattgtttg ttagcagttg   11880
tggaacagtt gtgtatacat taaactgtga aaatgtacac agttcagcct cagacggtgg   11940
taatattggt tttattggga gatgtgtcac ctcgaaaata ccctttacat ctgttgggat   12000
ctgaaaatga gtcacattga attgggttcc agctttataa tgagaaacgt tattcctaat   12060
ttttgagtta gccaatttgc attccacaaa ttgggatcct cataacccaa atatatcacc   12120
gtatgtgaga gggatttgaa agcgagtatt gaaaaactca cctttgcata tttaatttcc   12180
accaaaagga gttatttggg ctttatgctc atgaacttag acctaactgg ccatgtatat   12240
gtagatgcaa attcatctag ctgtggccct ctttgatctc tgcttgggaa tggctatttt   12300
tgactatgcg tggtttcttc tcgtattttg tgatcaggtc agctcccagt agaaactcaa   12360
atggcatcaa tattactaac tcttctctgc ccacttctct tttgtccact ctcctagaca   12420
ttcccaccaa ctgttccagt gatttgggca aaaatacgca gccatttccc aaaacttcac   12480
atgtgcagct atcatggctg tccctcccta gacttggagg tgactctcac ttaattttta   12540
cctgcccaac aatgttccat ctaccatcta aaaggtaata taagaagaag ttttgaaacc   12600
cactttagga aaaccatctt ctttaaatcc ttcaattatc tgaggcctct atatgtcaaa   12660
actattttc agttgcaggg gattgggcaa acttgttctt tcttatactt gggttcaaag   12720
acccattctc cagtttcata tttcccaaac caaaatgctt gacataaagc caaatcaact   12780
gccaagcaca ctttatttg cataggagta tgcagcctag ggaaccttgg ttgaaaagca   12840
gcagtctgct atgcaaaata ttggaaatca ctgacagtgt agcattcata ttatctgtca   12900
atgagggtat attgggaacg tgctctcgtg aataataaaa agcaacatat ttttatttgg   12960
ccttataaat taggttgtgg taatgtaaac tttgatatat agtctttta ttttctctt   13020
attaatctgc caaagatggg aacagataca agaattttc aaattggctt ttgtaagaca   13080
attgatgatt gtaatagtgt ttaatcttcc agaaagcttt atatgttgtt ccacaataaa   13140
attgatattt gtttcagcaa agttttcctg acactcacaa acccacaaac tgttcctctt   13200
aatgcagata ttgtagaatc tacaaagttc aaatccattt ttgatccaaa gaaagtagag   13260
gagtatttga gacatgagtg tacccagccc ttttttaat cacaggcaat gcatgggtct   13320
ggctggttac actttgccaa gaagacttgt cttatgaaac ccaaggtata ttttgttatg   13380
ccattttatg tccttttctt ttaacattgt ggaaagtggt atgttgaatc aagtgtaagc   13440
tgagttttcc agacaactga agtagctaca tcatgaatgt tattttgtta ttaaagggtt   13500
tttactcagt gctttgtgcc aatggatgtc cttttccttg gagacacata actacaaaat   13560
tacctcagct tggcctggtt ttctctcctg ccctcttggg gaaacatggg cctggcctgg   13620
gaaaaggcag gtcatgggct ggaaggtagg ttttggtact aggaagaaat ctctgtatct   13680
gtcagcttta aagagaactg ggccaaaaat ctctaacctc actctctctg gactccaaca   13740
cttccctgca atcctttggt cttgagcatg tgccagcatg aaggcagact ccagttcata   13800
catgaaaggc aagaaaaaga aaatagtaac cttgaatctt ctgtgggcca ccaggcactc   13860
acctttcccc accttgcaca ctatccagtc aaggctattg cagcccatct ggtggcttta   13920
catgggacat taccaaaggc ttcttcctcc atcctggggt tgcaaaggat ccaggtcccc   13980
tccatccagt ggggctcttc cacatcagaa gtccccctcc caccatcctc tgcatcctgt   14040
```

```
ttagctatcc catctatacc ttttggagat gattatttag aaaacaaaga aaggtatgga    14100
atggggtttc ctattgtttg ctaggttata ttttagcaat tctcaattct ttgatctgga    14160
aaaatacaag agggaaaagg agacccact atctccctgt gctttgctcc catctcaggg     14220
ggcaggggca gtgcacattg cctatgctgt tgatctgtct tgggcgacag gctgaatcac    14280
agctattgcc ccagccaaaa acatggccca tcaatgccta ctttatctct gcttgaaaat    14340
cctattcaaa aagttgtaga gtttgaggtt tttatccccc catatccttt gctttggtcc    14400
agtttggcct ttagcataag agtcagcttt atctctagga aagttttttc agattatgac    14460
aaggaacctg ccacctggga agaaaagagt ccgaagacta gcaatcggat aggtagtcat    14520
accattaaca gatacttcct tgaaggtaga atattatttc ctttctttac agttttgtgt    14580
tacacaagtc caagtggtgc cagcaaactt cttaccgtga aatgttgtaa aacacctggc    14640
atactgaaat ttctgaaaca aaaacacaag ctccacattg ataacttgat aaataaccac    14700
taaagtttag atgcagggac tgagatgata caggcaaaat cttggtgttg gtttctcttt    14760
taattcgtat cttcgatcac ctaaccttt tcaatccaag agcagttcag tcttttctcc     14820
ccaagtctag gatgccaaag agcatcatag gaaaagataa ttagggattg accagcattt    14880
caattagttc tcttcttcat ctttgcattt ctcaaaagtg ttctcctgga ccagagggaa    14940
agagctggtc catttttttt cattctttct attcaaattt ttccacccag acaatacttt    15000
attaacacag atactgtaga tccttccttg gtcagtgaat tattacaaga ggagctatcc    15060
ttccaccaaa gtgagtgaaa acaagttcca gtatcttttc ttccatccag ttttgttctc    15120
agaatccaag tcagtcctgg gtcttttctc actttagacc ctggcctcag atgtgtttat    15180
tcttgctatt taaaaatacc tttaaatttc acatgctggc ctgcagaact tgcatccttt    15240
gttctatact gttgactgct tgatggtatt gaaaggtgac tataatgagg gaagaaagga    15300
ggaggtaaag agagaagaat ttgtcccaga tctgtttaaa gtttcaaaat ttaaaaaggg    15360
acccattaaa ttatgggaaa atggctatag agtgtgagcc tccgttgacc atatgctcaa    15420
agaccgtact ctgccacctg ccttccaggt agctattcta gaaactcagt cctttgtgga    15480
aacccaacta ccttttaaaa gtctctttcc agattccaaa aggacaagag atcagagagt    15540
cacatatacg cctcttgttt tatttcttg ctttcacggg tattattgcc aagaaaatcg      15600
tagggaaaaa cttaaactt ttcttttcag ttgatcccctt tgacatcacc tctcatgttt      15660
aaaatcagga aaacacaccc ctaaaatttg cactctcttc cgttttgaaa aagaaaaccc    15720
acacacaaat gcacactatt accgtctttc accctgcgct atatttccaa agtgtattat    15780
aatccagata ttgccccatc tcaaacatgt taagtcagac tgtgctgaaa gactttccag    15840
ggacggtcaa cagggtatat gttcagtggc tgccctgaaa tcctggtggg gatgaggatc    15900
acgcttcatc atcaagggga tgcccatccc ctgataagct cccagtcctt tggaagatt     15960 tctttgaatg ttaattgcat tttcagtttt gctcatttcc cacccaatg ttttgtctgc     16020 aacatcgctt acactggatt ctttctattt ttattcctat cattaaatgg tagtgctgta    16080
aattctgcaa ttaatgttaa ataaactgct ttaattcatt gaaaaaaaaa aaaaaaaaa     16140 aa                                                                   16142
```

<210> SEQ ID NO 22
<211> LENGTH: 2379
<212> TYPE: DNA
<213> ORGANISM: Homo sapiens

<400> SEQUENCE: 22

```
gacccccgag ctgtgctgct cgcggccgcc accgccgggc ccggccgtc cctggctccc      60
ctcctgcctc gagaagggca gggcttctca gaggcttggc gggaaaaaga acggagggag    120
ggatcgcgct gagtataaaa gccggttttc gggcttttat ctaactcgct gtagtaattc    180
cagcgagagg cagagggagc gagcgggcgg ccggctaggg tggaagagcc gggcgagcag    240
agctgcgctg cgggcgtcct gggaagggag atcggagcg aatagggggc ttcgcctctg     300
gcccagccct cccgctgatc ccccagccag cggtccgcaa ccttgccgc atccacgaaa     360
ctttgcccat agcagcgggc gggcactttg cactggaact acaacaccc gagcaaggac     420
gcgactctcc cgacgcgggg aggctattct gcccatttgg ggacacttcc ccgccgctgc    480
caggacccgc ttctctgaaa ggctctcctt gcagctgctt agacgctgga ttttttcgg    540
gtagtggaaa accagcagcc tcccgcgacg atgcccctca acgttagctt caccaacagg    600
aactatgacc tcgactacga ctcggtgcag ccgtatttct actgcgacga ggaggagaac    660
ttctaccagc agcagcagca gagcgagctg cagcccccgg cgcccagcga ggatatctgg    720
aagaaattcg agctgctgcc cacccccgcc ctgtcccccta gccgccgctc cgggctctgc    780
tcgccctcct acgttgcggt cacacccttc tcccttcggg gagacaacga cggcggtggc    840
gggagcttct ccacggccga ccagctggag atggtgaccg agctgctggg aggagacatg    900
gtgaaccaga gtttcatctg cgacccggac gacgagacct tcatcaaaaa catcatcatc    960
caggactgta tgtggagcgg cttctcggcc gccgccaagc tcgtctcaga gaagctggcc   1020
tcctaccagc tgcgcgcaa agacagcggc agcccgcgcg ccacagcgtc                1080
tgctccacct ccagcttgta cctgcaggat ctgagcgccg ccgcctcaga gtgcatcgac   1140
ccctcggtgg tcttccccta ccctctcaac gacagcagct cgcccaagtc ctgcgcctcg   1200
caagactcca gcgccttctc tccgtcctcg gattctctgc tctcctcgac ggagtcctcc   1260
ccgcagggca gccccgagcc cctggtgctc catgaggaga ccgcccac accagcagc     1320
gactctgagg aggaacaaga agatgaggaa gaaatcgatg ttgtttctgt ggaaaagagg   1380
caggctcctg gcaaaaggtc agagtctgga tcaccttctg ctggaggcca cagcaaacct   1440
cctcacagcc cactggtcct caagaggtgc cacgtctcca cacatcagca caactacgca   1500
gcgcctccct ccactcggaa ggactatcct gctgccaaga gggtcaagtt ggacagtgtc   1560
agagtcctga cacagatcag caacaaccga aaatgcacca gccccaggtc ctcggacacc   1620
gaggagaatg tcaagaggcg aacacacaac gtcttggagc gccagaggag gaacgagcta   1680
aaacggagct tttttgccct gcgtgaccag atcccggagt tggaaaacaa tgaaaaggcc   1740
cccaaggtag ttatccttaa aaaagccaca gcatacatcc tgtccgtcca agcagaggag   1800
caaaagctca tttctgaaga ggacttgttg cggaaacgac gagaacagtt gaaacacaaa   1860
cttgaacagc tacggaactc ttgtgcgtaa ggaaaagtaa ggaaaacgat tccttctaac   1920
agaaatgtcc tgagcaatca cctatgaact tgtttcaaat gcatgatcaa atgcaacctc   1980
acaaccttgg ctgagtcttg agactgaaag atttagccat aatgtaaact gcctcaaatt   2040
ggactttggg cataaaagaa cttttttatg cttaccatct ttttttttc tttaacagat   2100
ttgtatttaa gaattgtttt taaaaatttt taagatttac acaatgtttc tctgtaaata   2160
ttgccattaa atgtaaataa ctttaataaa acgtttatag cagttacaca gaatttcaat   2220
cctagtatat agtacctagt attataggta ctataacccc taattttttt tatttaagta   2280
cattttgctt tttaaagttg attttttttct attgttttta gaaaaaataa aataactggc   2340
```

```
aaatatatca ttgagccaaa tcttaaaaaa aaaaaaaa                             2379
```

<210> SEQ ID NO 23
<211> LENGTH: 2046
<212> TYPE: DNA
<213> ORGANISM: Homo sapiens

<400> SEQUENCE: 23

```
ggagcccggg gcgggcgagg gcggggggtgt cccggctata aagcgtggcc gcctcccgcg     60
gcgctcggga cagccgtacc ccgggcggtc ggacgggcgg gcgccggtgg gagctcgggc    120
cgtgcccgct gagagatcca gagcgctccg ttcccccggg gccggagcgg gggcgggtgg    180
gggcgtaagc ccgggggatg ctgggctcag tgaagatgga ggcccatgac ctggccgagt    240
ggagctacta cccggaggcg ggcgaggtct actcgccggt gaccccagtg cccaccatgg    300
ccccccctcaa ctcctacatg accctgaatc ctctaagctc tccctatccc cctgggggc    360
tccctgcctc cccactgccc tcaggacccc tggcaccccc agcacctgca gccccctgg     420
ggcccacttt cccaggcctg ggtgtcagcg gtggcagcag cagctccggg tacggggccc    480
cgggtcctgg gctggtgcac gggaaggaga tgccgaaggg gtatcggcgg ccctggcac     540
acgccaagcc accgtattcc tatatctcac tcatcaccat ggccatccag caggcgccgg    600
gcaagatgct gaccttgagt gaaatctacc agtggatcat ggacctcttc ccttactacc    660
gggagaatca gcagcgctgg cagaactcca ttcgccactc gctgtctttc aacgactgct    720
tcgtcaaggt ggcgcgttcc ccagacaagc ctggcaaggg ctcctactgg gccctacacc    780
ccagctcagg gaacatgttt gagaatggct gctacctgcg ccgccagaaa cgcttcaagc    840
tggaggagaa ggtgaaaaaa gggggcagcg ggctgccac caccaccagg aacgggacag    900
ggtctgctgc ctcgaccacc accccgcgg ccacagtcac ctccccgccc cagcccccgc    960
ctccagcccc tgagcctgag gcccaggcg gggaagatgt gggggctctg gactgtggct   1020
cacccgcttc ctccacaccc tatttcactg gcctggagct cccaggggag ctgaagctgg   1080
acgcgcccta caacttcaac caccctttct ccatcaacaa cctaatgtca gaacagacac   1140
cagcacctcc caaactggac gtggggtttg gggctacgg ggctgaaggt ggggagcctg   1200
gagtctacta ccagggcctc tattcccgct ctttgcttaa tgcatcctag caggggttgg   1260
gaacatggtg gtgggtatgg ctggagctca caccacgaag ctcttggggc ctgatccttc   1320
tggtgacact tcacttgtcc cattggttaa catctgggtg ggtctattac ttactgtgat   1380
gactgctgtc tcagtgggca tggtgttgat ccacggggta ctgtgataac caccatggat   1440
acattttggt ggcccactgg gtactgtgag gactgctaca ttgatggatg ttattggcta   1500
atccactgca tggtttgatg gccaccatct cggttggccc tttgggtgtg atggtgatag   1560
catttcagtg acatcttctt tggcccccccc cattaggtgc tgtgcccact tcttttttgg   1620
tgtacttggc acagtaggtg ccaagttggc caccattctg tgtaacacct ttttggccc   1680
attgggtgct ttgatggaca tcatactggg taggtgacaa cgtcagtggg ccaccatgtg   1740
ccatgatggc tgctgcagcc ccgtgttggc catgtcgtca ccattctctc tggcatgggt   1800
tgggtagggg atggaggtga gaatactcct tggttttctc tgaagcccac cctttccccc   1860
aactctggtc caggagaaac cagaaaaggc tggttagggt gtgggaatt tctactgaag   1920
tctgattctt tcccgggaag cggggtactg gctgtgttta atcattaaag gtaccgtgtc   1980
cgcctcttaa aaaaaaaaa aaaaaaaaa aaaaaaaaa aaaaaaaaa aaaaaaaaa         2040
``` aaaaaa 2046

<210> SEQ ID NO 24
<211> LENGTH: 3239
<212> TYPE: DNA
<213> ORGANISM: Homo sapiens

<400> SEQUENCE: 24

| | | | | | |
|---|---|---|---|---|---|
| gggaggaggc | agtgggaggg | cggagggcgg | gggccttcgg | ggtgggcgcc | cagggtaggg | 60 |
| caggtggccg | cggcgtggag | gcagggagaa | tgcgactctc | caaaaccctc | gtcgacatgg | 120 |
| acatggccga | ctacagtgct | gcactggacc | cagcctacac | caccctggaa | tttgagaatg | 180 |
| tgcaggtgtt | gacgatgggc | aatgacacgt | ccccatcaga | aggcaccaac | ctcaacgcgc | 240 |
| ccaacagcct | gggtgtcagc | gccctgtgtg | ccatctgcgg | ggaccgggcc | acggcaaac | 300 |
| actacggtgc | ctcgagctgt | gacggctgca | agggcttctt | ccggaggagc | gtgcggaaga | 360 |
| accacatgta | ctcctgcaga | tttagccggc | agtgcgtggt | ggacaaagac | aagaggaacc | 420 |
| agtgccgcta | ctgcaggctc | aagaaatgct | tccgggctgg | catgaagaag | gaagccgtcc | 480 |
| agaatgagcg | ggaccggatc | agcactcgaa | ggtcaagcta | tgaggacagc | agcctgccct | 540 |
| ccatcaatgc | gctcctgcag | gcggaggtcc | tgtcccgaca | gatcacctcc | cccgtctccg | 600 |
| ggatcaacgg | cgacattcgg | gcgaagaaga | ttgccagcat | cgcagatgtg | tgtgagtcca | 660 |
| tgaaggagca | gctgctggtt | ctcgttgagt | gggccaagta | catcccagct | ttctgcgagc | 720 |
| tcccccctgga | cgaccaggtg | gccctgctca | gagcccatgc | tggcgagcac | ctgctgctcg | 780 |
| gagccaccaa | gagatccatg | gtgttcaagg | acgtgctgct | cctaggcaat | gactacattg | 840 |
| tccctcggca | ctgcccggag | ctggcggaga | tgagccgggt | gtccatacgc | atccttgacg | 900 |
| agctggtgct | gccccttccag | gagctgcaga | tcgatgacaa | tgagtatgcc | tacctcaaag | 960 |
| ccatcatctt | ctttgaccca | gatgccaagg | ggctgagcga | tccagggaag | atcaagcggc | 1020 |
| tgcgttccca | ggtgcaggtg | agcttggagg | actacatcaa | cgaccgccag | tatgactcgc | 1080 |
| gtggccgctt | tggagagctg | ctgctgctgc | tgcccacctt | gcagagcatc | acctggcaga | 1140 |
| tgatcgagca | gatccagttc | atcaagctct | tcggcatggc | caagattgac | aacctgttgc | 1200 |
| aggagatgct | gctgggaggg | tcccccagcg | atgcacccca | tgcccaccac | cccctgcacc | 1260 |
| ctcacctgat | gcaggaacat | atgggaacca | acgtcatcgt | tgccaacaca | atgcccactc | 1320 |
| acctcagcaa | cggacagatg | tgtgagtggc | ccgacccag | gggacaggca | gccaccctg | 1380 |
| agacccaca | gccctcaccg | ccaggtggct | cagggtctga | gccctataag | ctcctgccgg | 1440 |
| gagccgtcgc | cacaatcgtc | aagcccctct | ctgccatccc | cagccgacc | atcaccaagc | 1500 |
| aggaagttat | ctagcaagcc | gctgggcctt | ggggctcca | ctggctcccc | ccagcccct | 1560 |
| aagagagcac | ctggtgatca | cgtggtcacg | gcaaaggaag | acgtgatgcc | aggaccagtc | 1620 |
| ccagagcagg | aatgggaagg | atgaagggcc | cgagaacatg | gcctaagggc | cacatcccac | 1680 |
| tgccaccctt | gacgccctgc | tctggataac | aagactttga | cttggggaga | cctctactgc | 1740 |
| cttggacaac | ttttctcatg | ttgaagccac | tgccttcacc | ttcaccttca | tccatgtcca | 1800 |
| accccccgact | tcatcccaaa | ggacagccgc | ctggagatga | cttgaggcct | tacttaaacc | 1860 |
| cagctccctt | cttccctagc | ctggtgcttc | tcctctccta | gcccctgtca | tggtgtccag | 1920 |
| acagagccct | gtgaggctgg | gtccaattgt | ggcacttggg | gcaccttgct | cctccttctg | 1980 |
| ctgctgcccc | cacctctgct | gcctcccctct | gctgtcacct | tgctcagcca | tcccgtcttc | 2040 |
| tccaacacca | cctctccaga | ggccaaggag | gccttggaaa | cgattccccc | agtcattctg | 2100 |

```
ggaacatgtt gtaagcactg actgggacca ggcaccaggc agggtctaga aggctgtggt    2160
gagggaagac gcctttctcc tccaacccaa cctcatcctc cttcttcagg gacttgggtg    2220
ggtacttggg tgaggatccc tgaaggcctt caacccgaga aaacaaaccc aggttggcga    2280
ctgcaacagg aacttggagt ggagaggaaa agcatcagaa agaggcagac catccaccag    2340
gcctttgaga aagggtagaa ttctggctgg tagagcaggt gagatgggac attccaaaga    2400
acagcctgag ccaaggccta gtggtagtaa gaatctagca agaattgagg aagaatggtg    2460
tgggagaggg atgatgaaga gagagagggc ctgctggaga gcatagggtc tggaacacca    2520
ggctgaggtc ctgatcagct tcaaggagta tgcagggagc tgggcttcca gaaaatgaac    2580
acagcagttc tgcagaggac gggaggctgg aagctgggag gtcaggtggg gtggatgata    2640
taatgcgggt gagagtaatg aggcttgggg ctggagagga caagatgggt aaaccctcac    2700
atcagagtga catccaggag gaataagctc ccagggcctg tctcaagctc ttccttactc    2760
ccaggcactg tcttaaggca tctgacatgc atcatctcat ttaatcctcc cttcctccct    2820
attaacctag agattgtttt tgttttttat tctcctcctc cctccccgcc ctcacccgcc    2880
ccactccctc ctaacctaga gattgttaca gaagctgaaa ttgcgttcta agaggtgaag    2940
tgattttttt tctgaaactc acacaactag gaagtggctg agtcaggact tgaacccagg    3000
tctccctgga tcagaacagg agctcttaac tacagtggct gaatagcttc tccaaaggct    3060
ccctgtgttc tcaccgtgat caagttgagg ggcttccggc tcccttctac agcctcagaa    3120
accagactcg ttcttctggg aaccctgccc actcccagga ccaagattgg cctgaggctg    3180
cactaaaatt cacttagggt cgagcatcct gtttgctgat aaatattaag gagaattca     3239
```

<210> SEQ ID NO 25
<211> LENGTH: 3241
<212> TYPE: DNA
<213> ORGANISM: Homo sapiens
<400> SEQUENCE: 25

```
cgtggccctg tggcagccga gccatggttt ctaaactgag ccagctgcag acggagctcc      60
tggcggccct gctcgagtca gggctgagca aagaggcact gatccaggca ctgggtgagc     120
cggggcccta cctcctggct ggagaaggcc ccctggacaa gggggagtcc tgcggcggcg     180
gtcgagggga gctggctgag ctgcccaatg ggctggggga gactcgggggc tccgaggacg    240 agacggacga cgatggggaa gacttcacgc cacccatcct caaagagctg gagaacctca     300
gccctgagga ggcggcccac cagaaagccg tggtggagac ccttctgcag gaggacccgt     360
ggcgtgtggc gaagatggtc aagtcctacc tgcagcagca caacatccca cagcgggagg     420
tggtcgatac cactggcctc aaccagtccc acctgtccca acacctcaac aagggcactc     480
ccatgaagac gcagaagcgg gccgccctgt acacctggta cgtccgcaag cagcgagagg     540
tggcgcagca gttcaccat gcagggcagg gagggctgat tgaagagccc acaggtgatg     600
agctaccaac caagaagggg cggaggaacc gtttcaagtg gggcccagca tcccagcaga     660
tcctgttcca ggcctatgag aggcagaaga cccctagcaa ggaggagcga gagacgctag     720
tggaggagtg caatagggcg gaatgcatcc agagaggggt gtcccatca caggcacagg     780 ggctgggctc caacctcgtc acggaggtgc gtgtctacaa ctggtttgcc aaccggcgca     840
aagaagaagc cttccggcac aagctggcca tggacacgta cagcgggccc cccccagggc     900
caggcccggg acctgcgctg cccgctcaca gctcccctgg cctgcctcca cctgccctct    960
```

```
cccccagtaa ggtccacggt gtgcgctatg acagcctgc gaccagtgag actgcagaag    1020
taccctcaag cagcggcggt cccttagtga cagtgtctac accctccac caagtgtccc     1080
ccacgggcct ggagcccagc acagcctgc tgagtacaga agccaagctg gtctcagcag     1140
ctggggggccc cctcccccct gtcagcaccc tgacagcact gcacagcttg agcagacat    1200
ccccaggcct caaccagcag ccccagaacc tcatcatggc ctcacttcct ggggtcatga    1260
ccatcgggcc tggtgagcct gcctcccctgg gtcctacgtt caccaacaca ggtgcctcca   1320
ccctggtcat cggcctggcc tccacgcagg cacagagtgt gccggtcatc aacagcatgg    1380
gcagcagcct gaccaccctg cagcccgtcc agttctccca gccgctgcac ccctcctacc    1440
agcagccgct catgccacct gtgcagagcc atgtgaccca gagccccttc atggccacca    1500
tggctcagct gcagagcccc cacgccctct cagccacaa gcccgaggtg gcccagtaca    1560
cccacacggg cctgctcccg cagactatgc tcatcaccga caccaccaac ctgagcgccc   1620
tggccagcct cacgcccacc aagcaggtct tcacctcaga cactgaggcc tccagtgagt   1680
ccgggcttca cacgccggca tctcaggcca ccaccctcca cgtccccagc caggaccctg    1740
ccggcatcca gcacctgcag ccggcccacc ggctcagcgc cagccccaca gtgtcctcca   1800
gcagcctggt gctgtaccag agctcagact ccagcaatgg ccagagccac ctgctgccat   1860
ccaaccacag cgtcatcgag accttcatct ccacccagat ggcctcttcc tcccagtaac   1920
cacggcacct gggccctggg gcctgtactg cctgcttggg gggtgatgag ggcagcagcc   1980
agccctgcct ggaggacctg agcctgccga gcaaccgtgg cccttcctgg acagctgtgc   2040
ctcgctcccc actctgctct gatgcatcag aaagggaggg ctctgaggcg ccccaacccg    2100
tggaggctgc tcggggtgca caggaggggg tcgtggagag ctaggagcaa agcctgttca   2160
tggcagatgt aggagggact gtcgctgctt cgtgggatac agtcttctta cttggaactg   2220
aaggggggcgg cctatgactt gggcaccccc agcctgggcc tatggagagc cctgggaccg   2280
ctacaccact ctggcagcca cacttctcag gacacaggcc tgtgtagctg tgacctgctg   2340
agctctgaga ggccctggat cagcgtggcc ttgttctgtc accaatgtac ccaccgggcc   2400
actccttcct gccccaactc cttccagcta gtgacccaca tgccatttgt actgaccccca   2460
tcacctactc acacaggcat ttcctgggtg gctactctgt gccagagcct ggggctctaa   2520
cgcctgagcc cagggaggcc gaagctaaca gggaaggcag gcagggctct cctgcttcc    2580
catccccagc gattccctct cccaggcccc atgacctcca gctttcctgt atttgttccc    2640
aagagcatca tgcctctgag gccagcctgg cctcctgcct ctactgggaa ggctacttcg    2700
gggctgggaa gtcgtcctta ctcctgtggg agcctcgcaa cccgtgccaa gtccaggtcc   2760
tggtggggca gctcctctgt ctcgagcgcc ctgcagaccc tgcccttgtt tggggcagga    2820
gtagctgagc tcacaaggca gcaaggcccg agcagctgag cagggccggg gaactggcca    2880
agctgaggtg cccaggagaa gaaagaggtg accccagggc acaggagcta cctgtgtgga    2940
caggactaac actcagaagc ctgggggcct ggctggctga gggcagttcg cagccaccct    3000
gaggagtctg aggtcctgag cactgccagg aggacaaag gagcctgtga acccaggaca    3060
agcatggtcc cacatccctg ggcctgctgc tgagaacctg gccttcagtg taccgcgtct   3120
accctgggat tcaggaaaag gcctggggtg acccggcacc cctgcagct tgtagccagc    3180
cggggcgagt ggcacgttta tttaactttt agtaaagtca aggagaaatg cggtggaaaa    3240
a                                                                   3241
```

<210> SEQ ID NO 26
<211> LENGTH: 2842
<212> TYPE: DNA
<213> ORGANISM: Homo sapiens

<400> SEQUENCE: 26

```
aatttgcata tcttatatgg cctaatggtg gcgatcatgg caagttagaa gtttttctgac     60
tcctttcgga ggagcctccg ggaccccggg gagtaacagg tgtctggagg ctgaagggtg    120
gaggggttcc tggatttggg gtttgcttgt gaaactcccc tccaccctcc tctctcgcac    180
ccacccaccc cctcaccccc ttcttttttcc gtccttggaa aatggtgtcc aagctcacgt    240
cgctccagca agaactcctg agcgccctgc tgagctccgg ggtcaccaag gaggtgctgg    300
ttcaggcctt ggaggagttg ctgccatccc cgaacttcgg ggtgaagctg gagacgctgc    360
ccctgtcccc tggcagcggg gccgagcccg acaccaagcc ggtcttccat actctcacca    420
acggccacgc caagggccgc ttgtccggcg acgagggctc cgaggacggc gacgactatg    480
acacacctcc catcctcaag gagctgcagg cgctcaacac cgaggaggcg gcggagcagc    540
gggcggaggt ggaccggatg ctcagtgagg acccttggag ggctgctaaa atgatcaagg    600
gttacatgca gcaacacaac atcccccaga ggggaggtggt cgatgtcacc ggcctgaacc    660
agtcgcacct ctcccagcat ctcaacaagg gcaccctat gaagacccag aagcgtgccg    720
ctctgtacac ctggtacgtc agaaaagcaac gagagatcct ccgacaattc aaccagacag    780
tccagagttc tggaaatatg acagacaaaa gcagtcagga tcagctgctg tttctctttc    840
cagagttcag tcaacagagc catgggcctg gcagtccga tgatgcctgc tctgagccca    900
ccaacaagaa gatgcgccgc aaccggttca atgggggcc cgcgtcccag caaatcttgt    960
accaggccta cgatcggcaa aagaacccca gcaaggaaga gagagaggcc ttagtggagg   1020
aatgcaacag ggcagaatgt ttgcagcgag gggtgtcccc ctccaaagcc cacggcctgg   1080
gctccaactt ggtcactgag gtccgtgtct caactggtt tgcaaaccgc aggaaggagg   1140
aggcattccg gcaaaagctg gccatggacg cctatagctc caaccagact cacagcctga   1200
accctctgct ctcccacggc tcccccccacc accagcccag ctcctctcct ccaaacaagc   1260
tgtcaggagt gcgctacagc cagcagggaa acaatgagat cacttcctcc tcaacaatca   1320
gtcaccatgg caacagcgcc atggtgacca gccagtcggt tttacagcaa gtctccccag   1380
ccagcctgga cccaggccac aatctcctct cacctgatgg taaaatgatc tcagtctcag   1440
gaggaggttt gccccagtc agcaccttga cgaatatcca cagcctctcc caccataatc   1500
cccagcaatc tcaaaacctc atcatgacac ccctctctgg agtcatgca attgcacaaa   1560
gcctcaacac ctcccaagca cagagtgtcc ctgtcatcaa cagtgtggcc ggcagcctgg   1620
cagccctgca gcccgtccag ttctcccagc agctgcacag ccctcaccag cagccctca   1680
tgcagcagag cccaggcagc cacatggccc agcagccctt catggcagct gtgactcagc   1740
tgcagaactc acacatgtac gcacacaagc aggaaccccc ccagtattcc cacacctccc   1800
ggtttccatc tgcaatggtg gtcacagata ccagcagcat cagtacactc accaacatgt   1860
cttcaagtaa acagtgtcct ctacaagcct ggtgatgccc acacaccact tacttcgtgc   1920
gcaacaacaa ggaccctgtt ttccacacca tcaccctctg ggcagctgtc atggaaaagc   1980
ccagtgacct gaccggcacc tgcgagaggt ccctgcttac ctgacggacg tcctgctggc   2040
acctcagaca atccactctc aggaggcgca gcccgaagcc cagtttccct tctatgcagt   2100
attgccacaa tgcctctccc acgatgtcaa ggactcctgt ctgtcctgga ggtgggagac   2160
```

| aaggaaccac cgaagaggaa gcaagaaagc cgtactgtct atgttgtgat ccttcatcga | 2220 |
| acaaactgat gcgaaaactt gaatctgtta ctgaaatgag gagagaagga catgtgctat | 2280 |
| tgaactgagc caaacacact gtaaatatcc acagactccc tcccctgccc ccatcccaca | 2340 |
| tgatcttgag atttctttta aagaagtaaa tttgtccaat ggctgtaaac tataaactac | 2400 |
| tgtaattaag tgcaatttcc cctctgtgtc ctctcccctc tgccctgtat ataatactaa | 2460 |
| agtgtctatt agttttcttt gtaaaggtca gagtcaaaat ttcaaaagtg atctgtcccc | 2520 |
| tctcccctca tggagaaaca tcctaagtgg gaagtgaagc cccttgtcct ctcccgcggg | 2580 |
| cctggacact tatggggaca gcataccttg gactgactac cagctaactc cagtctcctg | 2640 |
| acattaagac acacctctgg atccctggag gggctgaatg tagtgtgtca gagtaacatg | 2700 |
| ccagcttcct gtgggccagg agctcagccg tgcactccct aagaaacccc agggcaggga | 2760 |
| aactggctgt ttgatagcag aagaaaaagt tgcagtctca gaaagccttc cattaaaaca | 2820 |
| atttatttta tcactaaaaa aa | 2842 |

<210> SEQ ID NO 27
<211> LENGTH: 2591
<212> TYPE: DNA
<213> ORGANISM: Homo sapiens

<400> SEQUENCE: 27

| cggaggtgcg cgggcgcggg cgagcagggt ctccgggtgg gcggcggcga cgccccgcgc | 60 |
| aggctggagg ccgccgaggc tcgccatgcc gggagaactc taactccccc atggagtcgg | 120 |
| ccgacttcta cgaggcggag ccgcggcccc cgatgagcag ccacctgcag agccccccgc | 180 |
| acgcgcccag cagcgccgcc ttcggctttc ccggggcgc gggccccgcg cagcctcccg | 240 |
| ccccacctgc cgccccggag ccgctgggcg gcatctgcga gcacgagacg tccatcgaca | 300 |
| tcagcgccta catcgacccg gccgccttca acgacgagtt cctggccgac ctgttccagc | 360 |
| acagccggca gcaggagaag gccaaggcgg ccgtgggccc cacgggcggc ggcggcggcg | 420 |
| gcgactttga ctacccgggc gcgcccgcgg gccccggcgg cgccgtcatg cccgggggag | 480 |
| cgcacgggcc cccgccccgg tacgctgcg cggccgccgg ctacctggac ggcaggctgg | 540 |
| agcccctgta cgagcgcgtc ggggcgccgg cgctgcggcc gctggtgatc aagcaggagc | 600 |
| cccgcgagga ggatgaagcc aagcagctgg cgctggccgg cctcttccct taccagccgc | 660 |
| cgccgccgcc gccgccctcg caccccgcacc cgcacccgcc gccgcgcac ctggccgccc | 720 |
| cgcacctgca gttccagatc gcgcactgcg gccagaccac catgcacctg cagccccgtc | 780 |
| accccacgcc gccgccacg cccgtgccca gcccgcaccc cgcgcccgcg ctcggtgccg | 840 |
| ccggcctgcc gggccctggc agcgcgctca aggggctggg cgccgcgcac cccgacctcc | 900 |
| gcgcgagtgg cggcagcggc gcgggcaagg ccaagaagtc ggtggacaag aacagcaacg | 960 |
| agtaccgggt gcggcgcgag cgcaacaaca tcgcggtgcg caagagccgc gacaaggcca | 1020 |
| agcagcgcaa cgtggagacg cagcagaagg tgctggagct gaccagtgac aatgaccgcc | 1080 |
| tgcgcaagcg ggtggaacag ctgagccgcg aactggacac gctgcggggc atcttccgcc | 1140 |
| agctgccaga gagctccttg gtcaaggcca tgggcaactg cgcgtgaggc gcgcggctgt | 1200 |
| gggaccgccc tgggccagcc tccggcgggg acccaggag tggtttgggg tcgccggatc | 1260 |
| tcgaggcttg cccgagccgt gcgagccagg actaggagat tccggtgcct cctgaaagcc | 1320 |
| tggcctgctc cgcgtgtccc ctcccttcct ctgcgccgga cttggtgcgt ctaagatgag | 1380 |
| ggggccaggc ggtggcttct ccctgcgagg aggggagaat tcttggggct gagctgggag | 1440 |

```
cccggcaact ctagtattta ggataacctt gtgccttgga aatgcaaact caccgctcca    1500
atgcctactg agtaggggga gcaaatcgtg ccttgtcatt ttatttggag gtttcctgcc    1560
tccttcccga ggctacagca gacccccatg agagaaggag gggagcaggc ccgtggcagg    1620
aggagggctc agggagctga gatcccgaca agcccgccag ccccagccgc tcctccacgc    1680
ctgtccttag aaaggggtgg aaacataggg acttggggct tggaacctaa ggttgttccc    1740
ctagttctac atgaaggtgg agggtctcta gttccacgcc tctcccacct ccctccgcac    1800
acaccccacc ccagcctgct ataggctggg cttcccctTg gggcggaact cactgcgatg    1860
ggggtcacca ggtgaccagt gggagccccc accccgagtc acaccagaaa gctaggtcgt    1920
gggtcagctc tgaggatgta tacccctggt gggagaggga gacctagaga tctggctgtg    1980
gggcgggcat gggggggtgaa gggccactgg gaccctcagc cttgtttgta ctgtatgcct    2040
tcagcattgc ctaggaacac gaagcacgat cagtccatcc cagagggacc ggagttatga    2100
caagcttttcc aaatattttg ctttatcagc cgatatcaac acttgtatct ggcctctgtg    2160
ccccagcagt gccttgtgca atgtgaatgt gcgcgtctct gctaaaccac cattttattt    2220
ggttttTgtt ttgttttggt tttgctcgga tacttgccaa aatgagactc tccgtcggca    2280
gctgggggaa gggtctgaga ctcccttTcc ttttggtttt gggattactt ttgatcctgg    2340
gggaccaatg aggtgagggg ggttctcctt tgccctcagc tttccccagc ccctccggcc    2400
tgggctgccc acaaggcttg tccccagag gccctggctc ctggtcggga agggaggtgg    2460
cctcccgcca acgcatcact ggggctggga gcagggaagg acggcttggt tctcttcttt    2520
tgggagaac gtagagtctc actctagatg ttttatgtat tatatctata atataaacat    2580
atcaaagtca a                                                        2591

<210> SEQ ID NO 28
<211> LENGTH: 1837
<212> TYPE: DNA
<213> ORGANISM: Homo sapiens

<400> SEQUENCE: 28
gagccgcgca cgggactggg aaggggaccc acccgagggt ccagccacca gcccctcac     60
taatagcggc caccccggca gcggcggcag cagcagcagc gacgcagcgg cgacagctca    120
gagcagggag gccgcgccac ctgcgggccg gccgagcgg gcagcccag gccccctccc     180
cgggcacccg cgttcatgca acgcctggtg gcctgggacc cagcatgtct cccctgccg    240
ccgccgccgc ctgcctttaa atccatgaa gtggccaact tctactacga gcggactgc     300
ttggctgctg cgtacggcgg caaggcggcc cccgcggcgc ccccgcggc cagacccggg    360
ccgcgcccc ccgccggcga gctgggcagc atcggcgacc acgagcgcgc catcgacttc    420
agcccgtacc tggagccgct gggcgcgccg caggccccgg cgcccgccac ggccacggac    480
accttcgagg cggctccgcc cgcgcccgcc ccgcgcccg cctcctccgg gcagcaccac    540
gacttcctct ccgacctctt ctccgacgac tacgggggca agaactgcaa gaagccggcc    600
gagtacggct acgtgagcct ggggcgcctg ggggccgcca agggcgcgct gcaccccggc    660
tgcttcgcgc cctgcaccc accgccccg ccgccgccgc cgccgccga gctcaaggcg    720
gagccgggct tcgagcccgc ggactgcaag cggaaggagg aggccggggc gccgggcggc    780
ggcgcaggca tggcggcggg cttcccgtac gcgctgcgcg cttacctcgg ctaccagcg    840
gtgccgagcg gcagcagcgg gagcctctcc acgtcctcct cgtccagccc gccggcacg    900
```

| | |
|---|---|
| ccgagccccg ctgacgccaa ggcgcccccg accgcctgct acgcgggggc cgcgccggcg | 960 |
| ccctcgcagg tcaagagcaa ggccaagaag accgtggaca agcacagcga cgagtacaag | 1020 |
| atccggcgcg agcgcaacaa catcgccgtg cgcaagagcc gcgacaaggc caagatgcgc | 1080 |
| aacctggaga cgcagcacaa ggtcctggag ctcacggccg agaacgagcg gctgcagaag | 1140 |
| aaggtggagc agctgtcgcg cgagctcagc accctgcgga acttgttcaa gcagctgccc | 1200 |
| gagcccctgc tcgcctcctc cggccactgc tagcgcggcc cccgcgcgcg tcccctgcc | 1260 |
| ggccggggct gagactccgg ggagcgcccg cgcccgcgcc ctcgccccg ccccggcgg | 1320 |
| cgccggcaaa actttggcac tgggcacttt ggcagcgcgg ggagcccgtc ggtaattta | 1380 |
| atattttatt atatatatat atctatattt ttgtccaaac caaccgcaca tgcagatggg | 1440 |
| gctcccgccc gtggtgttat ttaaagaaga aacgtctatg tgtacagatg aatgataaac | 1500 |
| tctctgcttc tccctctgcc cctctccagg cgccggcggg cgggccggtt tcgaagttga | 1560 |
| tgcaatcggt ttaaacatgg ctgaacgcgt gtgtacacgg gactgacgca acccacgtgt | 1620 |
| aactgtcagc cgggccctga gtaatcgctt aaagatgttc ctacgggctt gttgctgttg | 1680 |
| atgttttgtt ttgtttttgtt ttttggtctt ttttgtatt ataaaaaata atctatttct | 1740 |
| atgagaaaag aggcgtctgt atattttggg aatcttttcc gtttcaagca ttaagaacac | 1800 |
| ttttaataaa cttttttttg agaatggtta caaagcc | 1837 |

<210> SEQ ID NO 29
<211> LENGTH: 1658
<212> TYPE: DNA
<213> ORGANISM: Homo sapiens

<400> SEQUENCE: 29

| | |
|---|---|
| cgcgcacacc tctcggtgca gattgcaaag cgccttccgt tgcgagagct gcagattttg | 60 |
| caagagccag gctcgcccac cttgtagaag gagcgccttg agtcccctct caccctcggt | 120 |
| tgcaaagagc cgaccgcttg atctggacac ccctcgccc agattgcatg atctcccggg | 180 |
| accctcttga gttgcacgtt tctgcaccga ggaccctcaaa tccccgtcgc tcctaggatt | 240 |
| tgcagcgttc tggatactgg agggttgcag gctacactcg cccgcccctg ggcagacact | 300 |
| cgtccaaacc actggagtgt gctggtgact ggcaggccag cccttcgcct ctccatgaac | 360 |
| ccgtgagcct gggggcaggt gccaggcgat ggcgcggcct gtgagcgaca ggaccccggc | 420 |
| ccctctgctg ctgggcggcc cggccgggac accccctggc gggggagcgc tgcttgggtt | 480 |
| gcggagccttt ctgcagggga ccagcaagcc caaagagccg gccagctgtc tcctgaagga | 540 |
| aaaggagcgc aaggcggccc tgcctgcagc cacaacccct gggccaggcc tggagactgc | 600 |
| gggcccggcg gatgccccgg ctggggcagt ggtgggcgga gggtcccgc gggggcgccc | 660 |
| ggggccggtg cccgccccgg gtctgttggc gccactgctg tgggagcgca cgctgccgtt | 720 |
| cggcgatgtg gagtacgtag acctggacgc cttcctgctg gagcacgggc tcccgcccag | 780 |
| cccgccgccc cccggtggcc cgtcgccgga ccgtcgcccc gcgcggacgc ccgcacccct | 840 |
| cccagggccg ggttcgtgcg gctcggcttc ccccgctcc tctcctgggc acgccccgc | 900 |
| ccgggctgcc ctcgggaccg ccagcggcca ccgcgcaggc ctgacctctc gggacacacc | 960 |
| cagccctgtg gacccagaca ccgtggaggt gttgatgacc tttgaacccg acccagctga | 1020 |
| tcttgcccta tcaagcattc ctggccacga gacctttgac cctcgaagac atcgcttctc | 1080 |
| agaagaggaa cttaagcccc agccaatcat gaagaaggca agaaaaatcc aggtgccgga | 1140 |
| ggagcagaag gatgagaaat actggagccg gcggtacaag aacaacgagg cagccaagcg | 1200 |

| | |
|---|---|
| gtcccgtgac gcccggcggc tcaaggagaa ccagatatcg gtgcgggcgg ccttcctgga | 1260 |
| gaaggagaac gccctgctgc ggcaggaagt tgtggccgtg cgccaggagc tgtcccacta | 1320 |
| ccgcgccgtg ctgtcccgat accaggccca gcacggggcc ctgtgaggct gccccacatc | 1380 |
| cccacctggc ggagctctcc tccgccttgc tgagacttac gccctgttcc cttcctgccc | 1440 |
| tgtggcccac gggccggcca gctgggtgcc ccagggacgt gataatgcag ataaatacat | 1500 |
| ttatattttt aagaaaaagc gagcctcccc cctcccttgc gggggcgggg agggttctct | 1560 |
| gtgtgtgtcc ccggcacgtc agggacccta tcctcccacc gcctccgtta acacgatcct | 1620 |
| gaataaatct tgagaacccc agaaaaaaaa aaaaaaaa | 1658 |

<210> SEQ ID NO 30
<211> LENGTH: 3317
<212> TYPE: DNA
<213> ORGANISM: Homo sapiens

<400> SEQUENCE: 30

| | |
|---|---|
| gttgggaaac agcccagtgg tataaggatg aggaaactga agcccagaga ggtgaagtga | 60 |
| ggtgcccaag gccacacagc aagttagagg cacagctagt acggtagctc aagtctcctg | 120 |
| actcccagtc cagtgctcct cccattactc cacgagtcct gtctctaagc ttcctgacaa | 180 |
| atgctagaac ggaagaaacc caagacagct gaaaaccaga aggcatctga ggagaatgag | 240 |
| attactcagc cgggtggatc cagcgccaag ccgggccttc cctgcctgaa ctttgaagct | 300 |
| gttttgtctc cagacccagc cctcatccac tcaacacatt cactgacaaa ctctcacgct | 360 |
| cacaccgggt catctgattg tgacatcagt tgcaagggga tgaccgagcg cattcacagc | 420 |
| atcaaccttc acaacttcag caattccgtg ctcgagaccc tcaacgagca gcgcaaccgt | 480 |
| ggccacttct gtgacgtaac ggtgcgcatc cacgggagca tgctgcgcgc acaccgctgc | 540 |
| gtgctggcag ccggcagccc cttcttccag gacaaactgc tgcttggcta cagcgacatc | 600 |
| gagatcccgt cggtggtgtc agtgcagtca gtgcaaaagc tcattgactt catgtacagc | 660 |
| ggcgtgctac gggtctcgca gtcggaagct ctgcagatcc tcacggccgc cagcatcctg | 720 |
| cagatcaaaa cagtcatcga cgagtgcacg cgcatcgtgt cacagaacgt gggcgatgtg | 780 |
| ttcccgggga tccaggactc gggccaggac acgccgcggg gcactcccga gtcaggcacg | 840 |
| tcaggccaga gcagcgacac ggagtcgggc tacctgcaga gccacccaca gcacagcgtg | 900 |
| gacaggatct actcggcact ctacgcgtgc tccatgcaga atggcagcgg cgagcgctct | 960 |
| ttttacagcg gcgcagtggt cagccaccac gagactgcgc tcggcctgcc ccgcgaccac | 1020 |
| cacatggaag accccagctg gatcacacgc atccatgagc gctcgcagca gatggagcgc | 1080 |
| tacctgtcca ccaccccga gaccacgcac tgccgcaagc agcccggcc tgtgcgcatc | 1140 |
| cagaccctag tgggcaacat ccacatcaag caggagatgg aggacgatta cgactactac | 1200 |
| gggcagcaaa gggtgcagat cctggaacgc aacgaatccg aggagtgcac ggaagacaca | 1260 |
| gaccaggccg agggcaccga gagtgagccc aaaggtgaaa gcttcgactc gggcgtcagc | 1320 |
| tcctccatag gcaccgagcc tgactcggtg gagcagcagt ttgggcctgg ggcggcgcgg | 1380 |
| gacagccagg ctgaacccac ccaacccgag caggctgcag aagcccccgc tgagggtggt | 1440 |
| ccgcagacaa accagctaga aacaggtgct tcctctccgg agagaagcaa tgaagtggag | 1500 |
| atggacagca ctgttatcac tgtcagcaac agctccgaca gagcgtcct acaacagcct | 1560 |
| tcggtcaaca cgtccatcgg gcagccattg ccaagtaccc agctctactt acgccagaca | 1620 |

```
gaaaccctca ccagcaacct gaggatgcct ctgaccttga ccagcaacac gcaggtcatt    1680
ggcacagctg gcaacaccta cctgccagcc ctcttcacta cccagcccgc gggcagtggc    1740
cccaagcctt tcctcttcag cctgccacag cccctggcag gccagcagac ccagtttgtg    1800
acagtgtccc agcccggtct gtcgaccttt actgcacagc tgccagcgcc acagcccctg    1860
gcctcatccg caggccacag cacagccagt gggcaaggcg aaaaaaagcc ttatgagtgc    1920
actctctgca acaagacttt caccgccaaa cagaactacg tcaagcacat gttcgtacac    1980
acaggtgaga agccccacca atgcagcatc tgttggcgct ccttctcctt aaaggattac    2040
cttatcaagc acatggtgac acacacagga gtgagggcat accagtgtag tatctgcaac    2100
aagcgcttca cccagaagag ctccctcaac gtgcacatgc gcctccaccg gggagagaag    2160
tcctacgagt gctacatctg caaaaagaag ttctctcaca agaccctcct ggagcgacac    2220
gtggccctgc acagtgccag caatgggacc cccctgcag gcacacccc aggtgcccgc     2280 gctggccccc caggcgtggt ggcctgcacg gaggggacca cttacgtctg ctccgtctgc    2340
ccagcaaagt ttgaccaaat cgagcagttc aacgaccaca tgaggatgca tgtgtctgac    2400
ggataagtag tatcttttctc tctttcttat gaacaaaaca aaacaacaac aaaaaacaaa    2460
caaacaaaaa agctatggca ctagaattta agaaatgttt tggtttcatt tttacttttct   2520 gttttttgttt ttgtttcgtt tcattttgta ctacatgaag aactgttttt tgcctgctgg    2580
tacattacat ttccggaggc ttgggtgaat aatagttttc ccagtctccc tcggatggtg    2640
gccttaaggc ctggtagtgc ttcaagaggt ccactggttg gatctctagc tactggcctc    2700
taaatacaac ccttctttac aaaaaaatct tttaaaaaaa agtaaaaaaa aaaaaaaat     2760 ttccacttgt gaagagcact acaaaaaata tataacaaaa tctaaaaggc ctactgtctt    2820
taagtacacc gcttgcagtg tttcagtgga cattttcaca attctggccg cttggacttc    2880
acagtaacca gttaaaactg tggaatatca cttctggttg aaaacccaga ggaaaggccc    2940
tgctgttttc cacctaccac gttgtctgat ttcataaaag ggctgtgggg gtgggaaggg    3000
cagtgggttc ggtggtgtgg gaaagaaaga cgaatggcag gcttcttccc cagattctgc    3060
ccgggtccac acaccctggc ccaccttctc catatccccc tcttgcagca gaagccagga    3120
agacttggac aagcaacaag caacagtggc tatcgtattt attcagtgtc ttcgctgagc    3180
cacagcctca gcacaatcaa gagggacttt catgaaaggc aggaatgcag ataaaacaaa    3240
gatatcagaa atttgcacct atgtttctag gtacaagaga aggattattt ccaacaatct    3300
ttgcaaaaaa aaaaaaa                                                    3317

<210> SEQ ID NO 31
<211> LENGTH: 3779
<212> TYPE: DNA
<213> ORGANISM: Homo sapiens

<400> SEQUENCE: 31
gcactgccag gacttaccgt acaacactcc ttggcttctg gaattttatc tctgctcaca      60
gtctacatta caacattagt tcattctggg cactttagct tccttgaatc tccagttgat     120
ctcacaccca tgcctatgat attcttctcc tggttaatca agaattctct atttctgctc     180
cgtcatccat gccactacaa ataaaaagaa gtgttaagaa ttgcctttgg gactctgaag     240
gctgaagaat tgatgaattg caagtttgtg ccccatagct gcacagccta tgtctaagca    300
cagctcatct tcacaaactg aagtggatct tgatttctgg aaatgtccaa ataatgacaa    360
caaccccatg gaggtggata catcagagtc agctggaggt ggtcagaatt atttgcaatg    420
```

```
tttgggaaag cacctaccaa ggcttcctat tacctatttc acagaatgtt tcatcattac    480
taacaggata ttcctcatga cattgctgtc tgatctttga ccatcagtct gtgacctgcc    540
ccttctcttt acatgcagcc gctctctgct ccctgcccca atgaacatct gcactaggcc    600
caagccttgg agtaatttac ctgaagagtg acaccattga ttttgaaact actgaagaaa    660
cccaagacag ctgaaaacca gaaggcatct gaggagaatg agattactca gccgggtgga    720
tccagcgcca agccgggcct tccctgcctg aactttgaag ctgttttgtc tccagaccca    780
gccctcatcc actcaacaca ttcactgaca aactctcacg ctcacaccgg gtcatctgat    840
tgtgacatca gttgcaaggg gatgaccgag cgcattcaca gcatcaacct tcacaacttc    900
agcaattccg tgctcgagac cctcaacgag cagcgcaacc gtggccactt ctgtgacgta    960
acggtgcgca tccacgggag catgctgcgc gcacaccgct gcgtgctggc agccggcagc   1020
cccttcttcc aggacaaact gctgcttggc tacagcgaca tcgagatccc gtcggtggtg   1080
tcagtgcagt cagtgcaaaa gctcattgac ttcatgtaca gcggcgtgct acgggtctcg   1140
cagtcggaag ctctgcagat cctcacggcc gccagcatcc tgcagatcaa acagtcatc    1200
gacgagtgca cgcgcatcgt gtcacagaac gtgggcgatg tgttcccggg gatccaggac   1260
tcgggccagg acacgccgcg gggcactccc gagtcaggca cgtcaggcca gagcagcgac   1320
acggagtcgg gctacctgca gagccaccca cagcacagcg tggacaggat ctactcggca   1380
ctctacgcgt gctccatgca gaatggcagc ggcgagcgct cttttttacag cggcgcagtg   1440
gtcagccacc acgagactgc gctcggcctg ccccgcgacc accacatgga agaccccagc   1500
tggatcacac gcatccatga gcgctcgcag cagatggagc gctacctgtc caccaccccc   1560
gagaccacgc actgccgcaa gcagcccgg cctgtgcgca tccagaccct agtgggcaac    1620
atccacatca agcaggagat ggaggacgat tacgactact acgggcagca aagggtgcag   1680
atcctggaac gcaacgaatc cgaggagtgc acggaagaca cagaccaggc cgagggcacc   1740
gagagtgagc ccaaaggtga aagcttcgac tcgggcgtca gctcctccat aggcaccgag   1800
cctgactcgg tggagcagca gtttgggcct ggggcggcgc gggacagcca ggctgaaccc   1860
acccaaccccg agcaggctgc agaagccccc gctgagggtg gtccgcagac aaaccagcta   1920
gaaacaggtg cttcctctcc ggagagaagc aatgaagtgg agatggacag cactgttatc   1980
actgtcagca cagctccga caagagcgtc ctacaacagc cttcggtcaa cacgtccatc   2040
gggcagccat tgccaagtac ccagctctac ttacgccaga cagaaaccct caccagcaac   2100
ctgaggatgc ctctgacctt gaccagcaac acgcaggtca ttggcacagc tggcaacacc   2160
tacctgccag ccctcttcac tacccagccc gcgggcagtg gccccaagcc tttcctcttc   2220
agcctgccac agccctgggc aggcagcag acccagtttg tgacagtgtc ccagcccggt   2280
ctgtcgacct ttactgcaca gctgccagcg ccacagcccc tggcctcatc cgcaggccac   2340
agcacagcca gtgggcaagg cgaaaaaaag ccttatgagt gcactctctg caacaagact   2400
ttcaccgcca aacagaacta cgtcaagcac atgttcgtac acacaggtga aagcccccac   2460
caatgcagca tctgttggcg ctccttctcc ttaaaggatt accttatcaa gcacatggtg   2520
acacacacag gagtgagggc ataccagtgt agtatctgca acaagcgctt cacccagaag   2580
agctccctca acgtgcacat gcgcctccac cggggagaga agtcctacga gtgctacatc   2640
tgcaaaaaga gttctctcta caagaccctc ctggagcgac acgtggccct gcacagtgcc   2700
agcaatggga cccccctgc aggcacaccc ccaggtgccc gcgctggccc cccaggcgtg   2760
```

-continued

```
gtggcctgca cggaggggac cacttacgtc tgctccgtct gcccagcaaa gtttgaccaa    2820
atcgagcagt tcaacgacca catgaggatg catgtgtctg acggataagt agtatctttc    2880
tctctttctt atgaacaaaa caaaacaaca acaaaaaaca aacaaacaaa aaagctatgg    2940
cactagaatt taagaaatgt tttggtttca ttttttacttt ctgttttttgt ttttgtttcg    3000 tttcattttg tactacatga agaactgttt tttgcctgct ggtacattac atttccggag    3060
gcttgggtga ataatagttt tcccagtctc cctcggatgg tggccttaag gcctggtagt    3120
gcttcaagag gtccactggt tggatctcta gctactggcc tctaaataca acccttcttt    3180
acaaaaaaat cttttaaaaa aaagtaaaaa aaaaaaaaaa atttccactt gtgaagagca    3240
ctacaaaaaa tatataacaa atctaaaag gcctactgtc tttaagtaca ccgcttgcag    3300
tgtttcagtg gacattttca caattctggc cgcttggact tcacagtaac cagttaaaac    3360
tgtggaatat cacttctggt tgaaaaccca gaggaaaggc cctgctgttt tccacctacc    3420
acgttgtctg atttcataaa agggctgtgg gggtgggaag ggcagtgggt tcggtggtgt    3480
gggaaagaaa gacgaatggc aggcttcttc cccagattct gcccgggtcc acacaccctg    3540
gcccaccttc tccatatccc cctcttgcag cagaagccag gaagacttgg acaagcaaca    3600
agcaacagtg gctatcgtat ttattcagtg tcttcgctga gccacagcct cagcacaatc    3660
aagagggact ttcatgaaag gcaggaatgc agataaaaca aagatatcag aaatttgcac    3720
ctatgtttct aggtacaaga gaaggattat ttccaacaat ctttgcaaaa aaaaaaaaa    3779
```

<210> SEQ ID NO 32
<211> LENGTH: 4446
<212> TYPE: DNA
<213> ORGANISM: Homo sapiens

<400> SEQUENCE: 32

```
ttcttaaccc tttccagctt tcccaccctc tttggcttta gccatggcct tctgatctgt      60
gtttctcagg ggacctgcag gccccagata tagccccatg ctgtcctcct acccccagagc    120 acactgttca ggctacttcc actggtactg aaatccagta tttcacttac tcttttttctt    180 tccaatatcc tcatgacatt caatatttca cttactctag gtcctccctg cctaaggccc    240
aagtcaactt tctgtccagt gggatttgta atccaatacc tcctagccct agcagaatcc    300
catgtggata tcagaaatg tgactggaaa aaggacagag ctctatggct gtgggtccca    360
gtccccactg ctggcagtaa gtccccagca gtgagctgtg taagcacctt acattctgcg    420
cttggttgaa aacagcaagg caagcatcca cttgagaaat gtcaacccct aggaaatccc    480
agcctcaagt ctttctcatc ccttgggaag tgcaaattgg atagagaaga aaccaattaa    540
aaacaaaaca acaaatcat acttagatat tctggctttt ctcaccaggg ctggattaaa    600
gcatgtactt caaaataata acaacttaag tcaataaata aatgtaagga agtccaaatg    660
ttcacctgaa gacaactgtg gtcattttt ggcaatccca ggttctcttt tctacctgtt    720
tgctcaatcg tggtctccct ctccctctct tgttgggggcc catgccctg ctttactgtt    780 gccagaggct tgtacttgtt tgccttttag gtaggagcag ttacttccac tcccctcacc    840
tgccataaag catctttata aacaaagcaa gtagaagaaa cacatcctgg tatccaccac    900
attcggcttt tgttgattct gttcacttgg gagcacctgc tgctagggaa taagaaggtt    960
gaggctgaag agtgaggact cttcagctcc cctctggcag gacccgggag aggaaagagc   1020
cctcagctgg tccatcctcc ccactcctgg tcagccttct gttctgagat caaagtggtg   1080
gggtcacatt ctcgagaact gtgctcagcc ccctcatctc acacccttc cctctccctg    1140
```

```
tgtgcctgcc cccctcttac ataaccatgc tggtgattgg caccgtcata aatcaatact    1200
ttgctcactt tcacatcaag taacactatc cagggaggtg gtttcaacaa aggaggaagt    1260
ataaggagat ctaggttcaa attaatgttg ccctagtgg taaaggacag agaccctcag     1320
actgatgaaa tgcactcaga attacttaga caaagcggat atttgccact ctcttcccct    1380
tttcctgtgt ttttgtagtg aagagacctg aaagaaaaaa gtagggagaa cataatgaga    1440
acaaatacgg taatctcttc atttgctagt tcaagtgctg gacttgggac ttaggagggg    1500
caatggagcc gcttagtgcc tacatctgac ttggactgaa ataggtga gagacaagat      1560 tgtctcatat ccggggaaat cataacctat gactaggacg ggaagaggaa gcactgcctt    1620
tacttcagtg ggaatctcgg cctcagcctg caagccaagt gttcacagtg agaaaagcaa    1680
gagaataagc taatactcct gtcctgaaca aggcagcggc tccttggtaa agctactcct    1740
tgatcgatcc tttgcaccgg attgttcaaa gtggacccca ggggagaagt cggagcaaag    1800
aacttaccac caagcagtcc aagaggccca gaagcaaacc tggaggtgag acccaaagaa    1860
agctggaacc atgctgactt tgtacactgt gaggacacag agtctgttcc tggaaagccc    1920
agtgtcaacg cagatgagga agtcggaggt ccccaaatct gccgtgtatg tggggacaag    1980
gccactggct atcacttcaa tgtcatgaca tgtgaaggat gcaagggctt tttcaggagg    2040
gccatgaaac gcaacgcccg gctgaggtgc cccttccgga agggcgcctg cgagatcacc    2100
cggaagaccc ggcgacagtg ccaggcctgc cgcctgcgca agtgcctgga gagcggcatg    2160
aagaaggaga tgatcatgtc cgacgaggcc gtggaggaga gcggccctt gatcaagcgg     2220 aagaaaagtg aacggacagg gactcagcca ctgggagtgc aggggctgac agaggagcag    2280
cggatgatga tcagggagct gatggacgct cagatgaaaa cctttgacac taccttctcc    2340
catttcaaga atttccggct gccaggggtg cttagcagtg gctgcgagtt gccagagtct    2400
ctgcaggccc catcgaggga agaagctgcc aagtggagcc aggtccggaa agatctgtgc    2460
tctttgaagg tctctctgca gctgcggggg gaggatggca gtgtctggaa ctacaaaccc    2520
ccagccgaca gtggcgggaa agagatcttc tccctgctgc cccacatggc tgacatgtca    2580
acctacatgt tcaaaggcat catcagcttt gccaaagtca tctcctactt cagggacttg    2640
cccatcgagg accagatctc cctgctgaag ggggccgctt tcgagctgtg tcaactgaga    2700
ttcaacacag tgttcaacgc ggagactgga acctgggagt gtggccggct gtcctactgc    2760
ttggaagaca ctgcaggtgg cttccagcaa cttctactgg agcccatgct gaaattccac    2820
tacatgctga agaagctgca gctgcatgag gaggagtatg tgctgatgca ggccatctcc    2880
ctcttctccc cagaccgccc aggtgtgctg cagcaccgcg tggtggacca gctgcaggag    2940
caattcgcca ttactctgaa gtcctacatt gaatgcaatc ggccccagcc tgctcatagg    3000
ttcttgttcc tgaagatcat ggctatgctc accgagctcc gcagcatcaa tgctcagcac    3060
acccagcggc tgctgcgcat ccaggacata cccccctttg ctacgcccct catgcaggag    3120
ttgttcggca tcacaggtag ctgagcggct gcccttgggt gacacctccg agaggcagcc    3180
agacccagag ccctctgagc cgccactccc gggccaagac agatggacac tgccaagagc    3240
cgacaatgcc ctgctggcct gtctcccag ggaattcctg ctatgacagc tggctagcat     3300
tcctcaggaa ggacatgggt gcccccacc cccagttcag tctgtaggga gtgaagccac      3360
agactcttac gtggagagtg cactgacctg taggtcagga ccatcagaga ggcaaggttg    3420 cccttcctt ttaaaaggcc ctgtggtctg gggagaaatc cctcagatcc cactaaagtg     3480
```

| | |
|---|---|
| tcaaggtgtg gaagggacca agcgaccaag gatgggccat ctggggtcta tgcccacata | 3540 |
| cccacgtttg ttcgcttcct gagtcttttc attgctacct ctaatagtcc tgtctcccac | 3600 |
| ttcccactcg ttccctcct cttccgagct gctttgtggg ctccaggcct gtactcatcg | 3660 |
| gcaggcgcat gagtatctgt gggagtcctc tagagagatg agaagccagg aggcctgcac | 3720 |
| caaatgtcag aagcttggca tgacctcatt ccggccacat cattctgtgt ctctgcatcc | 3780 |
| atttgaacac attattaagc accgataata ggtagcctgc tgtggggtat acagcattga | 3840 |
| ctcagatata gatcctgagc tcacagagtt tatagttaaa aaacaaaca gaaacacaaa | 3900 |
| caatttggat caaaggaga atgataagt gacaaaagca gcacaaggaa tttccctgtg | 3960 |
| tggatgctga gctgtgatgg cgggcactgg gtacccaagt gaaggttccc gaggacatga | 4020 |
| gtctgtagga gcaagggcac aaactgcagc tgtgagtgcg tgtgtgtgat ttggtgtagg | 4080 |
| taggtctgtt tgccacttga tggggcctgg gtttgttcct ggggctggaa tgctgggtat | 4140 |
| gctctgtgac aaggctacgc tgacaatcag ttaaacacac cggagaagaa ccatttacat | 4200 |
| gcaccttata tttctgtgta cacatctatt ctcaaagcta aagggtatga aagtgcctgc | 4260 |
| cttgtttata gccacttgtg agtaaaaatt tttttgcatt ttcacaaatt atactttata | 4320 |
| taaggcattc cacacctaag aactagtttt gggaaatgta gccctgggtt taatgtcaaa | 4380 |
| tcaaggcaaa aggaattaaa taatgtactt ttggctaaaa aaaaaaaaaa aaaaaaaaa | 4440 |
| aaaaaa | 4446 |

<210> SEQ ID NO 33
<211> LENGTH: 2772
<212> TYPE: DNA
<213> ORGANISM: Homo sapiens

<400> SEQUENCE: 33

| | |
|---|---|
| ggcctgctgg gttagtgctg gcagccccct gaggccaagg acagcagcat gacagtcacc | 60 |
| aggactcacc acttcaagga ggggtccctc agagcacctg ccatacccct gcacagtgct | 120 |
| gcggctgagt tggcttcaaa ccatccaaga ggcccagaag caaacctgga ggtgagaccc | 180 |
| aaagaaagct ggaaccatgc tgactttgta cactgtgagg acacagagtc tgttcctgga | 240 |
| aagcccagtg tcaacgcaga tgaggaagtc ggaggtcccc aaatctgccg tgtatgtggg | 300 |
| gacaaggcca ctggctatca cttcaatgtc atgacatgtg aaggatgcaa gggctttttc | 360 |
| aggagggcca tgaaacgcaa cgcccggctg aggtgcccct tccggaaggg cgcctgcgag | 420 |
| atcacccgga agaccggcg acagtgccag gcctgccgcc tgcgcaagtg cctggagagc | 480 |
| ggcatgaaga aggagatgat catgtccgac gaggccgtgg aggagaggcg ggccttgatc | 540 |
| aagcggaaga aaagtgaacg gacagggact cagccactgg gagtgcaggg gctgacagag | 600 |
| gagcagcgga tgatgatcag ggagctgatg gacgctcaga tgaaaacctt tgacactacc | 660 |
| ttctcccatt tcaagaattt ccggctgcca ggggtgctta gcagtggctg cgagttgcca | 720 |
| gagtctctgc aggccccatc gagggaagaa gctgccaagt ggagccaggt ccggaaagat | 780 |
| ctgtgctctt tgaaggtctc tctgcagctg cgggggagg atggcagtgt ctggaactac | 840 |
| aaacccccag ccgacagtgg cgggaaagag atcttctccc tgctgcccca catggctgac | 900 |
| atgtcaacct acatgttcaa aggcatcatc agctttgcca aagtcatctc ctacttcagg | 960 |
| gacttgccca tcgaggacca gatctccctg ctgaaggggg ccgctttcga gctgtgtcaa | 1020 |
| ctgagattca acacagtgtt caacgcggag actggaacct gggagtgtgg ccggctgtcc | 1080 |
| tactgcttgg aagacactgc aggtggcttc cagcaacttc tactggagcc catgctgaaa | 1140 |

| | | | | | |
|---|---|---|---|---|---|
| ttccactaca | tgctgaagaa | gctgcagctg | catgaggagg | agtatgtgct | gatgcaggcc | 1200 |
| atctccctct | tctccccaga | ccgcccaggt | gtgctgcagc | accgcgtggt | ggaccagctg | 1260 |
| caggagcaat | tcgccattac | tctgaagtcc | tacattgaat | gcaatcggcc | ccagcctgct | 1320 |
| cataggttct | tgttcctgaa | gatcatggct | atgctcaccg | agctccgcag | catcaatgct | 1380 |
| cagcacaccc | agcggctgct | gcgcatccag | gacatacacc | cctttgctac | gcccctcatg | 1440 |
| caggagttgt | tcggcatcac | aggtagctga | gcggctgccc | ttgggtgaca | cctccgagag | 1500 |
| gcagccagac | ccagagccct | ctgagccgcc | actcccgggc | caagacagat | ggacactgcc | 1560 |
| aagagccgac | aatgccctgc | tggcctgtct | ccctagggaa | ttcctgctat | gacagctggc | 1620 |
| tagcattcct | caggaaggac | atgggtgccc | ccaccccca | gttcagtctg | tagggagtga | 1680 |
| agccacagac | tcttacgtgg | agagtgcact | gacctgtagg | tcaggaccat | cagagaggca | 1740 |
| aggttgccct | ttccttttaa | aaggccctgt | ggtctgggga | gaaatccctc | agatcccact | 1800 |
| aaagtgtcaa | ggtgtggaag | ggaccaagcg | accaaggatg | ggccatctgg | ggtctatgcc | 1860 |
| cacatacccα | cgtttgttcg | cttcctgagt | cttttcattg | ctacctctaa | tagtcctgtc | 1920 |
| tcccacttcc | cactcgttcc | cctcctcttc | cgagctgctt | tgtgggctcc | aggcctgtac | 1980 |
| tcatcggcag | gcgcatgagt | atctgtggga | gtcctctaga | gagatgagaa | gccaggaggc | 2040 |
| ctgcaccaaa | tgtcagaagc | ttggcatgac | ctcattccgg | ccacatcatt | ctgtgtctct | 2100 |
| gcatccattt | gaacacatta | ttaagcaccg | ataataggta | gcctgctgtg | gggtatacag | 2160 |
| cattgactca | gatatagatc | ctgagctcac | agagtttata | gttaaaaaaa | caaacagaaa | 2220 |
| cacaaacaat | ttggatcaaa | aggagaaatg | ataagtgaca | aaagcagcac | aaggaatttc | 2280 |
| cctgtgtgga | tgctgagctg | tgatggcggg | cactgggtac | ccaagtgaag | gttcccgagg | 2340 |
| acatgagtct | gtaggagcaa | gggcacaaac | tgcagctgtg | agtgcgtgtg | tgtgatttgg | 2400 |
| tgtaggtagg | tctgttttgcc | acttgatggg | gcctgggttt | gttcctgggg | ctggaatgct | 2460 |
| gggtatgctc | tgtgacaagg | ctacgctgac | aatcagttaa | acacaccgga | gaagaaccat | 2520 |
| ttacatgcac | cttatatttc | tgtgtacaca | tctattctca | aagctaaagg | gtatgaaagt | 2580 |
| gcctgccttg | tttatagcca | cttgtgagta | aaaattttt | tgcattttca | caaattatac | 2640 |
| tttatataag | gcattccaca | cctaagaact | agttttggga | aatgtagccc | tgggtttaat | 2700 |
| gtcaaatcaa | ggcaaaagga | attaaataat | gtacttttgg | ctaaaaaaa | aaaaaaaaa | 2760 |
| aaaaaaaaaa | aa | | | | | 2772 |

<210> SEQ ID NO 34
<211> LENGTH: 2213
<212> TYPE: DNA
<213> ORGANISM: Homo sapiens

<400> SEQUENCE: 34

| | | | | | |
|---|---|---|---|---|---|
| actctctcct | cctcctcacc | tcattgtctc | cccgacttat | cctaatgcga | aattggattc | 60 |
| tgagcatttg | tagcaaaatc | gctgggatct | ggagaggaag | actcagtcca | gaatcctccc | 120 |
| agggccttga | aagtccatct | ctgacccaaa | acaatccaag | gaggtagaag | acatcgtaga | 180 |
| aggagtgaaa | gaagaaaaga | agacttagaa | acatagctca | aagtgaacac | tgcttctctt | 240 |
| agtttcctgg | atttcttctg | gacatttcct | caagatgaaa | cttcagacac | tttggagttt | 300 |
| tttttgaaga | ccaccataaa | gaaagtgcat | tcaattgaa | aaatttggat | gggatcaaaa | 360 |
| atgaatctca | ttgaacattc | ccatttacct | accacagatg | aattttcttt | ttctgaaaat | 420 |

```
ttatttggtg ttttaacaga acaagtggca ggtcctctgg gacagaacct ggaagtggaa      480
ccatactcgc aatacagcaa tgttcagttt ccccaagttc aaccacagat tcctcgtca       540 tcctattatt ccaacctggg tttctacccc cagcagcctg aagagtggta ctctcctgga     600
atatatgaac tcaggcgtat gccagctgag actctctacc agggagaaac tgaggtagca      660
gagatgcctg taacaaagaa gccccgcatg ggcgcgtcag cagggaggat caaagggat       720 gagctgtgtg ttgtttgtgg agacagagcc tctggatacc actataatgc actgacctgt      780
gaggggtgta aaggtttctt caggagaagc attaccaaaa acgctgtgta caagtgtaaa      840
aacgggggca actgtgtgat ggatatgtac atgcgaagaa gtgtcaaga gtgtcgacta       900 aggaaatgca aagagatggg aatgttggct gaatgcttgt taactgaaat tcagtgtaaa      960
tctaagcgac tgagaaaaaa tgtgaagcag catgcagatc agaccgtgaa tgaagacagt     1020
gaaggtcgtg acttgcgaca agtgacctcg acaacaaagt catgcaggga gaaaactgaa     1080
ctcaccccag atcaacagac tcttctacat tttattatgg attcatataa caaacagagg     1140
atgcctcagg aaataacaaa taaaatttta aagaagaat tcagtgcaga agaaaatttt     1200
ctcattttga cggaaatggc aaccaatcat gtacaggttc ttgtagaatt cacaaaaaag    1260
ctaccaggat ttcagacttt ggaccatgaa gaccagattg ctttgctgaa agggtctgcg     1320
gttgaagcta tgttccttcg ttcagctgag atttcaata agaaacttcc gtctgggcat     1380
tctgacctat tggaagaaag aattcgaaat agtggtatct ctgatgaata tataacacct     1440
atgtttagtt tttataaaag tattggggaa ctgaaaatga ctcaagagga gtatgctctg     1500
cttacagcaa ttgttatcct gtctccagat agacaataca taaggatag agaggcagta     1560 gagaagcttc aggagccact tcttgatgtg ctacaaaagt tgtgtaagat tcaccagcct     1620
gaaaatcctc aacactttgc ctgtctcctg ggtcgcctga ctgaattacg gacattcaat     1680
catcaccacg ctgagatgct gatgtcatgg agagtaaacg accacaagtt taccccactt     1740
ctctgtgaaa tctgggacgt gcagtgatgg ggattacagg ggaggggtct agctccttt     1800 tctctctcat attaatctga tgtataactt tcctttattt cacttgtacc cagtttcact     1860
caagaaatct tgatgaatat ttatgttgta attcatgtg taacttccac aactgtaaat     1920
attgggctag atagaacaac tttctctaca ttgtgtttta aaaggctcca gggaatcctg     1980
cattctaatt ggcaagccct gttttgcctaa ttaaattgat tgttacttca attctatctg    2040
ttgaactagg gaaaatctca ttttgctcat cttaccatat tgcatatatt ttattaaaga     2100
gttgtattca atcttggcaa taaagcaaac ataatggcaa cagaaaaaa aaaaaaaaa      2160 aaaaaaaaa aaaaaaaaa aaaaaaaaa aaaaaaaaa aaaaaaaaaa aaa                2213
```

<210> SEQ ID NO 35
<211> LENGTH: 2293
<212> TYPE: DNA
<213> ORGANISM: Homo sapiens

<400> SEQUENCE: 35

```
atttgggaga gtgctgtgac tcatgctgga ctctaaccca cgagggtttc tcagagtcag      60
cagctggggg atgaagaagt gaaaagtgac tggcaggaaa ttctgcaagc aaggaagggg    120
aaagagaaat gaactggtgc aggtctgcgg gaagagaatg aggctggatc ctcaaaatca     180
caggaggaag caggcccaga cctcagaggc agaagagaa agaaaccaga gcttagagtc      240
aggaggagga aaccagaccc cggagccaca aggagaggc tggatccccg gctcagaggg     300
aagagtgtcg ccgcctctgc ctgcgtagcc ccggccatgg ctctgtagcc tcgaccccctt    360
```

```
tgtgccccg gccgtctcc gcgctcacca cgcctgcgct ctccgctccc accttctttc      420
ttcagccgag gccgccgccg cctctccttg ctgcagccat ggagtcttcc actttcgcct      480
tggtgcctgt cttcgcccac ctgagcatcc tccagagcct cgtgccagct gctggtgcag      540
cctctcctgt tgccatcagt gcccagcacc tgtgctacag ccatgtcact cctggcgacc      600
ctggggctgg agctggacag ggccctgctc ccagctagtg ggctgggatg gctcgtagac      660
tatgggaaac tcccccggc ccctgccccc tggctccct atgaggtcct tggggagcc       720 ctggagggcg gcttccagt gggggagag ccctggcag gtgatggctt ctctgactgg       780
atgactgagc gagttgattt cacagctctc ctccctctgg agcctccctt accccccggc      840
accctccccc aaccttcccc aaccccacct gacctggaag ctatggcctc cctcctcaag      900
aaggagctgg aacagatgga agacttcttc ctagatgccc cgcccctccc accacccc       960 ccgccgccac taccaccacc accactacca ccagcccct ccctcccct gtccctcccc      1020 tcctttgacc tcccccagcc ccctgtcttg gatactctgg acttgctggc catctactgc     1080
cgcaacgagg ccgggcagga ggaagtgggg atgccgcctc tgcccccgcc acagcagccc     1140
cctcctcctt ctccacctca accttctcgc ctggcccct acccacatcc tgccaccacc     1200
cgaggggacc gcaagcaaaa gaagagagac cagaacaagt cggcggctct gaggtaccgc     1260
cagcggaagc gggcagaggg tgaggccctg gaggcgagt gccaggggct ggaggcacgg     1320
aatcgcgagc tgaaggaacg ggcagagtcc gtggagcgcg agatccagta cgtcaaggac     1380
ctgctcatcg aggtttacaa ggcccggagc cagaggaccc gtagctgcta gaagggcagg     1440
ggtgtggctt ctgggggctg gtcttcagct ctggcgcctt catccccctg cctctacctt     1500
cattccaaac ccctctcggc cgggtgcagt ggcttatgct tgtaatccca gcactttggg     1560
aggccaaggc aggaggatcg tttgaggcca ggaggtcaat accagcctgg gcaacatagt     1620
aagaccctgt ctctattaaa aaaaaaaat caacccttct tccccaccaa accacccaac     1680
tcctctctac tcttatcctt ttatcctctg tctctgctta tcacctctct tgcgtatttc     1740
tggatctcct tccctccttt ctcgtccaaa tcatgaaatg tttggcctta gtcaatgtct     1800
atgcccgtca cataacagcc gaggcaccga ggcccacagg gaagcagctg ggagcttgga     1860
aacctggtct cttgaatttc aaacctggtt tcttacaggt ggttgtctgg ggtgggtgga     1920
gtggcgacag gatagagctg aaggactatg caaatgagga agtaagtcag ggcgggcttt     1980
gagaagggga cccatatcct acaggcaaaa agcaggctag gtgaccttgg gacactacgc     2040
taagggaggg aggctaaagg cggccaggtt tgcagtgcgg gaagatgagc aggccagtgg     2100
gaggaggggc agggcagggc tgtagttggt gactgggtgt tcattttagc tctaagaaaa     2160
aaaatcagtg tttcgtgaag gtgttggaga ggggctgtgt ctgggtgagg gatgcgggg      2220 tactgatttt tttgggaggt tatgagcaaa aataaaacga acatttcct ctggcaaaaa     2280 aaaaaaaaa aaa                                                         2293
```

<210> SEQ ID NO 36
<211> LENGTH: 4916
<212> TYPE: DNA
<213> ORGANISM: Homo sapiens

<400> SEQUENCE: 36

```
aaaaagtaca gagtccaggg aaagacttgc ttgtaacttt atgaattctg gattttttt       60 tttcctttgc ttttttcttaa ctttcactaa gggttactgt agtctgatgt gtccttccca     120
```

-continued

| | |
|---|---|
| aggccacgaa atttgacaag ctgcactttt cttttgctca atgatttctg ctttaagcca | 180 |
| aagaactgcc tataatttca ctaagaatgt cttctaattc agatactggg gatttacaag | 240 |
| agtcttttaaa gcacggactt acacctattg tgtctcaatt taaaatggtg aattactcct | 300 |
| atgatgaaga tctggaagag cttttgtccccg tgtgtggaga taaagtgtct gggtaccatt | 360 |
| atgggctcct cacctgtgaa agctgcaagg gatttttttaa gcgaacagtc caaaataata | 420 |
| aaaggtacac atgtatagaa aaccagaact gccaaattga caaaacacag agaaagcgtt | 480 |
| gtccttactg tcgttttcaa aaatgtctaa gtgttggaat gaagctagaa gctgtaaggg | 540 |
| ccgaccgaat gcgtggagga aggaataagt ttgggccaat gtacaagaga gacagggccc | 600 |
| tgaagcaaca gaaaaaagcc ctcatccgag ccaatggact taagctagaa gccatgtctc | 660 |
| aggtgatcca agctatgccc tctgacctga ccatttcctc tgcaattcaa aacatccact | 720 |
| ctgcctccaa aggcctacct ctgaaccatg ctgccttgcc tcctacagac tatgacagaa | 780 |
| gtcccctttgt aacatccccc attagcatga caatgccccc tcacggcagc ctgcaaggtt | 840 |
| accaaacata tggccacttt cctagccggg ccatcaagtc tgagtaccca gaccccctata | 900 |
| ccagctcacc cgagtccata atgggctatt catatatgga tagttaccag acgagctctc | 960 |
| cagcaagcat cccacatctg atactggaac ttttgaagtg tgagccagat gagcctcaag | 1020 |
| tccaggctaa aatcatggcc tatttgcagc aagagcaggc taaccgaagc aagcacgaaa | 1080 |
| agctgagcac ctttgggctt atgtgcaaaa tggcagatca aactctcttc tccattgtcg | 1140 |
| agtgggccag gagtagtatc ttcttcagag aacttaaggt tgatgaccaa atgaagctgc | 1200 |
| ttcagaactg ctggagtgag ctcttaatcc tcgaccacat ttaccgacaa gtggtacatg | 1260 |
| gaaaggaagg atccatcttc ctggttactg ggcaacaagt ggactattcc ataatagcat | 1320 |
| cacaagccgg agccaccctc aacaacctca tgagtcatgc acaggagtta gtggcaaaac | 1380 |
| ttcgttctct ccagtttgat caacgagagt tcgtatgtct gaaattcttg gtgctctttta | 1440 |
| gtttagatgt caaaaacctt gaaaacttcc agctggtaga aggtgtccag gaacaagtca | 1500 |
| atgccgccct gctggactac acaatgtgta actacccgca gcagacagag aaatttggac | 1560 |
| agctacttct tcgactaccc gaaatccggg ccatcagtat gcaggctgaa gaatacctct | 1620 |
| actacaagca cctgaacggg gatgtgccct ataataacct tctcattgaa atgttgcatg | 1680 |
| ccaaaagagc ataagttaca acccctagga gctctgcttt caaaacaaaa agagattggg | 1740 |
| ggagtgggga gggggaagaa gaacaggaag aaaaaaagta ctctgaactg ctccaagtaa | 1800 |
| cgctaattaa aaacttgctt taagatatt gaatttaaaa aggcataata atcaaatact | 1860 |
| taatagcaaa taaatgatgt atcagggtat ttgtattgca aactgtgaat caaaggcttc | 1920 |
| acagccccag aggattccat ataaaagaca ttgtaatgga gtggattgaa ctcacagatg | 1980 |
| gataccaaca cggtcagaag aaaaacggac agaacggttc ttgtatattt aaactgatct | 2040 |
| ccactatgaa gaaatttagg aactaatctt attaattagg cttatacagc gggggatttg | 2100 |
| agcttacagg attcctccat ggtaaagctg aactgaaaca attctcaaga atgcatcagc | 2160 |
| tgtacctaca atagcccctc cctcttcctt tgaaggcccc agcacctctg ccctgtggtc | 2220 |
| accgaatctg tactaaggac ctgtgttcag ccacacccag tggtagctcc accaaatcat | 2280 |
| gaacagccta attttgagtg tctgtgtctt agacctgcaa acagctaata ggaaattcta | 2340 |
| ttaatatgtt agcttgccat tttaaatatg ttctgagggt tgttttgtct cgtgttcatg | 2400 |
| atgttaagaa aatgcaggca gtatccctca tcttatgtaa gtgtgaatta atattaaggg | 2460 |
| aaatgactac aaactttcaa agcaaatgct ccatagctaa agcaacttag accttatttc | 2520 |

```
tgctactgtt gctgaaatgt ggctttggca ttgttggatt tcataaaaaa tttctggcag    2580
gaagtcttgt tagtatacat cagtcttttt catcatccaa gtttgtagtt catttaaaaa    2640
tacaacatta aacacatttt gctaggatgt caaatagtca cagttctaag tagttggaaa    2700
caaaattgac gcatgttaat ctatgcaaag agaaaggaaa ggatgaggtg atgtattgac    2760
tcaaggttca ttcttgctgc aattgaacat cctcaagagt tgggatggaa atggtgattt    2820
ttacatgtgt cctggaaaga tattaaagta attcaaatct tccccaaagg ggaaaggaag    2880
agagtgatac tgaccttttt aagtcataga ccaaagtctg ctgtagaaca aatatgggag    2940
gacaaagaat cgcaaattct tcaaatgact attatcagta ttattaacat gcgatgccac    3000
aggtatgaaa gtcttgcctt atttcacaat tttaaaggt agctgtgcag atgtggatca     3060
acatttgttt aaaataaagt attaatactt taaagtcaaa taagatatag tgtttacatt    3120
ctttaggtcc tgaggggcag ggggatctgt gatataacaa aatagcaaaa gcggtaattt    3180
ccttaatgtt attttctga ttggtaatta ttttaacag tacttaatta ttctatgtcg      3240
tgagacacta aaatcaaaaa cgggaatctc atttagactt taatttttt gagattatcg     3300 gcggcacaat cactttgtag aaactgtaaa aaataaagt atctcctagt cccttaattt     3360
tttcataaat atttctggct tttgagtagt gtatttatat tgtatatcat actttcaact   3420
gtagacaatt atgatgctaa tttattgttt cttggtttca cctttgtata agatatagcc    3480
aagactgaag aaaccaaata tatgtgttta ctgtagcatg tcttcaaatt agtggaactt    3540
agttcaggga catagaagag tcttaatgaa ttaaaatcat tcacttgatt aaatgtctgt    3600
aaatcttcat cattcctact gtagtttatt taatatctat tgtaaattat gtgacttgta   3660
gcttcctctg gttttcaagt aaactcaaca aggtggagtc ttacctggtt ttcctttcca   3720
agcattgtaa attgtatacc aaagatatta gttattactt ctgtgtgtac aaagaggatt   3780
attttattat gtttattaat cacctctaat actcatccac atgaagggta cacattaggt    3840
aagctgggcg ttgactcatg cgcagtctca gtcacccgtg ttatcttcgt ggctcaaagg    3900
acaatgcaaa atcgccgatc agagctcata cccaaagcat tacagagaac agcagcatca    3960
ttgccctccc cagctgaaaa acaagttggc tagaagatac atggagagga atggtgtggt    4020
caacagttaa tgaaacggtt ctatcatgca tgtgtaatgt ggatggagac aattataaga    4080
tttgactata actatttgga gggtctttaa cattgccaaa aaaacaaata tgttgatttt    4140
tattttattt tatttttat tttaagaggc gggatcttga tctcacatgt tgcccaggct     4200
ggccttgaac tcctgggctc aagcattcct cctgcctcag cctcccccat agctgggact    4260
aggggtgcat gccagcatac ctggctacgt tgactcttaa aatctatgtt ctcttatttt    4320
aaagatacag tgctccccac tgaaaattaa acctaaaaaa tgtcacatat tggtatgttg    4380
ttaacctggt agattaaatc atgagaatga ttagaaagac gggcaacaca gcgggttaca    4440
tccacactgc tgatcacacc aacgacagga gctgataagc aagaaagcgt cacagccagc    4500
gtctgttcac ccaaggttga caagtgaagt ttctctaatg ttgattgtta gccgatttgt    4560
aacctggcat ttacttagca actgccttat caattacagg attgccggt aaaagcagac     4620 tcaaatataa aggttttgg cttaacttgg tttattatag ttgctctatg tttgtaaaca     4680
gacaatctct aatgtctgat tatttgtatc acagatctgc agctgccttg gacttgaatc    4740
catgcaatgt ttagagtgtg aagtcagtta cttgttgatg tttcttact gtatcaatga     4800 aatacatatt gtcatgtcag tccttgccag gaacttctca acaaaatgga atttttttt     4860
```

```
tcagtatttc aataaatatt gatatgccca gcctgataat ttttaaaaaa aaaaaa    4916

<210> SEQ ID NO 37
<211> LENGTH: 1720
<212> TYPE: DNA
<213> ORGANISM: Homo sapiens

<400> SEQUENCE: 37
agtccctccc ctcagccttt ccccaaattg ctacttctct ggggctccag gtcctgcttg     60
tgctcagctc cagctcactg gctggccacc gagacttctg acaggaaac tgcaccatcc    120 tcttctccca gcaagggggc tccagagact gcccacccag gaagtctggt ggcctgggga    180
tttggacagt gccttggtaa tgaccagggc tccaggaaga gatgtccttg tggctggggg    240
cccctgtgcc tgacattcct cctgactctg cggtggagct gtggaagcca ggcgcacagg    300
atgcaagcag ccaggcccag ggaggcagca gctgcatcct cagagaggaa gccaggatgc    360
cccactctgc tggggtact gcaggggtgg ggctggaggc tgcagagccc acagccctgc    420
tcaccagggc agagcccct tcagaaccca cagagatccg tccacaaaag cggaaaaagg    480
ggccagcccc caaaatgctg gggaacgagc tatgcagcgt gtgtggggac aaggcctcgg    540
gcttccacta caatgttctg agctgcgagg gctgcaaggg attcttccgc cgcagcgtca    600
tcaagggagc gcactacatc tgccacagtg gcggccactg ccccatggac acctacatgc    660
gtcgcaagtg ccaggagtgt cggcttcgca atgccgtca ggctggcatg cgggaggagt    720
gtgtcctgtc agaagaacag atccgcctga agaaactgaa gcggcaagag gaggaacagg    780
ctcatgccac atccttgccc cccagggctt cctcaccccc ccaaatcctg ccccagctca    840
gcccggaaca actgggcatg atcgagaagc tcgtcgctgc ccagcaacag tgtaaccggc    900 gctcctttc tgaccggctt cgagtcacgc cttggcccat ggaccagat ccccatagcc    960 gggaggcccg tcagcagcgc tttgcccact tcactgagct ggccatcgtc tctgtgcagg   1020
agatagttga ctttgctaaa cagctacccg gcttcctgca gctcagccgg gaggaccaga   1080
ttgccctgct gaagacctct gcgatcgagg tgatgcttct ggagacatct cggaggtaca   1140
accctgggag tgagagtatc accttcctca aggatttcag ttataaccgg gaagactttg   1200
ccaaagcagg gctgcaagtg gaattcatca accccatctt cgagttctcc agggccatga   1260
atgagctgca actcaatgat gccgagtttg ccttgctcat tgctatcagc atcttctctg   1320
cagaccggcc caacgtgcag gaccagctcc aggtagagag gctgcagcac acatatgtgg   1380
aagccctgca tgcctacgtc tccatccacc atccccatga ccgactgatg ttcccacgga   1440
tgctaatgaa actggtgagc ctccggaccc tgagcagcgt ccactcagag caagtgtttg   1500
cactgcgtct gcaggacaaa aagctcccac cgctgctctc tgagatctgg gatgtgcacg   1560
aatgactgtt ctgtccccat atttttctgtt ttcttggccg gatggctgag gcctggtggc   1620
tgcctcctag aagtggaaca gactgagaag ggcaaacatt cctgggagct gggcaaggag   1680
atcctcccgt ggcattaaaa gagagtcaaa gggttgcgaa                         1720

<210> SEQ ID NO 38
<211> LENGTH: 2586
<212> TYPE: DNA
<213> ORGANISM: Homo sapiens

<400> SEQUENCE: 38
acagagccac agagggctgt gagcttgccc agcccaggt aacgctggcg gtgggtgggc     60
ctccagcttg gagcagagac cccccgaggc atctgcagac agaactggat ggacccatga    120
```

```
atacggattt agctgctgga aagatggctt ctgctgcctg ctccatggac cccatcgaca    180
gctttgagct cctggatctc ctgtttgacc ggcaggacgg catcctgaga cacgtggagc    240
tgggcgaggg ctggggtcac gtcaaggacc agcaggtcct gccaaacccc gactctgacg    300
acttcctcag ctccatcctg ggctctggag actcactgcc cagctcccca ctctggtccc    360
ccgaaggcag tgatagtggc atctccgaag acctcccctc cgaccccag gacaccctc     420
cacgcagcgg accagccacc tcccccgccg gctgccatcc tgcccagcct ggcaaggggc    480
cctgcctctc ctatcatcct ggcaactctt gctccaccac aaccccaggg ccagtgatcc    540
aagtacctga agcctctgtg accatagacc tggaaatgtg gagcccagga ggaaggatct    600
gtgctgagaa gccggctgat ccggtggacc tgtccccacg atgcaatctc accgtgaaag    660
acctcctcct ttcgggcagc agtggggacc tgcaacagca tcacctgggg gcctcctacc    720
tcctgcgacc tggggctggg cactgtcagg agctggtgct caccgaggat gagaagaagc    780
tgctggctaa agaaggcatc accctgccca ctcagctgcc cctcactaag tacgaggagc    840
gagtgctgaa aaaatccgc cggaaaatcc ggaacaagca gtcggcgcaa gaaagcagga    900
agaagaagaa ggaatatatc gatggcctgg agactcggat gtcagcttgc actgctcaga    960
atcaggagtt acagaggaaa gtcttgcatc tcgagaagca aaacctgtcc ctcttggagc    1020
aactgaagaa actccaggcc attgtggtgc agtccaccag caagtcagcc cagacaggca    1080
cctgtgtcgc agtcctgttg ctgtcctttg ccctcatcat cctcccctcc atcagccctt    1140
ttggccccaa caaaaccgag agccctgggg actttgcgcc tgtacgagtg ttctccagaa    1200
ctttgcacaa cgatgctgcc tcccgcgtgg ctgctgatgc tgtgccaggc tccgaggccc    1260
caggaccccg acccgaggct gacacaaccc gagaagagtc tccaggaagc cccgggcag    1320
actggggctt ccaggacacc gcgaacctga ccaattcgac ggaggagctg acaacgcca    1380
ccctggtcct gaggaatgca acagaggggc tgggccaggt cgccctgctg gactgggtgg    1440
cgcctgggcc gagcactggc tcaggacgtg cagggctgga ggcggcggga gacgagctgt    1500
gagccccgcc aggactatgc tcccaggccc ctctgcccag gggtgccttg gggatgctgc    1560
actgggcagc tacccacctg gggatgggac gtgaggccaa gaccccagca gagatgccag    1620
aatgggggag gcacagctca tagccacaca cccagggcct gactgaggcc cacgcaggaa    1680
ccgacactca gacacaaggc aaagagggcc acaggacccg ggaaatacac acagagccag    1740
gagcagaagc aaagagcaga cacacataca gcctgaaaca gacctggaca gacagacaca    1800
gcctgaaaca gacccggaca gacagacaca gcctgaaaca gacccagaca acagacaga    1860
cagacacagc ctgaaacaga cccagacaga cagacagaca gcctgaaaca gacccagaca    1920
cagcctgaaa cagatccgga cagacagaca gaaacagcct gaaacagacc cagacagaca    1980
gacagacaca gcctgaaaca gacccggaca gacagacaga cacagcctga acagacccg     2040
gacagacaga cagacacagc ctgaaacaga cccggacaga cagacagaca gcctgaaaca    2100
cagacctaga cagacagaca cagattgaaa cagacccaga caaacagaca gacacagcct    2160
gaaacagacc cagacacagc ctgaaacaga cccggacaga cagacagaca gcctgaaaca    2220
cagacccaga cagacagaca gacacagcct gaaacagacc cagacagaca gaccgacgca    2280
gcctgaaaga gacccagaca gagacacagg cagacacagc ctaaaacaga cctggacaga    2340
caggcagacg tagtctgaaa cagacctgaa cagacagaca gacgcacaca caacagat      2400
gcgcagcaac tccccgccca gggacccctc ccggcctccc tcgcacactg ggaggaggaa    2460
```

| | |
|---|---:|
| gccgccgaga ctgcagggag cctggccccg agccccggg tgcgccctgg tctttggagc | 2520 |
| agccacggcc cacaatcacc cccttttct aagactgcct gatccgaaat aaagtatttt | 2580 |
| gacaaa | 2586 |

<210> SEQ ID NO 39
<211> LENGTH: 1857
<212> TYPE: DNA
<213> ORGANISM: Homo sapiens

<400> SEQUENCE: 39

| | |
|---|---:|
| ccggacctcg gctttcaaag cggcctgggt gggaagagct gtttatataa acagagattc | 60 |
| cgctgtaaat gcgctaatat cccggctgcc agcgcatggc gagcgcctcc cacgcccatc | 120 |
| cgtaggagcg gcgtcccggc cgcccctccg ttcccagcct gccctgcccc cgcctccttc | 180 |
| ccctcctcgg ccatggccac ctctggacgc ctgagcttca ccgtgcgcag ccttctagat | 240 |
| ttacccgagc aggacgcgca acacctgccg aggcgggagc cagaaccacg cgcccccag | 300 |
| cccgacccct gcgccgcctg gctggattcg gagcgcggc actacccttc ctcggacgag | 360 |
| agcagcctgg agaccagccc gccagactcg tcgcagcggc cgtccgctag gcccgcgtct | 420 |
| ccgggctcga cgccgagaa aaggaagaag cggcgggtgc tattctccaa ggcgcagacg | 480 |
| ctggagttgg agcggcgctt ccggcagcag cggtacctgt ctgcgcccga gcgcgagcag | 540 |
| ctggcgagcc tgcttcgcct cacgcccacg caggtcaaga tctggttcca gaatcatcgc | 600 |
| tacaagctga agcgcgctcg cgctccaggg gcggcggagt cgcctgacct ggcagcatcc | 660 |
| gccgagctgc acgccgcgcc cggcctgctg cgtcgcgtgg tggtgccggt gcttgttcgc | 720 |
| gacgggcagc cgtgcggcgg cggcggcggt ggcgaggtgg gaaccgccgc ggcccaggag | 780 |
| aagtgcggcg ccctccagc cgccgcctgc cctctgccgg gctaccctgc cttcggtccc | 840 |
| ggctcggcgc ttggcctctt cccgcctac cagcacttag catccccgc cctggtctcc | 900 |
| tggaactggt gaggccgcag ggcggcacct ggggctaccc tcgactttgg agcgcgctct | 960 |
| gcgattggag cagggccgga ccgaacgcc tggaacgctc tccgtccgcc tccctgcagc | 1020 |
| cccatctcct tggcgccag ggtccctggc gcgccctcat cagccgtcgc gcaagcacac | 1080 |
| acgagggacg tgtgccagag cccctccct caccttccct ccaccgccag ccccagagtt | 1140 |
| agattttatg cttgggcctt atttgtatat tttaaatag cgatttgtat aggaagcaag | 1200 |
| ttatttttt aaaaaataga gtatttttcc tcgtagttcg agaataaaat gtgtggggtt | 1260 |
| gggtcccctg cgcgcctgcg gggaacgtag gcgggagtcg tgcccccag accggtgttc | 1320 |
| gcatcgctgg ctcgcccctt gactggctaa gtggggcccg gccccagctg gatcgaaggg | 1380 |
| cgggttgcag tcccgacacg gctttaggaa gatacctggg ggatggaggg gtggtgatgt | 1440 |
| cagggttggg cgcgggaaga aaaggagagg aggaagctga ggcaactttg ggattcttgt | 1500 |
| cagcgggagg cgtcactggc cccagagtga ctccgactct ccgctgggct cccagagctg | 1560 |
| ctggcgtttc gaataccgaa aagtcaaccc tgtggaccac gacagggcag aaggagtttc | 1620 |
| tccggagatg agccggcgag gccaggtgcg gggcgcgctg caccggagca gcccaggccg | 1680 |
| ggccgcaagc tgtttccaga gtgcaggagc caagtgctcg ggaccctttt gaaaagtgcc | 1740 |
| tggggacctg aagagcaccg gggaatttgt aaccccctatt taagcctgca agtgcctaag | 1800 |
| ttaaaaaaaa aaaaaaaaaa aaaaaaaaaa aaaaaaaaaa aaaaaaaaaa aaaaaaa | 1857 |

<210> SEQ ID NO 40
<211> LENGTH: 1269

```
<212> TYPE: DNA
<213> ORGANISM: Homo sapiens

<400> SEQUENCE: 40
aggtgacagc ctcgcttgga cgcagagccc ggcccgacgc cgccatgagc gccgcgctct    60
tcagcctgga cggcccggcg cgcggcgcgc cctggcctgc ggagcctgcg cccttctacg   120
aaccgggccg ggcgggcaag ccgggccgcg gggccgagcc aggggcccta ggcgagccag   180
gcgccgccgc ccccgccatg tacgacgacg agagcgccat cgacttcagc gcctacatcg   240
actccatggc cgccgtgccc accctggagc tgtgccacga cgagctcttc gccgacctct   300
tcaacagcaa tcacaaggcg ggcggcgcgg ggccctgga gcttcttccc ggcggccccg   360
cgcgcccctt gggcccgggc cctgccgctc ccgcctgct caagcgcgag cccgactggg   420
gcgacggcga cgcgccccgg ctgctgttgc ccgcgcaggt ggccgcgtgc gcacagaccg   480
tggtgagctt ggcggccgca gggcagccca ccccgcccac gtcgccggag ccgccgcgca   540
gcagccccag gcagacccccg cgcccgggcc cgcccgggga aagagcgcc ggcaagaggg   600
gcccggaccg cggcagcccc gagtaccggc agcggcgcga gcgcaacaac atcgccgtgc   660
gcaagagccg cgacaaggcc aagcggcgca accaggagat gcagcagaag ttggtggagc   720
tgtcggctga gaacgagaag ctgcaccagc gcgtggagca gctcacgcgg gacctggccg   780
gcctccggca gttcttcaag cagctgccca gcccgccctt cctgccggcc gccgggacag   840
cagactgccg gtaacgcgcg gccggggcgg gagagactca gcaacgaccc atacctcaga   900
cccgacggcc cggagcggag cgcgccctgc cctggcgcag ccagagccgc cgggtgcccg   960
ctgcagtttc ttgggacata ggagcgcaaa gaagctacag cctggactta ccaccactaa  1020
actgcgagag aagctaaacg tgtttatttt cccttaaatt attttttgtaa tggtagctt  1080
ttctacatct tactcctgtt gatgcagcta aggtacattt gtaaaagaa aaaaaccag   1140
accttttcaga caacccttt gtattgtaga taagaggaaa agactgagca tgctcacttt  1200
tttatattaa tttttacagt atttgtaaga ataaagcagc atttgaaatc gaaaaaaaaa  1260
aaaaaaaaa                                                           1269

<210> SEQ ID NO 41
<211> LENGTH: 5607
<212> TYPE: DNA
<213> ORGANISM: Homo sapiens

<400> SEQUENCE: 41
actcttgtca gggccgcggc acatgggcgg ccggatgcgc tgagcccggc gctgcggggc    60
cgcggagcgc tggggagcag cggccgccgg cgcggggagg ggggtggggt gggacggcgc   120
accgcctccg gtgctggcac taggggctgg ggtcggcgcg gtgtcttctg cccttctgca   180
gccgtcgaca ttttttttc ttctttttt tcaattttga acattttgca aaacgagggg   240
ttcgaggcag gtgagagcat cctgcacgtc gccgggagc ccgcgggcac ttggcgcgct   300
ctcctgggac cgtctgcact ggaaacccga agtttttttt ttaatatata tttttatgca   360
gatgtattta taaagatata agtaattttt ttcttccctt ttctccaccg ccttgagagc   420
gagtactttt ggcaaaggac ggaggaaaag ctcagcaaca ttttaggggg cggttgtttc   480
tttcttattt cttttttaa ggggaaaaaa tttgagtgca tcgcgatgga gaaaatgtcc   540
cgaccgctcc ccctgaatcc cacctttatc ccgcctccct acggcgtgct caggtccctg   600
ctggagaacc cgctgaagct ccccccttcac cacgaagacg catttagtaa agataaagac   660
```

```
aaggaaaaga agctggatga tgagagtaac agcccgacgg tcccccagtc ggcattcctg    720
gggcctacct tatgggacaa aacccttccc tatgacggag atactttcca gttggaatac    780
atggacctgg aggagttttt gtcagaaaat ggcattcccc ccagcccatc tcagcatgac    840
cacagccctc accctcctgg gctgcagcca gcttcctcgg ctgcccctc ggtcatggac     900 ctcagcagcc gggcctctgc acccttcac cctggcatcc catctccgaa ctgtatgcag     960
agccccatca gaccaggtca gctgttgcca gcaaaccgca atacaccaag tcccattgat    1020
cctgacacca tccaggtccc agtgggttat gagccagacc cagcagatct tgcccttcc    1080 agcatccctg ccaggaaat gtttgaccct cgcaaacgca agttctctga ggaagaactg    1140
aagccacagc ccatgatcaa gaaagctcgc aaagtcttca tccctgatga cctgaaggat   1200
gacaagtact gggcaaggcg cagaaagaac aacatggcag ccaagcgctc ccgcgacgcc   1260
cggaggctga aagagaacca gatcgccatc cgggcctcgt tcctggagaa ggagaactcg   1320
gccctccgcc aggaggtggc tgacttgagg aaggagctgg gcaaatgcaa gaacatactt   1380
gccaagtatg aggccaggca cgggcccctg taggatggca ttttttgcagg ctggctttgg  1440 aatagatgga cagtttgttt cctgtctgat agcaccacac gcaaaccaac ctttctgaca   1500
tcagcacttt accagaggca taaacacaac tgactcccat tttggtgtgc atctgtgtgt   1560
gtgtgcgtgt atatgtgctt gtgctcatgt gtgtggtcag cggtatgtgc gtgtgcgtgt   1620
tcctttgctc ttgccatttt aaggtagccc tctcatcgtc ttttagttcc aacaaagaaa   1680
ggtgccatgt ctttactaga ctgaggagcc ctctcgcggg tctcccatcc cctccctcct   1740
tcactcctgc ctcctcagct ttgcttcatg ttcgagctta cctactcttc caggactctc   1800
tgcttggatt cactaaaaag ggccctggta aaatagtgga tctcagtttt taagagtaca   1860
agctcttgtt tctgtttagt ccgtaagtta ccatgctaat gaggtgcaca caataactta   1920
gcactactcc gcagctctag tcctttataa gttgctttcc tcttactttc agttttggtg   1980
ataatcgtct tcaaattaaa gtgctgttta gatttattag atcccatatt tacttactgc   2040
tatctactaa gtttccttt aattctacca accccagata agtaagagta ctattaatag    2100
aacacagagt gtgttttgc actgtctgta cctaaagcaa taatcctatt gtacgctaga    2160
gcatgctgcc tgagtattac tagtggacgt aggatatttt ccctacctaa gaatttcact   2220
gtcttttaaa aaacaaaag taaagtaatg catttgagca tggccagact attccctagg    2280
acaaggaagc agagggaaat gggaggtcta aggatgaggg gttaatttat cagtacatga   2340
gccaaaaact gcgtcttgga ttagcctttg acattgatgt gttcggtttt gttgttcccc   2400
ttccctcaca ccctgcctcg ccccactttt tctagttaac ttttttccata tccctcttga   2460 cattcaaaac agttacttaa gattcagttt tcccactttt tggtaatata tatatttttg    2520
tgaattatac tttgttgttt ttaaaaagaa aatcagttga ttaagttaat aagttgatgt    2580
tttctaaggc cctttttcct agtggtgtca ttttttgaatg cctcataaat taatgattct   2640
gaagcttatg tttcttattc tctgtttgct tttgaacgta tgtgctctta taaagtggac   2700
ttctgaaaaa tgaatgtaaa agacactggt gtatctcaga aggggatggt gttgtcacaa   2760
actgtggtta atccaatcaa tttaaatgtt tactatagac caaaggaga gattattaaa    2820 tcgtttaatg tttatacaga gtaattatag gaagttcttt tttgtacagt attttcaga    2880 tataaatact gacaatgtat tttggaagac atatattata tatagaaaag aggagaggaa   2940
aactattcca tgtttttaaaa ttatatagca aagatatata ttcaccaatg ttgtacagag   3000
aagaagtgct tgggggtttt tgaagtcttt aatatttttaa gccctatcac tgacacatca  3060
```

```
gcatgttttc tgctttaaat taaaatttta tgacagtatc gaggcttgtg atgacgaatc   3120
ctgctctaaa atacacaagg agctttcttg tttcttatta ggcctcagaa agaagtcagt   3180
taacgtcacc caaaagcaca aaatggattt tagtcaaata tttattggat gatacagtgt   3240
tttttaggaa aagcatctgc cacaaaaatg ttcacttcga aattctgagt tcctggaatg   3300
gcacgttgct gccagtgccc cagacagttc ttttctaccc tgcgggcccg cacgttttat   3360
gaggttgata tcggtgctat gtgtttggtt tataatttga tagatgtttg actttaaaga   3420
tgattgttct tttgtttcat taagttgtaa aatgtcaaga aattctgctg ttacgacaaa   3480
gaaacatttt acgctagatt aaaatatcct ttcatcaatg ggattttcta gtttcctgcc   3540
ttcagagtat ctaatccttt aatgatctgg tggtctcctc gtcaatccat cagcaatgct   3600
tctctcatag tgtcatagac ttgggaaacc caaccagtag atatttcta caaggtgttc   3660 attttgtcac aagctgtaga taacagcaag agatgggggt gtattggaat tgcaatacat   3720
tgttcaggtg aataataaaa tcaaaaactt ttgcaatctt aagcagagat aaataaaaga   3780
tagcaatatg agacacaggt ggacgtagag ttggcctttt tacaggcaaa gaggcgaatt   3840
gtagaattgt tagatggcaa tagtcattaa aaacatagaa aaatgatgtc tttaagtgga   3900
gaattgtgga aggattgtaa catggaccat ccaaatttat ggccgtatca aatggtagct   3960
gaaaaaacta tatttgagca ctggtctctc ttggaattag atgtttatat caaatgagca   4020
tctcaaatgt tttctgcaga aaaaaataaa aagattctaa taaaatgtat tctcttgtgt   4080
gccaggagag gtttcagaaa cctacctcgt cttacaaatt taaacacttt ggagtctgta   4140
caggtgcctt atatgtaggt cattgtcacg atacacacac acgaacactc cctctggact   4200
ggctgcctct ccatccaggg cagttaacta gcaaacaagg cagatctgct tcatggagcg   4260
ggaggccatg gcttgactct gagtgatttg ggtcaaccgg agtcagacgc atgtctgcac   4320
gctgcagcta ttatgagagt ccctttgtca ttttcacct tttcatccta agcatctttc   4380
agagattaat tatttggcca ttaacaatga atccaaatca tatcatactg acatcatcta   4440
gacatgattt ggaaggaaca gcttaggacc tcctgatgag gtcacattgt tgtttctttt   4500
aactagactt ggcaaagaaa ggcaaaaatt gaccagccta tctttctgct ggtgctgcct   4560
taaggaggta gtttgttgag gggagggctg tagatcatta cttctttctc ttcaggaagt   4620
ggccactttg aaccattcaa ataccacatt aggcaagact gtgataggcc ttttgtcttc   4680
aaatacaaca ggcctccact gacccatccc tcaaagcaga aggaccctt gaggagagta   4740 cagatgggat tccacagtgg ggtgggtgga atggaaacct gtactagacc acccagaggt   4800
tccttctaac ccactggttt ggtggggaac tcacagtaat tccaaatgta caatcagatg   4860
tctagggtct gttttcggaa gaagcaagaa ttatcagtgg cacctcccc actgcccca   4920 gtgtaaaaca atagacattc tgtgaaatgc aaagctattc tttggttttt ctagtagttt   4980
atctcatttt accctattct tcctttaagg aaaactcaat ctttatcaca gtcaattaga   5040
gcgatcccaa ggcatgggac caggcctgct tgcctatgtg tgatggcaat tggagatctg   5100
gatttagcac tggggtctca gcaccctgca ggtgtctgag actaagtgat ctgcctcca   5160 ggtggcgatc accttctgct cctaggtacc cccactggca aggccaaggt ctcctccacg   5220 tttttttctgc aattaataat gtcatttaaa aaatgagcaa agccttatcc gaatcggata   5280
tagcaactaa agtcaataca ttttgcagga ggctaagtgt aagagtgtgt gtgtgtgtgt   5340
gtgcgtgcat gtgtgtgtgt gtgtatgtgt gtgaataagt cgacataaag tctttaattt   5400
```

| | |
|---|---:|
| tgagcacctt accaaacata acaataatcc attatccttt tggcaacacc acaaagatcg | 5460 |
| catctgttaa acaggtacaa gttgacatga ggttagttta attgtacacc atgatattgg | 5520 |
| tggtatttat gctgttaagt ccaaaccttt atctgtctgt tattcttaat gttgaataaa | 5580 |
| ctttgaatttt tttcctttca aaaaaaa | 5607 |

```
<210> SEQ ID NO 42
<211> LENGTH: 1277
<212> TYPE: DNA
<213> ORGANISM: Homo sapiens

<400> SEQUENCE: 42
```

| | |
|---|---:|
| ttttttttcaa tgaacatgac ttctggagtc aaggttgttg ggccattccc cccgttccac | 60 |
| tcactgggaa tataaatagc acccacagcg cagaacacag agccagagag ctggaagtga | 120 |
| gagcagatcc ctaaccatga gcaccagcca accaggggcc tgcccatgcc agggagctgc | 180 |
| aagccgcccc gccattctct acgcacttct gagctccagc ctcaaggctg tcccccgacc | 240 |
| ccgtagccgc tgcctatgta ggcagcaccg gcccgtccag ctatgtgcac ctcatcgcac | 300 |
| ctgccgggag gccttggatg ttctggccaa gacagtggcc ttcctcagga acctgccatc | 360 |
| cttctggcag ctgcctcccc aggaccgcg gcggctgctg cagggttgct ggggcccccct | 420 |
| cttcctgctt gggttggccc aagatgctgt gacctttgag gtggctgagg ccccggtgcc | 480 |
| cagcatactc aagaagattc tgctggagga gcccagcagc agtggaggca gtggccaact | 540 |
| gccagacaga ccccagccct cctggctgc ggtgcagtgg cttcaatgct gtctggagtc | 600 |
| cttctggagc ctggagctta gcccaagga atatgcctgc ctgaaaggga ccatcctctt | 660 |
| caaccccgat gtgccaggcc tccaagccgc ctcccacatt gggcacctgc agcaggaggc | 720 |
| tcactgggtg ctgtgtgaag tcctggaacc ctggtgccca gcagcccaag gccgcctgac | 780 |
| ccgtgtcctc ctcacggcct ccaccctcaa gtccattccg accagcctgc ttggggacct | 840 |
| cttctttcgc cctatcattg gagatgttga catcgctggc cttcttgggg acatgctttt | 900 |
| gctcaggtga cctgttccag cccaggcaga gatcaggtgg gcagaggctg gcagtgctga | 960 |
| ttcagcctgg ccatccccag aggtgaccca atgctcctgg aggggcaag cctgtataga | 1020 |
| cagcacttgg ctccttagga acagctcttc actcagccac accccacatt ggacttcctt | 1080 |
| ggtttggaca cagtgttcca gctgcctggg aggcttttgg tggtccccac agcctctggg | 1140 |
| ccaagactcc tgtcccttct tgggatgaga atgaaagctt aggctgctta ttggaccaga | 1200 |
| agtcctatcg actttataca gaactgaatt aagttattga ttttttgtaat aaaaggtatg | 1260 |
| aaacacttgg aaaaaaa | 1277 |

```
<210> SEQ ID NO 43
<211> LENGTH: 4335
<212> TYPE: DNA
<213> ORGANISM: Homo sapiens

<400> SEQUENCE: 43
```

| | |
|---|---:|
| gcgccccctg cgctgccaac ccgcgagccc gcatcatgga tgtcgagctc ccctatttcg | 60 |
| cattgctagc cctggaattc gagaccccag acgaggacca ggattcatga atcagtcgc | 120 |
| aggggccggg gcagggcct ctggctcccg acactggccg agaggtgatg agtgaggttc | 180 |
| gaagaacgga agatttaaaa agcagccggg gcctccgtat tgaatgaaag acccagtgca | 240 |
| aagacatcac catgaacact agcattcctt atcagcagaa tccttacaat ccacggggca | 300 |
| gctccaatgt catccagtgc taccgctgtg agacacctg caaaggggaa gtggtccgcg | 360 |

```
tgcacaacaa ccacttccac atcagatgct tcacctgtca agtatgtggc tgtggcctgg    420
cccagtcagg cttcttcttc aagaaccagg agtacatctg cacccaggac taccagcaac    480
tctatggcac ccgctgtgac agctgccggg acttcatcac aggcgaagtc atctcggccc    540
tgggccgcac ttaccacccc aagtgcttcg tgtgcagctt gtgcaggaag cctttcccca    600
ttggagacaa ggtgaccttc agcggtaaag aatgtgtgtg ccaaacgtgc tcccagtcca    660
tggccagcag taagcccatc aagattcgtg gaccaagcca ctgtgccggg tgcaaggagg    720
agatcaagca cggccagtca ctcctggctc tggacaagca gtggcacgtc agctgcttca    780
agtgccagac ctgcagcgtc atcctcaccg gggagtatat cagcaaggat ggtgttccat    840
actgtgagtc cgactaccat gcccagtttg gcattaaatg tgagacttgt gaccgataca    900
tcagtggcag agtcttggag caggaggga agcactacca cccaacctgt gccaggtgtg    960
tacgctgcca ccagatgttc accgaaggag aggaaatgta cctcacaggt tccgaggttt   1020
ggcaccccat ctgcaaacag gcagcccggg cagagaagaa gttaaagcat agacggacat   1080
ctgaaacctc catctcaccc cctggatcca gcattgggtc acccaaccga gtcatctgcg   1140
ctaaagtgga taatgagatc cttaattaca agacctggc ggctctcccc aaggttaagt    1200
ctatctacga ggtacaacgc cccgacctca tttcctatga gcctcattcc agatacatgt   1260
ccgacgagat gctggagaga tgtggctatg gagagtcgct gggaacatta tctccctact   1320
cccaggacat ctacgagaac ctggacctcc ggcagagacg ggcctccagc ccggggtaca   1380
tagactcccc cacctacagc cggcagggca tgtcccccac cttctcccgc tcacctcacc   1440
actactaccg ctctgggccc gagagtggcc ggagctctcc ataccatagc cagttagatg   1500
tgaggtcctc cactccaacc tcttaccagg ctcccaagca ctttcacatc ccagctggag   1560
acagtaacat ctaccggaaa cccccgatct acaaacggca tggtgatttg tctacagcaa   1620
ccaagagcaa aacaagtgaa gacatcagcc agacctccaa gtacagtccc atctactcgc   1680
cagaccccta ctatgcttcg gagtctgagt actggaccta ccatgggtcc cccaaagtgc   1740
cccgagccag aaggttctcg tctggaggag aggaggatga ttttgaccgc agcatgcaca   1800
agctccaaag tggaattggc cggctgattc tgaaggaaga aatgaaggcc cggtcgagct   1860
cctatgcaga tcctggacc cctcccccgga gctccaccag cagccgggaa gccctgcaca   1920
cagctggcta tgagatgtcc ctcaatggct cccctcggtc gcactacctg ctgacagtg    1980
atcctctcat ctccaaatct gcctccctgc ctgcctaccg aagaaatggg ctgcacagga   2040
cacccagcgc agacctcttc cactacgaca gcatgaacgc agtcaactgg ggcatgcgag   2100
agtacaagat ctacccttat gaactgctgc tggtgactac aagaggaaga aaccgactgc   2160
ccaaggatgt agacaggacc cgtttagagc gccaccgtgc ccaggaagag ttctaccaag   2220
tctttggcat gaccatctct gagtttgacc ggctggccct ctggaagagg aatgaactga   2280
agaagcaagc ccggctgttc taggcagagg ctctataaat atatatgcat ttatataaag   2340
atatatgtaa aatctctcta ctgaagctcg gtataatcct ctcttgtgta atgggacaca   2400
ctgcctgcca tgagacttgc ttttctgtac tgtcaggcaa gcccacgtca tcgagatatt   2460
tttatgctcc ttactttctc ttttctaagt gctgtgggat ctgggaaggg atttgagggg   2520
actctgtcct tttattgggg atcctttta tactgaaaca tctgtcctaa cttgagtgcc   2580
ccaaggtcca actctctttc ctaaagaagg tgcctgaaga agctctctt ctctctgctt    2640
cgtggccct ttcttaaatt tctagggctg atgctgacca tgtggtttcc acaccttatt    2700
```

| | | | | |
|---|---|---|---|---|
| ggccccagag | gggccctccc | atgggaagat | ctgcagcagt | ctccccaaat cagtgagcac | 2760 |
| ctttgagcgc | ccacgaagaa | ctttctcaac | accccaatt | aggagctcag tgctctcttg | 2820 |
| gggcaatgca | gttaaaaggg | tgagcctcaa | atctagtcat | acaccagtc aacagaagtg | 2880 |
| gacagggcct | aggcctctcc | tcagctcctt | aaccctcctc | cttctgccct ggattgtaac | 2940 |
| ctctcccttg | tccaaatcta | ggattcctgg | taggaaaagg | aaaaggccct tcccttccct | 3000 |
| ccaccacttc | caactggccc | ctttgcctga | cctggacttg | gagaaccaga ggaaaagaga | 3060 |
| gggagcggaa | gtgggagatg | gagcagggca | cctgttagaa | tcagagctgc aggatttctt | 3120 |
| gggaccctcc | tctctccctc | actgctccca | gcacctcctg | acccttccct ctttcaagga | 3180 |
| gaagcccatg | attgcagctt | gtattcttta | gccttattac | aatctatgtg cctgacaact | 3240 |
| caacacaccg | cagggctaat | gttcccacca | gagctccaac | tgaacaacca gacagacaac | 3300 |
| tctcatcatc | ctccagagag | aaaataggcc | gtgtctcaaa | gaaaggttct tggtctatgc | 3360 |
| ctctggtctg | tgggctggca | gggcaaccat | accataccc | cgccagtcct cggctcctgc | 3420 |
| tgcaaagttg | gccatgtttc | acagggaaac | ttttggaaga | gtggctgctt atgagattcc | 3480 |
| aaaatgaagt | gttggccaac | accgctcatg | gccatcctgg | attttcccag tggcttccct | 3540 |
| tcctgctcgc | ctccctgaac | aggggagaaa | gcttaacctc | tcttctcctc tccaaacctt | 3600 |
| tcaccttgaa | tgggtaatgt | ttggtggggg | ctgttccttc | ttggagaagc cttgagtcgg | 3660 |
| accattttga | gatcatggag | gaaggatgaa | gaagtgaaaa | tgacaataat gactctcaag | 3720 |
| aggctggcga | tgtgacatgg | caaatgtaga | actgacttaa | attgaacaaa ccctcactga | 3780 |
| gcacctctga | tgttgagcac | ctgctgaata | ctgagcactg | aatgggggag ggggagggga | 3840 |
| gcacggggtg | agtcaacctg | ggactcggtc | tcagggatat | gcctaccaat agcgggtatc | 3900 |
| gtaaggcatg | tacccaaaca | taacggatgt | aaggcagaaa | gtgatcggag aaggaatgag | 3960 |
| aaagtgtgcg | tgatgttaat | gaaaagtcat | atgcagctag | agcagaccca ggaaagcttt | 4020 |
| ctggaagaga | ttgcatctga | ggaaattcag | gaaggatctt | tgtagattgg ggggagattc | 4080 |
| taaattgaag | gggtgatggg | gtgaggggcc | agagggaagt | ctgctgtgtt ctcatgtagg | 4140 |
| atgtcagccc | tccctgcaac | ttctcttttt | ggccaatgtc | ttttcacttt cctgacccctt | 4200 |
| tagaatcatc | cccagccaga | cgcaatcatg | gaagttgcct | tattgtcact ggttaagaac | 4260 |
| ttggcgagat | tgaagggctt | ttgttattgt | tgttggatat | ttttgtttcc cataaaagca | 4320 |
| catcatttca | accct | | | | 4335 |

<210> SEQ ID NO 44
<211> LENGTH: 5873
<212> TYPE: DNA
<213> ORGANISM: Homo sapiens

<400> SEQUENCE: 44

| | | | | |
|---|---|---|---|---|
| gaaaaatgct | tcctgtttct | ttaaaggcgc | tcgcggctcg | gcggccggg gctggggagg | 60 |
| cggtggcggc | gggagctgcc | tcctctccgg | gcggcggcgc | tgactgatct cgcgaactgg | 120 |
| gcttctgtgt | aaactgaggc | taaacaaaca | cagatggagc | gcagcgggcg ttctccagaa | 180 |
| atgctggcaa | ggaggcagcg | acttcagatg | acactctgag | cgctccggga acggacagcc | 240 |
| cggcggcttc | ccgaagccgg | cggcgcagct | gcccggggcg | aggggagaa agggagagag | 300 |
| ggaggggag | ggcggggcgaa | gcgggagagc | cagagactcc | tcggcgctga gcgcggcggc | 360 |
| ggccccgggca | gccccacgcc | cctgcctcgc | gcgccgcccg | cgccatgaag cacatcccgg | 420 |
| tcctcgagga | cgggccgtgg | aagaccgtgt | gcgtgaagga | gctgaacggc cttaagaagc | 480 |

-continued

```
tcaagcggaa aggcaaggag ccggcgcggc gcgcgaacgg ctataaaact ttccgactgg      540
acttggaagc gcccgagccc cgcgccgtag ccaccaacgg gctgcgggac aggacccatc      600
ggctgcagcc ggtcccggta ccggtgccgg tgccagtccc agtggcgccg gccgttcccc      660
caagaggggg cacggacaca gccggggagc gcggggggctc tcgggcgccc gaggtctccg     720
acgcgcggaa acgctgcttc gccctaggcg cagtggggcc aggactcccc acgccgccgc      780
cgccgccgcc tcctgcgccc cagagccagg cacctggggg cccagaggca cagccttttcc    840 gggagccggg tctgcgtcct cgcatcttgc tgtgcgcacc gcccgcgcgc ccgcgccgt       900 cagcaccccc agcaccgcca gcgccccccgg agtccactgt gcgccctgcg cccccgacgc    960
gccccgggga aagttcctac tcgtcaattt cacacgtaat ttacaataac caccaggatt    1020
cctccgcgtc gcctaggaaa cgaccgggcg aagcgactgc cgcctcctcc gagatcaaag    1080
ccctgcagca gacccggagg ctcctggcga acgccaggga gcggacgcgg gtgcacacca    1140
tcagcgcagc cttcgaggcg ctcaggaagc aggtgccgtg ctactcatat gggcagaagc    1200
tgtccaaact ggccatcctg aggatcgcct gtaactacat cctgtccctg gcgcggctgg    1260
ctgaccttga ctacagtgcc gaccacagca acctcagctt ctccgagtgt gtgcagcgct    1320
gcacccgcac cctgcaggcc gagggacgtg ccaagaagcg caaggagtga ctggctgcag    1380
gcaagaccaa ggccaccact gtgggccctc cttccagtca ggcctgagga caaggtgagc    1440
tcgctgagtc cagcctcgtg gtcttctcca agatgccgcc agatgcccag cctacagcct    1500
ctcagggtcg gatcggagca cgcctgcctc cctctcccct ccgccctcac ccagccaatc    1560
cgaggctgct tcgcactttg ccctctgcct ggtggggagg ggagagctca gccccgact    1620 cactcagacc ccaaggccca ctgtccagct gcagaaattc gttgccaaag attggacaga    1680
gacaccgaag gaaatggggt ggtgaaaccc cacagcgaaa agccacaccg ttgctctgtg    1740
acttttgctc ctcctgttgc ctgagcccca tctcaagcca aagatgagtc agtggttctg    1800
ctaggaactc atggaatgga tgggcatttg atgacccctg ggggtcatct tggccctctg    1860
acctggtgct ctctctccac tgggccttgt gctggctgag tgcaagacaa gccttagggg    1920
ctgtgagagg gaggctgggg tgcctgggcg gggctggag tgggacctga tccctgcc      1980 cactctctcc ccttcattgg ctgcccaggc cactggcccc agttctcagt gtcccttggg    2040
tccaggctcc ttgggcccta agcatcacca gaagggagta agcagggaga gaagcaatat    2100
tactccctcc cctacaccag ggacttgccc cagggcagct acctatgggt ctttgcttcc    2160
ccagccagcc tctcctcact gtgacccacc cccatgggcc cccgtcccag gcagccagca    2220
ccatgggcag gccctgccat ggacagaaaa agagtttttc tcttgttcag cctgcacgtg    2280
gcctgaggaa ggagtagagg ctgggttggc tggagccgtc ctactgggca agatggcgcc    2340
ccacttggag ggcggtggtc tgttacaggg tgtgcagggg cagagaagga agggaccagg    2400
ggactgggcc agtatgtgga ggatggggcc tgcgtgttca agccaaggc ccgccccttc     2460 cttgtgctca aatggccaaa gctgttcacg tctgtgctca accatctgct tcaaattgaa    2520
gtaaaagccc caaaatgtca agaaaatact tgtgttgagt ggactctgtg ggtgaccagg    2580
actttggccg gtcatcagct ggggagtgtg agggaggggg ttggtttcta cctacaggtt    2640
gagagccctt caggatcagg cgctgtccga gtgagagtgt gtgtgtctgt gtgtggaagg    2700
gggtggaggg cggttcccac agtagtctca gcctggacta gtgaccagga ggcctggtca    2760
ggaacacatg aggagccctc tctgtccgca ctgcactcaa tctgtaccat ggatttatga    2820
```

```
gatagggcc cctattatta accccgtttc acagatgggg taactgaggc ctcaagtaga    2880
cagggtcagt cggtgacaga gccagtcatc gaatcaggat gggctcactt caaatcctgt    2940
gctctcaaac cttttccagc cccatcacca gtcccagccc aaagtctctt gtgtggcctt    3000
gtcacattgc ttcacctcag cgggcctaag gtagggacaa taaaggccca ttgggactgg    3060 gggaagggt gataagataa aaataggag agcactgtca aggcagaagg gacagggctg    3120
gccaaggaaa gggggatagg aggggaccgg aggctgcagc catacaggac acagtttgtc    3180
ccttggtttc accagtgtca ctttctcgtc tctgctgctc agactcctgg gctgggctgg    3240
ggctggctgc agggagcccc ccttgcagta gcgtttctca ggctggccct ttaccaagga    3300
ccacagtgtc catgctgtct tggatcccta ggctggcaca gaaacagggg acccaggtgg    3360
ccctgagcac tcctcagagc aaaggtgctc tggaagcaga ctggacagag tgggcatgga    3420
atggggccag gagggtctgt taggaaggtt cagccaccct gtgaagctgg cacagataac    3480
agcactgctc tgttgtccct cggagcctct gagtaaccct gatggcactt cctaaggcag    3540
caggacatgt ggactgacca gcatcaaact gttgacatag aagaccattt ctattaccaa    3600
agggagtgta ccccattctg ctgccaaggg agcaaaccca tggccttacc acccagaaag    3660
agcccatcct ccacctccca tccccctcct gcatacatac ttcattacat gtttcccttt    3720
cattctgaag catcattgat gaccagctgc ctgtcagaca ctaagatagg cagtgggaat    3780
gaagagatgg atcttgtgtc atgcatggca tcacggagct ctgggttctg tacgagggt    3840 gggacagaca ggtagacaag caaataatta tgattatagc agatgactaa ggtgttgtcg    3900
ggagcttcag gaaaggaaga actaactctt ggggaggttc tcaggaagga tttccctgga    3960
aagtagccat gggacttgcg tcttaaatgg tgagtaaaag ctttctgagc aggggagtag    4020
gaaaagggct ttctatgcag aggagcactc agcgctggca ggaaattgga atcacccaag    4080
gagattatta aatattaaat attgatatga agtattgatg cccaatttca tctccagaaa    4140
ttctgatgta ttggtctagg gtgttgcctg gtcattggga tttttacaag ctcctcaagt    4200
gatcttaatg tgcaggcaag gttgaagccg ctggtctaag tggggtctgg tctacgataa    4260
gaaagtgact ttgagccatc gatttgggag acaggctctg ggtggatgtg tgtgtgtgca    4320
cacatatgta tgtatgtgga tgactaaaag tgcatgctct cctctccttt cccagcttcc    4380
tctccagcac agcaacttgt gttcgtatgc acacacatgc atactctctc tcatgggcac    4440
atgcataccc acacacacac tcgtgtacat ttccagaaaa tggaattaca tttcagatag    4500
attcagattc caacggcagt cttctaaaca cttttatgca agcagccatt caaggagacc    4560
ctcagcaaaa tataaatgac gaggagctgc cctcatgggg ccctgtgaaa gcactttgca    4620
gtccagcctt gggtttgtgg tcacagagtc acctgtggat gtttgtagca cactctcctt    4680
gtcttgtctg ctctgggtca ccaggcacag gccataaagg gatgagggg ccctctccag    4740 ggacccgcaa gatcttcctg ggtatgtctg catgaagccc cacgtgtgca cacccatctt    4800
catgtgtgtg tgtgccagcc tcctgctctc tgcagaacaa aaccagaagg aatggctctg    4860
ggagttggag atctcagctc acaggccaag ctttgcaaga ctctccaaag actgcccaca    4920
gactgtgctg cttcctgggt ctggcctgag actatcccag aagagagggt taaattctgg    4980
aggtgaggtt ttgagcaagt gttcatcccc ccacactatg ctccttcctg tctccatggc    5040
cacatccttc aaggctctgt gctgttctct tttttctgg attttctccac ctccaccaag    5100 ttccccttc tcacagctag tggaggcatg agtaggcagg tcccagggc tgggaactgg    5160 gtagcattgc catgtgcagg gactgtgttg ggagctgcag gtacagagct cctctgtgct    5220
```

-continued

```
caagagcttg ccggtgagcc tggacggagg cataggtgca gctaattagg ataagacagg    5280
ggccgcgctg tggtcagccg tgggaagccg gcgaggggac tggagttggg gctacacttg    5340
cctccctcct atgctgcttc ctgagccacg aagtggtcat tgccagcatc ccaggcaaca    5400
aacagcaaga ctcagacatc tccaaggaaa cccttttgagt ggatctgtac cgttgttctc   5460
```

```
caagagcttg ccggtgagcc tggacggagg cataggtgca gctaattagg ataagacagg    5280
ggccgcgctg tggtcagccg tgggaagccg gcgaggggac tggagttggg gctacacttg    5340
cctccctcct atgctgcttc ctgagccacg aagtggtcat tgccagcatc ccaggcaaca    5400
aacagcaaga ctcagacatc tccaaggaaa ccctttgagt ggatctgtac cgttgttctc    5460
gtcttgctct cttgctgccc tgccaccttc acagctgctt tctgtttcct ggttccagga    5520
agacagcggg gcacagggtc cctgctttgt gaggagcagc tggcttctcc ctttgccccc    5580
aggttttgcc ctcccacatg tctcccttct ggtgacccgg accccagaca aactatgcct    5640
gcctccctga agccaggcat cctgaggaac ttgatagaca aacaatgaca gtgttttcca    5700
gaactgtggg tacgtgtcta atctcagatg gtactatgaa ttcctggaga tcaaagtttg    5760
gatctaattc aaccccctgat cctcgaaacg gctttcttgc aaagtgtata tattggtttc    5820
tttgctgaat gaatgaataa aacatggaaa atgtggtaat tcaaaaaaaa aaa           5873
```

```
<210> SEQ ID NO 45
<211> LENGTH: 2779
<212> TYPE: DNA
<213> ORGANISM: Homo sapiens

<400> SEQUENCE: 45
ccggggaccg tttgtagtta ggatccgctg tggcgtcctg agtggagttt gggaccccag      60
ggagggaggg tgtgggcgtt cgggtccaga ggagctgttt agtatccaag atgaatgaca     120
gcctgtttgt cagtttggac agacttttgc tagaatttgt cttccagtat gagcaagaca     180
taagtactaa agaagagatg attcaaagaa ttaataaatg ctgtgaagat attaaggaaa     240
acaaagtaac tatttgtagg atacacgaaa ctataaatgc aacagatgag gaaattgatc     300
attactgtaa acatagtgag gagattaaag acaactgtag aaactggaag ccaacatgtg     360
atgtttttcg taaacatgaa gattatatgc aggaccaatt tactgtttat caaggaactg     420
ttgaaaaaga caaagaaatg tatcatgatt atatatgtca gtataaagaa gttttgaagc     480
agtaccaact aaaatactca gaaacaccct tttcacgtga atattatgag aagaaaagag     540
aacatgaaga aattcaaagc agagtgttgg catgtactga caattaaaaa atgaatgaaa     600
caatttttat gaaatttcga gtgcctgctc cctttccatc acttactaaa tggactttaa     660
acattgttaa tttgagatgt gaaacacaag atattcttaa acatgccagc aatcttacca     720
aaagttcatc cgaattgaag aaagaagtag atgaaatgga aatagaaatt aattatttaa     780
accagcagat atctaggcat aatgaaacta aggctctttc agaaactctg gaagaaaaga     840
acaaaaatac agaaaacaga aaagaactga agaaagaat ttttggaaaa gatgagcatg      900
tacttacatt gaataaaact caaagcagtc aattatttct tccttatgaa tctcagaaat     960
tagtaagacc aataaagatg cattcttcag aaccaagagt tgcagatata aagaagaaa     1020 gttctgcgaa gcagtcaaag cttgccaata ttgactttag acaaaaagaa aatgatacac    1080
agatatttaa tgactctgct gtggataacc attcaaaatg ttcacatatt acgactatca    1140
caagttcaca aaagtttatg caagtcagat tgttaacccc acagaaacaa tcaaattcca    1200
atcagtggtc ggaaaaaggg gataaagatg ctgagtatgg agataaaggg acagtaagac    1260
aagtaagaga atcaaaatgt acttcacaag ctatatatac tgaacatttt gggaagtcaa    1320
tagaaaatga tagtgatgaa gtagaagaga gagctgagaa ttttccacga acgtctgaaa    1380
ttcctatatt tttaggaact cccaaagctg tgaaagcacc tgagtcattg gagaaaataa    1440
```

-continued

```
aattccctaa aaccccccg ttcgaaatta acagaaatag aaatgcagta cctgaagttc      1500
aaacagaaaa ggaatcccct ggactttctt ttcttatgag ttatacttct agatcacctg      1560
gattgaattt atttgattct tctgtatttg atacagaaat ctcatcagat cagtttaatg      1620
aacattattc tgcaagaaat ctaaatcctc tgtcatcaga gcaagagatt ggaaacttac      1680
ttgagaagcc agaaggagaa gatggcttta cattttcttt tccatcagac acttcaactc      1740
atacatttgg agctgaaaaa gatgatttta gttttccatt tcatttgga cagggtcaaa      1800 attcaatacc ttcttcttct ttaaaaggtt tttcatcttc ctcacaaaat acaacacagt      1860
ttactttttt ttgagctagt cattaattcc ttaaattatt ttactgttct gtgttcatga      1920
gggcataaat ttacattatt gcttaaaaca tgaagactgc tttcttttat tgattaaagc      1980
agtaatgttt acattatttg attatattta ttgaaatatt gaaatactga atattttggg      2040
ttttgtgtgt gctattaact aatcattatt tattttggtt ttgattttgc gagccgtggt      2100
caggtagaac ttttattaat cttaatagaa tttgatgctt ttttcattac tctttattta      2160
aatattaagc ctgcttctcc ttggaaccta aggttttttt ctggaagtat tgttggtact      2220
ttgataagaa caagaactgc agtagtaact ccagagttag tgctgaagcg tactttagct      2280
actaaaaatt tctattaaaa ttattgggtt tcacttctgc ttcactatgt agtatacaga      2340
gtggtactgt aataataatt tcaaataatt tatgttaata acaaaatctg tgttattttc      2400
ttctaatata acacatggta caattctaat tttatgagtt atgctaatgc tttcaatggc      2460
taaaaattaa atgtaaaggg caagagtaat ttctgaaaat tggattgttg tatcagtggt      2520
gatcctgtta atattctttt ttgcttaaat atttttgaa gaacatttac aattttgtct      2580
ccttcaataa caaaaatttc ttctttatgt tttgtgttca gtatttgtca attaattata      2640
tagcttaagt gaagatattt aagatttgat gaacttctgt aaacattttg ctcaatatca      2700
ttgtattttg tgctttgtaa attagctgta ctgagttacc aagtaataaa gggtttgact      2760
ccaaaaaaaa aaaaaaaaa                                                    2779
```

<210> SEQ ID NO 46
<211> LENGTH: 2923
<212> TYPE: DNA
<213> ORGANISM: Homo sapiens

<400> SEQUENCE: 46

```
gtcgcgggag ctctctgatc cactcagggg tcagggcatc actggtctcg cgtgcgcgtg       60
accaggcccg gttccggtg ccaggacctt tccgaagcgt cgagtggcct aacggtcaca      120
gctgtcgccc atcggagagg caggactact gcgagcagtt ttaccgcgac ctccggaggc      180
cggcgtgaca ggctctgtca ctaaaatagg agtagaggtt taccactctt aggtgactaa      240
gcagtatcac aaataaaccc tccagcaagt ttaaaaataa ttaggtccaa ctcagaggaa      300
gtggagtttc tcctgttgca caaaaatgat gtctaacagc tccagtgaaa tcgatgtgat      360
aaaaacaaga ataccctactt acgatgaaga tgacaacact attctttatg cgtatgaaac      420
aaaacctgaa tttgtcaata agaaccgaa tattgtatct gacgcatcct gtaatactga      480
agagcaactg aagacagttg atgatgtcct tattcattgc caggttatat atgatgctct      540
gcaaaacctg gataagaaga ttgatgtgat tcgtagaaag gtttcaaaaa tccaacgttt      600
ccatgcgaga tccctgtgga caaatcataa gcgatatgga tataaaaagc attcttaccg      660
gcttgttaaa aagcttaaac tccagaaaat gaagaaaaat gaggtttacg agacattctc      720
ctaccctgaa agttacagcc ccactttacc agtgtcaagg cgtgagaata attccccgag      780
```

| | |
|---|---|
| caaccttcca aggccatcct tttgcatgga agaataccag cgagctgagc tggaggagga | 840 |
| cccgatcctc agccgcactc cgagtccagt gcatccctca gatttctctg agcataattg | 900 |
| tcagccgtat tatgcatctg atggtgcaac gtatggttct tcttcagggc tctgccttgg | 960 |
| caaccctcgg gctgacagca tccacaacac ttactcaact gaccatgctt ctgcagcacc | 1020 |
| accttcagtt acaaggtcac cagttgaaaa tgacggttac atagaggaag gaagcatcac | 1080 |
| taagcaccct tcaacctggt cggtggaagc agtggtccta tttctaaaac aaacagatcc | 1140 |
| tcttgcatta tgccctcttg tcgacctctt cagaagccat gaaattgacg ggaaggctct | 1200 |
| gctcctactc acgagtgacg tgttgctgaa gcacttgggg gtgaagctgg aacggctgt | 1260 |
| gaagctatgc tactacattg accgacttaa caaggaaaa tgctttgaaa attgaaaaaa | 1320 |
| tccttgtgca aatttagatt gggccaactt ctagaggcac caatgccttc ttagtgtgga | 1380 |
| atcattttc tgccctttag tcgttttgt tttgtagaaa gtatctctca aaatatatta | 1440 |
| tagctagaat tgtagaacta tgttatagtc cagtctactt cttttaaaaac catttaaact | 1500 |
| gctagatagt attagaatag tccaatagaa aattcattct ttataggtct ttaaaaatta | 1560 |
| cttttattat attgtttaca aatatatttc atgcaagaaa cagaaaaaaa aaaaaaccct | 1620 |
| ttgattctgg ttcatctcga tacagagaac caaaacagct aagagaggta ttatcagggt | 1680 |
| tgacaactcc tatgattgaa tctatgggaa ttattcctca gaagagaatt taaaggtgta | 1740 |
| cccatatata tctctttctg gagtatttta tctgtctgat gttgcagtat tctacaagtt | 1800 |
| tccagaaaga gaatagccat ataaattatt ttcctttctg ctattatttc tctatatgtt | 1860 |
| ttatttattc agatttagag taaaaaataa gcatataaac ttttattatg tgctcttaac | 1920 |
| agttttaaga taaactatag gatagataga atggttattt tatgcaagaa atattgtacc | 1980 |
| gcaagggtgg tttggatgaa gtctgactac ttttttttcaa acaaactatt atattaaaac | 2040 |
| tgtcatattt tggctaagtt tggacctata actacacttt cattgtttgc atctctctat | 2100 |
| gaagatacgt ctgtccaaac ttttaaaagg cataactgta ttttatgtgt ttattcttta | 2160 |
| tatagatagt attttatatt ttattctcac ccgaagtatt cacacaatct ttttaaaaaa | 2220 |
| aatttgaaat ggcattttgt attgccacag aggtaggatg agccatatat tagtgaaatg | 2280 |
| ttttattttg taaatataa atggattatt tgccatcatt agtacctctc aacttacttt | 2340 |
| ttagaggaca agaaacaatc tgtagattgg tttccataca gggaagttct ccgtcctatg | 2400 |
| caatgtttct aattaatttg cttaattctg agccattaat cctgctacac tttgaatgat | 2460 |
| acattaattc agactaatct ttgggggctt tattttgtaa gttagaactt tcaagggaaa | 2520 |
| catgttcaac actattattt tgttataaat ttataacttt gttattacat tgtgtaacaa | 2580 |
| atataaggtt tacgagctat gagaattggt gctatcacca ttagctattt gctgtaatgt | 2640 |
| caagaaaatg ttcaccagat gcaagaatgt accttttctt tttagaaagc caaatgtact | 2700 |
| ttagacatga atgcaactat ttaaagaata gcttcatcaa tgttattcct tacatgtcat | 2760 |
| aagattctta cttaaacttg gtcttctttc aaattgtttg tatgaagatg ctgtacccac | 2820 |
| ttgaacagtc ctcaggtgtt tacataaata ctatgtttta cagttttcat attttaaaat | 2880 |
| attaataaag ttaaatcaca atagttcaaa aaaaaaaaaa aaa | 2923 |

<210> SEQ ID NO 47
<211> LENGTH: 2842
<212> TYPE: DNA
<213> ORGANISM: Homo sapiens

<400> SEQUENCE: 47

```
gtcgcgggag ctctctgatc cactcagggg tcagggcatc actggtctcg cgtgcgcgtg          60
accaggcccg gtttccggtg ccaggacctt tccgaagcgt cgagtggcct aacggtcaca         120
gctgtcgccc atcggagagg caggactact gcgagcagtt ttaccgcgac ctccggaggc         180
cggcgtgaca ggctctgtca ctaaaatagg agtagaggtt taccactctt aggtgactaa         240
gcagtatcac aaataaaccc tccagcaagt ttaaaaataa ttaggtccaa ctcagaggaa         300
gtggagtttc tcctgttgca caaaaatgat gtctaacagc tccagtgaaa tcgatgtgca         360
ggaaccgaat attgtatctg acgcatcctg taatactgaa gagcaactga agacagttga         420
tgatgtcctt attcattgcc aggttatata tgatgctctg caaaacctgg ataagaagat         480
tgatgtgatt cgtagaaagg tttcaaaaat ccaacgtttc catgcgagat ccctgtggac         540
aaatcataag cgatatggat ataaaagca ttcttaccgg cttgttaaaa agcttaaact          600
ccagaaaatg aagaaaaatg aggtttacga cattctcc tacctgaaa gttacagccc            660
cactttacca gtgtcaaggc gtgagaataa ttccccgagc aaccttccaa ggccatcctt         720
ttgcatggaa gaataccagc gagctgagct ggaggaggac ccgatcctca gccgcactcc         780
gagtccagtg catccctcag atttctctga gcataattgt cagccgtatt atgcatctga         840
tggtgcaacg tatggttctt cttcagggct ctgccttggc aaccctcggg ctgacagcat         900
ccacaacact tactcaactg accatgcttc tgcagcacca ccttcagtta caaggtcacc         960
agttgaaaat gacggttaca tagaggaagg aagcatcact aagcacccctt caacctggtc       1020
ggtggaagca gtggtcctat ttctaaaaca aacagatcct cttgcattat gccctcttgt        1080
cgacctcttc agaagccatg aaattgacgg gaaggctctg ctcctactca cgagtgacgt        1140
gttgctgaag cacttggggg tgaagctggg aacggctgtg aagctatgct actacattga        1200
ccgacttaaa caaggaaaat gctttgaaaa ttgaaaaaat ccttgtgcaa atttagattg        1260
ggccaacttc tagaggcacc aatgccttct tagtgtggaa tcattttttct gcccctttagt      1320
cgttttttgtt ttgtagaaag tatctctcaa aatatattat agctagaatt gtagaactat       1380
gttatagtcc agtctacttc tttaaaaacc atttaaactg ctagatagta ttagaatagt        1440
ccaatagaaa attcattctt tataggtctt taaaaattac ttttattata ttgtttacaa        1500
atatatttca tgcaagaaac agaaaaaaaa aaaaccctt tgattctggt tcatctcgat         1560
acagagaacc aaaacagcta agagaggtat tatcagggtt gacaactcct atgattgaat         1620
ctatgggaat tattcctcag aagagaattt aaaggtgtac ccatatatat ctctttctgg        1680
agtatttat ctgtctgatg ttgcagtatt ctacaagttt ccagaaagag aatagccata         1740
taaattattt tccttctgc tattatttct ctatatgttt tatttattca gatttagagt         1800
aaaaaataag catataaact tttattatgt gctcttaaca gttttaagat aaactatagg        1860
atagatagaa tggttatttt atgcaagaaa tattgtaccg caagggtggt ttggatgaag        1920
tctgactact ttttttcaaa caaactatta tattaaaact gtcatatttt ggctaagttt       1980
ggacctataa ctacacttttc attgtttgca tctctctatg aagatacgtc tgtccaaact       2040
tttaaaaggc ataactgtat tttatgtgtt tattctttat atagatagta ttttatatttt      2100
tattctcacc cgaagtattc acacaatctt tttaaaaaaa atttgaaatg gcattttgta       2160
ttgccacaga ggtaggatga gccatatatt agtgaaatgt tttattttgt aaaatataaa       2220
tggattattt gccatcatta gtacctctca acttactttt tagaggacaa gaaacaatct       2280
gtagattggt ttccatacag ggaagttctc cgtcctatgc aatgtttcta attaatttgc       2340
```

```
ttaattctga gccattaatc ctgctacact ttgaatgata cattaattca gactaatctt    2400
tgggggcttt attttgtaag ttagaacttt caagggaaac atgttcaaca ctattatttt    2460
gttataaatt tataactttg ttattacatt gtgtaacaaa tataaggttt acgagctatg    2520
agaattggtg ctatcaccat tagctatttg ctgtaatgtc aagaaaatgt tcaccagatg    2580
caagaatgta cctttctctt ttagaaagcc aaatgtactt tagacatgaa tgcaactatt    2640
taaagaatag cttcatcaat gttattcctt acatgtcata agattcttac ttaaacttgg    2700
tcttctttca aattgtttgt atgaagatgc tgtacccact tgaacagtcc tcaggtgttt    2760
acataaatac tatgttttac agttttcata tttttaaaata ttaataaagt taaatcacaa    2820
tagttcaaaa aaaaaaaaaa aa                                              2842

<210> SEQ ID NO 48
<211> LENGTH: 825
<212> TYPE: DNA
<213> ORGANISM: Homo sapiens

<400> SEQUENCE: 48
gcatggcacc ccgcccctcc ttggccaaga aacaaaggtt taggcatcgc aaccgcaaag      60
gctaccgttc acaacgaggc cacagccgtg gccgcaacca gaactcccgc cggccatccc     120
gcgccacgtg gctgtccttg ttctccagtg aggagagcaa cttgggagcc aacaactatg     180
atgactacag gatggactgg cttgtgcctg ccacctgtga acccatccag agtgtcttct     240
tcttctctgg agacaagtac taccgagtca atcttcgcac acgacggtgg cagcgggttg     300
ggttcccacc ggagaaagcg gaccaccttc agcaaagggc agctactgga gctggagagg     360
gcgtttgcag catggcccta ccccaacatc agcacccatg agcacctggc ctgggtcact     420
tgccttcctg aggccaaggt acaggtgtgg ttccagaagc gctgggccaa ataatcaag     480 aacaggaagt caggaattct aagccctggg tctgagtgcc cccagagctc ctgttctctt     540
ccagacaccc tccagcagcc ctgggatccc caaatgccag gccaacctcc accctccagc     600
ggcacacctc agcgcacctc agtgtgtcga catagctcct gtccagctcc tggcttgagt     660
ccacggcagg gctgggaagg ggctaaagct gtagcccccat ggggatcagc tggggcttca     720
gaggtccacc cttctttaga gcgagctact ccccagactt cactaggcag cctgtctgac     780
ctcatctatg ccttggccat tgtcgtcaat gtggaccact cctag                     825

<210> SEQ ID NO 49
<211> LENGTH: 2028
<212> TYPE: DNA
<213> ORGANISM: Homo sapiens

<400> SEQUENCE: 49
gcgcgccaag cacttccgga agcggcggcg ctcgggagga agtgccgatc ggctgctggg      60
gcgaaagggg ggcgccgggc cgctctagcc ggtgaggccg gcgggctctc tgtggctgcg     120
gctgggaaac cgcgcggagg aggtgcccgg ccggggacca gccctggtcc agcgcctccc     180
tctctcagca tggacgagga gagcctggag tcggccttgc agacctaccg tgcgcagctg     240
cagcaggtgg agctggcctt gggcgccggc ctggattcgt ctgagcaggc tgacctgcgc     300
cagctgcagg gggacctgaa ggagctcatc gagctcaccg aggccagcct ggtgtctgtc     360
aggaagagca gcttgttggc cgcgctggac gaagagcgcc cgggccgcca ggaagatgct     420
gagtaccagg ctttccggga ggccatcact gaggcggtgg aggcaccagc agcggcccgt     480
```

| | |
|---|---|
| gggtccggat cagagaccgt tcctaaagca gaggcggggc cagaatctgc ggcaggtggg | 540 |
| caggaggagg aagagggaga ggacgaggaa gagctgagtg ggacaaaggt gagcgcgccc | 600 |
| tactacagct cctggggcac tctggagtat cacaacgcca tggtggtggg aacggaagag | 660 |
| gcggaggatg gctcggcggg tgtccgtgtg ctttacctgt accccactca caagtctctg | 720 |
| aagccgtgcc cgttcttcct ggagggaaag tgccgcttta aggagaactg caggttctcc | 780 |
| catgggcagg tggtctctct ggatgagctg cgcccctttcc aggacccaga cctgagctcc | 840 |
| ctgcaggccg gctctgcgtg tctggccaag caccaggatg gcctctggca cgcagcacgc | 900 |
| atcaccgatg tggacaacgg ctactacaca gtcaagtttg actcgctgct gctgagggag | 960 |
| gccgtggtgg aggggacgg catcctgccc ccactgcgca cagaggccac agagtccgac | 1020 |
| tcagacagcg acgtacgggg tgactccagc tatgccagag tggtggggtc ggacgccgtg | 1080 |
| gactctgcac agtcctctgc cctctgtccg tctcttgcag tggtggggtc agatgctgtg | 1140 |
| gactctggga cctgcagctc tgcctttgct ggctgggagg tgcacacgcg aggtataggc | 1200 |
| tccagactcc tcaccaagat gggctatgag tttggcaagg gtttgggccg acacgcggaa | 1260 |
| ggccgggtgg agcccatcca tgctgtggtg ttgcctcgag ggaagtcgct ggaccagtgt | 1320 |
| gtggagaccc tgcagaagca gaccagggtt ggcaaggctg gcaccaacaa gccccccagg | 1380 |
| tgccggggaa gaggggccag gcctgggggc cgcccagctc ctcggaatgt gtttgacttc | 1440 |
| ctcaatgaaa agctgcaagg tcaggctcct ggggccctag aagccggggc ggccccagcg | 1500 |
| gggaggagga gcaaggacat gtaccatgcc agcaagagtg ccaagcgggc cctgagcctg | 1560 |
| cggctcttcc agactgagga gaagatcgag cgaacccagc gggacatcag gagcatccag | 1620 |
| gaggctctcg cccgcaacgc tggccggcat agcgtggcgt cagcccagct gcaggagaag | 1680 |
| ctggcaggag cccagcgcca gctggggcag ctccgggctc aggaagccgg cctgcagcag | 1740 |
| gagcagagga aggcagacac ccacaagaag atgactgagt tctagagacc ccacaagcac | 1800 |
| tatggacgaa gcgtgggacc ccagcacggg ctgccctcag gaagaccagt gttgcccgag | 1860 |
| gaggggccgg cctgctggcc tggggcgtgc agacactgct gagtggagac agagctgcgg | 1920 |
| ggtcccatct ggacacttac ttgcccacct gccagtgtct tgggcatttc cttggcaagg | 1980 |
| acattaaagt gatttcatca cagtgtcaaa aaaaaaaaa aaaaaaaa | 2028 |

```
<210> SEQ ID NO 50
<211> LENGTH: 1898
<212> TYPE: DNA
<213> ORGANISM: Homo sapiens

<400> SEQUENCE: 50
```

| | |
|---|---|
| gcgcgccaag cacttccgga agcggcggcg ctcgggagga agtgccgatc ggctgctggg | 60 |
| gcgaaaaggg ggcgccgggc cgctctagcc gccctggtcc agcgcctccc tctctcagca | 120 |
| tggacgagga gagcctggag tcggccttgc agacctaccg tgcgcagctg cagcaggtgg | 180 |
| agctggcctt gggcgccggc ctggattcgt ctgagcaggc tgacctgcgc cagctgcagg | 240 |
| gggacctgaa ggagctcatc gagctcaccg aggccagcct ggtgtctgtc aggaagagca | 300 |
| gcttgttggc cgcgctggac gaagagcgcc cgggccgcca ggaagatgct gagtaccagg | 360 |
| cttttccggga ggccatcact gaggcggtgg aggcaccagc agcggcccgt gggtccggat | 420 |
| cagagaccgt tcctaaagca gaggcggggc cagaatctgc ggcaggtggg caggaggagg | 480 |
| aagagggaga ggacgaggaa gagctgagtg ggacaaaggt gagcgcgccc tactacagct | 540 |
| cctggggcac tctggagtat cacaacgcca tggtggtggg aacggaagag gcggaggatg | 600 |

| | |
|---|---|
| gctcggcggg tgtccgtgtg ctttacctgt accccactca caagtctctg aagccgtgcc | 660 |
| cgttcttcct ggagggaaag tgccgcttta aggagaactg caggttctcc catgggcagg | 720 |
| tggtctctct ggatgagctg cgccccttcc aggacccaga cctgagctcc ctgcaggccg | 780 |
| gctctgcgtg tctggccaag caccaggatg gcctctggca cgcagcacgc atcaccgatg | 840 |
| tggacaacgg ctactacaca gtcaagtttg actcgctgct gctgagggag gccgtggtgg | 900 |
| aggggacgg catcctgccc ccactgcgca cagaggccac agagtccgac tcagacagcg | 960 |
| acggtacggg tgactccagc tatgccagag tggtggggtc agatgctgtg gactctggga | 1020 |
| cctgcagctc tgcctttgct ggctgggagg tgcacacgcg aggtataggc tccagactcc | 1080 |
| tcaccaagat gggctatgag tttggcaagg gtttgggccg acacgcggaa ggccgggtgg | 1140 |
| agcccatcca tgctgtggtg ttgcctcgag ggaagtcgct ggaccagtgt gtggagaccc | 1200 |
| tgcagaagca gaccagggtt ggcaaggctg gcaccaacaa gccccccagg tgccggggaa | 1260 |
| gaggggccag gcctggggc cgcccagctc ctcggaatgt gtttgacttc ctcaatgaaa | 1320 |
| agctgcaagg tcaggctcct ggggccctag aagccggggc ggccccagcg gggaggagga | 1380 |
| gcaaggacat gtaccatgcc agcaagagtg ccaagcgggc cctgagcctg cggctcttcc | 1440 |
| agactgagga gaagatcgag cgaacccagc gggacatcag gagcatccag gaggctctcg | 1500 |
| cccgcaacgc tggccggcat agcgtggcgt cagcccagct gcaggagaag ctggcaggag | 1560 |
| cccagcgcca gctggggcag ctccgggctc aggaagccgg cctgcagcag gagcagagga | 1620 |
| aggcagacac ccacaagaag atgactgagt tctagagacc ccacaagcac tatgacgaa | 1680 |
| gcgtgggacc ccagcacggg ctgccctcag gaagaccagt gttgcccgag gaggggccgg | 1740 |
| cctgctggcc tggggcgtgc agacactgct gagtggagac agagctgcgg ggtcccatct | 1800 |
| ggacacttac ttgcccacct gccagtgtct tgggcatttc cttggcaagg acattaaagt | 1860 |
| gatttcatca cagtgtcaaa aaaaaaaaaa aaaaaaaa | 1898 |

<210> SEQ ID NO 51
<211> LENGTH: 1596
<212> TYPE: DNA
<213> ORGANISM: Homo sapiens

<400> SEQUENCE: 51

| | |
|---|---|
| cgttgctcag tctcagtgtg gtctctgttt tgcaactggt cgtccgcgtc aggagactta | 60 |
| ggtccaggcg actgcccaga caatgactgg tcccgcatac cgagcagagc atgatcagca | 120 |
| gcagtctgag tggaagagtg cctgtgatct tagggaacct gatgggcgtt ggagcagcgg | 180 |
| ttcgacgcat gggtttctct ttaatccttc cgacttcccc aagcccagcg cactcaggtt | 240 |
| ccgctccaag tgcgggaccc gcccggggtg tgtcggggt actcggccgg aggcggccgg | 300 |
| tgagtgaggc ttacagggcc ccgggaccaa ggaacccag catgttaatt gaacttgatc | 360 |
| acccagttga aggaagaata atagtagatg ttggatcttc aggaagctga agagggcagt | 420 |
| gcccagaaat acctgtcttg ataggggat ttgagctgaa ccaaagcatc aacaccaatc | 480 |
| agactgtttc cgaagaacta gagttttctg ggtcagcaat ggaaagcctc agagggaata | 540 |
| ctgctcaggg tcctacaaat gaagaagact ataaaaacga aggccaatta tcaaggcaaa | 600 |
| caaaatgtcc tgcacagaag aaatcctctt ttgagaacac agtggtcaga aaagtgtcag | 660 |
| tgacactcaa agaatttttc acaggggagg aaggccctga atccagtgaa tttagtctaa | 720 |
| gcccaaacct tgacgcacaa cagaaaattc caaagggaca tggatcccca atatctagga | 780 |

```
aaaactccaa agataattca gacttaatta aacaccaaag acttttctca caaagaaaac    840
cttgtaaatg caatgaatgt gaaaaagcct ttagttacca atcagacctt cttgtacaca    900
gtagaattca tggtggagaa aagccttttg aatgcaacaa atgtgggaaa tctttcagcc    960
gaagtacaca ccttattgaa catcaaagaa ctcacactgg agagaaacct tatgaatgca   1020
atgaatgtgg aaaagctttt agccggagca cacatcttag tctacatcag agaatccata   1080
ctggagaaaa accatatgaa tgtagtgaat gtggaaaagc ctttagccga agcactaacc   1140
ttagtcagca tcagcgaact catactcaag aaaggcctta caaatgtaat gaatgtggga   1200
aagccttcgg tgaccgttca accataattc agcatcaacg aatacacact ggagagaatc   1260
cctatgaatg cagtaaatgt ggaaaagctt tcagttggat ctcatcgctt actgaacatc   1320
agagaacaca cactggggag aacccctatg agtgcagtga atgtgggaaa gtgttcagtc   1380
gaagctcgtc tcttacagaa catcagagaa tccacagtgg agaaaagcct cacgagtgta   1440
gagtgtgtgg aaagggcttc agtcgaagct catcccttat tattcatcag agaactcata   1500
ccggggagaa gccgtacaaa tgtaatgact gtggaaaagc ttctgtcag agttcaactc   1560 tgatcagaca tcagcacctt catactaaag agtaat                             1596
```

<210> SEQ ID NO 52
<211> LENGTH: 2320
<212> TYPE: DNA
<213> ORGANISM: Homo sapiens

<400> SEQUENCE: 52

```
gtgagcgcct gagagtcttt ttgcctttca gagttaaggc ctcactggcc tgggaaaata     60
attgctgcct tttgcatccg cgttggctcc gtccccagga tcttcccggt tcagggacct    120
ggcgatttct gagtgttccg gaatcccaat aaccctgttt aaagaggaat ggagattgcc    180
actgtccatt tagattaatg aggtgtcctg aagtgatggt gacatcaatg aaaggagggt    240
tctgacacgt tctcacctcg cgggatggca gctgctgatt tgtcccatgg acattatctt    300
tctggggacc cagtttgcct tcatgaagaa aagacaccag caggaagaat agtggctgac    360
tgcctaacag attgttatca ggattcagtg acctttgacg atgtggctgt ggacttcacc    420
caggaggagt ggactttact ggactcaact cagagaagcc tctacagtga cgtgatgctg    480
gagaactaca gaacctggc cacagtagga ggtcagatca tcaaacccag tctaatctct    540
tggttggaac aagaagagtc aaggacagtt cagggaggag ttctccaagg atgggaaatg    600
cgacttgaaa cccagtggtc tatacttcag caggactttt tgaggggtca gacatccatt    660
gggatacaat tggaaggaaa acacaatgga agggaactct gtgactgtga gcaatgtgga    720
gaagtcttca gtgaacactc atgccttaag acgcacgtga aactcaaag tacagggaac    780 actcatgact gtaatcagta tggaaaagat ttccttaccc tgtgtgagaa aacctctact    840
ggtgagaaac tttctgagtt taatcagagt gaaaaaatct tcagcctgac accaaatatt    900
gtataccaga gaactagcac acaagaaaag tcatttgaat gtagtcactg tggaaaatcc    960
ttcattaatg agtcataccct tcaggcacat atgagaactc acaatggaga aaaactctac   1020
gaatggagga attatgggcc aggttttatt gactctacaa gcctttctgt gcttatagaa   1080
accctcaatg caaaaaagcc ctacaaatgt aaggaatgtg gaaaaggcta tagatacccca  1140 gcctacctca gtattcacat gcgaaccccac actggggaga aaccatatga atgtaaggaa   1200
tgtgggaaag ccttcaatta ttccaactca tttcagatac atggaagaac tcacactgga   1260
gagaaaccct atgtatgtaa ggaatgtggg aaagccttca ctcagtactc gggccttagt   1320
```

```
atgcatgtac gatctcacag tggagacaag ccctatgaat gtaaggaatg tgggaaatcc    1380
ttccttacat cctcacgcct tattcaacat ataagaactc acactggaga gaagccttt     1440 gtatgtgttg aatgtgggaa agcctttgca gtttcctcaa atcttagtgg acatttgaga    1500
actcacactg aagagaaggc ctgtgagtgt aagatatgtg ggaaagtatt tgggtatccc    1560
tcatgtctta ataatcacat gcgaacgcac agtgcccaga aaccatacac ctgtaaggaa    1620
tgtgggaagg cttttaacta ttccacccac cttaaaattc acatgcgaat ccacactgga    1680
gaaaaaccct atgagtgtaa acaatgtgga aaggccttca gtcattccag ttcatttcaa    1740
atacatgaaa ggactcacac tggagagaaa ccctatgaat gcaaggagtg tgggaaagcc    1800
ttcacgtgtt ccagttcctt tagaattcat gaaaaaactc acacagaaga gaaaccctat    1860
aaatgtcagc aatgcgggaa agcttacagt catccccgtt cacttcgaag acatgaacaa    1920
attcactagt gagaaactgt ccatgtaata aatgtgggaa agctctcatt tgttccagtt    1980
cactttaaag acatgaatga actcactctg gagagaagaa gctgcatgaa aattacttaa    2040
ttcctgtaat cccagcattt tgagaggctg aggtgggtgg atcacttgag gtcaggagtt    2100
tgagaccacc ctggccaaca tggtgaaacc ttgtctctac tgaaaataca aaaaatttag    2160
ccaggtgtgg tgggcacctg taatcccagc tacttgggag gctgaggcaa gtgaatcact    2220
tgaacccagg aagcagaggt tgcagtgagc agagatcatg ccactgcact ccagcctggg    2280
cgatggagtg agactccatc tcaaaaaaaa aaaaaaaaa                           2320
```

<210> SEQ ID NO 53
<211> LENGTH: 2335
<212> TYPE: DNA
<213> ORGANISM: Homo sapiens

<400> SEQUENCE: 53

```
ggaaccggag cctgagagcc gggcgccgtg cgctcctccc cgcgctgtct cggcggccca     60
ggaattcact gtctgtagca tctgctcctc cacagaggga ccctggaatg gcgatggcac    120
tcccgatgcc tggacctcag gaggcggttg tgttcgagga tgtggctgtg tacttcacaa    180
ggatagagtg gagttgcctg gcccccgacc agcaggcact ctacagggac gtgatgctgg    240
agaactatgg gaacctggcc tcactaggct ttcttgttgc caaaccagca ctgatctccc    300
tattggagca aggagaggag ccgggggcct tgattctgca ggtggctgaa cagagcgtgg    360
ccaaagccag cctgtgcaca gattccagga tggaggctgg gatcatggag tctcctctgc    420
agagaaagct ctccaggcag gcaggactgc cgggcaccgt gtgggggtgc ctcccctggg    480
ggcaccctgt gggggggcac cctgcaccac cccacccgca tggcggtcct gaggacgggt    540
cagataaacc caccacccc cgggctcggg agcacagcgc ctccccaagg gttctgcagg    600
aagacctggg ccggcctgtg gggagctcag cccccgcta caggtgcgtg tgcggcaagg    660
cgttcagata caactcgctg cttctcaggc accagatcat ccacaccggc gccaagccct    720
tccagtgcac agagtgcggg aaggccttca gcaaagctc catcctgctg cggcaccagc    780
tgatccacac tgaggagaag ccgttccagt gcggcgagtg cgggaaggcc ttccggcaga    840
gcacgcagct ggctgcccac accgcgtcc acacccgcga gcggccctac gcatgcggcg    900 agtcggcaa ggccttcagc cgcagctccc ggctgctgca gcaccagaag ttccacaccg    960
gggagaagcc cttcgcgtgc acagagtgcg gcaaggcgtt ctgccgcagg ttcaccctca   1020
acgagcacgg ccgcatccac agcggggagc ggccctaccg gtgcctgcgg tgtgggcagc   1080
```

```
gcttcatccg agggtcctcg ctcctgaagc accaccggct gcacgcgcag gagggtgccc    1140
aggacggcgg cgtggggcag ggcgccctgc tcggagctgc gcagaggccc caggcggggg    1200
acccgcccca cgagtgcccg gtgtgcggga ggccgttccg acacaactcc ctgctgctgc    1260
tgcacctgcg cctacacacg ggcgagaagc cgttcgagtg cgcggagtgc ggcaaggcct    1320
tcggtcgcaa gtccaacctc actctgcacc agaagatcca caccaaggag aagcccttcg    1380
cgtgcaccga gtgcggcaag gcgttccgca ggagctacac gctgaacgag cactaccggc    1440
tccacagcgg cgagaggcca taccggtgcc gcgcctgcgg gagggcctgc agccggctgt    1500
ccaccctcat ccagcaccag aaggtgcacg gccgcgagcc cggggaggac acagagggca    1560
ggcgggcgcc ctgttgggct tcctgatgac ggggacgaca ggccgaggat tcacgctgga    1620
agcccaccca agccggcggg gccctagcgc agaaattcag aacccctgt cctgaaggtg     1680 aagcaaagtc taaagaaagg gccagctccc atcaggagct cggcttcttg ctccagccgg    1740
gcactgggga gggaaagggc accaggcagc ccgtggtgtg gcctcaggaa ccactatcag    1800
ccaccatttc ctggggcctt ccggaaatgt ccaggagcgg gcagaaggga gagagggagg    1860
ggcagctatg ctcagtcccc aaagagcagg gcacaggggg cgccacagac gcatatgcag    1920
ctgagctccc cacaggccgg cccgggtctt cgtgcagaac cattgggcac agccaggcct    1980
tagcgccagg ctccgtgtgg cggtcaattc caggtgctgt aaagccgact aacagggtac    2040
agggagcctt agctggctgc catgtctcct gcctgtaatc ccatcacttt gggaggctga    2100
ggtgggaggt ttgcttaagc ccaggagttt gagaccagct tgggcaacat ggtgaaactt    2160
ctctacaaaa aatttaaaaa taagtcaggt atcgtggtct gtgcctgtac gctgtagtcc    2220
cagctactca ggaggctgag gtgggaggat gggttgagcc tgggaagtca aggctgcagt    2280
gagctatgat agcaccacgg cactccaacc tggttgacag agtgacaccc tgttt          2335
```

HEPATOCYTE PRODUCTION BY FORWARD PROGRAMMING

The present application is a divisional of U.S. application Ser. No. 13/086,159, filed Apr. 13, 2011, which claims the priority benefit of U.S. Provisional Application No. 61/323,689, filed Apr. 13, 2010. The entire contents of each of the above referenced disclosures are incorporated herein by reference.

BACKGROUND OF THE INVENTION

1. Field of the Invention

The present invention relates generally to the field of molecular biology, stem cells and differentiated cells. More particularly, it concerns programming of somatic cells and undifferentiated cells toward specific cell lineages, particularly hepatic lineage cells.

2. Description of Related Art

In addition to their use in the transplantation therapies to treat various liver diseases, human hepatocytes are in high demand for drug toxicity screening and development due to their critical functions in the detoxification of drugs or other xenobiotics as well as endogenous substrates. Human primary hepatocytes, however, quickly lose their functions when cultured in vitro. Moreover, the drug metabolic ability of human primary hepatocytes exhibits significant difference between different individuals. The availability of an unlimited supply of patient-specific functional hepatocytes would greatly facilitate both the drug development and the eventual clinical application of hepatocyte transplantation.

Therefore, there is a need for production of hepatic lineage cells in therapeutic and research use, especially, human hepatocytes.

SUMMARY OF THE INVENTION

The present invention overcomes a major deficiency in the art in providing hepatocytes by forward programming to provide an unlimited supply of patient-specific hepatocytes. In a first embodiment there is provided a method of providing hepatocytes by forward programming of a variety of cell types, including somatic cells or stem cells. Forward programming into hepatocytes may comprise increasing the expression level of a sufficient number of hepatocyte programming factor genes capable of causing forward programming of non-hepatocytes to hepatocytes.

In another embodiment, there may also be provided a method of directly programming non-hepatocytes, such as differentiation of pluripotent stem cells, into hepatocytes, comprising increasing expression of a sufficient number of hepatocyte programming factor genes (e.g., genes in Table 1 and variants and isoforms thereof) capable of causing forward programming to a hepatic lineage or to hepatocyte cells, therefore directly programming the cells into hepatocytes.

"Forward programming," as used herein, refers to a process having essentially no requirement to culture cells through intermediate cellular stages using culture conditions that are adapted for each such stage and/or, optionally, having no need to add different growth factors during different time points between the starting cell source and the desired end cell product, e.g., hepatocytes, as exemplified in the upper part of FIG. 1. The terms "direct programming" or "direct differentiation," as used in the priority application provisional application 61/323,689, are intended to be commensurate with the term "forward programming," as used in the present application. "Forward programming" may include programming of a multipotent or pluripotent cell, as opposed to a differentiated somatic cell that has lost multipotency or pluripotency, by artificially increasing the expression of one or more specific lineage-determining genes in a multipotent or pluripotent cell. For example, forward programming may describe the process of programming embryonic stem cells (ESCs) or induced pluripotent stem cells (iPSCs) to hepatocyte-like cells or other differentiated precursor or somatic cells. In certain other aspects, "forward programming" may refer to "trans-differentiation," in which differentiated cells are programmed directly into another differentiated cell type without passing through an intermediate pluripotency stage.

On the other hand, the bottom part of FIG. 1 demonstrates various developmental stages present in a step-wise differentiation process and the need to add different growth factors at different times during the process, which costs more labor, time and expenses than methods described in certain aspects of the current invention. Therefore, the methods of forward programming in certain aspects of the present invention are advantageous by avoiding the need to add different growth factors at different stages of programming or differentiation to improve efficiency. For example, the medium for culturing the cells to be programmed or progeny cells thereof may be essentially free of one or more of fibroblast growth factors (FGFs), epidermal growth factors (EGFs), and nicotinamides, which are normally required for progressive programming (i.e., directed differentiation as defined below) along different developmental stages.

Forward programming as used in certain aspects of the present invention may be different from directed differentiation. In directed differentiation, growth factors or small molecules are added to the culture medium, thereby indirectly causing an increased expression of the endogenous genes. In directed differentiation, the added growth factors or small molecules signal though cell surface proteins and surface protein-mediated signaling to activate endogenous pathways toward the lineage desired. To the contrary, in forward programming, the programming factors that normally are only intra-cellular (e.g., transcription factors) are forced to have an increased expression by introducing or inducing the gene expression cassette or by being added directly (e.g., in the form of polypeptides or RNAs), thereby directly activating the programming factor genes for differentiation directly and by-passing the cell surface proteins and surface protein-mediated signaling pathways. These means for increasing the expression of programming factors may be defined as "artificial," and may be different from the directed differentiation which comprises adding growth factors or small molecules to the medium thereby indirectly causing increased expression of endogenous programming factor genes.

Sources of cells suitable for hepatic forward programming may include any stem cells or non-hepatocyte somatic cells. For example, the stem cells may be pluripotent stem cells or any non-pluripotent stem cells. The pluripotent stem cells may be induced pluripotent stem cells, embryonic stem cells, or pluripotent stem cells derived by nuclear transfer or cell fusion. The stem cells may also include multipotent stem cells, oligopotent stem cells, or unipotent stem cells. The stem cells may also include fetal stem cells or adult stem cells, such as hematopoietic stem cells, mesenchymal stem cells, neural stem cells, epithelial stem cells, skin stem cells. In certain aspects, the stem cells may be isolated from umbilical, placenta, amniotic fluid, chorion villi, blastocysts, bone marrow, adipose tissue, brain, peripheral blood, cord blood, menstrual blood, blood vessels, skeletal muscle, skin and liver.

In other aspects, hepatocytes may be produced by transdifferentiation of non-hepatocyte somatic cells. The somatic cells for hepatic lineage programming can be any cells forming the body of an organism other than hepatocytes. In some embodiments, the somatic cells are human somatic cells such as skin fibroblasts, adipose tissue-derived cells and human umbilical vein endothelial cells (HUVEC). In a particular aspect, the somatic cells may be immortalized to provide an unlimited supply of cells, for example, by increasing the level of telomerase reverse transcriptase (TERT). This can be effected by increasing the transcription of TERT from the endogenous gene, or by introducing a transgene through any gene delivery method or system.

Hepatocyte programming factor genes include any genes that, alone or in combination, directly impose hepatic fate upon non-hepatocytes, especially transcription factor genes or genes that are important in hepatic differentiation or hepatic function when expressed in cells. For example, one, two, three, four, five, six, seven, eight, nine, ten, or more of the exemplary genes and isoforms or variants thereof as listed in Table 1 may be used in certain aspects of the invention. Many of these genes have different isoforms, which might have similar functions and therefore are contemplated for use in certain aspects of the invention.

In a particular embodiment, the hepatocyte programming factor genes used herein may comprise one, two, three, four, five, or six of Forkhead box protein A1 (FOXA1), forkhead box A2 (FOXA2) (e.g., FOXA2-2; NM_153675.2), hematopoietically-expressed homeobox protein (HHEX), hepatocyte nuclear factor 1 homeobox A (HNF1A), hepatocyte nuclear factor 4 alpha (HNF4A) (e.g., HNF4A-2; NM_000457.3), GATA binding protein 4 (GATA4), NR0B2 (nuclear receptor subfamily 0, group B, member 2), sex comb on midleg-like 1 (SCML1), and T-box transcription factor (TBX3) (e.g., TBX3-1; NM_005996.3). In a more particular aspect, the hepatocyte programming factor genes include FOXA2, HHEX, HNF1A, and HNF4A. For example, the hepatocyte programming factor genes may be a combination of FOXA1, FOXA2, HHEX, HNF1A, HNF4A and TBX3. In another example, the hepatocyte programming factor genes may be a combination of FOXA2, HHEX, HNF4A, GATA4, NR0B2 and SCML1.

In certain aspects, there is provided a method of providing hepatocytes by forward programming of pluripotent stem cells, comprising: providing the hepatocytes by culturing the pluripotent stem cells under conditions to increasing the expression level of a sufficient number of hepatocyte programming factor genes capable of causing forward programming of the stem cells (e.g., pluripotent stem cells) to hepatocytes, thereby causing the pluripotent stem cells to directly differentiate into hepatocytes.

The skilled artisan will understand that methods for increasing the expression of the hepatocyte programming factor genes in the cells to be programmed into hepatocytes may include any method known in the art, for example, by induction of expression of one or more expression cassettes previously introduced into the cells, or by introduction of nucleic acids such as DNA or RNA, polypeptides, or small molecules to the cells. Increasing the expression of certain endogenous but transcriptionally repressed programming factor genes may also reverse the silencing or inhibitory effect on the expression of these programming factor genes by regulating the upstream transcription factor expression or epigenetic modulation.

In one aspect, the cells for hepatic lineage programming may comprise at least one exogenous expression cassette, wherein the expression cassette comprises the hepatocyte programming factor genes in a sufficient number to cause forward programming or transdifferentiation of non-hepatocytes to hepatocytes. The exogenous expression cassette may comprise an externally inducible transcriptional regulatory element for inducible expression of the hepatocyte programming factor genes, such as an inducible promoter comprising a tetracycline response element.

In a further aspect, one or more of the exogenous expression cassette for hepatocyte programming may be comprised in a gene delivery system. Non-limiting examples of a gene delivery system may include a transposon system, a viral gene delivery system, or an episomal gene delivery system. The viral gene delivery system may be an RNA-based or DNA-based viral vector. The episomal gene delivery system may be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or the like.

In another aspect, the cells for hepatic lineage programming may be contacted with hepatocyte programming factors in an amount sufficient to cause forward programming of the stem cells to hepatocytes. The hepatocyte programming factors may comprise gene products of the hepatocyte programming factor genes. The gene products may be polypeptides or RNA transcripts of the hepatocyte programming factor genes. In a further aspect, the hepatocyte programming factors may comprise one or more protein transduction domains to facilitate their intracellular entry and/or nuclear entry. Such protein transduction domains are well known in the art, such as an HIV TAT protein transduction domain, HSV VP22 protein transduction domain, *Drosophila* Antennapedia homeodomain or variants thereof.

The method may further comprise a selection or enrichment step for the hepatocytes provided from forward programming or transdifferentiation. To aid selection or enrichment, the cells for programming, such as the pluripotent stem cells or progeny cells thereof, may comprise a selectable or screenable reporter expression cassette comprising a reporter gene. The reporter expression cassette may comprise a hepatocyte-specific transcriptional regulatory element operably linked to a reporter gene. Non-limiting examples of hepatocyte-specific transcriptional regulatory element include a promoter of albumin, α-1-antitrypsin (AAT), cytochrome p450 3A4 (CYP3A4), apolipoprotein A-I, or apoE. Mature hepatocyte-specific transcriptional regulatory element may comprise a promoter of albumin, Δ1-antitrypsin, asialyglycoprotein receptor, cytokeratin 8 (CK8), cytokeratin 18 (CK18), CYP3A4, fumaryl acetoacetate hydrolase (FAH), glucose-6-phosphates, tyrosine aminotransferase, phosphoenolpyruvate carboxykinase, and tryptophan 2,3-dioxygenase.

Characteristics of the hepatocytes provided in certain aspects of the invention include, but are not limited to one or more of: (i) expression of one or more hepatocyte markers including glucose-6-phosphatase, albumin, α-1-antitrypsin (AAT), cytokeratin 8 (CK8), cytokeratin 18 (CK18), asialoglycoprotein receptor (ASGR), alcohol dehydrogenase 1, arginase Type I, cytochrome p450 3A4 (CYP3A4), liver-specific organic anion transporter (LST-1), or a combination thereof; (ii) activity of liver-specific enzymes such as glucose-6-phosphatase or CYP3A4, production of by-products such as bile and urea or bile secretion, or xenobiotic detoxification; (iii) hepatocyte morphological features; or (iv) in vivo liver engraftment in an immunodeficient subject.

For selection or enrichment of the hepatocytes, there may be further provided a step by identifying hepatocytes comprising expression of a hepatic reporter gene or one or more hepatocyte characteristics as described herein.

In particular aspects, the hepatocytes provided herein may be mature hepatocytes. The mature hepatocytes may be selected or enriched by using a screenable or selectable reporter expression cassette comprising a mature hepatocyte-specific transcriptional regulatory element operably linked to a reporter gene, or magnetic cell sorting using antibody against hepatocyte-specific cell surface antigens such as ASGR, or by assessing characteristic specific for mature hepatocytes as known in the art. For example, mature hepatocytes can be identified by one or more of: the presence of hepatocyte growth factor receptor, albumin, α1-antitrypsin, asialoglycoprotein receptor, cytokeratin 8 (CK8), cytokeratin 18 (CK18), CYP3A4, fumarylacetoacetate hydrolase (FAH), glucose-6-phosphates, tyrosine aminotransferase, phosphoenolpyruvate carboxykinase, and tryptophan 2,3-dioxygenase, and the absence of intracellular pancreas-associated insulin or proinsulin production. In further aspects, hepatocyte-like cells provided herein may be further forward programmed into mature hepatocytes by the artificially increased expression of genes detailed in Table 1.

For production of more mature hepatocytes, the starting cell population may be cultured in a medium comprising one or more growth factors such as Oncostain M (OSM), or further comprising hepatocyte growth factor (HGF). The culturing may be prior to, during, or after the effected expression of hepatocyte programming factors. Hepatocytes may be provided at least, about or up to 3, 4, 5, 6, 7, 8, 9, 10, 11, 12, 13, 14, 15, 16, 17, 18, 19, 20 days (or any range derivable therein) after the increased expression or culturing in the presence or absence of growth factors.

In a further embodiment, a hepatocyte may be produced by any of the methods set forth herein. In certain aspects, there may also be provided a tissue engineered liver comprising the hepatocytes provided by the methods described herein. In another aspect, there may be provided a hepatocyte-based bio-artificial liver (BAL) comprising the hepatocytes.

In certain aspects, the invention provides a cell comprising one or more exogenous expression cassettes comprising one or more hepatocyte programming factor genes (e.g., genes in Table 1 and isoforms or variants thereof). The exogenous expression cassettes may comprise two, three, four, five or six of the hepatocyte programming factor gene. For example, the exogenous expression cassettes may comprise FOXA2, HNF4A and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, ZNF391. In a particular example, the exogenous expression cassettes comprise FOXA1, FOXA2, HHEX, HNF1A, HNF4A, and TBX3. In another example, the hepatocyte programming factor genes may be a combination of FOXA2, HHEX, HNF4A, GATA4, NR0B2 and SCML1.

For inducible expression of the hepatocyte programming factor genes, at least one of the exogenous expression cassettes may comprise an externally inducible transcriptional regulatory element. In particular aspects, there may be provided a cell comprising one or more exogenous expression cassettes, wherein the one or more exogenous expression cassettes comprise FOXA2, HNF4A and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, ZNF391, and at least one of the exogenous expression cassettes is operably linked to an externally inducible transcriptional regulatory element.

The exogenous expression cassettes may be comprised in one or more gene delivery systems. The gene delivery system may be a transposon system; a viral gene delivery system; an episomal gene delivery system; or a homologous recombination system such as utilizing a zinc finger nuclease, a transcription activator-like effector (TALE) nuclease, or a meganuclease, or the like. The cell may further comprise a screenable or selectable reporter expression cassette comprising a hepatocyte-specific promoter operably linked to a reporter gene. The hepatocyte-specific transcriptional regulatory element may be a promoter of albumin, α-1-antitrypsin (AAT), cytochrome p450 3A4 (CYP3A4), apolipoprotein A-I, apoE, or any other hepatocyte-specific promoter or enhancer in the art.

In one aspect, the cell may be a stem cell or a progeny cell thereof. The stem cell may be a pluripotent stem cell or any non-pluripotent stem cell. The pluripotent stem cell may be an induced pluripotent stem cell, an embryonic stem cell, or a pluripotent stem cell derived by nuclear transfer or cell fusion. The stem cell may also be a multipotent stem cell, oligopotent stem cell, or unipotent stem cell. The stem cell may also be a fetal stem cell or an adult stem cell, for example, a hematopoietic stem cell, a mesenchymal stem cell, a neural stem cell, an epithelial stem cell or a skin stem cell. In another aspect, the cell may be a somatic cell, either immortalized or not. The cell may also be a hepatocyte, more particularly, a mature hepatocyte or an immature hepatocyte (e.g., hepatocyte-like cell).

There may also be provided a composition comprising a cell population comprising two cell types, i.e., the cells to be programmed to hepatocytes and hepatocytes, and essentially free of other intermediate cell types. For example, such a cell population may have two cell types including the stem cells and hepatocytes but essentially free of other cells types in the intermediate developmental stages along the hepatic differentiation process. In particular, a composition comprising a cell population consisting of stem cells and hepatocytes may be provided. The stem cells may be particularly pluripotent stem cells, e.g., induced pluripotent stem cells. Hepatocytes may be at least, about, or up to 1, 5, 10, 15, 20, 25, 30, 35, 40, 45, 50, 60, 70, 80, 85, 90, 91, 92, 93, 94, 95, 96, 97, 98, 99, 99.9% (or any intermediate ranges) of the cell population, or any range derivable therein.

There may be also provided a cell population comprising hepatocytes, wherein at least 20, 25, 30, 35, 40, 45, 50, 60, 70, 80, 85, 90, 91, 92, 93, 94, 95, 96, 97, 98, 99, 99.9% (or any intermediate ranges) of the hematopoietic precursor cells comprise one or more expression cassettes that comprise FOXA2, HNF4A and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, ZNF391.

The hepatocytes provided herein may be used in any methods and applications currently known in the art for hepatocytes. For example, a method of assessing a compound may be provided, comprising assaying a pharmacological or toxicological property of the compound on the hepatocyte or tissue engineered liver provided herein. There may also be provided a method of assessing a compound for an effect on a hepatocyte, comprising: a) contacting the hepatocyte provided herein with the compound; and b) assaying an effect of the compound on the hepatocyte.

In a further aspect, there may also be provided a method for treating a subject having or at risk of a liver dysfunction comprising administering to the subject with a therapeutically effective amount of hepatocytes or hepatocyte-containing cell population provided herein.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A-4B. Confirmation of restricted marker gene (mOrange) expression in hepatocytes during normal human ESC differentiation. (FIG. 4A) Cellular morphological changes during hepatic differentiation of human ESC R/I lines, and restricted expression of mOrange in maturing hepatocytes. (FIG. 4B) Flow cytometric analysis of hepatic marker Albumin and ASGPR1 (marker for mature hepatocytes) in d20 differentiated culture.

(FIG. 5A) A two-vector PiggyBac stable gene expression system. Ptight: an rtTET-responsive inducible promoter; pEF: the eukaryotic elongation factor 1α promoter; hPBase: the coding region for the PiggyBac transposase with codons optimized for expression in human cells. (FIG. 5B) EGFP induction in human ESC R/I lines. The EGFP driven by the Ptight promoter was introduced into human ESC R/I lines using Fugene HD-mediated transfection of both vectors in (FIG. 5A). Human ESCs with stable PiggyBac transposon integration were selected with geneticin (100 μg/ml). Images are shown with human ESC R/I lines after 2 days induction with or without Doxycycline (1 μg/ml). (FIG. 5C) Flow cytometric analysis of EGFP expression in human ESC R/I lines after 4 days induction with or without Doxycycline (1 μg/ml). Gray lines: Human ESC R/I lines without the transfection of the EGFP vector (negative control). Black lines: Human ESC R/I lines with stable PiggyBac transposon integration after 4 days induction with or without Doxycycline.

DESCRIPTION OF ILLUSTRATIVE EMBODIMENTS

Figure 1:
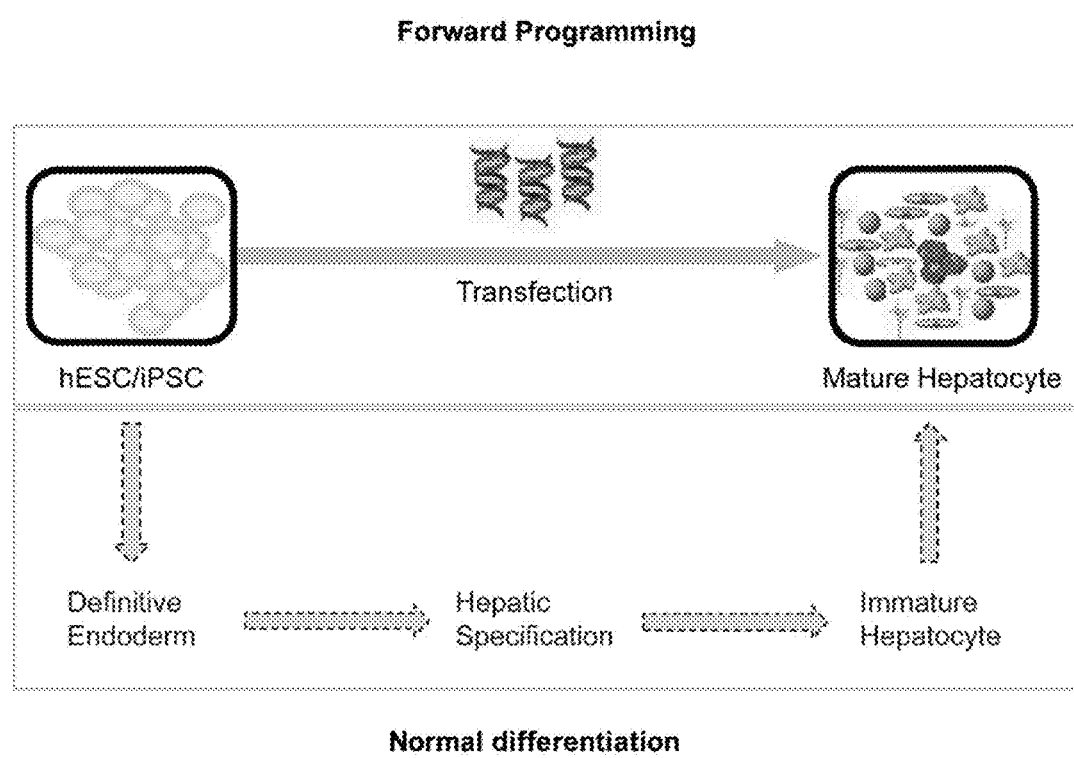
FIG. 1. Alternative approaches for hepatocyte differentiation from human ESC/iPSCs.

The instant invention overcomes several major problems with current technologies by providing methods and compositions for hepatocyte production by programming. In contrast to previous methods using step-wise differentiation protocols, certain aspects of these methods increase the level of hepatocyte programming transcription factors in non-hepatocytes to provide hepatocytes by forward programming. The extra steps including adding different growth factors during various intermediate developmental stages may be unnecessary in certain aspects the present methods. Therefore, certain aspects of the present methods may be more time- and cost-efficient and may enable manufacture of hepatocytes for therapeutics from a renewable source, for example, stem cells. Further embodiments and advantages of the invention are described below.

I. Definitions

"Programming" is a process that changes a cell to form progeny of at least one new cell type, either in culture or in vivo, than it would have under the same conditions without programming. This means that after sufficient proliferation, a measurable proportion of progeny having phenotypic characteristics of the new cell type if essentially no such progeny could form before programming; alternatively, the proportion having characteristics of the new cell type is measurably more than before programming. This process includes differentiation, dedifferentiation and transdifferentiation. "Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Under certain conditions, the proportion of progeny with characteristics of the new cell type may be at least about 1%, 5%, 25% or more in the in order of increasing preference.

The term "exogenous," when used in relation to a protein, gene, nucleic acid, or polynucleotide in a cell or organism refers to a protein, gene, nucleic acid, or polynucleotide which has been introduced into the cell or organism by artificial means, or in relation a cell refers to a cell which was isolated and subsequently introduced to other cells or to an organism by artificial means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

By "expression construct" or "expression cassette" is meant a nucleic acid molecule that is capable of directing transcription. An expression construct includes, at the least, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as gene delivery system or gene transfer "vehicle") refers to a macromolecule or complex of molecules comprising a polynucleotide to be delivered to a host cell, either in vitro or in vivo.

A "plasmid", a common type of a vector, is an extra-chromosomal DNA molecule separate from the chromosomal DNA which is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid, and/or a site at or near where DNA synthesis initiates. An ori for EBV includes FR sequences (20 imperfect copies of a 30 by repeat), and preferably DS sequences, however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of giving rising to at least one type of a more specialized cell. A stem cells has the ability to self-renew, i.e., to go through numerous cycles of cell division while maintaining the undifferentiated state, and has potency, i.e., the capacity to differentiate into specialized cell types. Typically, stem cells can regenerate an injured tissue. Stem cells herein may be, but are not limited to, embryonic stem (ES) cells, induced pluripotent stem cells, or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent stem cells or induced pluripotent stem cells.

As used herein "totipotent stem cells" refers to cells has the ability to differentiate into all cells constituting an organism, such as cells that are produced from the fusion of an egg and sperm cell. Cells produced by the first few divisions of the fertilized egg are also totipotent. These cells can differentiate into embryonic and extraembryonic cell types. Pluripotent stem cells can give rise to any fetal or adult cell type. However, alone they cannot develop into a fetal or adult animal because they lack the potential to contribute to extraembryonic tissue, such as the placenta.

In contrast, many progenitor cells are multipotent stem cells, i.e., they are capable of differentiating into a limited number of cell fates. Multipotent progenitor cells can give rise to several other cell types, but those types are limited in number. An example of a multipotent stem cell is a hematopoietic cell—a blood stem cell that can develop into several types of blood cells, but cannot develop into brain cells or other types of cells. At the end of the long series of cell divisions that form the embryo are cells that are terminally differentiated, or that are considered to be permanently committed to a specific function.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

Cells are "substantially free" of certain undesired cell types, as used herein, when they have less that 10% of the undesired cell types, and are "essentially free" of certain cell types when they have less than 1% of the undesired cell types. However, even more desirable are cell populations wherein less than 0.5% or less than 0.1% of the total cell population comprise the undesired cell types. Thus, cell populations wherein less than 0.1% to 1% (including all intermediate percentages) of the cells of the population comprise undesirable cell types are essentially free of these cell types. A medium may be "essentially free" of certain reagents, as used herein, when there is no externally addition of such agents. More preferably, these agents are absent or present at a undetectable amount.

The term "hepatocyte" as used herein is meant to include hepatocyte-like cells that exhibit some but not all characteristics of mature hepatocytes, as well as mature and fully functional hepatocytes. The cells produced by this method may be as at least as functional as the hepatocytes produced by directed differentiation to date. This technique may, as it is further improved, enable the production of completely fully functional hepatocytes, which have all characteristics of hepatocytes as determined by morphology, marker expression, in vitro and in vivo functional assays.

II. Cells Involved in Hepatocyte Programming

In certain embodiments of the invention, there are disclosed methods and compositions for producing hepatocytes by forward programming of cells which are not hepatocytes. There may be also provided cells that comprise exogenous expression cassettes including one or more hepatocyte programming factor genes and/or reporter expression cassettes specific for hepatocyte identification. In some embodiments, the cells may be stem cells, including but are not limited to, embryonic stem cells, fetal stem cells, or adult stem cells. In further embodiments, the cells may be any somatic cells.

A. Stem Cells

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

Human embryonic stem cells (ESCs) and induced pluripotent stem cells (iPSC) are capable of long-term proliferation in vitro, while retaining the potential to differentiate into all cell types of the body, including hepatocytes. Thus these cells could potentially provide an unlimited supply of patient-specific functional hepatocytes for both drug development and transplantation therapies. The differentiation of human ESC/iPSCs to hepatocytes in vitro recapitulates normal in vivo development, i.e. they undergo the following sequential developmental stages: definitive endoderm, hepatic specification, immature hepatocyte and mature hepatocyte (FIG. 1). This requires the addition of different growth factors at different stages of differentiation, and generally requires over 20 days of differentiation (FIG. 4). More importantly, the human ESC/iPSC-derived hepatocytes generally are yet to exhibit the full functional spectrum of human primary adult hepatocytes. Certain aspects of the invention provided that hepatocytes such as hepatocyte-like cells or fully functional hepatocytes could be induced directly from human ESC/iPSCs via expression of a combination of transcription factors important for hepatocyte differentiation/function, similar to the generation of iPSCs, bypassing most, if not all, normal developmental stages (FIG. 1). This approach could be more time- and cost-efficient, and generate hepatocytes with functions highly similar, if not identical, to human primary adult hepatocytes. In addition, human ESC/iPSCs, with their unlimited proliferation ability, have a unique advantage over somatic cells as the starting cell population for hepatocyte differentiation.

1. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may be also defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

2. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog as described above. The somatic cell for reprogramming may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, e.g., an EBV element-based system (see U.S. Application No. 61/058,858, incorporated herein by reference; Yu et al., 2009). In a further aspect, reprogramming proteins or RNA (such as mRNA or miRNA) could be introduced directly into somatic cells by protein transduction or RNA transfection (see U.S. Application No. 61/172,079, incorporated herein by reference; Yakubov et al., 2010).

3. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

4. Other Stem Cells

Fetal stem cells are cells with self-renewal capability and pluripotent differentiation potential. They can be isolated and expanded from fetal cytotrophoblast cells (European Patent EPO412700) and chorionic villi, amniotic fluid and the placenta (WO/2003/042405). These are hereby incorporated by reference in their entirety. Cell surface markers of fetal stem cells include $CD117/c\text{-kit}^+$, $SSEA3^+$, $SSEA4^+$ and $SSEA1^-$.

Somatic stem cells have been identified in most organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see U.S. Pat. Nos. 5,635,387; 5,460,964; 5,677,136; 5,750,397; 5,759,793; 5,681,599; 5,716,827; Hill et al., 1996). These are hereby incorporated by reference in their entirety. When transplanted into lethally irradiated animals or humans, hematopoietic stem cells can repopulate the erythroid, neutrophil-macrophage, megakaryocyte and lymphoid hematopoieticcell pool. In vitro, hematopoieticstem cells can be induced to undergo at least some self-renewing cell divisions and can be induced to differentiate to the same lineages as is seen in vivo. Therefore, this cell fulfills the criteria of a stem cell.

The next best characterized is the mesenchymal stem cells (MSC), originally derived from the embryonic mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A number of mesenchymal stem cells have been isolated (see, for example, U.S. Pat. Nos. 5,486,359; 5,827,735; 5,811,094; 5,736,396; 5,837,539; 5,837,670; 5,827,740; Jaiswal et al., 1997; Cassiede et al., 1996; Johnstone et al., 1998; Yoo et al., 1998; Gronthos, 1994; Makino et al., 1999). These are hereby incorporated by reference in their entirety. Of the many mesenchymal stem cells that have been described, all have demonstrated limited differentiation to form only those differentiated cells generally considered to be of mesenchymal origin. To date, the most multipotent mesenchymal stem cell expresses the $SH2^+$ $SH4^+$ $CD29^+$ $CD44^+$ $CD71^+$ $CD90^+$ $CD106^+$ $CD120a^+$ $CD124^+$ $CD14^-$ $CD34^-$ $CD45^-$ phenotype.

Other stem cells have been identified, including gastrointestinal stem cells, epidermal stem cells, neural and hepatic stem cells, also termed oval cells (Potten, 1998; Watt, 1997; Alison et al, 1998).

In some embodiments, the stem cells useful for the method described herein include but not limited to embryonic stem cells, induced pluripotent stem cells, mesenchymal stem cells, bone-marrow derived stem cells, hematopoietic stem cells, chondrocyte progenitor cells, epidermal stem cells, gastrointestinal stem cells, neural stem cells, hepatic stem cells adipose-derived mesenchymal stem cells, pancreatic progenitor cells, hair follicular stem cells, endothelial progenitor cells and smooth muscle progenitor cells.

In some embodiments, the stem cells used for the method described herein is isolated from umbilical cord, placenta, amniotic fluid, chorion villi, blastocysts, bone marrow, adipose tissue, brain, peripheral blood, the gastrointestinal tract, cord blood, blood vessels, skeletal muscle, skin, liver and menstrual blood. Stem cells prepared in the menstrual blood are called endometrial regenerative cells (Medistem Inc.).

One ordinary skilled artisan in the art can locate, isolate and expand such stem cells. The detailed procedures for the isolation of human stem cells from various sources are described in Current Protocols in Stem Cell Biology (2007) and it is hereby incorporated by reference in its entirety. Alternatively, commercial kits and isolation systems can be used. For example, the BD FACS Aria cell sorting system, BD IMag magnetic cell separation system, and BD IMag mouse hematopoietic progenitor cell enrichment set from BD Biosciences. Methods of isolating and culturing stem cells from various sources are also described in U.S. Pat. Nos. 5,486, 359, 6,991,897, 7,015,037, 7,422,736, 7,410,798, 7,410,773, 7,399,632 and these are hereby incorporated by reference in their entirety.

B. Somatic Cells

In certain aspects of the invention, there may also be provided methods of transdifferentiation, i.e., the direct conversion of one somatic cell type into another, e.g., deriving hepatocytes from other somatic cells. Transdifferentiation may involve the use of hepatocyte programming factor genes or gene products to increase expression levels of such genes in somatic cells for production of hepatocytes.

However, the human somatic cells may be limited in supply, especially those from living donors. In certain aspects to provide an unlimited supply of staring cells for programming, somatic cells may be immortalized by introduction of immortalizing genes or proteins, such as hTERT or oncoogenes. The immortalization of cells may be reversible (e.g., using removable expression cassettes) or inducible (e.g., using inducible promoters).

Somatic cells in certain aspects of the invention may be primary cells (non-immortalized cells), such as those freshly isolated from an animal, or may be derived from a cell line (immortalized cells). The cells may be maintained in cell culture following their isolation from a subject. In certain embodiments the cells are passaged once or more than once (e.g., between 2-5, 5-10, 10-20, 20-50, 50-100 times, or more) prior to their use in a method of the invention. In some embodiments the cells will have been passaged no more than 1, 2, 5, 10, 20, or 50 times prior to their use in a method of the invention. They may be frozen, thawed, etc.

The somatic cells used or described herein may be native somatic cells, or engineered somatic cells, i.e., somatic cells which have been genetically altered. Somatic cells of the present invention are typically mammalian cells, such as, for example, human cells, primate cells or mouse cells. They may be obtained by well-known methods and can be obtained from any organ or tissue containing live somatic cells, e.g., blood, bone marrow, skin, lung, pancreas, liver, stomach, intestine, heart, reproductive organs, bladder, kidney, urethra and other urinary organs, etc.

Mammalian somatic cells useful in the present invention include, but are not limited to, Sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, cardiac muscle cells, and other muscle cells, etc.

In some embodiments cells are selected based on their expression of an endogenous marker known to be expressed only or primarily in a desired cell type. For example, vimentin is a fibroblast marker. Other useful markers include various keratins, cell adhesion molecules such as cadherins, fibronectin, CD molecules, etc. The population of somatic cells may have an average cell cycle time of between 18 and 96 hours, e.g., between 24-48 hours, between 48-72 hours, etc. In some embodiments, at least 90%, 95%, 98%, 99%, or more of the cells would be expected to divide within a predetermined time such as 24, 48, 72, or 96 hours.

Methods described herein may be used to program one or more somatic cells, e.g., colonies or populations of somatic cells into hepatocytes. In some embodiments a population of cells of the present invention is substantially uniform in that at least 90% of the cells display a phenotype or characteristic of interest. In some embodiments at least 95%, 96%, 97%, 98%, 99%, 99.5%, 99.8%, 99.9, 99.95% or more of the cells display a phenotype or characteristic of interest. In certain embodiments of the invention the somatic cells have the capacity to divide, i.e., the somatic cells are not post-mitotic.

Somatic cells may be partially or completely differentiated. Differentiation is the process by which a less specialized cell becomes a more specialized cell type. Cell differentiation can involve changes in the size, shape, polarity, metabolic activity, gene expression and/or responsiveness to signals of the cell. For example, hematopoietic stem cells differentiate to give rise to all the blood cell types including myeloid (monocytes and macrophages, neutrophils, basophils, eosinophils, erythrocytes, megakaryocytes/platelets, dendritic cells) and lymphoid lineages (T-cells, B-cells, NK-cells). During progression along the path of differentiation, the ultimate fate of a cell becomes more fixed. As described herein, both partially differentiated somatic cells and fully differentiated somatic cells can be programmed as described herein to produce desired cell types such as hepatocytes.

III. Hepatocyte Programming Factors

Certain aspects of the invention provide hepatocyte programming factors for hepatocyte forward programming. The hepatocytes could be produced directly from other cell sources by increasing the level of hepatocyte programming factors in cells. The numerous functions of hepatocytes could be controlled at the transcriptional level by the concerted actions of a limited number of hepatocyte-enriched transcription factors. Any transcription factors important for hepatocyte differentiation or function may be used herein, like hepatocyte-enriched transcription factors, particularly the genes thereof listed in Table 1. All the isoforms and variants of the genes listed in Table 1 may be included in this invention, and non-limiting examples of accession numbers for certain isoforms or variants are provided.

For example, by effecting expression of a combination of transcription factors in Table 1, forward programming into hepatocytes from pluripotent stem cells may bypass most, if not all, normal developmental stages. Examples shown are a combination of the following transcription factors: FOXA1, FOXA2, HHEX, HNF1A, HNF4A and TBX3, or a combination of FOXA2, HHEX, HNF4A, GATA4, NR0B2 and SCML1.

TABLE 1

A list of genes for forward programming to hepatocytes.

| # | Symbol | Entrez Gene ID | Exemplary Accession No. | SEQ ID NO: | Name |
|---|---|---|---|---|---|
| 1 | SOX17 | 64321 | NM_022454.3 | 9 | SRY (sex determining region Y)-box 17 [*Homo sapiens*] |
| 2 | FOXA1 | 3169 | NM_004496.2 | 10 | forkhead box A1 [*Homo sapiens*] |
| 3 | FOXA2 | 3170 | NM_021784.4 | 11 | forkhead box A2 [*Homo sapiens*] |
|   |       |      | NM_153675.2 | 12 | |
| 4 | HHEX | 3087 | NM_002729.4 | 13 | hematopoietically expressed homeobox [*Homo sapiens*] |
| 5 | GATA4 | 2626 | NM_002052.3 | 14 | GATA binding protein 4 [*Homo sapiens*] |
| 6 | GATA6 | 2627 | NM_005257.3 | 15 | GATA binding protein 6 [*Homo sapiens*] |
| 7 | PROX1 | 5629 | NM_002763.3 | 16 | prospero homeobox 1 [*Homo sapiens*] |
| 8 | TBX3 | 6926 | NM_005996.3 | 17 | T-box 3 [*Homo sapiens*] |
|   |      |      | NM_016569.3 | 18 | |
| 9 | HLX | 3142 | NM_021958.3 | 19 | H2.0-like homeobox [*Homo sapiens*] |
| 10 | ONECUT1 | 3175 | NM_004498.1 | 20 | one cut homeobox 1 [*Homo sapiens*] |
| 11 | ONECUT2 | 9480 | NM_004852.2 | 21 | one cut homeobox 2 [*Homo sapiens*] |
| 12 | MYC | 4609 | NM_002467.4 | 22 | v-myc myelocytomatosis viral oncogene homolog (avian) [*Homo sapiens*] |
| 13 | FOXA3 | 3171 | NM_004497.2 | 23 | forkhead box A3 [*Homo sapiens*] |
| 14 | HNF4A | 3172 | NM_000457.3 | 24 | hepatocyte nuclear factor 4, alpha [*Homo sapiens*] |
| 15 | HNF1A | 6927 | NM_000545.5 | 25 | HNF1 homeobox A [*Homo sapiens*] |
| 16 | HNF1B | 6928 | NM_000458.2 | 26 | HNF1 homeobox B [*Homo sapiens*] |
| 17 | CEBPA | 1050 | NM_004364.3 | 27 | CCAAT/enhancer binding protein (C/EBP), alpha [*Homo sapiens*] |
| 18 | CEBPB | 1051 | NM_005194.2 | 28 | CCAAT/enhancer binding protein (C/EBP), beta [*Homo sapiens*] |
| 19 | DBP | 1628 | NM_001352.3 | 29 | D site of albumin promoter (albumin D-box) binding protein [*Homo sapiens*] |
| 20 | ZBTB20 | 26137 | NM_001164342.1 | 30 | zinc finger and BTB domain containing 20 [*Homo sapiens*] |
|    |        |       | NM_001164343.1 | 31 | |
| 21 | NR1I3 | 9970 |  |  | nuclear receptor subfamily 1, group I, member 3 [*Homo sapiens*] |
| 22 | NR1I2 | 8856 | NM_003889.3 | 32 | nuclear receptor subfamily 1, group I, member 2 [*Homo sapiens*] |
|    |       |      | NM_022002.2 | 33 | |
| 23 | NR1H4 | 9971 | NM_005123.2 | 34 | nuclear receptor subfamily 1, group H, member 4 [*Homo sapiens*] |
| 24 | ATF5 | 22809 | NM_012068.5 | 35 | activating transcription factor 5 [*Homo sapiens*] |
| 25 | NR5A2 | 2494 | NM_003822.3 | 36 | nuclear receptor subfamily 5, group A, member 2 [*Homo sapiens*] |
| 26 | NR1H3 | 10062 | NM_005693.2 | 37 | nuclear receptor subfamily 1, group H, member 3 [*Homo sapiens*] |
| 27 | CREB3L3 | 84699 | NM_032607.1 | 38 | cAMP responsive element binding protein 3-like 3 [*Homo sapiens*] |
| 28 | NKX2-8 | 26257 | NM_014360.2 | 39 | NK2 homeobox 8 [*Homo sapiens*] |
| 29 | CEBPD | 1052 | NM_005195.3 | 40 | CCAAT/enhancer binding protein (C/EBP), delta [*Homo sapiens*] |
| 30 | HLF | 3131 | NM_002126.4 | 41 | hepatic leukemia factor [*Homo sapiens*] |
| 31 | NR0B2 | 8431 | NM_021969.2 | 42 | nuclear receptor subfamily 0, group B, member 2 [*Homo sapiens*] |
| 32 | ABLIM3 | 22885 | NM_014945.2 | 43 | actin binding LIM protein family, member 3 [*Homo sapiens*] |
| 33 | ATOH8 | 84913 | NM_032827.6 | 44 | atonal homolog 8 (*Drosophila*) [*Homo sapiens*] |
| 34 | C14orf39 | 317761 | NM_174978.2 | 45 | chromosome 14 open reading frame 39 [*Homo sapiens*] |
| 35 | SCML1 | 6322 | NM_001037540.1 | 46 | sex comb on midleg-like 1 (*Drosophila*) [*Homo sapiens*] |
|    |       |      | NM_006746.4 | 47 | |
| 36 | SEBOX | 645832 | NM_001083896.1 | 48 | SEBOX homeobox [*Homo sapiens*] |

TABLE 1-continued

A list of genes for forward programming to hepatocytes.

| # | Symbol | Entrez Gene ID | Exemplary Accession No. | SEQ ID NO: | Name |
|---|--------|----------------|-------------------------|------------|------|
| 37 | ZBED3 | 84327 | NM_032527.3 | 49 | zinc finger, BED-type containing 3 [Homo sapiens] |
| 38 | ZGPAT | 84619 | NM_032527.3 NM_181485.2 | 49 50 | zinc finger, CCCH-type with G patch domain [Homo sapiens] |
| 39 | ZNF391 | 346157 | NM_001076781.1 | 51 | zinc finger protein 391 [Homo sapiens] |
| 40 | ZNF426 | 79088 | NM_024106.1 | 52 | zinc finger protein 426 [Homo sapiens] |
| 41 | ZNF517 | 340385 | NM_213605.2 | 53 | zinc finger protein 517 [Homo sapiens] |

The hepatocyte-enriched transcription factors include, but are not limited to, hepatocyte nuclear factor 1-α (HNF-1α), -1β, -3α, -3β, -3γ, -4α, and -6 and members of the c/ebp family). Hepatocyte nuclear factors (HNFs) are a group of phylogenetically unrelated transcription factors that regulate the transcription of a diverse group of genes into proteins. These proteins include blood clotting factors and in addition, enzymes and transporters involved with glucose, cholesterol, and fatty acid transport and metabolism. Of these, HNF4A (also known as HNF4a or nuclear receptor 2A1 or (NR2A1)) and HNF1A (i.e., HNF1α) appear to be correlated with the differentiated phenotype of cultured hepatoma cells. HNF1A-null mice are viable, indicating that this factor is not an absolute requirement for the formation of an active hepatic parenchyma. In contrast, HNF4A-null mice die during embryogenesis. HNF4A is expressed early in development, visible by in situ hybridization in the mouse visceral endoderm at embryonic day 4.5, long before liver development. Whereas HNF4A appears to be essential in the visceral endoderm it may not be necessary for the earliest steps in the development of the fetal liver (Li et al., 2000). HNF-4A is both essential for hepatocyte differentiation during mammalian liver development and also crucial for metabolic regulation and proper liver function (Hayhurst et al., 2001). HNF-4A is also known as TCF; HNF4; MODY; MODY1; NR2A1; TCF14; HNF4a7; HNF4a8; HNF4a9; NR2A21; and FLJ39654. Six transcriptional variants or isoforms are produced from the genomic gene, isoforms a, b c, d, d, e, and f (Genbank Accession NOs: NM_000457.3, NM_001030003.1, NM_001030004.1, NMJ75914.3, NM_178849.1, and NM_178850.1). All isoforms contain a zinc finger, C4 type DNA binding domain and ligand-binding domain. The encoded protein is a nuclear transcription factor which binds DNA as a homodimer and controls the expression of several genes, including HNF1A, a transcription factor which in turns regulates the expression of several hepatic genes. Over 55 distinct target genes have been identified for HNF4A. Since many of those genes contain more than one HNF4A binding site, the total number of distinct, non species redundant HNF4A binding sites is now 74. These genes can be grouped into several different categories, according to function, such as nutrient transport and metabolism, blood maintenance, immune function, liver differentiation and growth factors. The best characterized HNF-4A target genes are those involved in lipid transport (e.g., apolipoprotein genes) and glucose metabolism (e.g., L-PK and PEPCK). Nearly all of the target genes identified thus far are expressed primarily in the liver; several are expressed in other organs as well, such as the pancreas.

HNF1A is also known as HNF1, LFB1, TCF1, and MODY3. HNF1A is a transcription factor that is highly expressed in the liver and is involved in the regulation of the expression of several liver specific genes such as the human class I alcohol dehydrogenase. HNF-1A (Genbank Accession No: NM 000545.4) belongs to the homeobox gene family for it contains a homeobox DNA binding domain. A homeobox is a DNA sequence that binds DNA. The translated homeobox is a highly conserved stretch of 60 amino acid residues.

Forkhead box A2 (FOXA2), is also known as HNF-3β, HNF3B, TCF3B and MGC19807. FOXA2 is a member of the forkhead class of DNA-binding proteins. The forkhead box is a sequence of 80 to 100 amino acids that form a motif that binds to DNA. This forkhead motif is also known as the winged helix due to the butterfly-like appearance of the loops in the protein structure of the domain. These hepatocyte nuclear factors are transcriptional activators for liver-specific genes such as albumin and transthyretin, and they also interact with chromatin. Similar family members in mice have roles in the regulation of metabolism and in the differentiation of the pancreas and liver. This gene has been linked to sporadic cases of maturity-onset diabetes of the young. Transcript variants encoding different isoforms, isoform 1 and 2, have been identified for this gene (Genbank Accession Nos: NM 021784.4; FOXA2-1) and NM_153675.2; FOXA2-2).

CCAAT/enhancer binding protein (C/EBP) alpha is a CCAAT/enhancer-binding protein. C/EBPs are a family of transcription factors that are critical for cellular differentiation, terminal functions and inflammatory response. Six members of the family have been characterized (C/EBP alpha, C/EBP beta, C/EBP delta, C/EBP epsilon, C/EBP gamma and C/EBP zeta) and are distributed in a variety of tissues.

Hematopoietically-expressed homeobox protein HHEX is a protein that in humans is encoded by the HHEX gene. This gene encodes a member of the homeobox family of transcription factors, many of which are involved in developmental processes. HHEX is required for early development of the liver. A null mutation of HHEX results in a failure to form the liver bud and embryonic lethality.

T-box transcription factor TBX3 is a protein that in humans is encoded by the TBX3 gene. This gene is a member of a phylogenetically conserved family of genes that share a common DNA-binding domain, the T-box. T-box genes encode transcription factors involved in the regulation of developmental processes. This protein is a transcriptional repressor and is thought to play a role in the anterior/posterior axis of the tetrapod forelimb. Mutations in this gene cause ulnar-mammary syndrome, affecting limb, apocrine gland, tooth, hair, and genital development. Alternative splicing of this gene results in three transcript variants encoding different isoforms.

GATA4 gene encodes a member of the GATA family of zinc finger transcription factors. Members of this family recognize the GATA motif which is present in the promoters of many genes. GATA4 protein is thought to regulate genes involved in embryogenesis and in myocardial differentiation and function. Mutations in this gene have been associated with cardiac septal defects as well as reproductive defects.

NR0B2 gene (nuclear receptor subfamily 0, group B, member 1; previous name is dosage-sensitive sex reversal (DAX1)) encodes a protein that contains a DNA-binding domain. The encoded protein acts as a dominant-negative regulator of transcription which is mediated by the retinoic acid receptor. This protein also functions as an anti-testis gene by acting antagonistically to Sry. Mutations in this gene result in both X-linked congenital adrenal hypoplasia and hypogonadotropic hypogonadism. The encoded protein plays an important role in the normal development of several hormone-producing tissues. These tissues include the adrenal glands), the pituitary gland and hypothalamus which are located in the brain and the male and female reproductive structures (the testes and ovaries). The encoded protein controls the activity of certain genes in the cells that form these tissues during embryonic development. Proteins that control the activity of other genes are known as transcription factors. The encoded protein also plays a role in regulating hormone production in these tissues after they have been formed.

SCML1 (Sex comb on midleg-like protein 1) encodes a putative Polycomb group (PcG) protein. PcG proteins act by forming multiprotein complexes, which are required to maintain the transcriptionally repressive state of homeotic genes throughout development. The encoded protein may be involved in spermatogenesis during sexual maturation IV. Delivery Of Gene or Gene Products In certain embodiments, vectors for delivery of nucleic acids encoding hepatic lineage programming or differentiation factors could be constructed to express these factors in cells. Details of components of these vectors and delivery methods are disclosed below. In addition, protein transduction compositions or methods may be also used to effect expression of the hepatocyte programming factors.

In a further aspect, the following systems and methods may also be used in delivery of reporter expression cassette for identification of desired cell types, such as hepatocytes. In particular, a hepatocyte-specific regulatory element may be used to drive expression of a reporter gene, therefore hepatocytes derived from forward programming may be characterized, selected or enriched.

A. Nucleic Acid Delivery Systems

One of skill in the art would be well equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV, etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

1. Viral Vectors

In generating recombinant viral vectors, non-essential genes are typically replaced with a gene or coding sequence for a heterologous (or non-native) protein. Viral vectors are a kind of expression construct that utilizes viral sequences to introduce nucleic acid and possibly proteins into a cell. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviruses have promise as gene delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

2. Episomal Vectors

The use of plasmid- or liposome-based extra-chromosomal (i.e., episomal) vectors may be also provided in certain aspects of the invention. Such episomal vectors may include, e.g., oriP-based vectors, and/or vectors encoding a derivative of EBNA-1. These vectors may permit large fragments of DNA to be introduced to a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class 1 molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-base vectors are contemplated, such as yeast ARS, adenovirus, SV40, or BPV.

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Transposon-Based System

According to a particular embodiment the introduction of nucleic acids may use a transposon—transposase system. The used transposon—transposase system could be the well known Sleeping Beauty, the Frog Prince transposon—transposase system (for the description of the latter see e.g. EP1507865), or the TTAA-specific transposon piggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

4. Homologous Recombination Nuclease-Based Systems

Homologous recombination (HR) is a targeted genome modification technique that has been the standard method for genome engineering in mammalian cells since the mid 1980s. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002). Another path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606). Another class of such specificity molecules includes Transcription Activator Like Effector (TALE) DNA binding domains fused to the catalytic domain of a Type IIS restriction endonuclease such as FokI (Miller et al., 2011: PCT/IB2010/000154).

B. Regulatory Elements:

Eukaryotic expression cassettes included in the vectors preferably contain (in a 5'-to-3' direction) a eukaryotic transcriptional promoter operably linked to a protein-coding sequence, splice signals including intervening sequences, and a transcriptional termination/polyadenylation sequence.

1. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 by upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 by apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988; Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

Tissue-specific transgene expression, especially for reporter gene expression (such as antibiotic resistant gene expression) in hepatocytes produced from forward programming, is desirable as a way to identify produced hepatocytes. To increase both specificity and activity, the use of cis-acting regulatory elements has been contemplated. For example, a hepatocyte-specific promoter may be used, such as a promoter of albumin, α-1-antitrypsin (AAT), cytochrome p450 3A4 (CYP3A4), apolipoprotein A-I, or APOE.

In certain aspects, this also concerns enhancer sequences, i.e. nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter. For the liver, numerous approaches to incorporate such organ-specific regulatory sequences into retroviral, lentiviral, adenoviral and adeno-associated viral vectors or non-viral vectors (often in addition to house-keeping hepatocyte-specific cellular promoters) have been reported so far (Ferry et al., 1998; Ghosh et al., 2000; Miao et al., 2000; Follenzi et al., 2002).

Several enhancer sequences for liver-specific genes have been documented, WO2009130208 describes several liver-specific regulatory enhancer sequences. WO95/011308 describes a gene therapy vector comprising a hepatocyte-specific control region (HCR) enhancer linked to a promoter and a transgene. The human apolipoprotein E-Hepatocyte Control Region (ApoE-HCR) is a locus control region (LCR) for liver-specific expression of the apolipoprotein E (ApoE) gene. The ApoE-HCR is located in the ApoE/CI/CII locus, has a total length of 771 by and is important in expression of the genes ApoE and ApoC-1 in the liver (Simonet et al., 1993). In WO01/098482, the combination of this specific ApoE enhancer sequence or a truncated version thereof with hepatic promoters is suggested. It was shown that vector constructs combining the (non-truncated) ApoE-HCR enhancer with a human alpha-antitrypsin (AAT) promoter were able to produce the highest level of therapeutic protein in vivo (Miao et al., 2000) and may confer sustained expression when used in conjunction with a heterologous transgene (Miao et al., 2001).

This ApoE-HCR-AAT expression cassette as used, e.g., in the pAAV-ApoHCR-AAT-FIXIA construct (Vanden-Driessche et al., 2007) is one of the most potent liver-specific FIX expression constructs known, and has been successfully applied in a phase ½ dose-escalation clinical study in humans with severe hemophilia B (Manno et al., 2006). The expression of this hFIX minigene is driven from an ApoE-HCR joined to the human AAT promoter. The 5'-flanking sequence of the human AAT gene contains multiple cis-regulatory elements, including a distal enhancer and proximal sequences, with a total length of around 1.2 kb. It was shown to be sufficient to confer tissue specificity in vivo by driving gene expression primarily in the liver and also, to a lesser extent, in other tissues known to express AAT (Shen et al., 1989). A 347 by fragment of this 1.2 kb region in combination with the ApoE enhancer is capable of achieving long-term liver-specific gene expression in vivo (Le et al., 1997). Interestingly, this shorter promoter targets expression to the liver with a greater specificity than that reported for larger AAT promoter fragments (Yull et al., 1995).

Other chimeric liver-specific constructs have also been proposed in the literature, e.g., with the AAT promoter and the albumin or hepatitis B enhancers (Kramer et al., 2003), or the alcohol dehydrogenase 6 (ADH6) basal promoter linked to two tandem copies of the apolipoprotein E enhancer element (Gehrke et al., 2003). The authors of the latter publication stress the importance of the relatively small size (1068 bp) of this enhancer-promoter combination.

2. Initiation Signals and Internal Ribosome Binding Sites

A specific initiation signal also may be used for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

4. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select for hepatocytes after the programming factors have effected a desired programming change in those cells.

C. Nucleic acid Delivery

Introduction of a nucleic acid, such as DNA or RNA, into cells to be programmed with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L (A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

6. Microprojectile Bombardment

Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

B. Protein Transduction

In certain aspects of the present invention, the cells to be programmed into hepatocytes may be contacted with hepatocyte programming factors comprising polypeptides of hepatocyte transcription factor genes at a sufficient amount for forward programming. Protein transduction has been used as a method for enhancing the delivery of macromolecules into cells. Protein transduction domains may be used to introduce hepatocyte programming polypeptides or functional fragments thereof directly into cells. Research by many groups has shown that a region of the TAT protein which is derived from the HIV Tat protein can be fused to a target protein allowing the entry of the target protein into the cell. A particular exemplary protein sequence of this domain is RKKRRQRRR (SEQ ID NO:1) where R encodes Arginine, K encodes Lysine and Q encodes Glutamine. This sequence has been shown to enable the entry of a protein fusion both as an N-terminal or C-terminal fusion. The mechanism of TAT mediated entry is thought to be by macropinocytosis (Gump and Dowdy).

A "protein transduction domain" or "PTD" is an amino acid sequence that can cross a biological membrane, particularly a cell membrane. When attached to a heterologous polypeptide, a PTD can enhance the translocation of the heterologous polypeptide across a biological membrane. The PTD is typically covalently attached (e.g., by a peptide bond) to the heterologous DNA binding domain. For example, the PTD and the heterologous DNA binding domain can be encoded by a single nucleic acid, e.g., in a common open reading frame or in one or more exons of a common gene. An exemplary PTD can include between 10-30 amino acids and may form an amphipathic helix. Many PTD's are basic in character. For example, a basic PTD can include at least 4, 5, 6 or 8 basic residues (e.g., arginine or lysine). A PTD may be able to enhance the translocation of a polypeptide into a cell that lacks a cell wall or a cell from a particular species, e.g., a mammalian cell, such as a human, simian, murine, bovine, equine, feline, or ovine cell.

A PTD can be linked to an artificial transcription factor, for example, using a flexible linker. Flexible linkers can include one or more glycine residues to allow for free rotation. For example, the PTD can be spaced from a DNA binding domain of the transcription factor by at least 10, 20, or 50 amino acids. A PTD can be located N- or C-terminal relative to a DNA binding domain. Being located N- or C-terminal to a particular domain does not require being adjacent to that particular domain. For example, a PTD N-terminal to a DNA binding domain can be separated from the DNA binding domain by a spacer and/or other types of domains. A PTD can be chemically synthesized then conjugated chemically to separately prepared DNA binding domain with or without linker peptide. An artificial transcription factor can also include a plurality of PTD's, e.g., a plurality of different PTD's or at least two copies of one PTD.

Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the *Drosophila* Antennapedia (Antp) homeotic transcription factor. The small protein transduction domains (PTDs) from these proteins can be fused to other macromolecules, peptides or proteins to successfully transport them into a cell. Sequence alignments of the transduction domains from these proteins show a high basic amino acid content (Lys and Arg) which may facilitate interaction of these regions with negatively charged lipids in the membrane. Secondary structure analyses show no consistent structure between all three domains.

The advantages of using fusions of these transduction domains is that protein entry is rapid, concentration-dependent and appears to work with difficult cell types.

The Tat protein from human immunodeficiency virus type I (HIV-1) has the remarkable capacity to enter cells when added exogenously (Frankel and Pabo, 1988; Mann and Frankel, 1991; Fawell et al., 1994). A particular example of Tat PTD may include residues 47-57 of the human immunodeficiency virus Tat protein: YGRKKRRQRRR (SEQ ID NO:2). This peptide sequence is referred to as "TAT" herein. This peptide has been shown to successfully mediate the introduction of heterologous peptides and proteins in excess of 100 kDa into mammalian cells in vitro and in vivo (Ho et al., 2001). Schwarze et al. showed that when the 120 kDa β-galactosidase protein fused with TAT was injected into mouse intraperitoneally, the fusion proteins were found in all types of cells and tissues even including brain, which has been thought to be difficult because of the blood-brain-barrier (Schwarze et al., 1999).

The antennapedia homeodomain also includes a peptide that is a PTD (Derossi et al., 1994). This peptide, also referred to as "Penetratin", includes the amino acid sequence: AKIW-FQNRRMKWKKENN (SEQ ID NO:3).

The HSV VP22 protein also includes a PTD. This PTD is located at the VP22 C-terminal 34 amino acid residues: DAATATRGRSAASRPTERPRAPARSASRPRRPVE (SEQ ID NO:4). See, e.g., Elliott and O'Hare (1997) and U.S. Pat. No. 6,184,038.

In one embodiment, the PTD is obtained from a human or other mammalian protein. Exemplary mammalian PTD's are described in WO 03/059940 (human SIM-2) and WO 03/059941 (Mph). In certain embodiments, the PTD could be a synthetic PTD. The minimal Tat PTD (aa 47-57) was modified to optimize protein transduction potential (Ho et al., 2001). A FITC coupled with series of synthetic PTD's was tested with cultured T lymphocytes. Some synthetic PTD's showed enhanced protein transduction compared to Tat PTD. These PTD include: YARKARRQARR(SEQ ID NO:5); YARAARRAARR (SEQ ID NO:6); YARAARRAARA (SEQ ID NO:7); YARAAARQARA (SEQ ID NO:8). Especially, the FITC conjugated with synthetic PTD YARAAAR-QARA (SEQ ID NO:8); showed enhanced uptake by whole blood cells when the mice were i.p. injected.

The poly-arginine peptides composed of about 6-12 arginine residues also can mediate protein transduction in some cases. For additional information about poly-arginine, see, e.g., Rothbard et al. (2000); Wender et al. (2000).

For additional information about PTD's, see also U.S. 2003/0082561; U.S. 2002/0102265; U.S. 2003/0040038; Schwarze et al. (1999); Derossi et al. (1996); Hancock et al. (1991); Buss et al. (1988); Derossi et al. (1998); Lindgren et al. (2000); Kilic et al. (2003); Asoh et al. (2002); and Tanaka et al. (2003).

In addition to PTD's, cellular uptake signals can be used. Such signals include amino acid sequences which are specifically recognized by cellular receptors or other surface proteins. Interaction between the cellular uptake signal and the cell cause internalization of the artificial transcription factor that includes the cellular uptake signal. Some PTD's may also function by interaction with cellular receptors or other surface proteins.

A number of assays are available to determine if an amino acid sequence can function as a PTD. For example, the amino acid sequence can be fused to a reporter protein such as β-galactosidase to form a fusion protein. This fusion protein is contacted with culture cells. The cells are washed and then assayed for reporter activity. Another assay detects the presence of a fusion protein that includes the amino acid sequence in question and another detectable sequence, e.g., an epitope tag. This fusion protein is contacted with culture cells. The cells are washed and then analyzed by Western or immunofluorescence to detect presence of the detectable sequence in cells. Still other assays can be used to detect transcriptional regulatory activity of a fusion protein that includes the putative PTD, a DNA binding domain, and optionally an effector domain. For example, cells contacted with such fusion proteins can be assayed for the presence or level of mRNA or protein, e.g., using microarrays, mass spectroscopy, and high-throughput techniques.

V. Cell Culturing

Generally, cells of the present invention are cultured in a culture medium, which is a nutrient-rich buffered solution capable of sustaining cell growth.

Culture media suitable for isolating, expanding and differentiating stem cells into hepatocytes according to the method described herein include but not limited to high glucose Dulbecco's Modified Eagle's Medium (DMEM), DMEM/F-15, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transfernin, insulin, vitamins, essential and non essential amino acids, sodium pyruvate, glutamine and a mitogen is also suitable. As used herein, a mitogen refers to an agent that stimulates cell division of a cell. An agent can be a chemical, usually some form of a protein that encourages a cell to commence cell division, triggering mitosis. In one embodiment, serum free media such as those described in U.S. Ser. No. 08/464,599 and WO96/39487, and the "complete media" as described in U.S. Pat. No. 5,486,359 are contemplated for use with the method described herein. In some embodiments, the culture medium is supplemented with 10% Fetal Bovine Serum (FBS), human autologous serum, human AB serum or platelet rich plasma supplemented with heparin (2 U/ml). Cell cultures may be maintained in a $CO_2$ atmosphere, e.g., 5% to 12%, to maintain pH of the culture fluid, incubated at 37° C. in a humid atmosphere and passaged to maintain a confluence below 85%.

Pluripotent stem cells to be differentiated into hepatocytes may be cultured in a medium sufficient to maintain the pluripotency. Culturing of induced pluripotent stem (iPS) cells generated in certain aspects of this invention can use various medium and techniques developed to culture primate pluripotent stem cells, more specially, embryonic stem cells, as described in U.S. Pat. App. 20070238170 and U.S. Pat. App. 20030211603. For example, like human embryonic stem (hES) cells, iPS cells can be maintained in 80% DMEM (Gibco #10829-018 or #11965-092), 20% defined fetal bovine serum (FBS) not heat inactivated, 1% non-essential amino acids, 1 mM L-glutamine, and 0.1 mM .beta.-mercaptoethanol. Alternatively, ES cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM .beta.-mercaptoethanol. Just before use, human bFGF may be added to a final concentration of .about 4 ng/mL (WO 99/20741).

Hepatocytes of this invention can be made by culturing pluripotent stem cells or other non-hepatocytes in a medium under conditions that increase the intracellular level of hepatocyte programming factors to be sufficient to promote programming of the cells into hepatocytes. The medium may also contain one or more hepatocyte differentiation and maturation agents, like various kinds of growth factors. However, by increasing the intracellular level of hepatocyte programming transcription factors, aspects of the present invention bypass most stages toward mature hepatocytes without the need to change the medium for each of the stages. Therefore, in view of the advantages provided by the present invention, in particular aspects, the medium for culturing cells under hepatocyte programming may be essentially free of one or more of the hepatocyte differentiation and maturation agents, or may not undergo serial change with media containing different combination of such agents.

These agents may either help induce cells to commit to a more mature phenotype—or preferentially promote survival of the mature cells—or have a combination of both these effects. Hepatocyte differentiation and maturation agents illustrated in this disclosure may include soluble growth factors (peptide hormones, cytokines, ligand-receptor complexes, and other compounds) that are capable of promoting the growth of cells of the hepatocyte lineage. Non-limiting examples of such agents include but are not limited to epidermal growth factor (EGF), insulin, TGF-α, TGF-β, fibroblast growth factor (FGF), heparin, hepatocyte growth factor (HGF), Oncostatin M (OSM), IL-1, IL-6, insulin-like growth factors I and II (IGF-I, IGF-2), heparin binding growth factor 1 (HBGF-1), and glucagon. The skilled reader will already appreciate that Oncostatin M is structurally related to Leukemia inhibitory factor (LIF), Interleukin-6 (IL-6), and ciliary neurotrophic factor (CNTF).

An additional examples is n-butyrate, as described in previous patent disclosures (U.S. Pat. Nos. 6,458,589, 6,506,574; WO 01/81549). Homologs of n-butyrate can readily be identified that have a similar effect, and can be used as substitutes in the practice of this invention. Some homologs have similar structural and physicochemical properties to those of n-butyrate: acidic hydrocarbons comprising 3-10 carbon atoms, and a conjugate base selected from the group consisting of a carboxylate, a sulfonate, a phosphonate, and other proton donors. Examples include isobutyric acid, butenoic acid, propanoic acid, other short-chain fatty acids, and dimethylbutyrate. Also included are isoteric hydrocarbon sulfonates or phosphonates, such as propanesulfonic acid and propanephosphonic acid, and conjugates such as amides, saccharides, piperazine and cyclic derivatives. A further class of butyrate homologs is inhibitors of histone deacetylase. Non-limiting examples include trichostatin A, 5-azacytidine, trapoxin A, oxamflatin, FR901228, cisplatin, and MS-27-275. Another class of agents is organic solvents like DMSO. Alternatives with similar properties include but are not limited to dimethylacetamide (DMA), hexmethylene bisacetamide, and other polymethylene bisacetamides. Solvents in this class are related, in part, by the property of increasing membrane permeability of cells. Also of interest are solutes such as nicotinamide.

VI. Hepatocytes Characteristics

Cells can be characterized according to a number of phenotypic criteria. The criteria include but are not limited to the detection or quantitation of expressed cell markers, enzymatic activity, and the characterization of morphological features and intercellular signaling. In other aspects, cells to be programmed may comprise reporter gene expression cassette comprising tissue- or cell-specific transcriptional regulatory element, like hepatocyte-specific promoters for hepatocyte identification.

Hepatocytes embodied in certain aspects of this invention have morphological features characteristic of hepatocytes in the nature, such as primary hepatocytes from organ sources. The features are readily appreciated by those skilled in evaluating such things, and include any or all of the following: a polygonal cell shape, a binucleate phenotype, the presence of rough endoplasmic reticulum for synthesis of secreted protein, the presence of Golgi-endoplasmic reticulum lysosome complex for intracellular protein sorting, the presence of peroxisomes and glycogen granules, relatively abundant mitochondria, and the ability to form tight intercellular junctions resulting in creation of bile canalicular spaces. A number of these features present in a single cell are consistent with the cell being a member of the hepatocyte lineage. Unbiased determination of whether cells have morphologic features characteristic of hepatocytes can be made by coding micrographs of programming progeny cells, adult or fetal hepatocytes, and one or more negative control cells, such as a fibroblast, or RPE (Retinal pigment epithelial) cells—then evaluating the micrographs in a blinded fashion, and breaking the code to determine if the cells produced from forward programming are accurately identified.

Cells of this invention can also be characterized according to whether they express phenotypic markers characteristic of cells of the hepatocyte lineage. Non-limiting examples of cell markers useful in distinguishing hepatocytes include albumin, asialoglycoprotein receptor, α1-antitrypsin, α-fetoprotein, apoE, arginase I, apoAI, apoAII, apoB, apoCIII, apoCII, aldolase B, alcohol dehydrogenase 1, catalase, CYP3A4, glucokinase, glucose-6-phosphatase, insulin growth factors 1 and 2, IGF-1 receptor, insulin receptor, leptin, liver-specific organic anion transporter (LST-1), L-type fatty acid binding protein, phenylalanine hydroxylase, transferrin, retinol binding protein, and erythropoietin (EPO). Mature hepatocyte markers include, but are limited to, albumin, α1-antitrypsin, asialoglycoprotein receptor, cytokeratin 8 (CK8), cytokeratin 18 (CK18), CYP3A4, fumaryl acetoacetate hydrolase (FAH), glucose-6-phosphates, tyrosine aminotransferase, phosphoenolpyruvate carboxykinase, and tryptophan 2,3-dioxygenase.

Assessment of the level of expression of such markers can be determined in comparison with other cells. Positive controls for the markers of mature hepatocytes include adult hepatocytes of the species of interest, and established hepatocyte cell lines. The reader is cautioned that permanent cell lines or long-term liver cell cultures may be metabolically altered, and fail to express certain characteristics of primary hepatocytes. Negative controls include cells of a separate lineage, such as an adult fibroblast cell line, or retinal pigment epithelial (RPE) cells. Undifferentiated stem cells are positive for some of the markers listed above, but negative for markers of mature hepatocytes, as illustrated in the examples below.

Tissue-specific (e.g., hepatocyte-specific) protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific (e.g., hepatocyte-specific) markers can also be detected at the mRNA level by Northern blot analysis, dot-blot hybridization analysis, or by real time polymerase chain reaction (RT-PCR) using sequence-specific primers in standard amplification methods (U.S. Pat. No. 5,843,780). Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of tissue-specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

Cells can also be characterized according to whether they display enzymatic activity that is characteristic of cells of the hepatocyte lineage. For example, assays for glucose-6-phosphatase activity are described by Bublitz (1991); Yasmineh et al. (1992); and Ockerman (1968). Assays for alkaline phosphatase (ALP) and 5-nucleotidase (5'-Nase) in liver cells are described by Shiojiri (1981). A number of laboratories that serve the research and health care sectors provide assays for liver enzymes as a commercial service.

In other embodiments, cells of the invention are assayed for activity indicative of xenobiotic detoxification. Cytochrome p450 is a key catalytic component of the mono-oxygenase system. It constitutes a family of hemoproteins responsible for the oxidative metabolism of xenobiotics (administered drugs), and many endogenous compounds. Different cytochromes present characteristic and overlapping substrate specificity. Most of the biotransforming ability is attributable by the cytochromes designated 1A2, 2A6, 2B6, 3A4, 2C 9-11, 2D6, and 2E1 (Gomes-Lechon et al., 1997).

A number of assays are known in the art for measuring xenobiotic detoxification by cytochrome p450 enzyme activity. Detoxification by CYP3 A4 is demonstrated using the P450-Glo™ CYP3A4 DMSO-tolerance assay (Luciferin-PPXE) and the P450-Glo™ CYP3A4 cell-based/biochemical assay (Luciferin-PFBE) (Promega Inc, #V8911 and #V8901). Detoxification by CYP1A1 and or CYP1B1 is demonstrated using the P450-Glo™ assay (Luciferin-CEE) (Promega Inc., #V8762). Detoxification by CYP1A2 and or CYP4A is demonstrated using the P450-Glo™ assay (Luciferin-ME) (Promega Inc., #V8772) Detoxification by CYP2C9 is demonstrated using the P450-Glo™ CYP2C9 assay (Luciferin-H) (Promega Inc., #V8791).

In another aspect, the biological function of a hepatocyte cell provided by programming is evaluated, for example, by analysing glycogen storage. Glycogen storage is characterized by assaying Periodic Acid Schiff (PAS) functional staining for glycogen granules. The hepatocyte-like cells are first oxidized by periodic acid. The oxidative process results in the formation of aldehyde groupings through carbon-to-carbon bond cleavage. Free hydroxyl groups should be present for oxidation to take place. Oxidation is completed when it reaches the aldehyde stage. The aldehyde groups are detected by the Schiff reagent. A colorless, unstable dialdehyde compound is formed and then transformed to the colored final product by restoration of the quinoid chromophoric grouping (Thompson, 1966; Sheehan and Hrapchak, 1987). PAS staining can be performed according the protocol described at world wide web at jhu.edu/~iic/PDF jrotocols/LM/Glycogen Staining pdf and library.med.utah.edu/WebPath/HISTHTML/MANUALS/PAS.PDF with some modifications for an in vitro culture of hepatocyte-like cells. One of ordinary skill in the art should be able to make the appropriate modifications.

In another aspect, a hepatocyte cell produced by forward programming in certain aspects of the invention is characterized for urea production. Urea production can be assayed colorimetrically using kits from Sigma Diagnostic (Miyoshi et al, 1998) based on the biochemical reaction of urease reduction to urea and ammonia and the subsequent reaction with 2-oxoglutarate to form glutamate and NAD.

In another aspect, bile secretion is analyzed. Biliary secretion can be determined by fluorescein diacetate time lapse assay. Briefly, monolayer cultures of hepatocyte-like cells are rinsed with phosphate buffered saline (PBS) three times and incubated with serum-free hepatocyte growth media supplemented with doxycycline and fluorescein diacetate (20 µg/ml) (Sigma-Aldrich) at 37° C. for 35 minutes. The cells are washed with PBS three times and fluorescence imaging is carried out. Fluorescein diacetate is a non fluorescent precursor of fluorescein. The image is evaluated to determine that the compound had been taken up and metabolized in the hepatocyte-like cell to fluorescein. In some embodiments, the compound is secreted into intercellular clefts of the monolayer of cells. Alternatively, bile secretion is determined by a method using sodium fluorescein described by Gebhart and Wang (1982).

In yet another aspect, lipid synthesis is analyzed. Lipid synthesis in the hepatocyte-like cell can be determined by oil red O staining Oil Red O (Solvent Red 27, Sudan Red 5B, C.I. 26125, $C_{26}H_{24}N_4O$) is a lysochrome (fat-soluble dye) diazo dye used for staining of neutral triglycerides and lipids on frozen sections and some lipoproteins on paraffin sections. It has the appearance of a red powder with maximum absorption at 518(359) nm. Oil Red O is one of the dyes used for Sudan staining Similar dyes include Sudan III, Sudan IV, and Sudan Black B. The staining has to be performed on fresh samples and/or formalin fixed samples. Hepatocyte-like cells are cultured on microscope slides, rinsed in PBS three times, the slides are air dried for 30-60 minutes at room temperature, fixed in ice cold 10% formalin for 5-10 minutes, and then rinse immediately in 3 changes of distilled water. The slide is then placed in absolute propylene glycol for 2-5 minutes to avoid carrying water into Oil Red O and stained in pre-warmed Oil Red O solution for 8 minutes in 600° C. oven. The slide is then placed in 85% propylene glycol solution for 2-5 minutes and rinsed in 2 changes of distilled water. Oil red O staining can also be performed according the protocol described at library.med.utah.edu/WebPath/HISTHTML/MANUALS/OILRED.PDF with some modifications for an in vitro culture of hepatocyte-like cell by one of ordinary skill in the art.

In still another aspect, the cells are assayed for glycogen synthesis. Glycogen assays are well known to one of ordinary skill in the art, for example, in Passonneau and Lauderdale (1974). Alternatively, commercial glycogen assays can be used, for example, from BioVision, Inc. catalog #K646-100.

Cells of the hepatocyte lineage can also be evaluated by their ability to store glycogen. A suitable assay uses Periodic Acid Schiff (PAS) stain, which does not react with mono- and disaccharides, but stains long-chain polymers such as glycogen and dextran. PAS reaction provides quantitative estimations of complex carbohydrates as well as soluble and membrane-bound carbohydrate compounds. Kirkeby et al. (1992) describe a quantitative PAS assay of carbohydrate compounds and detergents. van der Laarse et al. (1992) describe a microdensitometric histochemical assay for glycogen using the PAS reaction. Evidence of glycogen storage is determined if the cells are PAS-positive at a level that is at least 2-fold, and preferably more than 10-fold above that of a control cell, such as a fibroblast The cells can also be characterized by karyotyping according to standard methods.

Assays are also available for enzymes involved in the conjugation, metabolism, or detoxification of small molecule drugs. For example, cells can be characterized by an ability to conjugate bilirubin, bile acids, and small molecule drugs, for excretion through the urinary or biliary tract. Cells are contacted with a suitable substrate, incubated for a suitable period, and then the medium is analyzed (by GCMS or other suitable technique) to determine whether a conjugation product has been formed. Drug metabolizing enzyme activities include de-ethylation, dealkylation, hydroxylation, demethylation, oxidation, glucuroconjugation, sulfoconjugation, glutathione conjugation, and N-acetyl transferase activity (A. Guillouzo, pp 411-431 in In vitro Methods in Pharmaceutical Research, Academic Press, 1997). Assays include peenacetin de-ethylation, procainamide N-acetylation, paracetamol sulfoconjugation, and paracetamol glucuronidation (Chesne et al., 1988).

A further feature of certain cell populations of this invention is that they are susceptible under appropriate circumstances to pathogenic agents that are tropic for primate liver cells. Such agents include hepatitis A, B, C, and delta, Epstein-Barr virus (EBV), cytomegalovirus (CMV), tuberculosis, and malaria. For example, infectivity by hepatitis B can be determined by combining cultured forward programming-derived hepatocytes with a source of infectious hepatitis B particles (such as serum from a human HBV carrier). The liver cells can then be tested for synthesis of viral core antigen (HBcAg) by immunohistochemistry or RT-PCR.

The skilled reader will readily appreciate that an advantage of forward programming-derived hepatocytes is that they will be essentially free of other cell types that typically contaminate primary hepatocyte cultures isolated from adult or fetal liver tissue. Markers characteristic of sinusoidal endothelial cells include Von Willebrand factor, CD4, CD14, and CD32. Markers characteristic of bile duct epithelial cells include cytokeratin-7, cytokeratin-19, and γ-glutamyl transpeptidase. Markers characteristic of stellate cells include α-smooth muscle actin (α-SMA), vimentin, synaptophysin, glial fibrillary acidic protein (GFAP), neural-cell adhesion molecule (N-CAM), and presence of lipid droplets (detectable by autofluorescence or staining by oil red O). Markers characteristic of Kupffer cells include CD68, certain lectins, and markers for cells of the macrophage lineage (such as HLA Class II, and mediators of phagocytosis). Forward rogramming-derived hepatocytes can be characterized as essentially free of some or all of these cell types if less than 0.1% (preferably less than 100 or 10 ppm) bear markers or other features of the undesired cell type, as determined by immunostaining and fluorescence-activated quantitation, or other appropriate technique.

Hepatocytes provided by forward programming according to certain aspects of this invention can have a number of the features of the stage of cell they are intended to represent. The more of these features that are present in a particular cell, the more it can be characterized as a cell of the hepatocyte lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

Other desirable features of hepatocytes provided in certain aspects of this invention are an ability to act as target cells in drug screening assays, and an ability to reconstitute liver function, both in vivo, and as part of an extracorporeal device. These features are described further in sections that follow.

VII. Use of Hepatocytes

The hepatocytes provided by methods and compositions of certain aspects of the invention can be used in a variety of applications. These include but not limited to transplantation or implantation of the hepatocytes in vivo; screening cytotoxic compounds, carcinogens, mutagens growth/regulatory factors, pharmaceutical compounds, etc., in vitro; elucidating the mechanism of liver diseases and infections; studying the mechanism by which drugs and/or growth factors operate; diagnosing and monitoring cancer in a patient; gene therapy; and the production of biologically active products, to name but a few.

A. Test Compound Screening

Forward programming-derived hepatocytes of this invention can be used to screen for factors (such as solvents, small molecule drugs, peptides, and polynucleotides) or environmental conditions (such as culture conditions or manipulation) that affect the characteristics of hepatocytes provided herein.

In some applications, stem cells (differentiated or undifferentiated) are used to screen factors that promote maturation of cells along the hepatocyte lineage, or promote proliferation and maintenance of such cells in long-term culture. For example, candidate hepatocyte maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of this invention, cell programmed to the hepatocyte lineage play the role of test cells for standard drug screening and toxicity assays, as have been previously performed on hepatocyte cell lines or primary hepatocytes in short-term culture. Assessment of the activity of candidate pharmaceutical compounds generally involves combining the hepatocytes provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on liver cells, or because a compound designed to have effects elsewhere may have unintended hepatic side effects. Two or more drugs can be tested in combination (by combining with the cells either simultaneously or sequentially), to detect possible drug-drug interaction effects.

In some applications, compounds are screened initially for potential hepatotoxicity (Castell et al., 1997). Cytotoxicity can be determined in the first instance by the effect on cell viability, survival, morphology, and leakage of enzymes into the culture medium. More detailed analysis is conducted to determine whether compounds affect cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al. (1996) describes a microassay for measuring glycogen, which can be used to measure the effect of pharmaceutical compounds on hepatocyte gluconeogenesis.

Other current methods to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of α-glutathione s-transferase; ATP, ADP, and AMP metabolism; intracellular $K^+$ and $Ca^{2+}$ concentrations; the release of nuclear matrix proteins or oligonucleosomes; and induction of apoptosis (indicated by cell rounding, condensation of chromatin, and nuclear fragmentation). DNA synthesis can be measured as $[^3H]$-thymidine or BrdU incorporation. Effects of a drug on DNA synthesis or structure can be determined by measuring DNA synthesis or repair. $[^3H]$-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to Vickers (1997) for further elaboration.

B. Liver Therapy and Transplantation

This invention also provides for the use of hepatocytes provided herein to restore a degree of liver function to a subject needing such therapy, perhaps due to an acute, chronic, or inherited impairment of liver function.

To determine the suitability of hepatocytes provided herein for therapeutic applications, the cells can first be tested in a suitable animal model. At one level, cells are assessed for their ability to survive and maintain their phenotype in vivo. Hepatocytes provided herein are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether starting cell typess such as pluripotent stem cells are still present. This can be performed by providing the administered cells with a detectable label (such as green fluorescent protein, or β-galactosidase); or by measuring a constitutive marker specific for the administered cells. Where hepatocytes provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure. General descriptions for determining the fate of hepatocyte-like cells in animal models is provided in Grompe et al. (1999); Peeters et al., (1997); and Ohashi et al. (2000).

At another level, hepatocytes provided herein are assessed for their ability to restore liver function in an animal lacking full liver function. Braun et al. (2000) outline a model for toxin-induced liver disease in mice transgenic for the HSV-tk gene. Rhim et al. (1995) and Lieber et al. (1995) outline models for liver disease by expression of urokinase. Mignon et al. (1998) outline liver disease induced by antibody to the cell-surface marker Fas. Overturf et al. (1998) have developed a model for Hereditary Tyrosinemia Type I in mice by targeted disruption of the Fah gene. The animals can be rescued from the deficiency by providing a supply of 2-(2-nitro-4-fluoro-methyl-benzyol)-1,3-cyclohexanedione (NTBC), but they develop liver disease when NTBC is withdrawn. Acute liver disease can be modeled by 90% hepatectomy (Kobayashi et al., 2000). Acute liver disease can also be modeled by treating animals with a hepatotoxin such as galactosamine, $CCl_4$, or thioacetamide.

Chronic liver diseases such as cirrhosis can be modeled by treating animals with a sub-lethal dose of a hepatotoxin long enough to induce fibrosis (Rudolph et al., 2000). Assessing the ability of hepatocytes provided herein to reconstitute liver function involves administering the cells to such animals, and then determining survival over a 1 to 8 week period or more, while monitoring the animals for progress of the condition. Effects on hepatic function can be determined by evaluating markers expressed in liver tissue, cytochrome p450 activity, and blood indicators, such as alkaline phosphatase activity, bilirubin conjugation, and prothrombin time), and survival of the host Any improvement in survival, disease progression, or maintenance of hepatic function according to any of these criteria relates to effectiveness of the therapy, and can lead to further optimization.

Hepatocytes provided in certain aspects of this invention that demonstrate desirable functional characteristics according to their profile of metabolic enzymes, or efficacy in animal models, may also be suitable for direct administration to human subjects with impaired liver function. For purposes of hemostasis, the cells can be administered at any site that has adequate access to the circulation, typically within the abdominal cavity. For some metabolic and detoxification functions, it is advantageous for the cells to have access to the biliary tract. Accordingly, the cells are administered near the liver (e.g., in the treatment of chronic liver disease) or the spleen (e.g., in the treatment of fulminant hepatic failure). In one method, the cells administered into the hepatic circulation either through the hepatic artery, or through the portal vein, by infusion through an in-dwelling catheter. A catheter in the portal vein can be manipulated so that the cells flow principally into the spleen, or the liver, or a combination of both. In another method, the cells are administered by placing a bolus in a cavity near the target organ, typically in an excipient or matrix that will keep the bolus in place. In another method, the cells are injected directly into a lobe of the liver or the spleen.

The hepatocytes provided in certain aspects of this invention can be used for therapy of any subject in need of having hepatic function restored or supplemented. Human conditions that may be appropriate for such therapy include fulminant hepatic failure due to any cause, viral hepatitis, drug-induced liver injury, cirrhosis, inherited hepatic insufficiency (such as Wilson's disease, Gilbert's syndrome, or $\alpha_1$-antitrypsin deficiency), hepatobiliary carcinoma, autoimmune liver disease (such as autoimmune chronic hepatitis or primary biliary cirrhosis), and any other condition that results in impaired hepatic function. For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

C. Use in a Liver Assist Device

Certain aspects of this invention include hepatocytes provided herein that are encapsulated or part of a bioartificial liver device. Various forms of encapsulation are described in *Cell Encapsulation Technology and Therapeutics*, 1999. Hepatocytes provided in certain aspects of this invention can be encapsulated according to such methods for use either in vitro or in vivo.

Bioartificial organs for clinical use are designed to support an individual with impaired liver function—either as a part of long-term therapy, or to bridge the time between a fulminant hepatic failure and hepatic reconstitution or liver transplant. Bioartificial liver devices are reviewed by Macdonald et al., pp. 252-286 of "Cell Encapsulation Technology and Therapeutics", op cit., and exemplified in U.S. Pat. Nos. 5,290,684, 5,624,840, 5,837,234, 5,853,717, and 5,935,849. Suspension-type bioartificial livers comprise cells suspended in plate dialysers, microencapsulated in a suitable substrate, or attached to microcarrier beads coated with extracellular matrix. Alternatively, hepatocytes can be placed on a solid support in a packed bed, in a multiplate flat bed, on a microchannel screen, or surrounding hollow fiber capillaries. The device has an inlet and outlet through which the subject's blood is passed, and sometimes a separate set of ports for supplying nutrients to the cells.

Hepatocytes are prepared according to the methods described earlier, and then plated into the device on a suitable substrate, such as a matrix of Matrigel® or collagen. The efficacy of the device can be assessed by comparing the composition of blood in the afferent channel with that in the efferent channel—in terms of metabolites removed from the afferent flow, and newly synthesized proteins in the efferent flow.

Devices of this kind can be used to detoxify a fluid such as blood, wherein the fluid comes into contact with the hepatocytes provided in certain aspects of this invention under conditions that permit the cell to remove or modify a toxin in the fluid. The detoxification will involve removing or altering at least one ligand, metabolite, or other compound (either natural and synthetic) that is usually processed by the liver. Such compounds include but are not limited to bilirubin, bile acids, urea, heme, lipoprotein, carbohydrates, transferrin, hemopexin, asialoglycoproteins, hormones like insulin and glucagon, and a variety of small molecule drugs. The device can also be used to enrich the efferent fluid with synthesized proteins such as albumin, acute phase reactants, and unloaded carrier proteins. The device can be optimized so that a variety of these functions is performed, thereby restoring as many hepatic functions as are needed. In the context of therapeutic care, the device processes blood flowing from a patient in hepatocyte failure, and then the blood is returned to the patient.

D. Distribution for Commercial, Therapeutic, and Research Purposes

For purposes of manufacture, distribution, and use, the hepatocyte lineage cells of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to programming-derived cells (hepatocyte lineage cells, their precursors and subtypes), in combination with undifferentiated stem cells, somatic cell-derived hepatocytes, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. Cells and Methods for Testing Candidate Gene in Programming

The ability of a particular candidate gene or a combination of candidate genes to act as forward programming factors for a specific cell type, such as hepatocytes, can be tested using the methods and cells provided in this disclosure. Efficacy of particular candidate genes or combinations of candidate genes in forward programming can be assessed by their effect on cell morphology, marker expression, enzymatic activity, proliferative capacity, or other features of interest, which is then determined in comparison with parallel cultures that did not include the candidate genes or combinations. Candidate genes may be transcription factors important for differentiation into desired cell types or for function of the desired cell types.

In certain embodiments, starting cells, such as pluripotent stem cells, comprising at least one expression cassette for expression of a candidate gene or a combination of candidate genes may be provided. The expression cassette may comprise an externally controllable transcriptional regulatory element, such as an inducible promoter. The activity of these promoters may be induced by the presence or absence of biotic or abiotic factors. Inducible promoters are a very powerful tool in genetic engineering because the expression of genes operably linked to them can be turned on or off at certain stages of development of an organism or in a particular tissue. Tet-On and Tet-Off inducible gene expression systems based on the essential regulatory components of the *E. coli* tetracycline-resistance operon may be used. Once established in the starting cells, the inducer doxycycline (Dox, a tetracycline derivative) could controls the expression system in a dose-dependent manner, allowing to precisely modulate the expression levels of candidate genes.

To aid identification of desired cell types, the starting cells may further comprise a cell-specific or tissue-specific reporter expression cassette. The reporter expression cassette may comprise a reporter gene operably linked to a transcriptional regulatory element specific for the desired cell types. For example, the reporter expression cassette may comprise a hepatocyte-specific promoter for hepatocyte production, isolation, selection, or enrichment. The reporter gene may be any selectable or screenable marker gene known in the art and exemplified in the preceding disclosure.

VIII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Forward Programming into Hepatocytes

Alternative approaches for hepatocyte differentiation from human ESC/iPSCs are shown in FIG. 1. Hepatic lineage cells such as mature hepatocytes can likely be efficiently induced from human ESC/iPSCs via expression of appropriate transgene combination (top box), bypassing most, if not all, developmental stages required during normal differentiation (bottom box).

Figure 2:
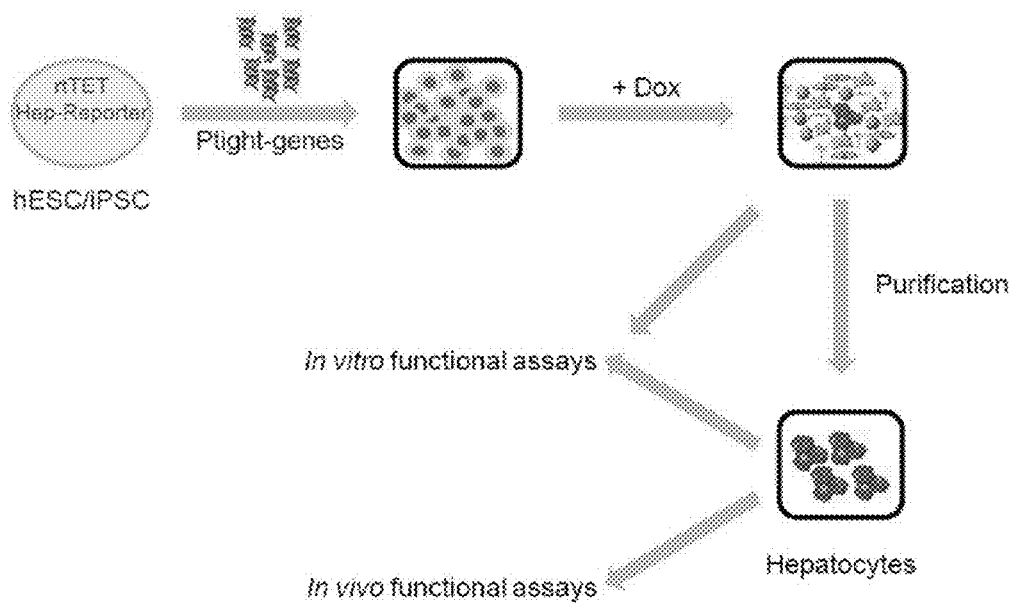
FIG. 2. The strategy employed for identifying transgenes that could forward program human ESC/iPSCs to mature hepatocytes.

The strategy employed for identifying transgenes that could directly convert human ESC/iPSCs to hepatic lineage cells including mature hepatocytes is shown in FIG. 2. Human ESC/iPSCs were engineered to carry reporters under the control of a hepatocyte-specific promoter, and to constitutively express rtTET protein for inducible gene expression. Transgenes under the control of the inducible promoter Ptight will be introduced into the engineered hESC/iPSCs either by lipid-mediated transfection or electroporation. Upon doxycycline (Dox) addition, transgene expression will be induced, and hepatocyte differentiation will be monitored by the expression of reporters and hepatocyte-specific marker genes, and additional hepatocyte-specific function analyses. Once the right transgene combination is identified, the hepatocytes will be purified for both in vitro and in vivo functional assays.

Figure 3:
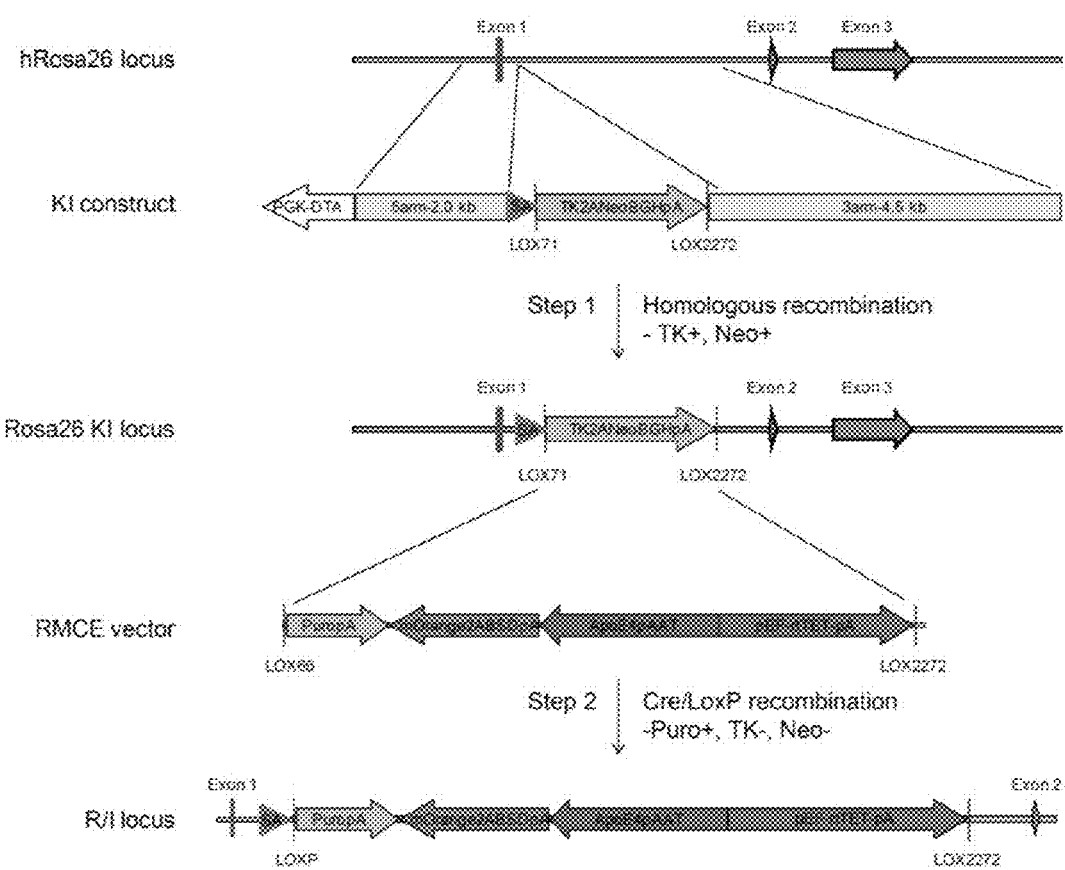
FIG. 3. The establishment of human ESC/iPSC reporter/inducible (R/I) lines for hepatocyte differentiation.

Human ESC/iPSC reporter/inducible (R/I) lines were established for hepatocyte differentiation (FIG. 3). The human Rosa26 locus on chromosome 3 was selected to allow the expression of both hepatocyte-specific reporter and rtTET, while minimizing the chromosome location-dependent silencing effect. First, the LoxP recombination sites (LOX71 and LOX2272) were introduced into a site between exon 1 and exon 2 of human ROSA 26 gene via homologous recombination. The targeting construct (KI construct) used the phosphoglycerate kinase promoter (PGK)-driven expression of diphtheria toxin A fragment gene (DTA) for negative selection, and contains a ~2.0 kb 5' arm and a 4.5 kb 3' arm. A splicing acceptor signal from human BCL2 gene (SA) was placed in front of LOX71 site to allow the expression of selection markers from the endogenous human ROSA26 promoter. The coding region for thymidine kinase (TK) was included to enable negative selection against incorrect Cre/LoxP recombination events at step 2 using ganciclovir. The neomycin phosphotransferase (Neo) was used for positive selection during homologous recombination (step 1). The foot-and-mouth disease virus peptide (F2A) was used to co-express the TK and Neo genes from the endogenous human ROSA26 promotor. BGHpA is polyadenylation signal derived from bovine growth hormone gene. The homologous recombination yielded parental human ESC/iPSC lines for efficient cassette exchange via Cre/LoxP recombination. To establish reporter/inducible cell lines for hepatocyte differentiation, F2A peptide linked marker gene mOrange and Blasticidin S deaminase (BSD) (driven by a hepatocyte-specific promoter ApoE4pAAT) and rtTET (driven by the constitutively active eukaryotic elongation factor 1α promoter—pEF) was introduced into the $Rosa$ 26 locus by lipid-mediated cotransfection of the recombination mediated cassette exchange (RMCE) vector and a Cre-expressing plasmid. The puromycin N-acetyl-transferase (Puro) was used to select for recombination events. The correctly recombined R/I cells are resistant to puromycin (Puro$^+$) and ganciclovir (TK$^-$), and sensitive to geneticin selection (Neo$^-$).

Restricted marker gene (mOrange) expression in hepatocytes during normal human ESC differentiation were confirmed (FIGS. 4A-4B). Human H1 ESC R/I lines were routinely maintained in MEF-conditioned human ES cell medium supplemented with 100 ng/ml bFGF (CM100) on matrigel (Growth Factor Reduced; BD Bioscience). For differentiation, human ESCs were harvested using Accutase (Invitrogen), and plated on matrigel-coated 10-cm dishes at a density of 0.5×10$^5$ cells/cm$^2$ in CM100 for 3 days. Hepatocyte differentiation was initiated by culture for 5 days with 100 ng/ml Activin A (R&D Systems) in RPMI/B27 medium (Invitrogen) (definitive endoderm differentiation), followed by 5 days with 20 ng/ml BMP4 (Peprotech) and 10 ng/ml FGF-2 (Invitrogen) in RPMI/B27 (hepatic specification), then 5 days with 20 ng/ml HGF (Peprotech) in RPMI/B27 (immature hepatocyte differentiation) and finally for 5 days with 20 ng/ml Oncostatin-M (R&D Systems) in Hepatocyte Culture Media (Lonza) supplemented with SingleQuots (hepatocyte maturation).

Figure 5A:
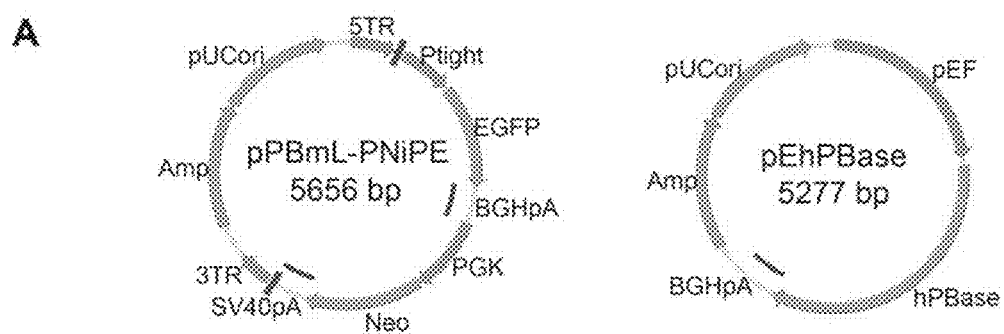
FIGS. 5A-5C. Confirmation of the Tet-On inducible gene expression in human H1 ESC R/I lines.
Figure 5B:
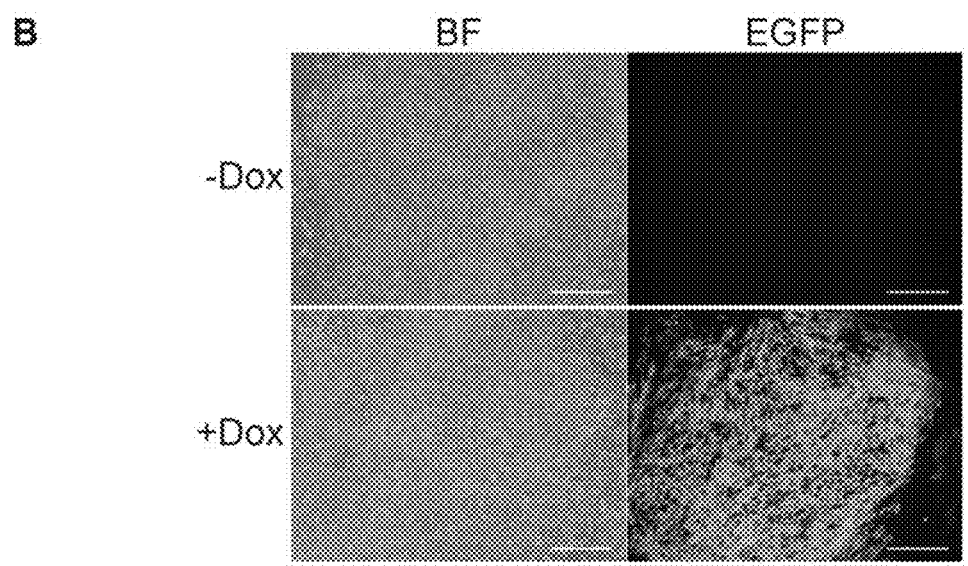
Figure 5C:
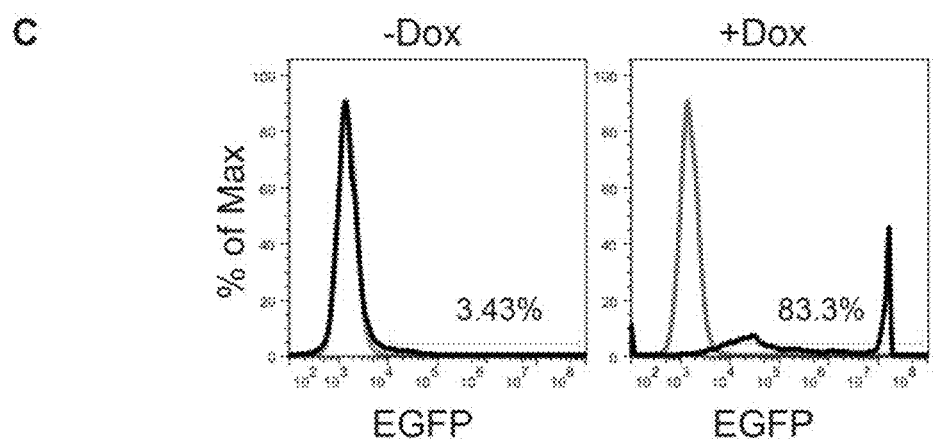

The Tet-On inducible gene expression was confirmed in human H1 ESC R/I lines (FIGS. 5A-5C). The EGFP driven by the Ptight promoter (an rtTET-responsive inducible promoter) was introduced into human ESC R/I lines using Fugene HD-mediated transfection of both vectors in FIG. 5A. Human ESCs with stable PiggyBac transposon integration were selected with geneticin (100 μg/ml). Images are shown in FIG. 5B with human ESC R/I lines after 2 days induction with or without Doxycycline (1 μg/ml). EGFP expression was analyzed by flow cytometry in human ESC R/I lines after 4 days induction with or without Doxycycline (1 μg/ml) (FIG. 5C). After 4 days of Doxycycline induction, 83.3% human ESC R/I lines showed stable PiggyBac transposon integration by EGFP expression.

Figure 6:
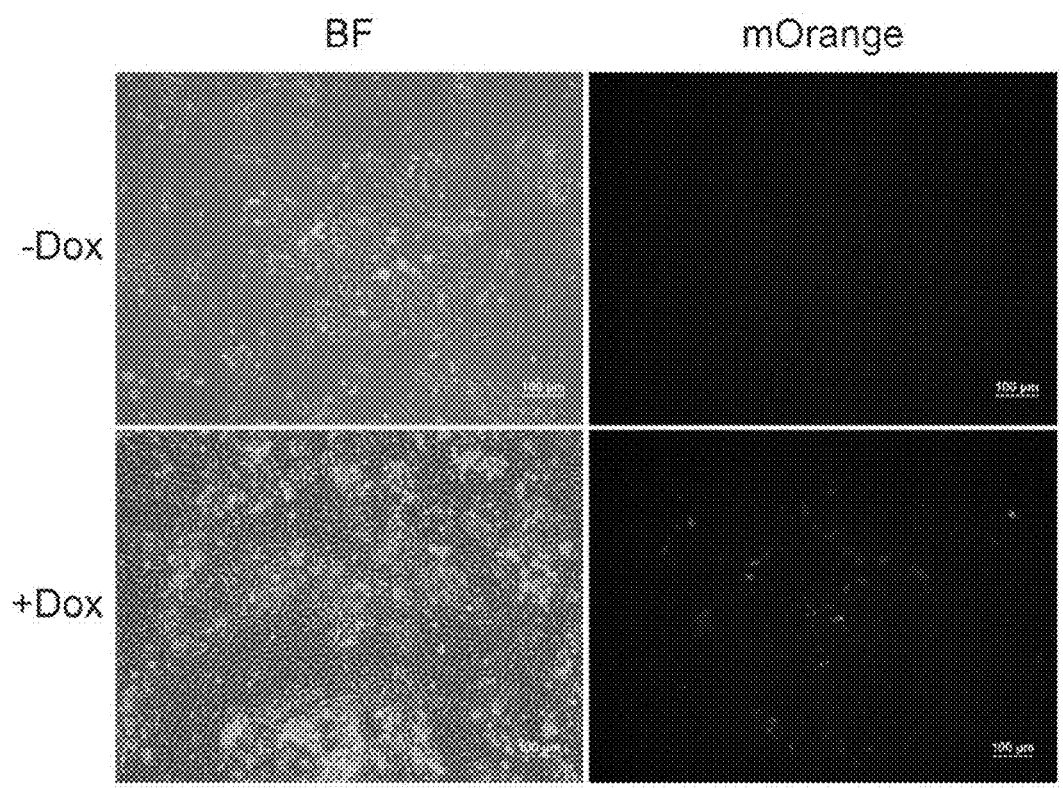
FIG. 6. Direct induction of hepatocytes from human ESC R/I lines through transgene expression.

Hepatocytes were directly induced from human ESC R1 lines through transgene expression (FIG. 6). Genes that are either implicated in hepatic differentiation during normal mammalian development or enriched in adult hepatocytes were cloned into the PiggyBac vector (FIG. 5A) under the control of the Ptight promoter (Table 1). These genes were further prioritized based on their known functional importance during normal hepatic differentiation or hepatic functions. To screen for transcription factors that are able to directly impose hepatic fate upon human ESCs, various combinations of transgene-expressing PiggyBac vectors along with the hPBase-expressing vector were introduced into the human ESC R/I lines cultured in CM100 on matrigel via Fugene HD-mediated transfection or electroporation. Following Geneticin (100 µg/ml) selection for stable genomic transgene integration, Doxycycline (1 µg/ml) was added to induce transgene expression, and the CM100 was replaced with Hepatocyte Culture Media (Lonza) supplemented with SingleQuots, 20 ng/ml HGF and 50 ng/ml Oncostatin-M (HCM). Hepatic lineage induction was monitored with mOrange marker gene expression between day 3-5 post induction. In the absence of Doxycycline induction, significant cell death was observed after 3-day culture in HCM medium in contrast to those with Doxycycline induction. The combination of transcription factors used herein are from the following: FOXA1, FOXA2-2, HHEX, HNF1A, HNF4A-2 and TBX3-1 (Table 1). Significant number of hepatocyte-specific promoter-driven mOrange-expressing cells were observed after five days of Doxycycline induction in HCM.

Figures 7A, 7B, 7C:
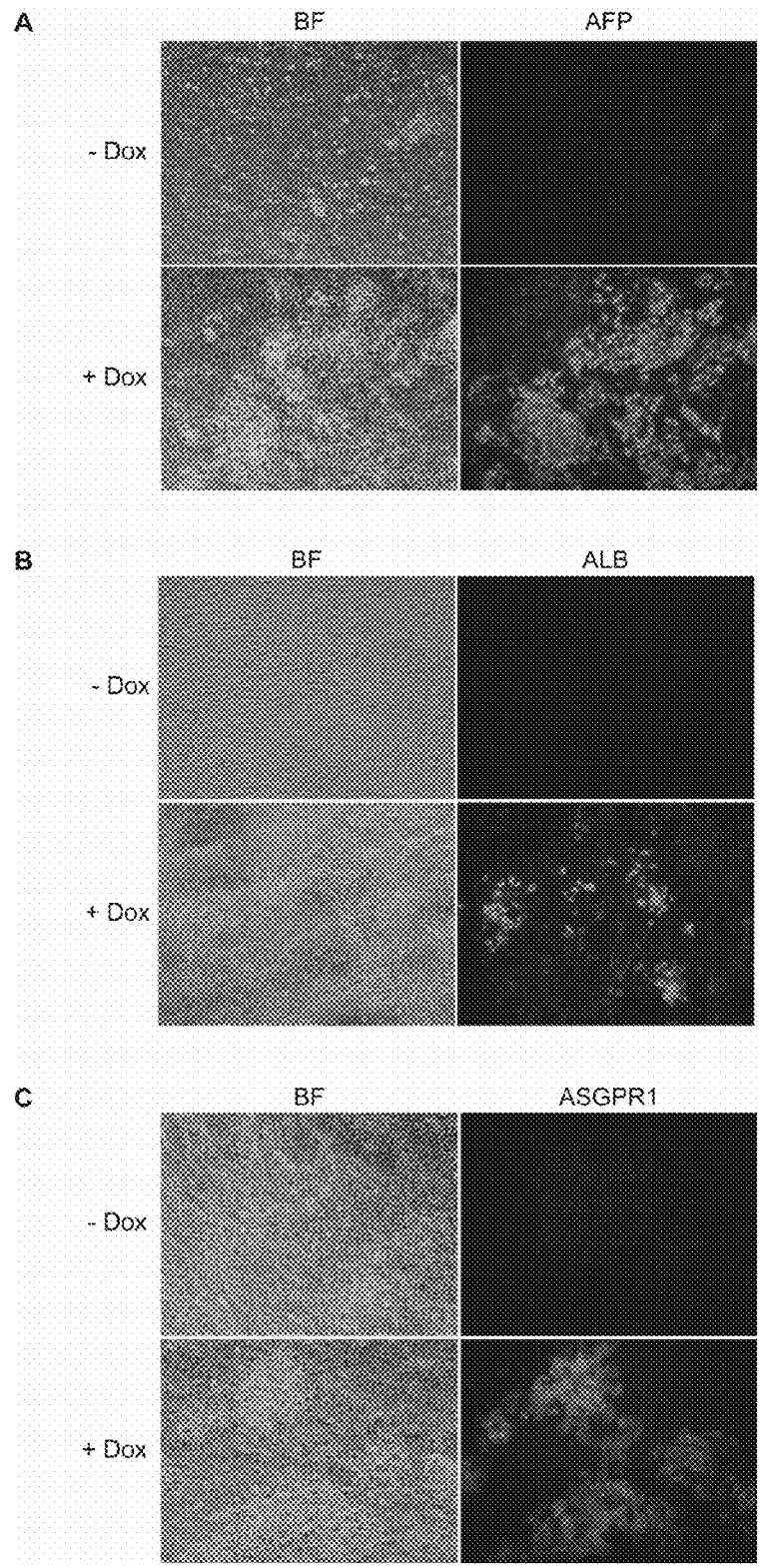
FIGS. 7A-7C. Forward programming of human ESC R/I lines to hepatocyte-like cells by transgene expression. Among genes that are either implicated in hepatic differentiation during normal mammalian development or enriched in adult hepatocytes (Table 1), a combination of genes (FOXA2, HHEX, HNF4A, GATA4, NR0B2 and SCML1) were identified that are sufficient to convert human ESCs directly into hepatocyte-like cells.

Another combination of genes (FOXA2, HHEX, HNF4A, GATA4, NROB2 and SCML1) were identified that are sufficient to convert human ESCs directly into hepatocyte-like cells (FIGS. 7A-7C). Briefly, the transgene-expressing PiggyBac vectors (2 µg each) along with the hPBase-expressing vector (4 µg) were introduced into the human ESC R/I lines cultured in mTeSR1 on matrigel via nucleofection. About 2-3×10⁶ ESCs were used for each nucleofection (nucleofection solution: 100 µA of Ingenio® Electroporation solution from Minis, Madison, Wis.; program: Amaxa B-016). Following Geneticin (100 µg/ml) selection for stable genomic transgene integration, cells were plated into 12-well matrigel plates for forward programming. The next day following plating, Doxycycline (1 µg/ml) was added to induce transgene expression, initially in mTeSR1 for 1 day followed by Hepatocyte Maintenance Medium supplemented with SingleQuot (HMM, Lonza), 20 ng/ml HGF and 20 ng/ml Oncostatin-M (OSM) for 5 days. After 6-day transgene induction, cells were further cultured in HMM supplemented with OSM for an additional 10-11 days prior to analysis. Hepatic induction was examined by immunological staining with antibodies for hepatocyte-specific markers alpha-fetoprotein (AFP) (FIG. 7A), albumin (ALB) (FIG. 7B), and asiologlycoprotein receptor 1 (ASGPR1) (FIG. 7C). Expression of additional genes (Table 1) may improve either the efficiency of hepatic lineage programming from human ESCs or hepatic functions.

Additional combinations that could induce hepatocyte-like cells from human ESC R/I lines via forward programming are presented in Table 2.

TABLE 2

Additional transgene combinations for hepatocyte forward programming

| # | | | | |
|---|---|---|---|---|
| C1 | FOXA2 | HNF1A | HNF4A | CEBPB |
| C2 | FOXA2 | HNF1A | HNF4A | FOXA1 |
| C3 | FOXA2 | HNF1A | HNF4A | GATA4 |
| C4 | FOXA2 | HNF1A | HNF4A | HHEX |
| C5 | FOXA2 | HNF1A | HNF4A | HLF |
| C6 | FOXA2 | HNF1A | HNF4A | HLX |
| C7 | FOXA2 | HNF1A | HNF4A | NR0B2 |
| C8 | FOXA2 | HNF1A | HNF4A | NR1H3 |
| C9 | FOXA2 | HNF1A | HNF4A | NR1H4 |
| C10 | FOXA2 | HNF1A | HNF4A | NR1I2 |
| C11 | FOXA2 | HNF1A | HNF4A | NR1I3 |
| C12 | FOXA2 | HNF1A | HNF4A | NR5A2 |

TABLE 2-continued

Additional transgene combinations for hepatocyte forward programming

| # | | | | |
|---|---|---|---|---|
| C13 | FOXA2 | HNF1A | HNF4A | SCML1 |
| C14 | FOXA2 | HNF1A | HNF4A | SEBOX |
| C15 | FOXA2 | HNF1A | HNF4A | ZNF391 |
| C16 | FOXA2 | HNF1A | HNF4A | ZNF517 |

Figure 8:
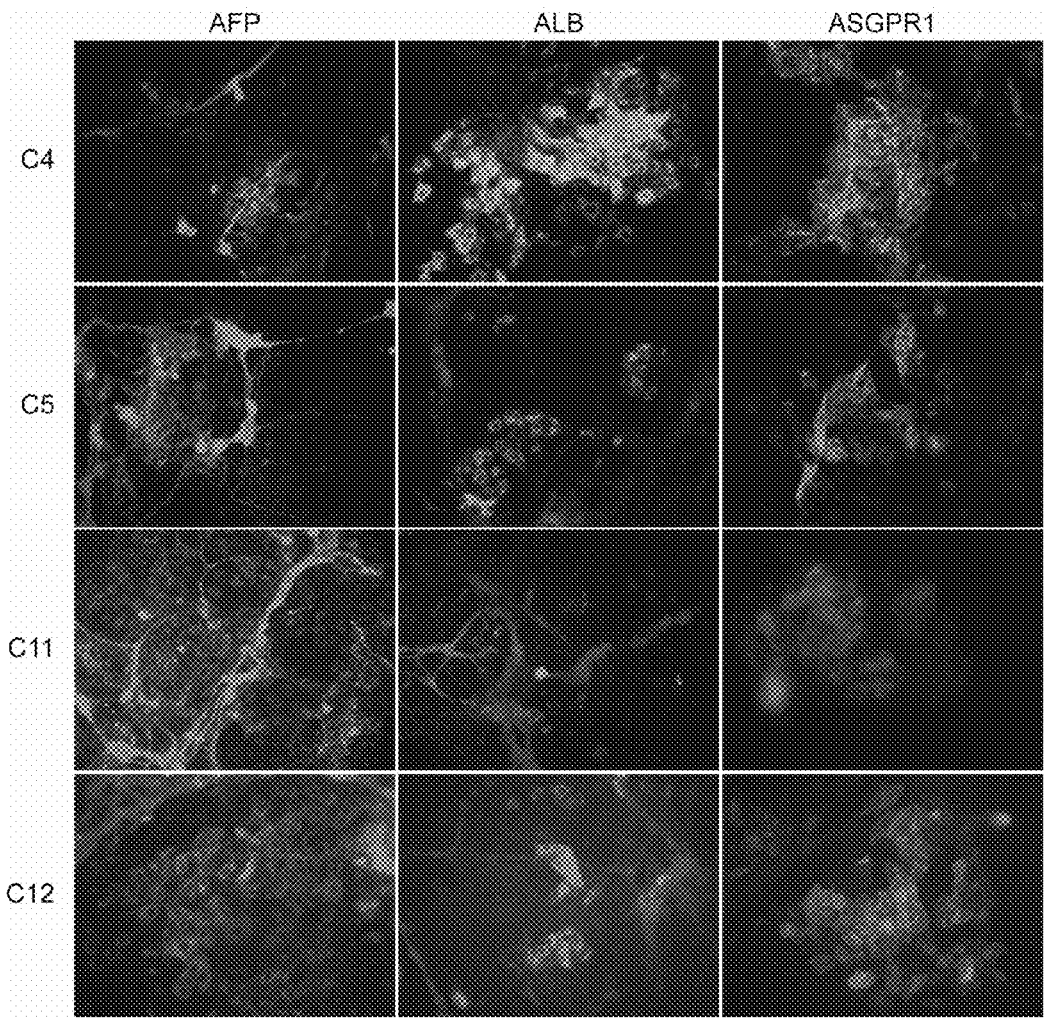
FIG. 8. Examples of additional combinations (Table 2) that could induce hepatocyte-like cells from human ESC R/I lines via forward programming. AFP, ALB, ASGPR1 expression of cells by forward programming using combinations 4, 5, 11, 12 (C4, C5, C11, C12) in Table 2 were shown.

Examples of additional combinations for forward programming are shown in FIG. 8. The transgene-expressing PiggyBac vectors (2 µg each) along with the hPBase-expressing vector (4 µg) were introduced into the human ESC R/I lines cultured in mTeSR1 on matrigel via nuleofection. About 2-3×10⁶ ESCs were used for each nucleofection (nucleofection solution: 100 µl of Ingenio® Electroporation solution from Minis, Madison, Wis.; program: Amaxa B-016). Following Geneticin (100 µg/ml) selection for stable genomic transgene integration, cells were plated into 12-well matrigel plates for forward programming. The next day following plating, Doxycycline (1 µg/ml) was added to induce transgene expression, in Hepatocyte Maintenance Medium supplemented with SingleQuot (HMM, Lonza), 20 ng/ml HGF and 20 ng/ml Oncostatin-M (OSM) for 4 days. After 4-day transgene induction, cells were further cultured in HMM supplemented with OSM for an additional 12 days prior to analysis. Hepatic induction was examined by immunostaining with antibodies for hepatocyte-specific markers alpha-fetoprotein (AFP), albumin (ALB), and asiologlycoprotein receptor 1 (ASGPR1).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,030,015
U.S. Pat. No. 5,290,684
U.S. Pat. No. 5,302,523
U.S. Pat. No. 5,322,783
U.S. Pat. No. 5,384,253
U.S. Pat. No. 5,460,964
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,563,055
U.S. Pat. No. 5,580,859

U.S. Pat. No. 5,589,466
U.S. Pat. No. 5,591,616
U.S. Pat. No. 5,610,042
U.S. Pat. No. 5,624,840
U.S. Pat. No. 5,635,387
U.S. Pat. No. 5,656,610
U.S. Pat. No. 5,677,136
U.S. Pat. No. 5,681,599
U.S. Pat. No. 5,702,932
U.S. Pat. No. 5,716,827
U.S. Pat. No. 5,736,396
U.S. Pat. No. 5,736,524
U.S. Pat. No. 5,750,397
U.S. Pat. No. 5,759,793
U.S. Pat. No. 5,780,448
U.S. Pat. No. 5,789,215
U.S. Pat. No. 5,811,094
U.S. Pat. No. 5,827,735
U.S. Pat. No. 5,827,740
U.S. Pat. No. 5,837,234
U.S. Pat. No. 5,837,539
U.S. Pat. No. 5,837,670
U.S. Pat. No. 5,843,780
U.S. Pat. No. 5,853,717
U.S. Pat. No. 5,925,565
U.S. Pat. No. 5,928,906
U.S. Pat. No. 5,935,819
U.S. Pat. No. 5,935,849
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,184,038
U.S. Pat. No. 6,458,589
U.S. Pat. No. 6,506,574
U.S. Pat. No. 6,833,269
U.S. Pat. No. 6,991,897
U.S. Pat. No. 7,015,037
U.S. Pat. No. 7,399,632
U.S. Pat. No. 7,410,773
U.S. Pat. No. 7,410,798
U.S. Pat. No. 7,422,736
U.S. Patent Pubin. 2002/0102265
U.S. Patent Pubin. 2003/0040038
U.S. Patent Pubin. 2003/0082561
U.S. Patent Pubin. 20030211603
U.S. Patent Pubin. 20070238170
U.S. application Ser. No. 08/464,599
U.S. Appln. Ser. 61/058,858
U.S. Appln. Ser. 61/172,079
U.S. Appln. Ser. 61/184,546
Alexander et al., *Proc. Nat. Acad. Sci. USA*, 85:5092-5096, 1988.
Alison et al, *Hepatol.*, 29:678-83, 1998.
Amit et al., *Dev. Bio.*, 227:271-278, 2000.
Andrews et al., In: *Teratocarcinomas and Embryonic Stem Cells*, Robertson (Ed.), IRL Press, 207-246, 1987.
Asoh et al., *Proc. Natl. Acad. Sci. USA*, 99(26):17107-12, 2002.
Ausubel et al., *Current Protocols in Molecular Biology*, Greene Publ. Assoc. Inc. & John Wiley & Sons, Inc., MA, 1996.
Ausubel et al., In: *Current Protocols in Molecular Biology*, John, Wiley & Sons, Inc, New York, 1994.
Blomer et al., *J. Virol.*, 71(9):6641-6649, 1997.
Boyer et al., *Cell*, 122(6):947-56, 2005.
Braun et al., *Nature Med.*, 6:320, 2000.
Bublitz, *Mol. Cell. Biochem.*, 108:141, 1991.
Buss et al., *Mol. Cell. Biol.*, 8:3960-3963, 1988.
Byrne et al., *Nature*, 450(7169):497-502, 2007.
Capecchi, *Nature*, 348:109, 1990.
Cassiede et al., *J. Bone Miner. Res.*, 11(9):1264-1273, 1996.
Castell et al., In: *In vitro Methods in Pharmaceutical Research*, Academic Press, 375-410, 1997.
Cell Encapsulation Technology and Therapeutics, Kuhtreiber et al. eds., Birkhauser, Boston Mass., 1999.
Chambers et al., *Cell*, 113(5):643-55, 2003.
Chen and Okayama, *Mol. Cell. Biol.*, 7(8):2745-2752, 1987.
Chesne et al., In: *Liver Cells and Drugs*, Guillouzo (Ed.), John Libbey Eurotext, London, 343-350, 1988.
Chevalier et al., *Mol. Cell.*, 10:895-905, 2002.
*Current Protocols in Stem Cell Biology*, Bhatia et. al. (Ed.), John Wiley and Sons, Inc., 2007.
Derossi et al., *J. Bio. Chem.*, 269:10444-10450, 1994.
Derossi et al., *J. Biol. Chem.*, 271:18188, 1996.
Derossi et al., *Trends in Cell Biol.*, 8:84-87, 1998.
Durai et al., *Nucleic Acids Res.*, 33:5978-5990, 2005.
Elliott and O'Hare, *Cell*, 88:223-234, 1997.
EP 1507865
EP0412700
Ercolani et al., *J. Biol. Chem.*, 263:15335-15341, 1988.
Evans, et al., In: *Cancer Principles and Practice of Oncology*, Devita et al. (Eds.), Lippincot-Raven, N.Y., 1054-1087, 1997.
Fawell et al., *Proc. Natl. Acad. Sci. USA*, 91:664-668, 1994.
Fechheimer et al., *Proc Natl. Acad. Sci. USA*, 84:8463-8467, 1987.
Ferry et al., *Hum. Gene Ther.*, 9(14):1975-81, 1998.
Follenzi et al., *Hum. Gene Ther.*, 13(2):243-60, 2002.
Fraley et al., *Proc. Natl. Acad. Sci. USA*, 76:3348-3352, 1979.
Frankel and Pabo, *Cell*, 55(6):1189-1193, 1988.
Gebhart and Wang, *J. Cell Sci.*, 56233-244, 1982.
Gehrke et al., *Gene*, 322:137-43, 2003.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh et al., *J. Hepatol.*, 32(1Suppl):238-52, 2000.
Gomes-Lechon et al., In: *In vitro Methods in Pharmaceutical Research*, Academic Press, 129-153, 1997
Gomez-Lechon et al., *Anal. Biochem.*, 236:296, 1996.
Gopal, *Mol. Cell. Biol.*, 5:1188-1190, 1985.
Graham and Van Der Eb, *Virology*, 52:456-467, 1973.
Grompe et al., *Sem. Liver Dis.*, 19:7, 1999.
Gronthos, *Blood*, 84(12):41644173, 1994.
Hancock et al., *EMBO J.*, 10:4033-4039, 1991.
Harland and Weintraub, *J. Cell Biol.*, 101(3):1094-1099, 1985.
Hayhurst et al., *Mol. Cell. Biol.*, 21(4):1393-403, 2001.
Hill et al., *Exp. Hematol.*, 24(8):936-943, 1996.
Ho et al., *Cancer Res.*, 61(2):474-7, 2001.
*In vitro Methods in Pharmaceutical Research*, Academic Press, 1997.
Jaiswal et al., *J. Cell Biochem.*, 64(2):295-312, 1997.
Johnstone et al., 238(1):265-272, 1998.
Kaeppler et al., *Plant Cell Rep.*, 8:415-418, 1990.
Kaneda et al., *Science*, 243:375-378, 1989.
Karin et al. *Cell*, 36: 371-379, 1989.
Kato et al, *J. Biol. Chem.*, 266:3361-3364, 1991.
Kilic et al., *Stroke*, 34:1304-10, 2003.

Kirchmaier and Sugden, *J. Virol.*, 72(6):4657-4666, 1998.
Kirkeby et al., *Biochem. Biophys. Meth.*, 24:225, 1992.
Klein et al., *Nature*, 327:70-73, 1987.
Kobayashi et al., *Science*, 287:1258, 2000.
Kramer et al., *Mol. Ther.*, 7(3):375-85, 2003.
Laarse et al., *Biotech Histochem.*, 67:303, 1992.
Langle-Rouault et al., *J. Virol.*, 72(7):6181-6185, 1998.
Le et al., *Blood*, 89(4):1254-9, 1997.
Levitskaya et al., *Proc. Natl. Acad. Sci. USA*, 94(23):12616-12621, 1997.
Li et al., *Genes Dev.*, 14:464-74, 2000.
Lieber et al., *Proc. Natl. Acad. Sci. USA*, 92:6210, 1995.
Lindgren et al., *Trends in Pharmacol. Sci.*, 21:99-103, 2000.
Lindner et.al., *J. Virol.*, 82(12):5693-702, 2008.
Macdonald et al., pp. 252-286, *Cell Encapsulation Technology and Therapeutics*
Macejak and Sarnow, *Nature*, 353:90-94, 1991.
Makino et al., *J. Clin. Invest.*, 103(5):697-705, 1999.
Maniatis, et al., *Molecular Cloning, A Laboratory Manual*, Cold Spring Harbor Press, Cold Spring Harbor, N.Y., 1988.
Mann and Frankel, *EMBO J.*, 10:1733-1739, 1991. Mann et al., *Cell*, 33:153-159, 1983.
Manno et al., *Nat. Med.*, 12(3):342-7, 2006.
Miao et al., *Mol. Ther.*, 1(6):522-32, 2000.
Mignon et al., *Nature Med.*, 4:1185, 1998.
Miller et al., *Am. J. Clin. Oncol.*, 15(3):216-221, 1992.
Miller et al., *Nat. Biotechnol.*, 29:143-148, 2011.
Miyoshi et al, *J. Biomater. Sci. Polym. Ed.*, 9:227-237, 1998.
Nabel et al., *Science*, 244(4910):1342-1344, 1989.
Naldini et al., *Science*, 272(5259):263-267, 1996.
Ng, *Nuc. Acid Res.*, 17:601-615, 1989.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Ockerman, *Clin. Chim. Acta*, 17:201, 1968.
Ohashi et al., *Nature Med.*, 6:327, 2000.
Overturf et al., *Human Gene Ther.*, 9:295, 1998.
Paskind et al., *Virology*, 67:242-248, 1975.
Passonneau and Lauderdale, *Anal. Biochem.*, 60:405-415, 1974.
Pingoud and Silva, *Nat. Biotechnol.*, 25:743-744, 2007.
PCT Appln. WO 01/81549
PCT Appln. WO 03/059940
PCT Appln. WO 03/059941
PCT Appln. WO 94/09699
PCT Appln. WO 94/09699
PCT Appln. WO 95/06128
PCT Appln. WO 99/20741
PCT Appln. WO/2003/042405
PCT Appln. WO 01/098482
PCT Appln. WO 95/011308
PCT Appln. WO 96/39487
PCT/US2004/030606
PCT/IB2010/000154
Peeters et al., *Hepatology*, 25:884, 1997.
Pelletier and Sonenberg, *Nature*, 334:320-325, 1988.
Potrykus et al., *Mol. Gen. Genet.*, 199(2):169-177, 1985.
Potten, *Philos. Trans. R Soc. Lond. B Biol. Sci.*, 353:821-30, 1998.
Potter et al., *Proc. Natl. Acad. Sci. USA*, 81:7161-7165, 1984.
Quitsche et al., *J. Biol. Chem.*, 264:9539-9545, 1989.
Reubinoff et al., *Nat. Biotechnol.*, 18:399 B404, 2000.
Rhim et al., *Proc. Natl. Acad. Sci. USA*, 92:4942, 1995.
Richards et al., *Cell*, 37: 263-272, 1984.
Rippe, et al., *Mol. Cell. Biol.*, 10:689-695, 1990.
Rothbard et al., *Nat. Med.*, 6(11):1253-7, 2000.
Rudolph et al., *Science*, 287:1253, 2000.
Sambrook and Russell, *Molecular Cloning: A Laboratory Manual*, $3^{rd}$ Ed. Cold Spring Harbor Lab. Press, 2001.
Sambrook et al., *In:Molecular Cloning: A Laboratory Manual*, Vol. 1, Cold Spring Harbor Laboratory Press, Cold Spring Harbor, N.Y., (7)7:19-17.29, 1989.
Schwarze et al., *Science*, 285(5433):1466-7, 1999.
Schwarze et al., *Science*, 285:1569-1572, 1999.
Sheehan and Hrapchak, In: *Theory and Practise of Histotechnology*, $2^{nd}$ Ed., Battelle Memorial Institute, Columbus, Ohio, 1987.
Shen et al., *DNA*, 8(2):101-8, 1989.
Shiojiri, *J. Embryo'. Exp. Morph.*, 62:139, 1981.
Simonet et al., *J. Biol. Chem.*, 268(11):8221-9, 1993.
Smith, In: *Origins and Properties of Mouse Embryonic Stem Cells*, Annu Rev. Cell. Dev. Biol., 2000.
Takahashi and Yamanaka, *Cell*, 126:663-676, 2006.
Takahashi et al., *Cell*, 126(4):663-76, 2007.
Takahashi et al., *Cell*, 131:861-872, 2007.
Tanaka et al., *J. Immunol.*, 170(3):1291-8, 2003.
Temin, In: *Gene Transfer*, Kucherlapati (Ed.), NY, Plenum Press, 149-188, 1986.
Thompson, In: *Selected Histochemical and Histopathological Methods*, Tomas (Ed.), Sprungfield, Ill., 1966.
Thomson and Marshall, *Curr. Top. Dev. Biol.*, 38:133-165, 1998.
Thomson and Odorico, *J. Trends. Biotechnol.*, 18:53 B57, 2000.
Thomson et al. *Proc. Natl. Acad. Scie. USA*, 92:7844-7848, 1995.
Thomson et al., *Science*, 282:1145, 1998.
Tur-Kaspa et al., *Mol. Cell. Biol.*, 6:716-718, 1986.
VandenDriessche et al., *J. Thromb. Haemost.*, 5(1):16-24, 2007.
Vickers In: *In vitro Methods in Pharmaceutical Research*, Academic Press, 375-410, 1997
Watt, *Philos. Trans. R. Soc. Lond. B. Biol. Sci.*, 353:831, 1997.
Wender et al., *Proc. Natl. Acad. Sci. USA*, 97(24):13003-8, 2000.
Wilson et al., *Science*, 244:1344-1346, 1989.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Xu et al., *Nat. Biotechnol.*, 19:971-974, 2001.
Yakubov et al., *Biochemical and Biophysical Research Communications* 394: 189-193, 2010.
Yang and Russell, *Proc. Natl. Acad. Sci. USA*, 87:4144-4148, 1990.
Yasmineh et al., *Clin. Biochem.*, 25:109, 1992.
Ying et al., *Cell*, 115:281-292, 2003.
Yoo et al., *J. Bone Joint Sure. Am.*, 80(12):1745-1757, 1998.
Yu and Thompson, *Genes Dev.*, 22(15):1987-97, 2008.
Yu et al., *Science*, 318:1917-1920, 2007.
Yu et al., *Science*, 324(5928):797-801, 2009.
Yull et al., *Transgenic Res.*, 4(1):70-4, 1995.
Zufferey et al., *Nat. Biotechnol.*, 15(9):871-875, 1997.

What is claimed is:

1. A hepatocyte or stem cell comprising:
    a) one or more exogenous expression cassettes comprising a FOXA2 gene, a HNF1A gene and one or more additional hepatocyte programming factor genes selected from the group consisting of HHEX, HNF4A, FOXA1, TBX3-1, GATA4, NR0B2, SCML1, CEBPB, HLF, HLX, NR1H3, NR1H4, NR1I2, NR1I3, NR5A2, SEBOX, and ZNF391 genes; and
    b) a reporter expression cassette comprising a hepatocyte-specific promoter operably linked to a reporter gene.

2. A hepatocyte or stem cell comprising one or more exogenous expression cassettes, wherein the one or more exogenous expression cassettes comprise a FOXA2 gene, a HNF1A gene and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, and ZNF391 genes, and at least one of the exogenous expression cassettes is operably linked to an externally inducible transcriptional regulatory element.

3. A cell population comprising hepatocytes, wherein at least 80% of the hepatocytes comprise one or more exogenous expression cassettes that comprise a FOXA2 gene, a HNF1A gene and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, and ZNF391 genes.

* * * * *